US009884896B2

(12) United States Patent
Broglie et al.

(10) Patent No.: US 9,884,896 B2
(45) Date of Patent: Feb. 6, 2018

(54) POLYNUCLEOTIDES AND METHODS FOR MAKING PLANTS RESISTANT TO FUNGAL PATHOGENS

(71) Applicants: PIONEER HI-BRED INTERNATIONAL INC, Johnston, IA (US); E I DU PONT DE NEMOURS AND COMPANY, Wilmington, DE (US); UNIVERSITY OF DELAWARE, Newark, DE (US)

(72) Inventors: Karen E. Broglie, Landenberg, PA (US); Karlene H. Butler, Newark, DE (US); Marymar G. Butruille, Urbandale, IA (US); Alexandre Da Silva Conceicao, Wilmington, DE (US); Travis James Frey, Huxley, IA (US); James A. Hawk, Newark, DE (US); Jennifer S. Jaqueth, Wilmington, DE (US); Elizabeth S. Jones, Raleigh, NC (US); Dilbag S. Multani, Urbandale, IA (US); Petra Johanna Cecilia Christina Wolters, Kennett Square, PA (US)

(73) Assignees: PIONEER HI-BRED INTERNATIONAL, INC., Johnston, IA (US); E. I. DU PONT DE NEMOURS AND COMPANY, Wilmington, DE (US); UNIVERSITY OF DELAWARE, Newark, DE (US)

( * ) Notice: Subject to any disclaimer, the term of this patent is extended or adjusted under 35 U.S.C. 154(b) by 343 days.

(21) Appl. No.: 14/538,238

(22) Filed: Nov. 11, 2014

(65) Prior Publication Data

US 2016/0201079 A1    Jul. 14, 2016

Related U.S. Application Data

(63) Continuation of application No. 13/270,722, filed on Oct. 11, 2011, now Pat. No. 8,884,126, which is a continuation of application No. 11/774,121, filed on Jul. 6, 2007, now Pat. No. 8,084,671, which is a continuation of application No. 11/397,247, filed on Apr. 4, 2006, now abandoned.

(60) Provisional application No. 60/675,664, filed on Apr. 28, 2005, provisional application No. 60/668,241, filed on Apr. 4, 2005.

(51) Int. Cl.
*A01H 5/10* (2006.01)
*C12N 15/82* (2006.01)
*C12N 15/29* (2006.01)
*C07K 14/415* (2006.01)
*A01H 1/04* (2006.01)
*C12Q 1/68* (2006.01)

(52) U.S. Cl.
CPC ............. *C07K 14/415* (2013.01); *A01H 1/04* (2013.01); *A01H 5/10* (2013.01); *C12N 15/8282* (2013.01); *C12Q 1/6895* (2013.01); *C12Q 2600/13* (2013.01); *C12Q 2600/156* (2013.01); *C12Q 2600/172* (2013.01)

(58) Field of Classification Search
CPC .......................... C12N 15/8282; C07K 14/415
See application file for complete search history.

(56) References Cited

U.S. PATENT DOCUMENTS

| 6,479,731 | B1 | 11/2002 | Valent et al. | |
|---|---|---|---|---|
| 8,084,671 | B2 * | 12/2011 | Broglie | A01H 1/04 800/275 |
| 8,884,126 | B2 * | 11/2014 | Broglie | A01H 1/04 435/412 |
| 2009/0307796 | A1 | 12/2009 | Broglie et al. | |

OTHER PUBLICATIONS

Campa et al. BMC Plant Biology 2014, 14:115.*
Gonzalez et al (Front. Plant Sci.(2015) 6:141).*
McHale et al (Genome Biology 2006, 7:212).*
Jung et al (Theor Appl Genet (1994) 89:413-418).*
Salvi et al., 2003, Tuberosa, Phillips et Gale (eds.), Proceedings of the International Congress "In the Wake of the Double-Helix: From the Green Revolution to the Gene Revolution", 327-345.
Leister, 2004, Trends in Genetics, vol. 20, No. 3:116-122.
Young et al., 1989, Theor. Appl. Genet., vol. 77:353-359.
Zeven et al., 1983, Euphytica, vol. 32:319-327.
Opposition Against Patent EP 1 874 935, Aug. 1, 2014.
CPVO Variety data Sheet of PH705.
CPVO Variety data Sheet of PH5W4.
CPVO Variety data Sheet of PH87P.
CPVO Variety data Sheet of PH51K.
Response to Opposition Against Patent EP 1 874 935, May 22, 2015.
Flaque et al , "Linkage Mapping of 1454 New Maize Candidate Gene Loci", Genetics, vol. 170: 1957-1966 (2005).
Cone et al, "Genetic, Physical, and Informatics Resources for Maize on the Road to an Integrated Map", vol. 130: 1598-1605 (2002).
Williams, et al, "The genetic structure of recombinant inbred mice: high-resolution consensus maps for complex trait analysis", vol. 2(11): 0046.1-0046.18.

(Continued)

*Primary Examiner* — Lee A Visone

(57) ABSTRACT

This invention relates to polynucleotide sequences encoding a gene that can confer resistance to the plant pathogen *Colletotrichum*, which causes anthracnose stalk rot, leaf blight and top dieback in corn and other cereals. It further relates to plants and seeds of plants carrying chimeric genes comprising said polynucleotide sequences, which enhance or confer resistance to the plant pathogen *Colletotrichum*, and processes of making said plants and seeds. The invention further presents sequences that can be used as molecular markers that in turn can be used to identify the region of interest in corn lines resulting from new crosses and to quickly and efficiently introgress the gene from corn lines carrying said gene into other corn lines that do not carry said gene, in order to make them resistant to *Colletotrichum* and resistant to stalk rot.

16 Claims, 31 Drawing Sheets

(56) References Cited

OTHER PUBLICATIONS

Declaration of Petra J. Wolters, Ph.D. filed in Responst to Opposition Against Patent EP 1 874 935, May 22, 2015.
Summons to attend oral proceedings pursuant to Rule 115(1) EPC for Patent EP 1 874 935, Aug. 10, 2015.
Lee et al., Expanding the genetic map of maize with the intermated B73 x Mo17 (IBM) Population, Plant Molecular Biology, vol. 48: 453-461 (2002).
Gardiner et al., Development of a Core RFLP Map in Maize Using an Immortalized F2 Population, Genetics, vol. 134:914-930 (1993).
Chao et al., RFLP mapping of partially sequenced leaf cDNA clones in maize, Theor Appl Genet, vol. 88 :717-721 (1994).
Coe et al, MaizeGDB Map Record p. 97584 (1995).
Davis et al, MaizeGDB Map Record p. 129755 (1996).
Springer et al, Maize Inbreds Exhibit High Levels of Copy Number Variation (CNV) and Presence/Absence Variation (PAV) in Genome Content, PLOS Genetics, vol. 5 : e1000734 (1999).
Slides that may be presented during the oral proceedings submitted on Mar. 11, 2016.
Declaration of Jean-Pierre Martinant.
Response to the Summons to Oral Proceedings dated Aug. 10, 2015.
Minutes of Oral Proceeding held on Apr. 11, 2016.
Interlocutory Decision in Opposition Proceedings Jun. 8, 2016.
Notice of Grounds for Appeal regarding Opposition to patent EP 187935; document dated Oct. 18, 2016.
Letter Dated Aug. 18, 2016 notifying Appeal against interlocutory decision of Opposition Division regarding patent EP 187935.
Fehr ("Principles of Cultivar Development," vol. 1 Theory and Technique Publishing Company, New York, pp. 360-376, 1987).
Hawk, J.A., Registration of DE811 Germplasm Line of Maize, Crop Science, (1985), 25:716.
Cowen, N. et al., Mapping of Anthracnose Stalk Rot resistance in maize using RFLP analysis, Maize Genetics Conference Abstracts 33, (1991).
Toman, et al., Inheritenace of Resistance to Anthracnose Stalk Rot of Corn, Phytopathology, (1993), 83: 981-986.
Weldekidan and Hawk, Inheritance of Anthracnose Stalk Rot Resistance in Maize, Maydica, (1993), 38:189-192.
Jung, et al., Generation-means analysis and quantitative trait locus mapping of anthracnose stalk rot genes in maize, Theor Appl Genet, (1994), 89:413-418.

Polacco, et al., IBM2 Neighbors 4 (Map), (2002), Maize Genetics and Genomics Database.
Wu, Gusui, Molecular Breeding and Breeding Molecules, Charlie Rick Symposium Presentation, (2006).
Collins, et al., The Isolation and Mapping of Disease Resistance Gene Analogs in Maize, MPMI, (1998), 11 (10): 968-978.
Travis, J. Frey, Finemapping, Cloning, Verification, and Fitness Evaluation of a QTL, RCG1, Which Confers Resistance to Colletotricum Graminicola in Maize, (2005), Dissertation to Faculty of University of Delaware.
Frey, et al., Fine mapping and cloning of a maize QTL for resistance to Colletotrichum graminicola, (2005), Poster presented at IPS Meeting.
Gerdes, et al., Compilation of North American Maize Breeding Germplasm, (1993), p. 4, 37.
Jung, Mark T., Generation Means Analysis and Molecular Mapping of Anthracnose Stalkrot Resistance Genes in Maize, (1993), Thesis submitted to Faculty of University of Delaware.
Toman, Jr., Joseph, Ineheritance of Resistance to Anthracnose Stalk Rot of Corn, (1991), Thesis submitted to Graduate College of University of Illinois.
Hawk, J.A., Weldekidan, T., Inheritance of Antracnose Stalk Rot Resistance in Maize, 48th Annual Northeastern Corn Improvement Conference (NEC-29), (1993) p. 8.
Jung, et al., Generation means analysis and QTL mapping of anthracnose stalk rot resistance genes in maize, 48th Annual Northeastern Corn Improvement Conference (NEC-29), (1993) p. 40.
Badu-Apraku, et al., A Major Gene for Resistance to Anthracnose Stalk Rot in Maize, Phytopathology, (1987), 77 (6): 957-959.
Badu-Apraku, et al., A Major Gene for Resistance to Anthracnose Leaf Blight in Maize, (1987), 98(3): 194-199.
Sharopova et al. Development and mapping of SSR markers for maize. Plant Mol Biol 48:463-481, (2002).
Falcon-Perez, JM et al. 1999, J. Biol Chem. 274: 23584-90.
Lazar et al. 1988, Mol. Cell. Biol. 8:1247-1252.
Hill et al. 1998, Biochem. Biophys. Res. Comm. 244:573-577.
Guo et al. 2004, Proc. Natl. Acad. Sci. USA 101: 9205-9210.
King et al. A Dictionary of Genetics, 5th ed., p. 275, 1997.
Poehlman, J.M. and Sleper, D.A., 1995. Breeding Field Crops. 4th ed. Iowa State University Press, Ames,Iowa p. 473.
Ferrier-Cana, et al., Distinct post-transcriptional modifications result into seven alternative transcripts of the CC-NBS-LRR gene JA1tr of Phaseolus vulgaris, Theor. Appl. Genet (2005) 110:895-905 gene.

* cited by examiner

Figure 2a

```
              1                                                           60
SEQ ID NO: 3  MEAALLS---GFIKTILPRLFSLV-QGRYKLHKGLKSDIKSLEKELHMIAVTID--EQIS
SEQ ID NO: 17 METAVLS---AVLRTLGPKLYAFLRDGHDLLRRDLERDVHYIRNELAMIAAAIE--EHDR
SEQ ID NO: 15 MEGAIFSVAEGTVRSLLSKLSSLLSQE-SWFVRGVHGDIQYIKDELESMNAFLRYLTVLE
SEQ ID NO: 14 MEGAVFSLTEGAVRSLLCKLGCLLTED-TWLVQGVHGEIQYIKDELECMNAFLRNLTISQ
SEQ ID NO: 16 MEGAIVSLTEGAVRGLLRKLAGVLAQE-SSPAQRVHGEVQYIKDELESMNAFLRSVSTSP
SEQ ID NO: 18 MD------IVTGAISNLIPKLGELLTEE-FKLHKGVKKNIEDLGKELESMNAAL--IKIGE 61                                                          120
SEQ ID NO: 3  LGRKDQGAVLSLSIDELHELAHQIEDSIDRFLYHVTREQQ---------ASFFRRTVRSPK
SEQ ID NO: 17 RPPPAAGDVRSAWIRGVRDLACDMEDCVDRFVH--------------------RATGHGLA
SEQ ID NO: 15 D----HDTQVRIWMKQVREIAYDAEDCIDQFTHHLGESSGI-GFLYRLIYILGKLC----
SEQ ID NO: 14 I----HDDQVRIWMKQVREIAYDSEDCIDEFIHNLGESSEM-GFFGGLISMLRKLA----
SEQ ID NO: 16 EDAAGHDDQVRVWMKQVREIAYDAEDCIDVFVRGRSHPAAAAGDEGRLVASLRRFVRLLA
SEQ ID NO: 18 VPREQLDSQDKLWADEVRELSYVIEDVVDKFLVQV-DGIQFDDNNNKFKGFMKRTTELLK 121                                                         180
SEQ ID NO: 3  TLLS----RQRLAAEVQFLKKIPEEAHQREKRYRVFAGLSSSTRHTESSS---CSSVSDP
SEQ ID NO: 17 SMGA----RAKFAAVIQELRRKSEELSRLASYAAAAGEPSCWVATGSSALTLPASSSEA
SEQ ID NO: 15 -------CRHRIAMQLQELKARAQDVSERRSRYEVM--LPKTTLQGAGPRLTRHASRHLD
SEQ ID NO: 14 -------CRHRIALQLQELKARAQDVGDRRSRYGVE--LAKATHEEAHPRLTRHASLHID
SEQ ID NO: 16 GALGVGGGDRSVAAQLRELKARARDAGERRTRYGVS--LAAAAVRGGG---GSSSSGRLD
SEQ ID NO: 18 KV----KHKHGIAHAIKDIQEQLQKVADRRDRNKVF--VPHPTRTIA-----------ID 181                                                         240
SEQ ID NO: 3  HTL------KADVVGIDGPRDELVQQLTEEA--EGLTKQLKVISIVGIHGSGKTVLAREV
SEQ ID NO: 17 HTL------ASDIVGMDGPRDEILE-LIGET--QG---QLKVISIVGFGGLGKTLLARQI
SEQ ID NO: 15 PQLHALFTEEAQLVGLDEPRDKLVRWVMEAD------PCRRVLAIVGFGGLGKTTLARMV
SEQ ID NO: 14 PQLHALFAEEAQLVGIDEPRNELVSWLMEED------LRLRVLAIVGFGGLGKTTLARMV
SEQ ID NO: 16 PRLHALFTEEAQLVGIDGPREELVGWVMEEE------PRLRVLAVVGFGGLGKTTLARMV
SEQ ID NO: 18 PCLRALYAEATELVGIYGKRDQDLMRLLSMEGDDASNKRLKKVSIVGFGGLGKTTLARAV 241                                                         300
SEQ ID NO: 3  YESD-V--GRQFS--LRAWVSATDRGPREVLMEILRNF------GRPVVDSSS-------
SEQ ID NO: 17 YESDAV--AAQFH--PRIWVRAAGKNAEDVLMDILQQL------GMPVHHCHA-------
SEQ ID NO: 15 CENPMVKGA-DFHCCP-LFIVSQTFNIRTLFQYMIRELIQRPNKAMAV-----AGGKHGHT
SEQ ID NO: 14 CGSPVVKSA-DFQCCP-LFIISQTFNIRALFQHMVRELIQEPHKAMAI-----AGCKHGLI
SEQ ID NO: 16 CGSPRVKGAADFQCSPPLVVVSQTFSITALFQHLLRELIQRPRKAMAAVAAAGGGGGDLV
SEQ ID NO: 18 YE--KIKG--DFDC-RAFVPVGQNPHMKKVLRDILIDL-GNPHSDLAML-----------

301                                                         360
SEQ ID NO: 3  -------------IDQLTVDL-----RKHLGEK-------RYFIVIDGM-QTDQW-STIET
SEQ ID NO: 17 -------------SNLVVNL------RNCLESK-------RFFVVIDDM-QREYWNSSFRN
SEQ ID NO: 15 MDGNMDGMERWEVAVLAEKV-----RQYLLDK--------YIVIFDDIWTISAWES-IRC
SEQ ID NO: 14 TDDYLEGMERWEVAALTKNL-----RRYFQDK--------RYIVILDDIWTVSAWES-IRC
SEQ ID NO: 16 AYDALQGMERWETAALASKAEGIPARQKFVHICGTITLYRYIVILDDIWSSSAWES-IKC
SEQ ID NO: 18 -----------DANQLIKKL-----REFLENK--------RYLVIIDDIWDEKLWEG-INF
```

Figure 2b

```
                      361                                                         420
SEQ ID NO: 3     AFPENNVVSSRVIVTTTIRSVANSCSSS-NGYVHKMKRLSDEHSEQLFIKK-----ACPT
SEQ ID NO: 17    AFPSDTGLSSIVIVTTAIQSIANACSSR-NSHVYVMRTLNEEHSRQLFLKE-----ASWK
SEQ ID NO: 15    ALPDNKK-GSRVIITTRNEDVANTCCSGPQDQVYKMQRLSDAASRELFFKRIFG-SADIS
SEQ ID NO: 14    ALPDNLK-GSRIIVTTRNADVANTCCSRPQDRIYNIQRLSETTSRELFFKKIFGFADDKS
SEQ ID NO: 16    AFPDNKK-GSRIIVTTRNEDVANTCCCRPQDRIYKIQRLSDAASRELFFKRIFGMADAGA
SEQ ID NO: 18    AFSNRNNLGSRLITTTRIVSVSNSCCSSHGDSVYQMEPLSVDDSRILFWKRIF---PDEN 421                                                         480
SEQ ID NO: 3     KYSGYTRPESKEVLKKCDGQPLALVTMGQFLRKNGWPTGPNC-ENVCRDLRRHLEQDDTL
SEQ ID NO: 17    DYP-----PGSEAILKKCDGLPLALVTTAQFLQSRCQQQPLGC-AKLCDNLGKHLVTEDTL
SEQ ID NO: 15    SNE-ELDEVSNSILKKCGGLPLAIVSIGSLVASKTN-RTKEEWQKICDNLGSELETNPTL
SEQ ID NO: 14    PTD-EPEEVSNSVLKKCGGLPLAIVNIGSLLASKTN-RTKEEWQKVCNNLGSELENNPTL
SEQ ID NO: 16    PDDDELKQVSDSILKKCGGLPLAIVSIGSLLASKPN-RSKEEWQKVCDNLGSELESNPTL
SEQ ID NO: 18    GCLNEFEQVSRDILKKCGGVPLAIITIASALAGDQKMKPKCEWDILLQSLGSGLTEDNSL 481                                                         540
SEQ ID NO: 3     ERMRRVLIHSLSSLPSHVPKACLLYFGMFPCDHPIKRKSLMRRWLAEGFVQTQPSSS----
SEQ ID NO: 17    ARMKRVLVHHYSSLPGHVIKACLLYLGIFPSGHPVRRKTLIRRWSAEGFVGADHHRSSLD
SEQ ID NO: 15    EVAKQVLTLSYNDLPYHL-KACFLYLSIFPENYVIRRGPLVRRWIAEGFVNQ-RHGLSME
SEQ ID NO: 14    EGVKQVLTLSYNDLPYHL-KACFLYLSIFPENYVIKRGPLVRRWIAEGFVSQ-RHGQSME
SEQ ID NO: 16    EGTKQVLTLSYNDLPYHL-KACFLYLSIFPENHVIKRGPLVRMWIAEGFVTQ-RHGLSME
SEQ ID NO: 18    EEMRRILSFSYSNLPSHL-KTCLLYLCIYPEDSKIHRDELIWKWVAEGFVHHENQGNSLY 541                                                         600
SEQ ID NO: 3     ----ENFNTLIDRNIIEPIGICNDDQVKTCKTYGMMHEFILLMSTSHDFITLLCNNKVE-
SEQ ID NO: 17    --VAIDSFEELVNRSIIQPVDVSSNTEVKTCQTHGMMLEFILHKSICDNFITFLYGQARL-
SEQ ID NO: 15    EVAESYFDEFVARSIVQPVKIDWSGKVRTCRVHDMMLEVIISKSLEENFASFLCDNGHPL
SEQ ID NO: 14    QLAESYFDEFVARSIVQPVRTDWTGKVRSCRVHDLMLDVIVSRSIEENFASFLCDNGSTL
SEQ ID NO: 16    QVGERYFDEFVSRSMVHLVRIDWSGKVRSCKVHDIMLEVIVSKSLEENFASFFCDNGTEL
SEQ ID NO: 18    LLGLNYFNQLINRSMIQPI-YGFNDEVYVCRVHDMVLDLICNLSREAKFVNLLDGSGNSM 601                                                         660
SEQ ID NO: 3     --HKYVRRLSLHHHS-ATSGSF-SVID-LSLVRSLMVFGEAGKTILSFRKYELLRVLDLE
SEQ ID NO: 17    --PDKIRCVSIQQNS-GSKTRVDSDID-LSLVRSLTIFGKAHKSFLNFSRYKLLRVLDLE
SEQ ID NO: 15    VCHDKIRRLSIHNS-HNSVQRTRVSV---SHVRSFTMSASVEEVPMFFPQMRLLRVLDLQ
SEQ ID NO: 14    ASHDKIRRLSIHSS-YNSSQKTSANV---SHARSFTMSASVEEVPFFFPQLRLLRVLDLQ
SEQ ID NO: 16    VSHDKIRRLSIRSSSYSSAQRTSNSV---AHVRTFRMSPSIDNIPFFFPQLRLLRVLDMQ
SEQ ID NO: 18    SSQGNCRRLSLQKRNEDHQAKPITDIKSMSRVRSITIFPPAIEVMPSLSRFDVLRVLDL- 661                                                         720
SEQ ID NO: 3     QCT-DLEDD-----HLKDICNLFLMKYLSL-GETIRSLPKEIEKLKLLETLDLRRTK-VK
SEQ ID NO: 17    ECD-ELEDE-----HLKKICKRLLLKYLSL-GRGITVLPKEIAKLKFLETLDLRRTV-IK
SEQ ID NO: 15    GSSC-LNNST-----LNYICKFYQLKYLTLRKTNIGKLPRLIGNLKYLETLDIRATR-IK
SEQ ID NO: 14    GCSC-LSNET-----LHCMCRFFQLKYLSLRNTNVSKLPHLLGNLKHLETLDIRATL-IK
SEQ ID NO: 16    GSRC-MSNKN-----LDCICRFFQLKYLSLRNTSVSILPRLIGNLNHLETLDIRETL-IK
SEQ ID NO: 18    -SRCNLGENSSLQLNLKDVGHLTHLRYLGLEGTNISKLPAEIGKLQFLEVLDLGNNHNLK
```

Figure 2c

```
              721                                                          780
SEQ ID NO: 3  TLPIEVLLLPCLLHLFGKFQFSDKIKITSD---------MQKFFLTGQSNLETLSGFITD
SEQ ID NO: 17 FLPIQVLELPCLIHLFGVFKIQDADQQMRK---------L-KSFLTEKSKLETLAGFVTD
SEQ ID NO: 15 RLPASASNLSCLKHLLVGHKVQLTRTTSVKCFRPDSGLEMTAGVVKNMMALQSLAHIVVK
SEQ ID NO: 14 KLPASAGNLSCLKHLFAGHKVQLTRTASVKFLRQSSGLEVATGVVKNMVALQSLVHIVVK
SEQ ID NO: 16 KLPSSAANLTCLKHLLAGHKEQLTRTSSVKFLRPSSGLKMSHGVIRNMAKLQSLVHVEIK
SEQ ID NO: 18 ELPSTVCNFRRLIYL---------------NLF--GCPVVPPVGVLQNLTSIEVLRGILVS 781                                                          840
SEQ ID NO: 3  GSQGLPQMMNYM-NLRKLKIWFERSKRS--TNFTD-----LVNAVQKFIHDDKESNDPRSL
SEQ ID NO: 17 RCQTFPQLMKHMTNLAKVKIWCENTADA--SSSSNSDVHLSEAIQEFIQRGTDVNDVRSL
SEQ ID NO: 15 ERPAVLSEIGQLQKLQKLNVLFRGVEEN-WNAFLQSLVKLTGSLRSLSIHILDEKE-HSS
SEQ ID NO: 14 DKSPVLREIGLLQNLTKLNVLLRGVEEN-WNAFLESLSKLPGPLRSLSIHTLDEKE-HSL
SEQ ID NO: 16 EHPSVFQEIALLQNLRKLSVLFYGIEVN-WKPFLELLNMLSGSVRSLSIDIFDAQG-N-I
SEQ ID NO: 18 VNI-IAQELGNLERLRVLDICFRDGSLDLYKDFVKSLCNLH-HIESLRIEC--NSR-ETS 841                                                          900
SEQ ID NO: 3  SLHFDDGTENILN-SLKAPCYLRSLKLKGNLL-ELPQFV----ISMRGLREICLSST-KL
SEQ ID NO: 17 SLDVGECSQEFLNFSLGDSCYLSSLKLKGNKICRLPPFV----TSLAVLTDLCLSSSDRL
SEQ ID NO: 15 SLEYLALIAE--SPPLFIRNF--SLK---GKLQRLPPWI----PSLRNVSRITFRDT-GL
SEQ ID NO: 14 SLDNLAFV-E--SPPLFITKF--SLA---GELERLPPWI----PSLRNVSRFALRRT-EL
SEQ ID NO: 16 SISSLEMLSSLVSPPIFITSF--SLT---GKLGSLPPWV----ASLRSVSRLTLRRS-QL
SEQ ID NO: 18 SFELVDLLGERWVPPVHFREFVSSMP---SQLSALRGWIKRDPSHLSNLSELILSSVKDV 901                                                          960
SEQ ID NO: 3  TSGLLATLANLKGLQHLKLI-----ADVLEDFIIEGQAFLGLLHLCFVLERATL-----P
SEQ ID NO: 17 SSDVLAALSNVRALRYLKLI-----ARHLDRFVIERGDLQSLRRLHIVVVSMTTMSKQQP
SEQ ID NO: 15 HAEAIGVLGDLPNLLCLK-LYQRSYADD--HIFFAHGNFLKLR----MLVIDNMENIRNV
SEQ ID NO: 14 HADAIGVLGDLPNLLCLK-LYHKSYADN--CIVFCHGKFVKLK----LLIIDNLERIEKM
SEQ ID NO: 16 RADAIHVLGGLQNLLCLK-LYHKSYADD--RLVFPQGGFARVK----LLIDDNLVNLEKL
SEQ ID NO: 18 QQDDVEIIGGL---LCLRRLFIITSTDQTQRLLVIRADGFRCT-----VDFRLDCGSATQI 961                                                          1020
SEQ ID NO: 3  IIEGGALPYLISLKLICKDLVG---LGDIKINRLK--CLKEVSLDHRVASETREIWEKAA
SEQ ID NO: 17 EIQEGALPNLESFHLLCKDLDGPCGHGGIRIDSLGLGCLREIVLDDGVRETAKEQWKDAA
SEQ ID NO: 15 HFEKGSVPNLE--------------------WLTIAFLQEP--KDGITG----------
SEQ ID NO: 14 QFDAGSVTNLE--------------------RLTLSFLREP--KYGISG----------
SEQ ID NO: 16 HFNEGSMPNLE--------------------RLTLSFLREP--KDGISG----------
SEQ ID NO: 18 LFEPGALPRAVRV------------------WFSLGVRVTK--EDGNRG----------

1021                                                         1080
SEQ ID NO: 3  EKHPNRPKVLLVNSSDESEIKAVDCSVASRPAVSEANGTSPMSEVD--VREDDIQMI---
SEQ ID NO: 17 RRHPKRPKVVFVGAGDVVDRRRVGAAAAAPAAGESNSAMAPAAVASVVAAGDVKRPARE
SEQ ID NO: 15 --------LE-----NLLKLKEIE-----------------------FFGDIILSMTKV
SEQ ID NO: 14 --------LE-----NLPKLKEIE-----------------------FFGDIILSVVTKV
SEQ ID NO: 16 --------LN-----NLLKLKEVE-----------------------PFGNIVSSVVSKV
SEQ ID NO: 18 --------FDLGLQGNLFSLREFVS------------------VYMYCGGARVGEAKEA 1081                                       1128
SEQ ID NO: 3  ---LNQGLSAAAEKQMNCAVQPSSKAELNSDFNNISFPEVALGLTEL.
SEQ ID NO: 17 ESDISAALASLPAK-MARLLGAASIHQSSGTQGELSCGGNGASQRHFS
SEQ ID NO: 15 ASCMK----AHPNR--PRVIGDKWNNVT-----------------EYA
SEQ ID NO: 14 ASCVK----AHPNH--PRVIGDKWNIVT-----------------EYA
SEQ ID NO: 16 VSCVK----DHPNH--PRVVGDKWNIVT-----------------VYN
SEQ ID NO: 18 EAAVR
```

Figure 10
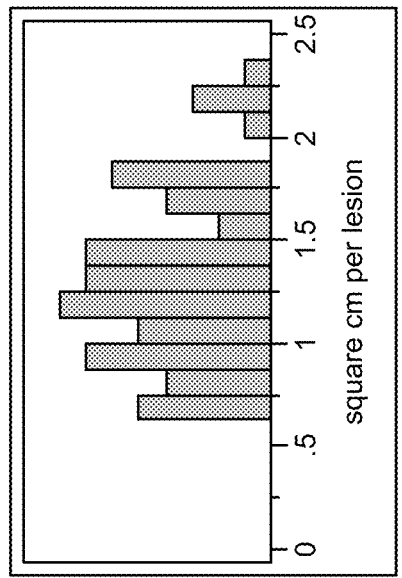
a) DE811ASR(BC5)
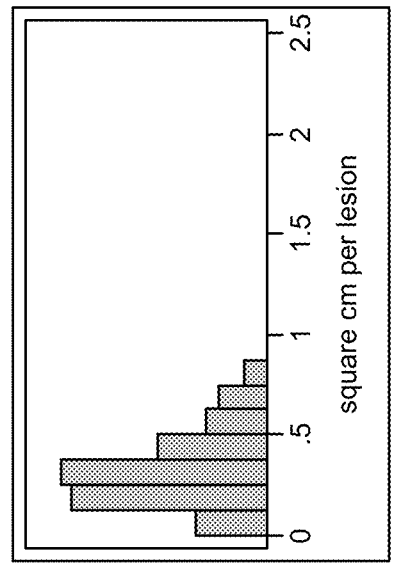
b) DE811

SEQUENCE LISTING

```
<160> NUMBER OF SEQ ID NOS: 232

<210> SEQ ID NO 1
<211> LENGTH: 4212
<212> TYPE: DNA
<213> ORGANISM: Zea mays
<220> FEATURE:
<221> NAME/KEY: gene
<222> LOCATION: (0)...(0)
<223> OTHER INFORMATION: Nucleotide sequence for Rcg1:
      bac811h.pk257.m04
<221> NAME/KEY: exon
<222> LOCATION: (143)...(948)
<223> OTHER INFORMATION: exon 1
<221> NAME/KEY: exon
<222> LOCATION: (1452)...(3588)
<223> OTHER INFORMATION: exon 2
<221> NAME/KEY: intron
<222> LOCATION: (949)...(1451)
<223> OTHER INFORMATION: intron 1
<221> NAME/KEY: CDS
<222> LOCATION: (143)...(948)
<221> NAME/KEY: CDS
<222> LOCATION: (1452)...(3588)

<400> SEQUENCE: 1
aaaaccctca ccacattttc ctcaaccaca tgatggagat tggggctact agatactatg      60
cctggtggta gactggtagc tgatgtcttt ggaccagtag ttggtgctag atttgtgaac     120
tctaccaagg tgagaaacgg ag atg gag gct gcc ctg ctg agc ggg ttc atc     172
                        Met Glu Ala Ala Leu Leu Ser Gly Phe Ile
                          1               5                  10 aaa acc atc ctg cca agg ctc ttc tca ctg gta caa ggg aga tac aag     220
Lys Thr Ile Leu Pro Arg Leu Phe Ser Leu Val Gln Gly Arg Tyr Lys
             15                  20                  25 ctg cac aag ggc ctc aag agc gac atc aaa tcg ctg gag aaa gag ctc     268
Leu His Lys Gly Leu Lys Ser Asp Ile Lys Ser Leu Glu Lys Glu Leu
         30                  35                  40 cat atg atc gct gtt aca atc gat gaa caa atc tcg ctg ggg agg aag     316
His Met Ile Ala Val Thr Ile Asp Glu Gln Ile Ser Leu Gly Arg Lys
     45                  50                  55 gat cag gga gct gtg ctg agc ctc tca att gat gag ctg cat gaa ctg     364
Asp Gln Gly Ala Val Leu Ser Leu Ser Ile Asp Glu Leu His Glu Leu
 60                  65                  70 gct cac caa atc gag gac tcc ata gat cgc ttc ttg tac cat gtg acc     412
Ala His Gln Ile Glu Asp Ser Ile Asp Arg Phe Leu Tyr His Val Thr
 75                  80                  85                  90 agg gag cag caa gca tcc ttt ttt cgt cgg act gta cgg tcg ccg aag     460
Arg Glu Gln Gln Ala Ser Phe Phe Arg Arg Thr Val Arg Ser Pro Lys
                 95                 100                 105 act ctg ttg tca cgt cag cgg ctg gct gcc gag gtt cag ttc ctg aag     508
Thr Leu Leu Ser Arg Gln Arg Leu Ala Ala Glu Val Gln Phe Leu Lys
             110                 115                 120
```

```
aag ata ccg gag gag gcg cac cag cga gag aag agg tac agg gtc ttc      556
Lys Ile Pro Glu Glu Ala His Gln Arg Glu Lys Arg Tyr Arg Val Phe
        125                 130                 135 gcc ggc ctt tct tcc tct acc cgg cac act gaa tcg tct tcc tgt tcg      604
Ala Gly Leu Ser Ser Ser Thr Arg His Thr Glu Ser Ser Ser Cys Ser
    140                 145                 150 tct gta tct gat ccg cac aca ctt aag gcc gac gtc gtc ggc atc gac      652
Ser Val Ser Asp Pro His Thr Leu Lys Ala Asp Val Val Gly Ile Asp
155                 160                 165                 170 ggt ccc agg gac gag ctt gtg cag cag tta acc gaa gag gca gag ggc      700
Gly Pro Arg Asp Glu Leu Val Gln Gln Leu Thr Glu Glu Ala Glu Gly
                175                 180                 185 cta aca aag cag ctc aag gtg atc tcc atc gtc ggg atc cat ggc tcc      748
Leu Thr Lys Gln Leu Lys Val Ile Ser Ile Val Gly Ile His Gly Ser
            190                 195                 200 ggc aag acc gtc ctt gcc aga gag gta tac gag agc gac gtc ggc cgg      796
Gly Lys Thr Val Leu Ala Arg Glu Val Tyr Glu Ser Asp Val Gly Arg
        205                 210                 215 cag ttc agt ctc cgg gca tgg gtt tct gct act gac aga ggt ccg aga      844
Gln Phe Ser Leu Arg Ala Trp Val Ser Ala Thr Asp Arg Gly Pro Arg
    220                 225                 230 gag gtg ctc atg gag atc ctc cga aat ttt ggt agg cca gtg gtg gat      892
Glu Val Leu Met Glu Ile Leu Arg Asn Phe Gly Arg Pro Val Val Asp
235                 240                 245                 250 agc tct agt att gac cag ctt acg gta gat ctc agg aaa cac ttg ggt      940
Ser Ser Ser Ile Asp Gln Leu Thr Val Asp Leu Arg Lys His Leu Gly
                255                 260                 265 gag aaa ag gtgaaaaaaa cctcttcttt atgttattta ttatttatga agtttcttca    998
Glu Lys Ser actacgggtt ttcatgttca aattgcctct ctgaacttcg aaaacgttta ataccaattg   1058
aattgaggat cttagctttg gaaaagcggt agtgttttga cgttttgcat acatttctca   1118
ccgttatttt attcatttat aatttagagt ttaagcagta tattcatttt gaaatttatg   1178
agatttctgt ctgcacgctt acttccatgc ccaaaacatg tccgattgag aacagaaggt   1238
aattttgttt gatctttgag atcagacaca ctgattgagt agtaacagga aacaagtgct   1298
caccaatcac ccaagtcact tacaaagaat ttcatgctta caaaacacac tgattgttaa   1358
ggatagagac tatgtttgat ctgcatagtt tgaattttga ttatgtcatc gtcgattgtt   1418
atcattaact tttgttggaa atttctcttg tag c tat ttc att gta atc gat      1470
                                     Tyr Phe Ile Val Ile Asp
                                                     270 ggc atg caa aca gat cag tgg agc acc att gaa act gcc ttc cca gaa     1518
Gly Met Gln Thr Asp Gln Trp Ser Thr Ile Glu Thr Ala Phe Pro Glu
            280                 285                 290 aac aat gtt gtt agc agc aga gta att gtt aca aca aca atc cgg tca     1566
Asn Asn Val Val Ser Ser Arg Val Ile Val Thr Thr Thr Ile Arg Ser
        295                 300                 305 gta gct aat tct tgc agc tct tct aac ggt tat gtg cac aaa atg aaa     1614
Val Ala Asn Ser Cys Ser Ser Ser Asn Gly Tyr Val His Lys Met Lys
    310                 315                 320 aga ctt agt gac gaa cac tca gag caa ttg ttt atc aag aaa gct tgc     1662
Arg Leu Ser Asp Glu His Ser Glu Gln Leu Phe Ile Lys Lys Ala Cys
325                 330                 335 cca aca aaa tat tca ggt tat act cga ccg gaa tca aaa gaa gtt ctg     1710
Pro Thr Lys Tyr Ser Gly Tyr Thr Arg Pro Glu Ser Lys Glu Val Leu
340                 345                 350                 355 aag aaa tgt gat ggt caa cca ctt gct ctt gtt act atg ggc caa ttc     1758
Lys Lys Cys Asp Gly Gln Pro Leu Ala Leu Val Thr Met Gly Gln Phe
```

-continued

|     |     |     | 360 |     |     |     | 365 |     |     |     | 370 |     |     |     |      |
| --- | --- | --- | --- | --- | --- | --- | --- | --- | --- | --- | --- | --- | --- | --- | ---- |
| ttg | agg | aaa | aat | ggt | tgg | ccc | aca | gga | ccc | aac | tgc | gaa | aat | gtg | tgt  | 1806
| Leu | Arg | Lys | Asn | Gly | Trp | Pro | Thr | Gly | Pro | Asn | Cys | Glu | Asn | Val | Cys  |
|     |     |     | 375 |     |     |     | 380 |     |     |     | 385 |     |     |     |      |

| aga | gat | ctt | aga | cga | cat | ctg | gag | cag | gat | gat | aca | ttg | gag | aga | atg | 1854
| Arg | Asp | Leu | Arg | Arg | His | Leu | Glu | Gln | Asp | Asp | Thr | Leu | Glu | Arg | Met |
|     |     | 390 |     |     |     | 395 |     |     |     | 400 |     |     |     |     |     |

| cga | agg | gtg | ctt | atc | cac | agc | tta | tct | agt | ctt | cct | agc | cat | gtt | ccc | 1902
| Arg | Arg | Val | Leu | Ile | His | Ser | Leu | Ser | Ser | Leu | Pro | Ser | His | Val | Pro |
| 405 |     |     |     |     | 410 |     |     |     |     | 415 |     |     |     |     |     |

| aaa | gcc | tgc | ctt | ttg | tat | ttt | ggt | atg | ttt | cca | tgt | gat | cat | ccc | ata | 1950
| Lys | Ala | Cys | Leu | Leu | Tyr | Phe | Gly | Met | Phe | Pro | Cys | Asp | His | Pro | Ile |
| 420 |     |     |     |     | 425 |     |     |     |     | 430 |     |     |     |     | 435 |

| aag | agg | aag | agc | ctg | atg | agg | cga | tgg | tta | gca | gag | gga | ttt | gta | caa | 1998
| Lys | Arg | Lys | Ser | Leu | Met | Arg | Arg | Trp | Leu | Ala | Glu | Gly | Phe | Val | Gln |
|     |     |     |     | 440 |     |     |     |     | 445 |     |     |     |     | 450 |     |

| aca | cag | cct | tca | tct | agt | gaa | aac | ttc | aac | acc | ctc | ata | gac | cgg | aat | 2046
| Thr | Gln | Pro | Ser | Ser | Ser | Glu | Asn | Phe | Asn | Thr | Leu | Ile | Asp | Arg | Asn |
|     |     |     |     | 455 |     |     |     |     | 460 |     |     |     |     | 465 |     |

| att | att | gag | ccc | atc | ggc | ata | tgt | aac | gat | gat | cag | gta | aag | aca | tgc | 2094
| Ile | Ile | Glu | Pro | Ile | Gly | Ile | Cys | Asn | Asp | Asp | Gln | Val | Lys | Thr | Cys |
|     |     |     |     | 470 |     |     |     |     | 475 |     |     |     |     | 480 |     |

| aaa | aca | tat | ggc | atg | atg | cac | gag | ttc | att | ttg | tta | atg | tcc | acc | tcc | 2142
| Lys | Thr | Tyr | Gly | Met | Met | His | Glu | Phe | Ile | Leu | Leu | Met | Ser | Thr | Ser |
|     | 485 |     |     |     |     | 490 |     |     |     |     | 495 |     |     |     |     |

| cat | gac | ttc | att | acc | ctg | ctt | tgt | aat | aat | aaa | gtt | gaa | cac | aaa | tat | 2190
| His | Asp | Phe | Ile | Thr | Leu | Leu | Cys | Asn | Asn | Lys | Val | Glu | His | Lys | Tyr |
| 500 |     |     |     |     | 505 |     |     |     |     | 510 |     |     |     |     | 515 |

| gtg | cgt | cgg | ctt | tct | ctc | cat | cat | cat | agt | gct | aca | agt | ggc | agt | ttt | 2238
| Val | Arg | Arg | Leu | Ser | Leu | His | His | His | Ser | Ala | Thr | Ser | Gly | Ser | Phe |
|     |     |     |     | 520 |     |     |     |     | 525 |     |     |     |     | 530 |     |

| tcg | gtc | atc | gac | tta | tct | ctt | gtt | aga | tct | ctg | atg | gtt | ttt | ggg | gag | 2286
| Ser | Val | Ile | Asp | Leu | Ser | Leu | Val | Arg | Ser | Leu | Met | Val | Phe | Gly | Glu |
|     |     |     | 535 |     |     |     |     | 540 |     |     |     |     | 545 |     |     |

| gct | ggc | aaa | act | att | ttg | agt | ttc | cga | aag | tac | gag | cta | ttg | aga | gtc | 2334
| Ala | Gly | Lys | Thr | Ile | Leu | Ser | Phe | Arg | Lys | Tyr | Glu | Leu | Leu | Arg | Val |
|     |     | 550 |     |     |     |     | 555 |     |     |     |     | 560 |     |     |     |

| ttg | gat | ctt | gaa | caa | tgt | acc | gac | ttg | gaa | gat | gat | cac | ctc | aaa | gac | 2382
| Leu | Asp | Leu | Glu | Gln | Cys | Thr | Asp | Leu | Glu | Asp | Asp | His | Leu | Lys | Asp |
|     | 565 |     |     |     |     | 570 |     |     |     |     | 575 |     |     |     |     |

| ata | tgc | aac | ctt | ttt | ctt | atg | aaa | tat | cta | agc | ctc | gga | gaa | act | att | 2430
| Ile | Cys | Asn | Leu | Phe | Leu | Met | Lys | Tyr | Leu | Ser | Leu | Gly | Glu | Thr | Ile |
| 580 |     |     |     |     | 585 |     |     |     |     | 590 |     |     |     |     | 595 |

| aga | agt | ctt | cca | aag | gag | ata | gaa | aaa | ctg | aag | ctc | ttg | gag | aca | ctt | 2478
| Arg | Ser | Leu | Pro | Lys | Glu | Ile | Glu | Lys | Leu | Lys | Leu | Leu | Glu | Thr | Leu |
|     |     |     |     | 600 |     |     |     |     | 605 |     |     |     |     | 610 |     |

| gac | ttg | agg | aga | aca | aag | gtg | aaa | aca | cta | cct | ata | gag | gtc | ctc | ctg | 2526
| Asp | Leu | Arg | Arg | Thr | Lys | Val | Lys | Thr | Leu | Pro | Ile | Glu | Val | Leu | Leu |
|     |     |     |     | 615 |     |     |     |     | 620 |     |     |     |     | 625 |     |

| ctc | ccc | tgt | tta | ctc | cat | ctg | ttt | ggg | aag | ttc | caa | ttt | tct | gat | aaa | 2574
| Leu | Pro | Cys | Leu | Leu | His | Leu | Phe | Gly | Lys | Phe | Gln | Phe | Ser | Asp | Lys |
|     |     |     |     | 630 |     |     |     |     | 635 |     |     |     |     | 640 |     |

| atc | aag | ata | aca | agt | gac | atg | cag | aag | ttt | ttc | tta | act | gga | cag | agt | 2622
| Ile | Lys | Ile | Thr | Ser | Asp | Met | Gln | Lys | Phe | Phe | Leu | Thr | Gly | Gln | Ser |
|     |     |     | 645 |     |     |     |     | 650 |     |     |     |     | 655 |     |     |

| aac | tta | gag | aca | ctt | tca | gga | ttt | atc | aca | gat | ggg | tct | caa | gga | ttg | 2670
| Asn | Leu | Glu | Thr | Leu | Ser | Gly | Phe | Ile | Thr | Asp | Gly | Ser | Gln | Gly | Leu |
| 660 |     |     |     |     | 665 |     |     |     |     | 670 |     |     |     |     | 675 |

| cca | cag | atg | atg | aat | tac | atg | aat | tta | aga | aag | ctt | aag | ata | tgg | ttt | 2718

```
                Pro Gln Met Met Asn Tyr Met Asn Leu Arg Lys Leu Lys Ile Trp Phe
                                    680             685             690 gag agg agt aag aga agc acc aac ttc acc gat ctt gtg aat gct gtc           2766
Glu Arg Ser Lys Arg Ser Thr Asn Phe Thr Asp Leu Val Asn Ala Val
                    695             700             705 caa aag ttc atc cat gat gac aaa gag agc aat gat cca cgt tct cta           2814
Gln Lys Phe Ile His Asp Asp Lys Glu Ser Asn Asp Pro Arg Ser Leu
            710             715             720 tca ctt cat ttc gat gac ggc act gaa aac atc ctg aac tct ttg aag           2862
Ser Leu His Phe Asp Asp Gly Thr Glu Asn Ile Leu Asn Ser Leu Lys
        725             730             735 gct cct tgt tac ctt agg tca ttg aag tta aaa ggg aat ttg ctg gaa           2910
Ala Pro Cys Tyr Leu Arg Ser Leu Lys Leu Lys Gly Asn Leu Leu Glu
740             745             750             755 ctt ccc cag ttt gtc ata tca atg cgg ggt ctc cgg gag ata tgc ctt           2958
Leu Pro Gln Phe Val Ile Ser Met Arg Gly Leu Arg Glu Ile Cys Leu
                    760             765             770 tca tca aca aaa ttg aca tcg ggc ctc ctt gca aca ctc gct aac ttg           3006
Ser Ser Thr Lys Leu Thr Ser Gly Leu Leu Ala Thr Leu Ala Asn Leu
            775             780             785 aaa ggc ttg cag cat ctc aag ctg att gca gat gtc ctt gaa gat ttt           3054
Lys Gly Leu Gln His Leu Lys Leu Ile Ala Asp Val Leu Glu Asp Phe
        790             795             800 atc att gaa ggt cag gca ttc ctg ggg ctg cta cac cta tgt ttt gtc           3102
Ile Ile Glu Gly Gln Ala Phe Leu Gly Leu Leu His Leu Cys Phe Val
805             810             815 cta gaa cgt gcc acc tta cca ata att gaa gga gga gct ttg ccg tac           3150
Leu Glu Arg Ala Thr Leu Pro Ile Ile Glu Gly Gly Ala Leu Pro Tyr
820             825             830             835 ctc atc tca ctt aag cta atc tgc aaa gat cta gtt ggc ctc ggt gac           3198
Leu Ile Ser Leu Lys Leu Ile Cys Lys Asp Leu Val Gly Leu Gly Asp
                    840             845             850 atc aaa atc aac cgc ctc aaa tgt ctt aag gaa gtc agt cta gat cat           3246
Ile Lys Ile Asn Arg Leu Lys Cys Leu Lys Glu Val Ser Leu Asp His
            855             860             865 aga gtc gct tcg gaa aca aga gaa atc tgg gaa aaa gct gcc gag aag           3294
Arg Val Ala Ser Glu Thr Arg Glu Ile Trp Glu Lys Ala Ala Glu Lys
        870             875             880 cat cca aac cgg ccg aaa gta ttg ttg gtc aac tca tct gat gaa agc           3342
His Pro Asn Arg Pro Lys Val Leu Leu Val Asn Ser Ser Asp Glu Ser
885             890             895 gaa att aag gct gta gac tgt tct gtt gct tca aga cca gct gtg agt           3390
Glu Ile Lys Ala Val Asp Cys Ser Val Ala Ser Arg Pro Ala Val Ser
900             905             910             915 gag gct aat gga act tct ccc atg tca gag gtt gat gta cga gag gat           3438
Glu Ala Asn Gly Thr Ser Pro Met Ser Glu Val Asp Val Arg Glu Asp
                    920             925             930 gac att cag atg ata ctt aac cag ggg ctc tct gcc gct gct gag aaa           3486
Asp Ile Gln Met Ile Leu Asn Gln Gly Leu Ser Ala Ala Ala Glu Lys
            935             940             945 cag atg aat tgt gca gtt cag cca agt tca aaa gct gaa ctg aac tct           3534
Gln Met Asn Cys Ala Val Gln Pro Ser Ser Lys Ala Glu Leu Asn Ser
        950             955             960 gat ttc aat aat att agt ttc cca gag gtt gcg ctt ggt tta acc gag           3582
Asp Phe Asn Asn Ile Ser Phe Pro Glu Val Ala Leu Gly Leu Thr Glu
965             970             975 ctg tga attgcttgga attgaaatgt gtcttcatac acctattgat ccttgattgt           3638
Leu *
980
```

-continued

```
ccatggtcag tttcgttgca cttgcagcat attactatga ggctagtatc atgtaaatta      3698
caaatctttt gttgttaagg ccataaattg catattatag cacaacaagc tggtatgtct      3758
caacaatggc attaattttt tttctgcttg aatctacaaa tttcatcatt attttgcaat      3818
ttcgctttta tacagatatg gtgatgccat gtcattttga ctttgcagca tatatgcaag      3878
caacggtttg agttgctgga gttgctagaa tattgataca acttcagttt actcgaaggc      3938
tacagggatc tcataactag gatggttgaa gataatttgc gattgtttcc ttcagtgtca      3998
ctgaaaagac ttttgtaaca ataaagcata cctttgcttc ctactttttt gaagttactt      4058
cagatgctaa gttcgcagtt gggcctggac tttatcatgt ttatccagct gtttatttgt      4118
ttcatgtaca ataataccgg tgattgctgt tgttatataa tctatattta tactatagtt      4178
aaagtatcag tttcaacggt tgtcccgcgc catc                                   4212
```

<210> SEQ ID NO 2
<211> LENGTH: 2943
<212> TYPE: DNA
<213> ORGANISM: Zea mays
<220> FEATURE:
<221> NAME/KEY: gene
<222> LOCATION: (1)...(2943)
<223> OTHER INFORMATION: Coding region only of Cgr1 gene
<221> NAME/KEY: CDS
<222> LOCATION: (1)...(2943)

<400> SEQUENCE: 2

```
atg gag gct gcc ctg ctg agc ggg ttc atc aaa acc atc ctg cca agg        48
Met Glu Ala Ala Leu Leu Ser Gly Phe Ile Lys Thr Ile Leu Pro Arg
1               5                   10                  15 ctc ttc tca ctg gta caa ggg aga tac aag ctg cac aag ggc ctc aag        96
Leu Phe Ser Leu Val Gln Gly Arg Tyr Lys Leu His Lys Gly Leu Lys
                20                  25                  30 agc gac atc aaa tcg ctg gag aaa gag ctc cat atg atc gct gtt aca       144
Ser Asp Ile Lys Ser Leu Glu Lys Glu Leu His Met Ile Ala Val Thr
            35                  40                  45 atc gat gaa caa atc tcg ctg ggg agg aag gat cag gga gct gtg ctg       192
Ile Asp Glu Gln Ile Ser Leu Gly Arg Lys Asp Gln Gly Ala Val Leu
        50                  55                  60 agc ctc tca att gat gag ctg cat gaa ctg gct cac caa atc gag gac       240
Ser Leu Ser Ile Asp Glu Leu His Glu Leu Ala His Gln Ile Glu Asp
65                  70                  75                  80 tcc ata gat cgc ttc ttg tac cat gtg acc agg gag cag caa gca tcc       288
Ser Ile Asp Arg Phe Leu Tyr His Val Thr Arg Glu Gln Gln Ala Ser
                85                  90                  95 ttt ttt cgt cgg act gta cgg tcg ccg aag act ctg ttg tca cgt cag       336
Phe Phe Arg Arg Thr Val Arg Ser Pro Lys Thr Leu Leu Ser Arg Gln
                100                 105                 110 cgg ctg gct gcc gag gtt cag ttc ctg aag aag ata ccg gag gag gcg       384
Arg Leu Ala Ala Glu Val Gln Phe Leu Lys Lys Ile Pro Glu Glu Ala
            115                 120                 125 cac cag cga gag aag agg tac agg gtc ttc gcc ggc ctt tct tcc tct       432
His Gln Arg Glu Lys Arg Tyr Arg Val Phe Ala Gly Leu Ser Ser Ser
        130                 135                 140 acc cgg cac act gaa tcg tct tcc tgt tcg tct gta tct gat ccg cac       480
Thr Arg His Thr Glu Ser Ser Ser Cys Ser Ser Val Ser Asp Pro His
145                 150                 155                 160 aca ctt aag gcc gac gtc gtc ggc atc gac ggt ccc agg gac gag ctt       528
Thr Leu Lys Ala Asp Val Val Gly Ile Asp Gly Pro Arg Asp Glu Leu
                165                 170                 175 gtg cag cag tta acc gaa gag gca gag ggc cta aca aag cag ctc aag       576
Val Gln Gln Leu Thr Glu Glu Ala Glu Gly Leu Thr Lys Gln Leu Lys
```

```
                Val Gln Gln Leu Thr Glu Glu Ala Glu Gly Leu Thr Lys Gln Leu Lys
                                180                 185                 190 gtg atc tcc atc gtc ggg atc cat ggc tcc ggc aag acc gtc ctt gcc        624
Val Ile Ser Ile Val Gly Ile His Gly Ser Gly Lys Thr Val Leu Ala
            195                 200                 205 aga gag gta tac gag agc gac gtc ggc cgg cag ttc agt ctc cgg gca        672
Arg Glu Val Tyr Glu Ser Asp Val Gly Arg Gln Phe Ser Leu Arg Ala
210                 215                 220 tgg gtt tct gct act gac aga ggt ccg aga gag gtg ctc atg gag atc        720
Trp Val Ser Ala Thr Asp Arg Gly Pro Arg Glu Val Leu Met Glu Ile
225                 230                 235                 240 ctc cga aat ttt ggt agg cca gtg gtg gat agc tct agt att gac cag        768
Leu Arg Asn Phe Gly Arg Pro Val Val Asp Ser Ser Ile Asp Gln
                245                 250                 255 ctt acg gta gat ctc agg aaa cac ttg ggt gag aaa agg tat ttc att        816
Leu Thr Val Asp Leu Arg Lys His Leu Gly Glu Lys Arg Tyr Phe Ile
            260                 265                 270 gta atc gat ggc atg caa aca gat cag tgg agc acc att gaa act gcc        864
Val Ile Asp Gly Met Gln Thr Asp Gln Trp Ser Thr Ile Glu Thr Ala
        275                 280                 285 ttc cca gaa aac aat gtt gtt agc agc aga gta att gtt aca aca aca        912
Phe Pro Glu Asn Asn Val Val Ser Ser Arg Val Ile Val Thr Thr Thr
            290                 295                 300 atc cgg tca gta gct aat tct tgc agc tct tct aac ggt tat gtg cac        960
Ile Arg Ser Val Ala Asn Ser Cys Ser Ser Ser Asn Gly Tyr Val His
305                 310                 315                 320 aaa atg aaa aga ctt agt gac gaa cac tca gag caa ttg ttt atc aag       1008
Lys Met Lys Arg Leu Ser Asp Glu His Ser Glu Gln Leu Phe Ile Lys
                325                 330                 335 aaa gct tgc cca aca aaa tat tca ggt tat act cga ccg gaa tca aaa       1056
Lys Ala Cys Pro Thr Lys Tyr Ser Gly Tyr Thr Arg Pro Glu Ser Lys
            340                 345                 350 gaa gtt ctg aag aaa tgt gat ggt caa cca ctt gct ctt gtt act atg       1104
Glu Val Leu Lys Lys Cys Asp Gly Gln Pro Leu Ala Leu Val Thr Met
        355                 360                 365 ggc caa ttc ttg agg aaa aat ggt tgg ccc aca gga ccc aac tgc gaa       1152
Gly Gln Phe Leu Arg Lys Asn Gly Trp Pro Thr Gly Pro Asn Cys Glu
370                 375                 380 aat gtg tgt aga gat ctt aga cga cat ctg gag cag gat gat aca ttg       1200
Asn Val Cys Arg Asp Leu Arg Arg His Leu Glu Gln Asp Asp Thr Leu
385                 390                 395                 400 gag aga atg cga agg gtg ctt atc cac agc tta tct agt ctt cct ag        1248
Glu Arg Met Arg Arg Val Leu Ile His Ser Leu Ser Ser Leu Pro Ser
                405                 410                 415 cat gtt ccc aaa gcc tgc ctt ttg tat ttt ggt atg ttt cca tgt ga        1296
His Val Pro Lys Ala Cys Leu Leu Tyr Phe Gly Met Phe Pro Cys Asp
            420                 425                 430 cat ccc ata aag agg aag agc ctg atg agg cga tgg tta gca gag gg        1344
His Pro Ile Lys Arg Lys Ser Leu Met Arg Arg Trp Leu Ala Glu Gly
        435                 440                 445 ttt gta caa aca cag cct tca tct agt gaa aac ttc aac acc ctc at        1392
Phe Val Gln Thr Gln Pro Ser Ser Ser Glu Asn Phe Asn Thr Leu Ile
450                 455                 460 gac cgg aat att att gag ccc atc ggc ata tgt aac gat gat cag ga        1440
Asp Arg Asn Ile Ile Glu Pro Ile Gly Ile Cys Asn Asp Asp Gln Val
465                 470                 475                 480 aag aca tgc aaa aca tat ggc atg atg cac gag ttc att ttg tta ag        1488
Lys Thr Cys Lys Thr Tyr Gly Met Met His Glu Phe Ile Leu Leu Met
                485                 490                 495
```

```
tcc acc tcc cat gac ttc att acc ctg ctt tgt aat aat aaa gtt ga      1536
Ser Thr Ser His Asp Phe Ile Thr Leu Leu Cys Asn Asn Lys Val Glu
            500                 505                 510 cac aaa tat gtg cgt cgg ctt tct ctc cat cat cat agt gct aca at      1584
His Lys Tyr Val Arg Arg Leu Ser Leu His His His Ser Ala Thr Ser
        515                 520                 525 ggc agt ttt tcg gtc atc gac tta tct ctt gtt aga tct ctg atg tt      1632
Gly Ser Phe Ser Val Ile Asp Leu Ser Leu Val Arg Ser Leu Met Val
    530                 535                 540 ttt ggg gag gct ggc aaa act att ttg agt ttc cga aag tac gag ta      1680
Phe Gly Glu Ala Gly Lys Thr Ile Leu Ser Phe Arg Lys Tyr Glu Leu
545                 550                 555                 560 ttg aga gtc ttg gat ctt gaa caa tgt acc gac ttg gaa gat gat ac      1728
Leu Arg Val Leu Asp Leu Glu Gln Cys Thr Asp Leu Glu Asp Asp His
                565                 570                 575 ctc aaa gac ata tgc aac ctt ttt ctt atg aaa tat cta agc ctc gga    1776
Leu Lys Asp Ile Cys Asn Leu Phe Leu Met Lys Tyr Leu Ser Leu Gly
            580                 585                 590 gaa act att aga agt ctt cca aag gag ata gaa aaa ctg aag ctc ttg    1824
Glu Thr Ile Arg Ser Leu Pro Lys Glu Ile Glu Lys Leu Lys Leu Leu
        595                 600                 605 gag aca ctt gac ttg agg aga aca aag gtg aaa aca cta cct ata gag    1872
Glu Thr Leu Asp Leu Arg Arg Thr Lys Val Lys Thr Leu Pro Ile Glu
    610                 615                 620 gtc ctc ctg ctc ccc tgt tta ctc cat ctg ttt ggg aag ttc caa ttt    1920
Val Leu Leu Leu Pro Cys Leu Leu His Leu Phe Gly Lys Phe Gln Phe
625                 630                 635                 640 tct gat aaa atc aag ata aca agt gac atg cag aag ttt ttc tta act    1968
Ser Asp Lys Ile Lys Ile Thr Ser Asp Met Gln Lys Phe Phe Leu Thr
                645                 650                 655 gga cag agt aac tta gag aca ctt tca gga ttt atc aca gat ggg tc     2016
Gly Gln Ser Asn Leu Glu Thr Leu Ser Gly Phe Ile Thr Asp Gly Ser
            660                 665                 670 caa gga ttg cca cag atg atg aat tac atg aat tta aga aag ctt aa     2064
Gln Gly Leu Pro Gln Met Met Asn Tyr Met Asn Leu Arg Lys Leu Lys
        675                 680                 685 ata tgg ttt gag agg agt aag aga agc acc aac ttc acc gat ctt gt     2112
Ile Trp Phe Glu Arg Ser Lys Arg Ser Thr Asn Phe Thr Asp Leu Val
    690                 695                 700 aat gct gtc caa aag ttc atc cat gat gac aaa gag agc aat gat cca    2160
Asn Ala Val Gln Lys Phe Ile His Asp Asp Lys Glu Ser Asn Asp Pro
705                 710                 715                 720 cgt tct cta tca ctt cat ttc gat gac ggc act gaa aac atc ctg aa     2208
Arg Ser Leu Ser Leu His Phe Asp Asp Gly Thr Glu Asn Ile Leu Asn
                725                 730                 735 tct ttg aag gct cct tgt tac ctt agg tca ttg aag tta aaa ggg aa     2256
Ser Leu Lys Ala Pro Cys Tyr Leu Arg Ser Leu Lys Leu Lys Gly Asn
            740                 745                 750 ttg ctg gaa ctt ccc cag ttt gtc ata tca atg cgg ggt ctc cgg ga     2304
Leu Leu Glu Leu Pro Gln Phe Val Ile Ser Met Arg Gly Leu Arg Glu
        755                 760                 765 ata tgc ctt tca tca aca aaa ttg aca tcg ggc ctc ctt gca aca ctc    2352
Ile Cys Leu Ser Ser Thr Lys Leu Thr Ser Gly Leu Leu Ala Thr Leu
    770                 775                 780 gct aac ttg aaa ggc ttg cag cat ctc aag ctg att gca gat gtc ctt    2400
Ala Asn Leu Lys Gly Leu Gln His Leu Lys Leu Ile Ala Asp Val Leu
785                 790                 795                 800 gaa gat ttt atc att gaa ggt cag gca ttc ctg ggg ctg cta cac cta    2448
Glu Asp Phe Ile Ile Glu Gly Gln Ala Phe Leu Gly Leu Leu His Leu
                805                 810                 815
```

-continued

```
tgt ttt gtc cta gaa cgt gcc acc tta cca ata att gaa gga gga gct      2496
Cys Phe Val Leu Glu Arg Ala Thr Leu Pro Ile Ile Glu Gly Gly Ala
        820                 825                 830 ttg ccg tac ctc atc tca ctt aag cta atc tgc aaa gat cta gtt ggc      2544
Leu Pro Tyr Leu Ile Ser Leu Lys Leu Ile Cys Lys Asp Leu Val Gly
835                 840                 845 ctc ggt gac atc aaa atc aac cgc ctc aaa tgt ctt aag gaa gtc agt      2592
Leu Gly Asp Ile Lys Ile Asn Arg Leu Lys Cys Leu Lys Glu Val Ser
850                 855                 860 cta gat cat aga gtc gct tcg gaa aca aga gaa atc tgg gaa aaa gct      2640
Leu Asp His Arg Val Ala Ser Glu Thr Arg Glu Ile Trp Glu Lys Ala
865                 870                 875                 880 gcc gag aag cat cca aac cgg ccg aaa gta ttg ttg gtc aac tca tct      2688
Ala Glu Lys His Pro Asn Arg Pro Lys Val Leu Leu Val Asn Ser Ser
                885                 890                 895 gat gaa agc gaa att aag gct gta gac tgt tct gtt gct tca aga cca      2736
Asp Glu Ser Glu Ile Lys Ala Val Asp Cys Ser Val Ala Ser Arg Pro
            900                 905                 910 gct gtg agt gag gct aat gga act tct ccc atg tca gag gtt gat gta      2784
Ala Val Ser Glu Ala Asn Gly Thr Ser Pro Met Ser Glu Val Asp Val
        915                 920                 925 cga gag gat gac att cag atg ata ctt aac cag ggg ctc tct gcc gct      2832
Arg Glu Asp Asp Ile Gln Met Ile Leu Asn Gln Gly Leu Ser Ala Ala
930                 935                 940 gct gag aaa cag atg aat tgt gca gtt cag cca agt tca aaa gct gaa      2880
Ala Glu Lys Gln Met Asn Cys Ala Val Gln Pro Ser Ser Lys Ala Glu
945                 950                 955                 960 ctg aac tct gat ttc aat aat att agt ttc cca gag gtt gcg ctt ggt      2928
Leu Asn Ser Asp Phe Asn Asn Ile Ser Phe Pro Glu Val Ala Leu Gly
                965                 970                 975 tta acc gag ctg tga                                                   2943
Leu Thr Glu Leu *
            980

<210> SEQ ID NO 3
<211> LENGTH: 980
<212> TYPE: PRT
<213> ORGANISM: Zea mays
<220> FEATURE:
<221> NAME/KEY: DOMAIN
<222> LOCATION: (157)...(404)
<223> OTHER INFORMATION: Region showing homology to nucleotide binding
      site (NBS) domain.
<221> NAME/KEY: DOMAIN
<222> LOCATION: (528)...(846)
<223> OTHER INFORMATION: Region showing loose homology to leucine-rich
      repeat (LRR) domain.

<400> SEQUENCE: 3

Met Glu Ala Ala Leu Leu Ser Gly Phe Ile Lys Thr Ile Leu Pro Arg
  1               5                  10                  15

Leu Phe Ser Leu Val Gln Gly Arg Tyr Lys Leu His Lys Gly Leu Lys
             20                  25                  30

Ser Asp Ile Lys Ser Leu Glu Lys Glu Leu His Met Ile Ala Val Thr
         35                  40                  45

Ile Asp Glu Gln Ile Ser Leu Gly Arg Lys Asp Gln Gly Ala Val Leu
     50                  55                  60

Ser Leu Ser Ile Asp Glu Leu His Gly Leu Ala His Gln Ile Glu Asp
 65                  70                  75                  80

Ser Ile Asp Arg Phe Leu Tyr His Val Thr Arg Glu Gln Gln Ala Ser
                 85                  90                  95
```

```
Phe Phe Arg Arg Thr Val Arg Ser Pro Lys Thr Leu Leu Ser Arg Gln
            100                 105                 110

Arg Leu Ala Ala Glu Val Gln Phe Leu Lys Lys Ile Pro Glu Glu Ala
            115                 120                 125

His Gln Arg Glu Lys Arg Tyr Arg Val Phe Ala Gly Leu Ser Ser Ser
            130                 135                 140

Thr Arg His Thr Glu Ser Ser Ser Cys Ser Ser Val Ser Asp Pro His
145                 150                 155                 160

Thr Leu Lys Ala Asp Val Val Gly Ile Asp Gly Pro Arg Asp Glu Leu
            165                 170                 175

Val Gln Gln Leu Thr Glu Glu Ala Glu Gly Leu Thr Lys Gln Leu Lys
            180                 185                 190

Val Ile Ser Ile Val Gly Ile His Gly Ser Gly Lys Thr Val Leu Ala
            195                 200                 205

Arg Glu Val Tyr Glu Ser Asp Val Gly Arg Gln Phe Ser Leu Arg Ala
            210                 215                 220

Trp Val Ser Ala Thr Asp Arg Gly Pro Arg Glu Val Leu Met Glu Ile
225                 230                 235                 240

Leu Arg Asn Phe Gly Arg Pro Val Val Asp Ser Ser Ile Asp Gln
            245                 250                 255

Leu Thr Val Asp Leu Arg Lys His Leu Gly Glu Lys Arg Tyr Phe Ile
            260                 265                 270

Val Ile Asp Gly Met Gln Thr Asp Gln Trp Ser Thr Ile Glu Thr Ala
            275                 280                 285

Phe Pro Glu Asn Asn Val Val Ser Ser Arg Val Ile Val Thr Thr Thr
            290                 295                 300

Ile Arg Ser Val Ala Asn Ser Cys Ser Ser Ser Asn Gly Tyr Val His
305                 310                 315                 320

Lys Met Lys Arg Leu Ser Asp Glu His Ser Glu Gln Leu Phe Ile Lys
            325                 330                 335

Lys Ala Cys Pro Thr Lys Tyr Ser Gly Tyr Thr Arg Pro Glu Ser Lys
            340                 345                 350

Glu Val Leu Lys Lys Cys Asp Gly Gln Pro Leu Ala Leu Val Thr Met
            355                 360                 365

Gly Gln Phe Leu Arg Lys Asn Gly Trp Pro Thr Gly Pro Asn Cys Glu
            370                 375                 380

Asn Val Cys Arg Asp Leu Arg Arg His Leu Glu Gln Asp Asp Thr Leu
385                 390                 395                 400

Glu Arg Met Arg Arg Val Leu Ile His Ser Leu Ser Ser Leu Pro Ser
            405                 410                 415

His Val Pro Lys Ala Cys Leu Leu Tyr Phe Gly Met Phe Pro Cys Asp
            420                 425                 430

His Pro Ile Lys Arg Lys Ser Leu Met Arg Arg Trp Leu Ala Glu Gly
            435                 440                 445

Phe Val Gln Thr Gln Pro Ser Ser Glu Asn Phe Asn Thr Leu Ile
            450                 455                 460

Asp Arg Asn Ile Ile Glu Pro Ile Gly Ile Cys Asn Asp Asp Gln Val
465                 470                 475                 480

Lys Thr Cys Lys Thr Tyr Gly Met Met His Glu Phe Ile Leu Leu Met
            485                 490                 495

Ser Thr Ser His Asp Phe Ile Thr Leu Leu Cys Asn Asn Lys Val Glu
            500                 505                 510
```

-continued

```
His Lys Tyr Val Arg Arg Leu Ser Leu His His Ser Ala Thr Ser
            515                 520                 525

Gly Ser Phe Ser Val Ile Asp Leu Ser Leu Val Arg Ser Leu Met Val
530                 535                 540

Phe Gly Glu Ala Gly Lys Thr Ile Leu Ser Phe Arg Lys Tyr Glu Leu
545                 550                 555                 560

Leu Arg Val Leu Asp Leu Glu Gln Cys Thr Asp Leu Glu Asp Asp His
                565                 570                 575

Leu Lys Asp Ile Cys Asn Leu Phe Leu Met Lys Tyr Leu Ser Leu Gly
                580                 585                 590

Glu Thr Ile Arg Ser Leu Pro Lys Glu Ile Glu Lys Leu Lys Leu Leu
            595                 600                 605

Glu Thr Leu Asp Leu Arg Arg Thr Lys Val Lys Thr Leu Pro Ile Glu
            610                 615                 620

Val Leu Leu Leu Pro Cys Leu Leu His Leu Phe Gly Lys Phe Gln Phe
625                 630                 635                 640

Ser Asp Lys Ile Lys Ile Thr Ser Asp Met Gln Lys Phe Phe Leu Thr
                645                 650                 655

Gly Gln Ser Asn Leu Glu Thr Leu Ser Gly Phe Ile Thr Asp Gly Ser
            660                 665                 670

Gln Gly Leu Pro Gln Met Met Asn Tyr Met Asn Leu Arg Lys Leu Lys
            675                 680                 685

Ile Trp Phe Glu Arg Ser Lys Arg Ser Thr Asn Phe Thr Asp Leu Val
            690                 695                 700

Asn Ala Val Gln Lys Phe Ile His Asp Lys Glu Ser Asn Asp Pro
705                 710                 715                 720

Arg Ser Leu Ser Leu His Phe Asp Asp Gly Thr Glu Asn Ile Leu Asn
                725                 730                 735

Ser Leu Lys Ala Pro Cys Tyr Leu Arg Ser Leu Lys Leu Lys Gly Asn
            740                 745                 750

Leu Leu Glu Leu Pro Gln Phe Val Ile Ser Met Arg Gly Leu Arg Glu
            755                 760                 765

Ile Cys Leu Ser Ser Thr Lys Leu Thr Ser Gly Leu Leu Ala Thr Leu
770                 775                 780

Ala Asn Leu Lys Gly Leu Gln His Leu Lys Leu Ile Ala Asp Val Leu
785                 790                 795                 800

Glu Asp Phe Ile Ile Glu Gly Gln Ala Phe Leu Gly Leu Leu His Leu
                805                 810                 815

Cys Phe Val Leu Glu Arg Ala Thr Leu Pro Ile Ile Glu Gly Gly Ala
                820                 825                 830

Leu Pro Tyr Leu Ile Ser Leu Lys Leu Ile Cys Lys Asp Leu Val Gly
            835                 840                 845

Leu Gly Asp Ile Lys Ile Asn Arg Leu Lys Cys Leu Lys Glu Val Ser
850                 855                 860

Leu Asp His Arg Val Ala Ser Glu Thr Arg Glu Ile Trp Glu Lys Ala
865                 870                 875                 880

Ala Glu Lys His Pro Asn Arg Pro Lys Val Leu Leu Val Asn Ser Ser
                885                 890                 895

Asp Glu Ser Glu Ile Lys Ala Val Asp Cys Ser Val Ala Ser Arg Pro
            900                 905                 910

Ala Val Ser Glu Ala Asn Gly Thr Ser Pro Met Ser Glu Val Asp Val
            915                 920                 925

Arg Glu Asp Asp Ile Gln Met Ile Leu Asn Gln Gly Leu Ser Ala Ala
```

```
            930                 935                 940
Ala Glu Lys Gln Met Asn Cys Ala Val Gln Pro Ser Ser Lys Ala Glu
945                 950                 955                 960

Leu Asn Ser Asp Phe Asn Asn Ile Ser Phe Pro Glu Val Ala Leu Gly
                965                 970                 975

Leu Thr Glu Leu
          980

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide Primer a20Cforw4881

<400> SEQUENCE: 4
cagggcctac ttggtttagt aata                                      24

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide Primer a20Crev4920

<400> SEQUENCE: 5
gggtactaca ctagcctatt acta                                      24

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide Primer a20fis19forw1110

<400> SEQUENCE: 6
cggttacaag gtctacccaa tctg                                      24

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide Primer a20fis19rev1149

<400> SEQUENCE: 7
gtcaaacaga tagccgcaga ttgg                                      24

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide Primer n07fis13forw51524

<400> SEQUENCE: 8
tacaaaacta ctgcaacgcc tata                                      24

<210> SEQ ID NO 9
<211> LENGTH: 24
<212> TYPE: DNA
<213> ORGANISM: Artificial Sequence
<220> FEATURE:
<223> OTHER INFORMATION: Oligonucleotide Primer n07fis13rev51563
```

-continued

```
<400> SEQUENCE: 9 cctcaccccca agtatatata ggcg                                             24

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide Primer n07Bforw10439/53434

<400> SEQUENCE: 10
cattggacct cttccccact aaga                                              24

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide Primer n07Brev10478/53473

<400> SEQUENCE: 11
tccttgagtc cagtgctctt agtg                                              24

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide Primer n07Aforw4333

<400> SEQUENCE: 12
gaaactaggc gcgtcaggtt ttat                                              24

<210> SEQ ID NO 13
<211> LENGTH: 24
<212> TYPE: DNA
<213> ORGANISM: Artificial Sequence
<220> FEATURE:
<223> OTHER INFORMATION: Oligonucleotide Primer n07Arev4372

<400> SEQUENCE: 13
aaggcagcca ctgaaaataa aacc                                              24

<210> SEQ ID NO 14
<211> LENGTH: 954
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No: NP_910480, Rice NBS-LRR

<400> SEQUENCE: 14

Met Glu Gly Ala Val Phe Ser Leu Thr Glu Gly Ala Val Arg Ser Leu
1               5                   10                  15

Leu Cys Lys Leu Gly Cys Leu Leu Thr Glu Asp Thr Trp Leu Val Gln
            20                  25                  30

Gly Val His Gly Glu Ile Gln Tyr Ile Lys Asp Glu Leu Glu Cys Met
        35                  40                  45

Asn Ala Phe Leu Arg Asn Leu Thr Ile Ser Gln Ile His Asp Asp Gln
    50                  55                  60

Val Arg Ile Trp Met Lys Gln Val Arg Glu Ile Ala Tyr Asp Ser Glu
65                  70                  75                  80
```

-continued

```
Asp Cys Ile Asp Glu Phe Ile His Asn Leu Gly Ser Ser Glu Met
                85                  90                  95
Gly Phe Phe Gly Gly Leu Ile Ser Met Leu Arg Lys Leu Ala Cys Arg
            100                 105                 110
His Arg Ile Ala Leu Gln Leu Gln Glu Leu Lys Ala Arg Ala Gln Asp
            115                 120                 125
Val Gly Asp Arg Arg Ser Arg Tyr Gly Val Glu Leu Ala Lys Ala Thr
    130                 135                 140
His Glu Glu Ala His Pro Arg Leu Thr Arg His Ala Ser Leu His Ile
145                 150                 155                 160
Asp Pro Gln Leu His Ala Leu Phe Ala Glu Glu Ala Gln Leu Val Gly
                165                 170                 175
Ile Asp Glu Pro Arg Asn Glu Leu Val Ser Trp Leu Met Glu Glu Asp
            180                 185                 190
Leu Arg Leu Arg Val Leu Ala Ile Val Gly Phe Gly Gly Leu Gly Lys
            195                 200                 205
Thr Thr Leu Ala Arg Met Val Cys Gly Ser Pro Val Val Lys Ser Ala
    210                 215                 220
Asp Phe Gln Cys Cys Pro Leu Phe Ile Ile Ser Gln Thr Phe Asn Ile
225                 230                 235                 240
Arg Ala Leu Phe Gln His Met Val Arg Glu Leu Ile Gln Glu Pro His
                245                 250                 255
Lys Ala Met Ala Ile Ala Gly Cys Lys His Gly Leu Ile Thr Asp Asp
            260                 265                 270
Tyr Leu Glu Gly Met Glu Arg Trp Glu Val Ala Ala Leu Thr Lys Asn
    275                 280                 285
Leu Arg Arg Tyr Phe Gln Asp Lys Arg Tyr Ile Val Ile Leu Asp Asp
    290                 295                 300
Ile Trp Thr Val Ser Ala Trp Glu Ser Ile Arg Cys Ala Leu Pro Asp
305                 310                 315                 320
Asn Leu Lys Gly Ser Arg Ile Ile Val Thr Thr Arg Asn Ala Asp Val
                325                 330                 335
Ala Asn Thr Cys Cys Ser Arg Pro Gln Asp Arg Ile Tyr Asn Ile Gln
            340                 345                 350
Arg Leu Ser Glu Thr Thr Ser Arg Glu Leu Phe Phe Lys Lys Ile Phe
    355                 360                 365
Gly Phe Ala Asp Asp Lys Ser Pro Thr Asp Glu Phe Glu Glu Val Ser
    370                 375                 380
Asn Ser Val Leu Lys Lys Cys Gly Gly Leu Pro Leu Ala Ile Val Asn
385                 390                 395                 400
Ile Gly Ser Leu Leu Ala Ser Lys Thr Asn Arg Thr Lys Glu Glu Trp
                405                 410                 415
Gln Lys Val Cys Asn Asn Leu Gly Ser Glu Leu Glu Asn Asn Pro Thr
            420                 425                 430
Leu Glu Gly Val Lys Gln Val Leu Thr Leu Ser Tyr Asn Asp Leu Pro
    435                 440                 445
Tyr His Leu Lys Ala Cys Phe Leu Tyr Leu Ser Ile Phe Pro Glu Asn
    450                 455                 460
Tyr Val Ile Lys Arg Gly Pro Leu Val Arg Arg Trp Ile Ala Glu Gly
465                 470                 475                 480
Phe Val Ser Gln Arg His Gly Gln Ser Met Glu Gln Leu Ala Glu Ser
                485                 490                 495
Tyr Phe Asp Glu Phe Val Ala Arg Ser Ile Val Gln Pro Val Arg Thr
```

```
                500                 505                 510
Asp Trp Thr Gly Lys Val Arg Ser Cys Arg Val His Asp Leu Met Leu
        515                 520                 525

Asp Val Ile Val Ser Arg Ser Ile Glu Glu Asn Phe Ala Ser Phe Leu
    530                 535                 540

Cys Asp Asn Gly Ser Thr Leu Ala Ser His Asp Lys Ile Arg Arg Leu
545                 550                 555                 560

Ser Ile His Ser Ser Tyr Asn Ser Ser Gln Lys Thr Ser Ala Asn Val
                565                 570                 575

Ser His Ala Arg Ser Phe Thr Met Ser Ala Ser Val Glu Glu Val Pro
            580                 585                 590

Phe Phe Phe Pro Gln Leu Arg Leu Leu Arg Val Leu Asp Leu Gln Gly
        595                 600                 605

Cys Ser Cys Leu Ser Asn Glu Thr Leu His Cys Met Cys Arg Phe Phe
    610                 615                 620

Gln Leu Lys Tyr Leu Ser Leu Arg Asn Thr Asn Val Ser Lys Leu Pro
625                 630                 635                 640

His Leu Leu Gly Asn Leu Lys His Leu Glu Thr Leu Asp Ile Arg Ala
                645                 650                 655

Thr Leu Ile Lys Lys Leu Pro Ala Ser Ala Gly Asn Leu Ser Cys Leu
            660                 665                 670

Lys His Leu Phe Ala Gly His Lys Val Gln Leu Thr Arg Thr Ala Ser
        675                 680                 685

Val Lys Phe Leu Arg Gln Ser Ser Gly Leu Glu Val Ala Thr Gly Val
    690                 695                 700

Val Lys Asn Met Val Ala Leu Gln Ser Leu Val His Ile Val Val Lys
705                 710                 715                 720

Asp Lys Ser Pro Val Leu Arg Glu Ile Gly Leu Leu Gln Asn Leu Thr
                725                 730                 735

Lys Leu Asn Val Leu Leu Arg Gly Val Glu Glu Asn Trp Asn Ala Phe
            740                 745                 750

Leu Glu Ser Leu Ser Lys Leu Pro Gly Pro Leu Arg Ser Leu Ser Ile
        755                 760                 765

His Thr Leu Asp Glu Lys Glu His Ser Leu Ser Leu Asp Asn Leu Ala
    770                 775                 780

Phe Val Glu Ser Pro Pro Leu Phe Ile Thr Lys Phe Ser Leu Ala Gly
785                 790                 795                 800

Glu Leu Glu Arg Leu Pro Pro Trp Ile Pro Ser Leu Arg Asn Val Ser
                805                 810                 815

Arg Phe Ala Leu Arg Arg Thr Glu Leu His Ala Asp Ala Ile Gly Val
            820                 825                 830

Leu Gly Asp Leu Pro Asn Leu Leu Cys Leu Lys Leu Tyr His Lys Ser
        835                 840                 845

Tyr Ala Asp Asn Cys Ile Val Phe Cys His Gly Lys Phe Val Lys Leu
    850                 855                 860

Lys Leu Leu Ile Ile Asp Asn Leu Glu Arg Ile Glu Lys Met Gln Phe
865                 870                 875                 880

Asp Ala Gly Ser Val Thr Asn Leu Glu Arg Leu Thr Leu Ser Phe Leu
                885                 890                 895

Arg Glu Pro Lys Tyr Gly Ile Ser Gly Leu Glu Asn Leu Pro Lys Leu
            900                 905                 910

Lys Glu Ile Glu Phe Phe Gly Asp Ile Ile Leu Ser Val Val Thr Lys
        915                 920                 925
```

-continued

Val Ala Ser Cys Val Lys Ala His Pro Asn His Pro Arg Val Ile Gly
            930                 935                 940

Asp Lys Trp Asn Ile Val Thr Glu Tyr Ala
945                 950

<210> SEQ ID NO 15
<211> LENGTH: 953
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No. NP_910483 Rice NBS-LRR

<400> SEQUENCE: 15

Met Glu Gly Ala Ile Phe Ser Val Ala Glu Gly Thr Val Arg Ser Leu
  1                 5                  10                  15

Leu Ser Lys Leu Ser Ser Leu Leu Ser Gln Glu Ser Trp Phe Val Arg
             20                  25                  30

Gly Val His Gly Asp Ile Gln Tyr Ile Lys Asp Glu Leu Glu Ser Met
         35                  40                  45

Asn Ala Phe Leu Arg Tyr Leu Thr Val Leu Glu Asp His Asp Thr Gln
 50                  55                  60

Val Arg Ile Trp Met Lys Gln Val Arg Glu Ile Ala Tyr Asp Ala Glu
65                  70                  75                  80

Asp Cys Ile Asp Gln Phe Thr His His Leu Gly Glu Ser Ser Gly Ile
                 85                  90                  95

Gly Phe Leu Tyr Arg Leu Ile Tyr Ile Leu Gly Lys Leu Cys Cys Arg
            100                 105                 110

His Arg Ile Ala Met Gln Leu Gln Glu Leu Lys Ala Arg Ala Gln Asp
        115                 120                 125

Val Ser Glu Arg Arg Ser Arg Tyr Glu Val Met Leu Pro Lys Thr Thr
    130                 135                 140

Leu Gln Gly Ala Gly Pro Arg Leu Thr Arg His Ala Ser Arg His Leu
145                 150                 155                 160

Asp Pro Gln Leu His Ala Leu Phe Thr Glu Glu Ala Gln Leu Val Gly
                165                 170                 175

Leu Asp Glu Pro Arg Asp Lys Leu Val Arg Trp Val Met Glu Ala Asp
            180                 185                 190

Pro Cys Arg Arg Val Leu Ala Ile Val Gly Phe Gly Gly Leu Gly Lys
        195                 200                 205

Thr Thr Leu Ala Arg Met Val Cys Glu Asn Pro Met Val Lys Gly Ala
    210                 215                 220

Asp Phe His Cys Cys Pro Leu Phe Ile Val Ser Gln Thr Phe Asn Ile
225                 230                 235                 240

Arg Thr Leu Phe Gln Tyr Met Ile Arg Glu Leu Ile Gln Arg Pro Asn
                245                 250                 255

Lys Ala Met Ala Val Ala Gly Gly Lys His Gly His Thr Met Asp Gly
            260                 265                 270

Asn Met Asp Gly Met Glu Arg Trp Glu Val Ala Val Leu Ala Glu Lys
        275                 280                 285

Val Arg Gln Tyr Leu Leu Asp Lys Tyr Ile Val Ile Phe Asp Asp Ile
    290                 295                 300

Trp Thr Ile Ser Ala Trp Glu Ser Ile Arg Cys Ala Leu Pro Asp Asn
305                 310                 315                 320

```
Lys Lys Gly Ser Arg Val Ile Ile Thr Thr Arg Asn Glu Asp Val Ala
                325                 330                 335

Asn Thr Cys Cys Ser Gly Pro Gln Asp Gln Val Tyr Lys Met Gln Arg
            340                 345                 350

Leu Ser Asp Ala Ala Ser Arg Glu Leu Phe Phe Lys Arg Ile Phe Gly
        355                 360                 365

Ser Ala Asp Ile Ser Ser Asn Glu Glu Leu Asp Glu Val Ser Asn Ser
    370                 375                 380

Ile Leu Lys Lys Cys Gly Gly Leu Pro Leu Ala Ile Val Ser Ile Gly
385                 390                 395                 400

Ser Leu Val Ala Ser Lys Thr Asn Arg Thr Lys Glu Glu Trp Gln Lys
                405                 410                 415

Ile Cys Asp Asn Leu Gly Ser Glu Leu Glu Thr Asn Pro Thr Leu Glu
            420                 425                 430

Val Ala Lys Gln Val Leu Thr Leu Ser Tyr Asn Asp Leu Pro Tyr His
        435                 440                 445

Leu Lys Ala Cys Phe Leu Tyr Leu Ser Ile Phe Pro Glu Asn Tyr Val
    450                 455                 460

Ile Arg Arg Gly Pro Leu Val Arg Arg Trp Ile Ala Glu Gly Phe Val
465                 470                 475                 480

Asn Gln Arg His Gly Leu Ser Met Glu Glu Val Ala Glu Ser Tyr Phe
                485                 490                 495

Asp Glu Phe Val Ala Arg Ser Ile Val Gln Pro Val Lys Ile Asp Trp
            500                 505                 510

Ser Gly Lys Val Arg Thr Cys Arg Val His Asp Met Met Leu Glu Val
        515                 520                 525

Ile Ile Ser Lys Ser Leu Glu Glu Asn Phe Ala Ser Phe Leu Cys Asp
    530                 535                 540

Asn Gly His Pro Leu Val Cys His Asp Lys Ile Arg Arg Leu Ser Ile
545                 550                 555                 560

His Asn Ser His Asn Ser Val Gln Arg Thr Arg Val Ser Val Ser His
                565                 570                 575

Val Arg Ser Phe Thr Met Ser Ala Ser Val Glu Glu Val Pro Met Phe
            580                 585                 590

Phe Pro Gln Met Arg Leu Leu Arg Val Leu Asp Leu Gln Gly Ser Ser
        595                 600                 605

Cys Leu Asn Asn Ser Thr Leu Asn Tyr Ile Cys Lys Phe Tyr Gln Leu
    610                 615                 620

Lys Tyr Leu Thr Leu Arg Lys Thr Asn Ile Gly Lys Leu Pro Arg Leu
625                 630                 635                 640

Ile Gly Asn Leu Lys Tyr Leu Glu Thr Leu Asp Ile Arg Ala Thr Arg
                645                 650                 655

Ile Lys Arg Leu Pro Ala Ser Ala Ser Asn Leu Ser Cys Leu Lys His
            660                 665                 670

Leu Leu Val Gly His Lys Val Gln Leu Thr Arg Thr Thr Ser Val Lys
        675                 680                 685

Cys Phe Arg Pro Asp Ser Gly Leu Glu Met Thr Ala Gly Val Val Lys
    690                 695                 700

Asn Met Met Ala Leu Gln Ser Leu Ala His Ile Val Val Lys Glu Arg
705                 710                 715                 720

Pro Ala Val Leu Ser Glu Ile Gly Gln Leu Gln Lys Leu Gln Lys Leu
                725                 730                 735

Asn Val Leu Phe Arg Gly Val Glu Glu Asn Trp Asn Ala Phe Leu Gln
```

740                 745                 750
Ser Leu Val Lys Leu Thr Gly Ser Leu Arg Ser Leu Ser Ile His Ile
            755                 760                 765

Leu Asp Glu Lys Glu His Ser Ser Leu Glu Tyr Leu Ala Leu Ile
770                 775                 780

Ala Glu Ser Pro Pro Leu Phe Ile Arg Asn Phe Ser Leu Lys Gly Lys
785                 790                 795                 800

Leu Gln Arg Leu Pro Pro Trp Ile Pro Ser Leu Arg Asn Val Ser Arg
            805                 810                 815

Ile Thr Phe Arg Asp Thr Gly Leu His Ala Glu Ala Ile Gly Val Leu
            820                 825                 830

Gly Asp Leu Pro Asn Leu Leu Cys Leu Lys Leu Tyr Gln Arg Ser Tyr
            835                 840                 845

Ala Asp Asp His Ile Phe Phe Ala His Gly Asn Phe Leu Lys Leu Arg
            850                 855                 860

Met Leu Val Ile Asp Asn Met Glu Asn Ile Arg Asn Val His Phe Glu
865                 870                 875                 880

Lys Gly Ser Val Pro Asn Leu Glu Trp Leu Thr Ile Ala Phe Leu Gln
            885                 890                 895

Glu Pro Lys Asp Gly Ile Thr Gly Leu Glu Asn Leu Leu Lys Leu Lys
            900                 905                 910

Glu Ile Glu Phe Phe Gly Asp Ile Ile Leu Ser Met Val Thr Lys Val
            915                 920                 925

Ala Ser Cys Met Lys Ala His Pro Asn Arg Pro Arg Val Ile Gly Asp
            930                 935                 940

Lys Trp Asn Asn Val Thr Glu Tyr Ala
945                 950

<210> SEQ ID NO 16
<211> LENGTH: 989
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No: NP_910482 Rice NBS-LRR

<400> SEQUENCE: 16

Met Glu Gly Ala Ile Val Ser Leu Thr Glu Gly Ala Val Arg Gly Leu
1               5                   10                  15

Leu Arg Lys Leu Ala Gly Val Leu Ala Gln Glu Ser Ser Pro Ala Gln
            20                  25                  30

Arg Val His Gly Glu Val Gln Tyr Ile Lys Asp Glu Leu Glu Ser Met
            35                  40                  45

Asn Ala Phe Leu Arg Ser Val Ser Thr Ser Pro Glu Asp Ala Ala Gly
            50                  55                  60

His Asp Asp Gln Val Arg Val Trp Met Lys Gln Val Arg Glu Ile Ala
65                  70                  75                  80

Tyr Asp Ala Glu Asp Cys Ile Asp Val Phe Val Arg Gly Arg Ser His
                85                  90                  95

Pro Ala Ala Ala Gly Asp Glu Gly Arg Leu Val Ala Ser Leu Arg
            100                 105                 110

Arg Phe Val Arg Leu Leu Ala Gly Ala Leu Gly Val Gly Gly Gly Asp
            115                 120                 125

Arg Ser Val Ala Ala Gln Leu Arg Glu Leu Lys Ala Arg Ala Arg Asp
            130                 135                 140

```
Ala Gly Glu Arg Arg Thr Arg Tyr Gly Val Ser Leu Ala Ala Ala Ala
145                 150                 155                 160

Val Arg Gly Gly Gly Ser Ser Ser Gly Arg Leu Asp Pro Arg
            165                 170                 175

Leu His Ala Leu Phe Thr Glu Ala Gln Leu Val Gly Ile Asp Gly
            180                 185                 190

Pro Arg Glu Glu Leu Val Gly Trp Val Met Glu Glu Pro Arg Leu
            195                 200                 205

Arg Val Leu Ala Val Val Gly Phe Gly Gly Leu Gly Lys Thr Thr Leu
    210                 215                 220

Ala Arg Met Val Cys Gly Ser Pro Arg Val Lys Gly Ala Ala Asp Phe
225                 230                 235                 240

Gln Cys Ser Pro Pro Leu Val Val Ser Gln Thr Phe Ser Ile Thr
            245                 250                 255

Ala Leu Phe Gln His Leu Leu Arg Glu Leu Ile Gln Arg Pro Arg Lys
            260                 265                 270

Ala Met Ala Ala Val Ala Ala Ala Gly Gly Gly Gly Asp Leu Val
            275                 280                 285

Ala Tyr Asp Ala Leu Gln Gly Met Glu Arg Trp Glu Thr Ala Ala Leu
            290                 295                 300

Ala Ser Lys Ala Glu Gly Ile Pro Ala Arg Gln Lys Phe Val His Ile
305                 310                 315                 320

Cys Gly Thr Ile Thr Leu Tyr Arg Tyr Ile Val Ile Leu Asp Asp Ile
                325                 330                 335

Trp Ser Ser Ser Ala Trp Glu Ser Ile Lys Cys Ala Phe Pro Asp Asn
                340                 345                 350

Lys Lys Gly Ser Arg Ile Ile Val Thr Thr Arg Asn Glu Asp Val Ala
            355                 360                 365

Asn Thr Cys Cys Cys Arg Pro Gln Asp Arg Ile Tyr Lys Ile Gln Arg
370                 375                 380

Leu Ser Asp Ala Ala Ser Arg Glu Leu Phe Phe Lys Arg Ile Phe Gly
385                 390                 395                 400

Met Ala Asp Ala Gly Ala Pro Asp Asp Glu Leu Lys Gln Val Ser
            405                 410                 415

Asp Ser Ile Leu Lys Lys Cys Gly Gly Leu Pro Leu Ala Ile Val Ser
            420                 425                 430

Ile Gly Ser Leu Leu Ala Ser Lys Pro Asn Arg Ser Lys Glu Glu Trp
            435                 440                 445

Gln Lys Val Cys Asp Asn Leu Gly Ser Glu Leu Glu Ser Asn Pro Thr
            450                 455                 460

Leu Glu Gly Thr Lys Gln Val Leu Thr Leu Ser Tyr Asn Asp Leu Pro
465                 470                 475                 480

Tyr His Leu Lys Ala Cys Phe Leu Tyr Leu Ser Ile Phe Pro Glu Asn
                485                 490                 495

His Val Ile Lys Arg Gly Pro Leu Val Arg Met Trp Ile Ala Glu Gly
            500                 505                 510

Phe Val Thr Gln Arg His Gly Leu Ser Met Glu Gln Val Gly Glu Arg
            515                 520                 525

Tyr Phe Asp Glu Phe Val Ser Arg Ser Met Val His Leu Val Arg Ile
            530                 535                 540

Asp Trp Ser Gly Lys Val Arg Ser Cys Lys Val His Asp Ile Met Leu
545                 550                 555                 560
```

```
Glu Val Ile Val Ser Lys Ser Leu Glu Glu Asn Phe Ala Ser Phe
                565                 570                 575
Cys Asp Asn Gly Thr Glu Leu Val Ser His Lys Ile Arg Arg Leu
            580                 585                 590
Ser Ile Arg Ser Ser Ser Tyr Ser Ser Ala Gln Arg Thr Ser Asn Ser
        595                 600                 605
Val Ala His Val Arg Thr Phe Arg Met Ser Pro Ser Ile Asp Asn Ile
610                 615                 620
Pro Phe Phe Phe Pro Gln Leu Arg Leu Leu Arg Val Leu Asp Met Gln
625                 630                 635                 640
Gly Ser Arg Cys Met Ser Asn Lys Asn Leu Asp Cys Ile Cys Arg Phe
                645                 650                 655
Phe Gln Leu Lys Tyr Leu Ser Leu Arg Asn Thr Ser Val Ser Ile Leu
            660                 665                 670
Pro Arg Leu Ile Gly Asn Leu Asn His Leu Glu Thr Leu Asp Ile Arg
        675                 680                 685
Glu Thr Leu Ile Lys Lys Leu Pro Ser Ser Ala Ala Asn Leu Thr Cys
690                 695                 700
Leu Lys His Leu Leu Ala Gly His Lys Glu Gln Leu Thr Arg Thr Ser
705                 710                 715                 720
Ser Val Lys Phe Leu Arg Pro Ser Ser Gly Leu Lys Met Ser His Gly
                725                 730                 735
Val Ile Arg Asn Met Ala Lys Leu Gln Ser Leu Val His Val Glu Ile
            740                 745                 750
Lys Glu His Pro Ser Val Phe Gln Glu Ile Ala Leu Leu Gln Asn Leu
        755                 760                 765
Arg Lys Leu Ser Val Leu Phe Tyr Gly Ile Glu Val Asn Trp Lys Pro
770                 775                 780
Phe Leu Glu Leu Leu Asn Met Leu Ser Gly Ser Val Arg Ser Leu Ser
785                 790                 795                 800
Ile Asp Ile Phe Asp Ala Gln Gly Asn Ile Ser Ile Ser Ser Leu Glu
                805                 810                 815
Met Leu Ser Ser Leu Val Ser Pro Pro Ile Phe Ile Thr Ser Phe Ser
            820                 825                 830
Leu Thr Gly Lys Leu Gly Ser Leu Pro Pro Trp Val Ala Ser Leu Arg
        835                 840                 845
Ser Val Ser Arg Leu Thr Leu Arg Arg Ser Gln Leu Arg Ala Asp Ala
850                 855                 860
Ile His Val Leu Gly Gly Leu Gln Asn Leu Leu Cys Leu Lys Leu Tyr
865                 870                 875                 880
His Lys Ser Tyr Ala Asp Asp Arg Leu Val Phe Pro Gln Gly Gly Phe
                885                 890                 895
Ala Arg Val Lys Leu Leu Ile Asp Asp Asn Leu Val Asn Leu Glu Lys
            900                 905                 910
Leu His Phe Asn Glu Gly Ser Met Pro Asn Leu Glu Arg Leu Thr Leu
        915                 920                 925
Ser Phe Leu Arg Glu Pro Lys Asp Gly Ile Ser Gly Leu Asn Asn Leu
930                 935                 940
Leu Lys Leu Lys Glu Val Glu Phe Phe Gly Asn Ile Val Ser Ser Val
945                 950                 955                 960
Val Ser Lys Val Val Ser Cys Val Lys Asp His Pro Asn His Pro Arg
                965                 970                 975
Val Val Gly Asp Lys Trp Asn Ile Val Thr Val Tyr Asn
```

<210> SEQ ID NO 17
<211> LENGTH: 998
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Accession No. NP_921091.1 Rice disease resistance protein

<400> SEQUENCE: 17

```
Met Glu Thr Ala Val Leu Ser Ala Val Leu Arg Thr Leu Gly Pro Lys
 1               5                  10                  15

Leu Tyr Ala Phe Leu Arg Asp Gly His Asp Leu Leu Arg Arg Asp Leu
            20                  25                  30

Glu Arg Asp Val His Tyr Ile Arg Asn Glu Leu Ala Met Ile Ala Ala
        35                  40                  45

Ala Ile Glu Glu His Asp Arg Arg Pro Pro Ala Ala Gly Asp Val
    50                  55                  60

Arg Ser Ala Trp Ile Arg Gly Val Arg Asp Leu Ala Cys Asp Met Glu
65                  70                  75                  80

Asp Cys Val Asp Arg Phe Val His Arg Ala Thr Gly His Gly Leu Ala
                85                  90                  95

Ser Met Gly Ala Arg Ala Lys Phe Ala Ala Val Ile Gln Glu Leu Arg
            100                 105                 110

Arg Lys Ser Glu Glu Leu Ser Arg Leu Arg Ala Ser Tyr Ala Ala Ala
        115                 120                 125

Ala Gly Glu Pro Ser Cys Trp Val Ala Thr Gly Ser Ser Ala Leu Thr
    130                 135                 140

Leu Pro Ala Ser Ser Glu Ala His Thr Leu Ala Ser Asp Ile Val
145                 150                 155                 160

Gly Met Asp Gly Pro Arg Asp Glu Ile Leu Glu Leu Ile Gly Glu Thr
                165                 170                 175

Gln Gly Gln Leu Lys Val Ile Ser Ile Val Gly Phe Gly Leu Gly
            180                 185                 190

Lys Thr Leu Leu Ala Arg Gln Ile Tyr Glu Ser Asp Ala Val Ala Ala
        195                 200                 205

Gln Phe His Pro Arg Ile Trp Val Arg Ala Ala Gly Lys Asn Ala Glu
    210                 215                 220

Asp Val Leu Met Asp Ile Leu Gln Gln Leu Gly Met Pro Val His His
225                 230                 235                 240

Cys His Ala Ser Asn Leu Val Val Asn Leu Arg Asn Cys Leu Glu Ser
                245                 250                 255

Lys Arg Phe Phe Val Val Ile Asp Asp Met Gln Arg Glu Tyr Trp Asn
            260                 265                 270

Ser Ser Phe Arg Asn Ala Phe Pro Ser Asp Thr Gly Leu Ser Ser Ile
        275                 280                 285

Val Ile Val Thr Thr Ala Ile Gln Ser Ile Ala Asn Ala Cys Ser Ser
    290                 295                 300

Arg Asn Ser His Val Tyr Val Met Arg Thr Leu Asn Glu Glu His Ser
305                 310                 315                 320

Arg Gln Leu Phe Leu Lys Glu Ala Ser Trp Lys Asp Tyr Pro Pro Gly
                325                 330                 335

Ser Glu Ala Ile Leu Lys Lys Cys Asp Gly Leu Pro Leu Ala Leu Val
```

```
                340                 345                 350
Thr Thr Ala Gln Phe Leu Gln Ser Arg Cys Gln Gln Pro Leu Gly
            355                 360                 365
Cys Ala Lys Leu Cys Asp Asn Leu Gly Lys His Leu Val Thr Glu Asp
            370                 375                 380
Thr Leu Ala Arg Met Lys Arg Val Leu Val His His Tyr Ser Ser Leu
385                 390                 395                 400
Pro Gly His Val Ile Lys Ala Cys Leu Leu Tyr Leu Gly Ile Phe Pro
                405                 410                 415
Ser Gly His Pro Val Arg Arg Lys Thr Leu Ile Arg Arg Trp Ser Ala
                420                 425                 430
Glu Gly Phe Val Gly Ala Asp His His Arg Ser Ser Leu Asp Val Ala
            435                 440                 445
Ile Asp Ser Phe Glu Glu Leu Val Asn Arg Ser Ile Ile Gln Pro Val
            450                 455                 460
Asp Val Ser Ser Asn Thr Glu Val Lys Thr Cys Gln Thr His Gly Met
465                 470                 475                 480
Met Leu Glu Phe Ile Leu His Lys Ser Ile Cys Asp Asn Phe Ile Thr
                485                 490                 495
Phe Leu Tyr Gly Gln Ala Arg Leu Pro Asp Lys Ile Arg Cys Val Ser
                500                 505                 510
Ile Gln Gln Asn Ser Gly Ser Lys Thr Arg Val Asp Ser Asp Ile Asp
            515                 520                 525
Leu Ser Leu Val Arg Ser Leu Thr Ile Phe Gly Lys Ala His Lys Ser
            530                 535                 540
Phe Leu Asn Phe Ser Arg Tyr Lys Leu Leu Arg Val Leu Asp Leu Glu
545                 550                 555                 560
Glu Cys Asp Glu Leu Glu Asp Glu His Leu Lys Lys Ile Cys Lys Arg
                565                 570                 575
Leu Leu Leu Lys Tyr Leu Ser Leu Gly Arg Gly Ile Thr Val Leu Pro
            580                 585                 590
Lys Glu Ile Ala Lys Leu Lys Phe Leu Glu Thr Leu Asp Leu Arg Arg
            595                 600                 605
Thr Val Ile Lys Phe Leu Pro Ile Gln Val Leu Glu Leu Pro Cys Leu
            610                 615                 620
Ile His Leu Phe Gly Val Phe Lys Ile Gln Asp Ala Asp Gln Gln Met
625                 630                 635                 640
Arg Lys Leu Lys Ser Phe Leu Thr Glu Lys Ser Lys Leu Glu Thr Leu
                645                 650                 655
Ala Gly Phe Val Thr Asp Arg Cys Gln Thr Phe Pro Gln Leu Met Lys
                660                 665                 670
His Met Thr Asn Leu Ala Lys Val Lys Ile Trp Cys Glu Asn Thr Ala
            675                 680                 685
Asp Ala Ser Ser Ser Asn Ser Asp Val His Leu Ser Glu Ala Ile
            690                 695                 700
Gln Glu Phe Ile Gln Arg Gly Thr Asp Val Asn Asp Val Arg Ser Leu
705                 710                 715                 720
Ser Leu Asp Val Gly Glu Cys Ser Gln Glu Phe Leu Asn Phe Ser Leu
                725                 730                 735
Gly Asp Ser Cys Tyr Leu Ser Ser Leu Lys Leu Lys Gly Asn Lys Ile
            740                 745                 750
Cys Arg Leu Pro Pro Phe Val Thr Ser Leu Ala Val Leu Thr Asp Leu
            755                 760                 765
```

-continued

```
Cys Leu Ser Ser Ser Asp Arg Leu Ser Ser Asp Val Leu Ala Ala Leu
        770                 775                 780

Ser Asn Val Arg Ala Leu Arg Tyr Leu Lys Leu Ile Ala Arg His Leu
785                 790                 795                 800

Asp Arg Phe Val Ile Glu Arg Gly Asp Leu Gln Ser Leu Arg Arg Leu
                805                 810                 815

His Ile Val Val Val Ser Met Thr Thr Met Ser Lys Gln Gln Pro Glu
            820                 825                 830

Ile Gln Glu Gly Ala Leu Pro Asn Leu Glu Ser Phe His Leu Leu Cys
        835                 840                 845

Lys Asp Leu Asp Gly Pro Cys Gly His Gly Gly Ile Arg Ile Asp Ser
850                 855                 860

Leu Gly Leu Gly Cys Leu Arg Glu Ile Val Leu Asp Asp Gly Val Arg
865                 870                 875                 880

Glu Thr Ala Lys Glu Gln Trp Lys Asp Ala Ala Arg Arg His Pro Lys
                885                 890                 895

Arg Pro Lys Val Val Phe Val Gly Ala Gly Asp Val Val Asp Arg Arg
                900                 905                 910

Arg Val Gly Ala Ala Ala Ala Ala Pro Ala Ala Gly Glu Ser Asn
            915                 920                 925

Ser Ala Met Ala Pro Ala Ala Val Ala Ser Val Val Ala Ala Gly Asp
        930                 935                 940

Val Lys Arg Pro Ala Arg Glu Glu Ser Asp Ile Ser Ala Ala Leu Ala
945                 950                 955                 960

Ser Leu Pro Ala Lys Met Ala Arg Leu Leu Gly Ala Ala Ser Ile His
                965                 970                 975

Gln Ser Ser Gly Thr Gln Gly Leu Ser Cys Gly Gly Asn Gly Ala
            980                 985                 990

Ser Gln Arg His Phe Ser
        995
```

<210> SEQ ID NO 18
<211> LENGTH: 958
<212> TYPE: PRT
<213> ORGANISM: Hordeum vulgare
<220> FEATURE:
<221> NAME/KEY: PEPTIDE
<222> LOCATION: (0)...(0)
<223> OTHER INFORMATION: Accession No. AAG37354, Barley powdery mildew
      resistance protein

<400> SEQUENCE: 18

```
Met Asp Ile Val Thr Gly Ala Ile Ser Asn Leu Ile Pro Lys Leu Gly
1               5                   10                  15

Glu Leu Leu Thr Glu Glu Phe Lys Leu His Lys Gly Val Lys Lys Asn
            20                  25                  30

Ile Glu Asp Leu Gly Lys Glu Leu Glu Ser Met Asn Ala Ala Leu Ile
        35                  40                  45

Lys Ile Gly Glu Val Pro Arg Glu Gln Leu Asp Ser Gln Asp Lys Leu
    50                  55                  60

Trp Ala Asp Glu Val Arg Glu Leu Ser Tyr Val Ile Glu Asp Val Val
65                  70                  75                  80

Asp Lys Phe Leu Val Gln Val Asp Gly Ile Gln Phe Asp Asp Asn Asn
                85                  90                  95

Asn Lys Phe Lys Gly Phe Met Lys Arg Thr Thr Glu Leu Leu Lys Lys
                100                 105                 110
```

```
Val Lys His Lys His Gly Ile Ala His Ala Ile Lys Asp Ile Gln Glu
        115                 120                 125

Gln Leu Gln Lys Val Ala Asp Arg Arg Asp Arg Asn Lys Val Phe Val
130                 135                 140

Pro His Pro Thr Arg Thr Ile Ala Ile Asp Pro Cys Leu Arg Ala Leu
145                 150                 155                 160

Tyr Ala Glu Ala Thr Glu Leu Val Gly Ile Tyr Gly Lys Arg Asp Gln
                165                 170                 175

Asp Leu Met Arg Leu Leu Ser Met Glu Gly Asp Ala Ser Asn Lys
                180                 185                 190

Arg Leu Lys Lys Val Ser Ile Val Gly Phe Gly Gly Leu Gly Lys Thr
                195                 200                 205

Thr Leu Ala Arg Ala Val Tyr Glu Lys Ile Lys Gly Asp Phe Asp Cys
210                 215                 220

Arg Ala Phe Val Pro Val Gly Gln Asn Pro His Met Lys Lys Val Leu
225                 230                 235                 240

Arg Asp Ile Leu Ile Asp Leu Gly Asn Pro His Ser Asp Leu Ala Met
                245                 250                 255

Leu Asp Ala Asn Gln Leu Ile Lys Lys Leu Arg Glu Phe Leu Glu Asn
                260                 265                 270

Lys Arg Tyr Leu Val Ile Ile Asp Asp Ile Trp Asp Glu Lys Leu Trp
        275                 280                 285

Glu Gly Ile Asn Phe Ala Phe Ser Asn Arg Asn Asn Leu Gly Ser Arg
        290                 295                 300

Leu Ile Thr Thr Thr Arg Ile Val Ser Val Ser Asn Ser Cys Cys Ser
305                 310                 315                 320

Ser His Gly Asp Ser Val Tyr Gln Met Glu Pro Leu Ser Val Asp Asp
                325                 330                 335

Ser Arg Ile Leu Phe Trp Lys Arg Ile Phe Pro Asp Glu Asn Gly Cys
                340                 345                 350

Leu Asn Glu Phe Glu Gln Val Ser Arg Asp Ile Leu Lys Lys Cys Gly
                355                 360                 365

Gly Val Pro Leu Ala Ile Ile Thr Ile Ala Ser Ala Leu Ala Gly Asp
                370                 375                 380

Gln Lys Met Lys Pro Lys Cys Glu Trp Asp Ile Leu Leu Gln Ser Leu
385                 390                 395                 400

Gly Ser Gly Leu Thr Glu Asp Asn Ser Leu Glu Glu Met Arg Arg Ile
                405                 410                 415

Leu Ser Phe Ser Tyr Ser Asn Leu Pro Ser His Leu Lys Thr Cys Leu
                420                 425                 430

Leu Tyr Leu Cys Ile Tyr Pro Glu Asp Ser Lys Ile His Arg Asp Glu
                435                 440                 445

Leu Ile Trp Lys Trp Val Ala Glu Gly Phe Val His His Glu Asn Gln
        450                 455                 460

Gly Asn Ser Leu Tyr Leu Leu Gly Leu Asn Tyr Phe Asn Gln Leu Ile
465                 470                 475                 480

Asn Arg Ser Met Ile Gln Pro Ile Tyr Gly Phe Asn Asp Glu Val Tyr
                485                 490                 495

Val Cys Arg Val His Asp Met Val Leu Asp Leu Ile Cys Asn Leu Ser
                500                 505                 510

Arg Glu Ala Lys Phe Val Asn Leu Leu Asp Gly Ser Gly Asn Ser Met
                515                 520                 525
```

```
Ser Ser Gln Gly Asn Cys Arg Arg Leu Ser Leu Gln Lys Arg Asn Glu
    530                 535                 540

Asp His Gln Ala Lys Pro Ile Thr Asp Ile Lys Ser Met Ser Arg Val
545                 550                 555                 560

Arg Ser Ile Thr Ile Phe Pro Pro Ala Ile Glu Val Met Pro Ser Leu
                565                 570                 575

Ser Arg Phe Asp Val Leu Arg Val Leu Asp Leu Ser Arg Cys Asn Leu
            580                 585                 590

Gly Glu Asn Ser Ser Leu Gln Leu Asn Leu Lys Asp Val Gly His Leu
        595                 600                 605

Thr His Leu Arg Tyr Leu Gly Leu Glu Gly Thr Asn Ile Ser Lys Leu
    610                 615                 620

Pro Ala Glu Ile Gly Lys Leu Gln Phe Leu Glu Val Leu Asp Leu Gly
625                 630                 635                 640

Asn Asn His Asn Leu Lys Glu Leu Pro Ser Thr Val Cys Asn Phe Arg
                645                 650                 655

Arg Leu Ile Tyr Leu Asn Leu Phe Gly Cys Pro Val Val Pro Pro Val
            660                 665                 670

Gly Val Leu Gln Asn Leu Thr Ser Ile Glu Val Leu Arg Gly Ile Leu
        675                 680                 685

Val Ser Val Asn Ile Ile Ala Gln Glu Leu Gly Asn Leu Glu Arg Leu
    690                 695                 700

Arg Val Leu Asp Ile Cys Phe Arg Asp Gly Ser Leu Asp Leu Tyr Lys
705                 710                 715                 720

Asp Phe Val Lys Ser Leu Cys Asn Leu His His Ile Glu Ser Leu Arg
                725                 730                 735

Ile Glu Cys Asn Ser Arg Glu Thr Ser Ser Phe Glu Leu Val Asp Leu
            740                 745                 750

Leu Gly Glu Arg Trp Val Pro Pro Val His Phe Arg Glu Phe Val Ser
        755                 760                 765

Ser Met Pro Ser Gln Leu Ser Ala Leu Arg Gly Trp Ile Lys Arg Asp
    770                 775                 780

Pro Ser His Leu Ser Asn Leu Ser Glu Leu Ile Leu Ser Ser Val Lys
785                 790                 795                 800

Asp Val Gln Gln Asp Asp Val Glu Ile Ile Gly Gly Leu Leu Cys Leu
                805                 810                 815

Arg Arg Leu Phe Ile Ile Thr Ser Thr Asp Gln Thr Gln Arg Leu Leu
            820                 825                 830

Val Ile Arg Ala Asp Gly Phe Arg Cys Thr Val Asp Phe Arg Leu Asp
    835                 840                 845

Cys Gly Ser Ala Thr Gln Ile Leu Phe Glu Pro Gly Ala Leu Pro Arg
850                 855                 860

Ala Val Arg Val Trp Phe Ser Leu Gly Val Arg Val Thr Lys Glu Asp
865                 870                 875                 880

Gly Asn Arg Gly Phe Asp Leu Gly Leu Gln Asn Leu Phe Ser Leu
                885                 890                 895

Arg Glu Phe Val Ser Val Tyr Met Tyr Cys Gly Gly Ala Arg Val Gly
                900                 905                 910

Glu Ala Lys Glu Ala Glu Ala Val Arg Arg Ala Leu Glu Ala His
        915                 920                 925

Pro Ser His Pro Arg Ile Tyr Ile Gln Met Arg Pro His Ile Ala Lys
930                 935                 940

Gly Ala His Asp Asp Asp Leu Cys Glu Asp Glu Glu Asn
```

<210> SEQ ID NO 19
<211> LENGTH: 17
<212> TYPE: DNA
<213> ORGANISM: Artificial Sequence
<220> FEATURE:
<223> OTHER INFORMATION: MPSS Signature Sequence Tag

<400> SEQUENCE: 19
gatctcataa ctaggat                                                    17

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide Primer KEB131

<400> SEQUENCE: 20
tgatccttga ttgtccatgg                                                 20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide Primer KEB138

<400> SEQUENCE: 21
ccgttgcttg catatatgct                                                 20

<210> SEQ ID NO 22
<211> LENGTH: 1684
<212> TYPE: DNA
<213> ORGANISM: Zea mays
<220> FEATURE:
<221> NAME/KEY: promoter
<222> LOCATION: (0)...(0)
<223> OTHER INFORMATION: Rcg1 Promoter Region

<400> SEQUENCE: 22
actgtcgggg accataatta ggggtaccct caagacgcct aattctcagc tggtaacccc      60
catcagcata aagctgcaaa ggcctgatgg gcacgattaa gtcagggatc agtccacacg     120
agtgactcga tcgcgcttca cccgagccta gcctcggccg aaggcagccg acctcgagag     180
acttccgtct cgcccgaggc cccccttttt atggcggaca catcaccggc ttgcccaagg     240
ccttggcttc gctcagaagc aaccttgact aaatcaccac accgactgac caaattgcag     300
gggcatttaa cgcaaaggtg gcctgacacc tctatcctga cacgcgcccc cggcagagcc     360
gaggtgaccg ccgtcactcc accgctccac tggccagtct gacagaagga cagcgccgcc     420
tgcgccactc cgactgcagt gccactcgac agagtgagtc tgacaggcaa ctaggccttg     480
ccgaaggcgc cacggcgaac tccgctccgc ccgaccccag ggctcggact cgggctaaga     540
cccggaagac ggcgaactcc gctccgcccg accccagggc tcggactcgg ctaagaccc     600 ggaagacggc gaactccgct ccgcccgacc ccagggctcg gactcgggct aagacccgga     660
agacggcgaa ctccgctccg cccgacccca gggctcggac tcgggctaag acccggaaga     720
cggcgaactc cgctccgccc gaccccaggg ctcggactcg gctaagacc cggaagacgg     780 cgaactccgc tccgcccgac cccagggctc agactcaggc taagacccgg aagacgacga     840
aactccgcct cgcccgaccc cagggctcgg actccgcct ggcctcggcc ggacgacttc      900

```
cgcctcgccc gacccctgg ctcgggctcg gccacagcaa ctgaaggcaa gactcaacct    960
cggcttcgga ggaaacccca cgtcgccctg cctagagcac agaccgccac gtcaacagga   1020
aacgtcatca tcaccctacc ccgaatcgac tcgggtcacg gagaacaaga ccggcgtctc   1080
gtccggccag ctccgccaga gggcaatga tggcgctcca cgagctctat gacgacggcg    1140
gcccccagct ctcttacggc agcaggacaa cgtcagcagg gactcgaccg ctccaacagc   1200
tgtccctcca tcaggctccg ccgcaccacc gatagccacg acatcacgcc agcaggatgc   1260
ccagatctct ccggctgcca catcggcatg tacctagggc actagctctc cctccgctag   1320
acacgtagca ctctgctaca tccccattgt acacctgggt cctctcctta cgactataaa   1380
aggaaggacc agggtcttct cagagaaggt tggccgcgcg ggaccgagga cgggacaggc   1440
gctctcttgg ggccgctcgc ttccctcacc cgcgtggacg cttgtaaccc ccctactgca   1500
agcgcacctg acctgggcgc gggacgaaca cgaaggccgc gggacttcca cctctctcac   1560
gctcggctcc ggccgcctcg cctctccccc ctccgcgctc gcccacgcgc tcgacccatc   1620
tgggctgggg cacgcagcac actcactcgt cggcttaggg accccctgtc tcgaaacgcc   1680
gaca                                                                1684

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide Primer Frey8 Forward

<400> SEQUENCE: 23
acatgggtcc aaagatcgac                                                 20

<210> SEQ ID NO 24
<211> LENGTH: 20
<212> TYPE: DNA
<213> ORGANISM: Artificial Sequence
<220> FEATURE:
<223> OTHER INFORMATION: Oligonucleotide Primer Frey8 Reverse

<400> SEQUENCE: 24
catggaagcc ccacaataac                                                 20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide Primer Frey27 Forward

<400> SEQUENCE: 25
gcatgcccca tctggtatag                                                 20

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide Primer Frey27 Reverse

<400> SEQUENCE: 26
agccctattt cctgctcctg                                                 20

<210> SEQ ID NO 27
```

```
<211> LENGTH: 20
<212> TYPE: DNA
<213> ORGANISM: Artificial Sequence
<220> FEATURE:
<223> OTHER INFORMATION: Oligonucleotide Primer Frey33 Forward

<400> SEQUENCE: 27
gcattcacat gttcctcacc                                               20

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide Primer Frey33 Reverse

<400> SEQUENCE: 28
ctgtcgttcg gttttgcttc                                               20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide Primer Frey41 Forward

<400> SEQUENCE: 29
ctgtaaggca cccgatgttt                                               20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide Primer Frey41 Reverse

<400> SEQUENCE: 30
tgtgttcgca tcaaaggtgt                                               20

<210> SEQ ID NO 31
<211> LENGTH: 21
<212> TYPE: DNA
<213> ORGANISM: Artificial Sequence
<220> FEATURE:
<223> OTHER INFORMATION: Oligonucleotide Primer Frey56 Forward

<400> SEQUENCE: 31
tgtccagggt tacagaaaac g                                             21

<210> SEQ ID NO 32
<211> LENGTH: 21
<212> TYPE: DNA
<213> ORGANISM: Artificial Sequence
<220> FEATURE:
<223> OTHER INFORMATION: Oligonucleotide Primer Frey56 Reverse

<400> SEQUENCE: 32
ggtctgggaa tgctaaagag g                                             21

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide Primer Frey95 Forward

<400> SEQUENCE: 33
```

-continued atttcgacgg agggttcttc 20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide Primer Frey95 Reverse

<400> SEQUENCE: 34
gcagcaggag gagctcatag 20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide Primer Frey110 Forward

<400> SEQUENCE: 35
atggaggctg ccctgctgag 20

<210> SEQ ID NO 36
<211> LENGTH: 24
<212> TYPE: DNA
<213> ORGANISM: Artificial Sequence
<220> FEATURE:
<223> OTHER INFORMATION: Oligonucleotide Primer Frey110 Reverse

<400> SEQUENCE: 36
cgtatacctc tctggcaagg acgg 24

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide Primer Frey111 Forward

<400> SEQUENCE: 37
ttcctgttcg tctgtatctg atccg 25

<210> SEQ ID NO 38
<211> LENGTH: 25
<212> TYPE: DNA
<213> ORGANISM: Artificial Sequence
<220> FEATURE:
<223> OTHER INFORMATION: Oligonucleotide Primer Frey111 Reverse

<400> SEQUENCE: 38
tttgattccg gtcgagtata acctg 25

<210> SEQ ID NO 39
<211> LENGTH: 25
<212> TYPE: DNA
<213> ORGANISM: Artificial Sequence
<220> FEATURE:
<223> OTHER INFORMATION: Oligonucleotide Primer Frey112 Forward

<400> SEQUENCE: 39
gaaactgcct tcccagaaaa caatg 25

<210> SEQ ID NO 40
<211> LENGTH: 24
<212> TYPE: DNA

```
<213> ORGANISM: Artificial Sequence
<220> FEATURE:
<223> OTHER INFORMATION: Oligonucleotide Primer Frey112 Reverse

<400> SEQUENCE: 40
caagatcggt gaagttggtg cttc                                            24

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide Primer Frey113F Forward

<400> SEQUENCE: 41
atcacagatg ggtctcaagg attgc                                           25

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide Primer Alex1R Reverse

<400> SEQUENCE: 42
ttccaagcaa ttcacagctc                                                 20

<210> SEQ ID NO 43
<211> LENGTH: 24
<212> TYPE: DNA
<213> ORGANISM: Artificial Sequence
<220> FEATURE:
<223> OTHER INFORMATION: Oligonucleotide Primer umc1612 Forward

<400> SEQUENCE: 43
aggtccaggt tacagagcaa gaga                                            24

<210> SEQ ID NO 44
<211> LENGTH: 24
<212> TYPE: DNA
<213> ORGANISM: Artificial Sequence
<220> FEATURE:
<223> OTHER INFORMATION: Oligonucleotide Primer umc1612 Reverse

<400> SEQUENCE: 44
gctagtaggt gcatggtggt ttct                                            24

<210> SEQ ID NO 45
<211> LENGTH: 24
<212> TYPE: DNA
<213> ORGANISM: Artificial Sequence
<220> FEATURE:
<223> OTHER INFORMATION: Oligonucleotide Primer umc2041 Forward

<400> SEQUENCE: 45
ctacacaagc atagaggcct ggag                                            24

<210> SEQ ID NO 46
<211> LENGTH: 23
<212> TYPE: DNA
<213> ORGANISM: Artificial Sequence
<220> FEATURE:
<223> OTHER INFORMATION: Oligonucleotide Primer umc2041 Reverse

<400> SEQUENCE: 46
cagtacgaga cgatggagga cat                                             23
```

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide Primer cdo127 Forward

<400> SEQUENCE: 47
tgctgttgtt actcgggttg                                               20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide Primer cdo127 Reverse

<400> SEQUENCE: 48
ctctgcctca gcacaaattc                                               20

<210> SEQ ID NO 49
<211> LENGTH: 26
<212> TYPE: DNA
<213> ORGANISM: Artificial Sequence
<220> FEATURE:
<223> OTHER INFORMATION: Oligonucleotide Primer phi093 Forward

<400> SEQUENCE: 49
agtgcgtcag cttcatcgcc tacaag                                        26

<210> SEQ ID NO 50
<211> LENGTH: 30
<212> TYPE: DNA
<213> ORGANISM: Artificial Sequence
<220> FEATURE:
<223> OTHER INFORMATION: Oligonucleotide Primer phi093 Reverse

<400> SEQUENCE: 50
aggccatgca tgcttgcaac aatggataca                                    30

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide Primer cdo365 Forward

<400> SEQUENCE: 51
cttccagagg caaagcgtag                                               20

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide Primer cdo365 Reverse

<400> SEQUENCE: 52
tgtcacccat gatccagttg                                               20

<210> SEQ ID NO 53
<211> LENGTH: 20
<212> TYPE: DNA
<213> ORGANISM: Artificial Sequence
<220> FEATURE:

```
<223> OTHER INFORMATION: Oligonucleotide Primer csu166 Forward

<400> SEQUENCE: 53
tattgtgcac gtcaccttgg                                                20

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide Primer csu166 Reverse

<400> SEQUENCE: 54
gggcagactt actgctggag                                                20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide Primer umc2285 Forward

<400> SEQUENCE: 55
atctgcctcc ttttccttgg                                                20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide Primer umc2285 Reverse

<400> SEQUENCE: 56
aagtagctgg gcttggaggg                                                20

<210> SEQ ID NO 57
<211> LENGTH: 20
<212> TYPE: DNA
<213> ORGANISM: Artificial Sequence
<220> FEATURE:
<223> OTHER INFORMATION: Oligonucleotide Primer MZA11455 Forward

<400> SEQUENCE: 57
acgaagcaat ttcaccttcc                                                20

<210> SEQ ID NO 58
<211> LENGTH: 23
<212> TYPE: DNA
<213> ORGANISM: Artificial Sequence
<220> FEATURE:
<223> OTHER INFORMATION: Oligonucleotide Primer MZA11455 Reverse

<400> SEQUENCE: 58
tgtggaacta accctcagca tag                                            23

<210> SEQ ID NO 59
<211> LENGTH: 19
<212> TYPE: DNA
<213> ORGANISM: Artificial Sequence
<220> FEATURE:
<223> OTHER INFORMATION: Oligonucleotide Primer MZA6064 Forward

<400> SEQUENCE: 59
cgagaaccgg agaagaagg                                                 19
```

```
<210> SEQ ID NO 60
<211> LENGTH: 20
<212> TYPE: DNA
<213> ORGANISM: Artificial Sequence
<220> FEATURE:
<223> OTHER INFORMATION: Oligonucleotide Primer MZA6064 Reverse

<400> SEQUENCE: 60
ttgggctgct gtattttgtg                                              20

<210> SEQ ID NO 61
<211> LENGTH: 19
<212> TYPE: DNA
<213> ORGANISM: Artificial Sequence
<220> FEATURE:
<223> OTHER INFORMATION: Oligonucleotide Primer MZA15842 Forward

<400> SEQUENCE: 61
gacgcagctg tgaagttgg                                               19

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide Primer MZA15842 Reverse

<400> SEQUENCE: 62
caccggaata ccttgaccac                                              20

<210> SEQ ID NO 63
<211> LENGTH: 24
<212> TYPE: DNA
<213> ORGANISM: Artificial Sequence
<220> FEATURE:
<223> OTHER INFORMATION: Oligonucleotide Primer umc1086 Forward

<400> SEQUENCE: 63
catgaaagtt ttcctgtgca gatt                                         24

<210> SEQ ID NO 64
<211> LENGTH: 25
<212> TYPE: DNA
<213> ORGANISM: Artificial Sequence
<220> FEATURE:
<223> OTHER INFORMATION: Oligonucleotide Primer umc1086 Reverse

<400> SEQUENCE: 64
gggcaacttt agaggtcgat ttatt                                        25

<210> SEQ ID NO 65
<211> LENGTH: 21
<212> TYPE: DNA
<213> ORGANISM: Artificial Sequence
<220> FEATURE:
<223> OTHER INFORMATION: Oligonucleotide Primer umc1466-FA Forward

<400> SEQUENCE: 65
gatccactag ggtttcgggg t                                            21

<210> SEQ ID NO 66
<211> LENGTH: 24
<212> TYPE: DNA
<213> ORGANISM: Artificial Sequence
<220> FEATURE:
<223> OTHER INFORMATION: Oligonucleotide Primer umc1466-FA Reverse
```

```
<400> SEQUENCE: 66
cgaatagtgg tctcgcgtct atct                                          24

<210> SEQ ID NO 67
<211> LENGTH: 21
<212> TYPE: DNA
<213> ORGANISM: Artificial Sequence
<220> FEATURE:
<223> OTHER INFORMATION: Oligonucleotide Primer umc1418-PA Forward

<400> SEQUENCE: 67
gagccaagag ccagagcaaa g                                             21

<210> SEQ ID NO 68
<211> LENGTH: 24
<212> TYPE: DNA
<213> ORGANISM: Artificial Sequence
<220> FEATURE:
<223> OTHER INFORMATION: Oligonucleotide Primer umc1418-PA Reverse

<400> SEQUENCE: 68
tcacacacac actacactcg caat                                          24

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide Primer BNLG2162-DA Forward

<400> SEQUENCE: 69
caccggcatt cgatatcttt                                               20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotide Primer BNLG2162-DA Reverse

<400> SEQUENCE: 70
gtctgctgct agtggtggtg                                               20

<210> SEQ ID NO 71
<211> LENGTH: 20
<212> TYPE: DNA
<213> ORGANISM: Artificial Sequence
<220> FEATURE:
<223> OTHER INFORMATION: Oligonucleotide Primer csu166-IA Forward

<400> SEQUENCE: 71
aaatatcggc tttggtcacg                                               20

<210> SEQ ID NO 72
<211> LENGTH: 20
<212> TYPE: DNA
<213> ORGANISM: Artificial Sequence
<220> FEATURE:
<223> OTHER INFORMATION: Oligonucleotide Primer csu166-IA

<400> SEQUENCE: 72
tcgtccttcc tcaattcgac                                               20

<210> SEQ ID NO 73
<211> LENGTH: 24
```

-continued

```
<212> TYPE: DNA
<213> ORGANISM: Artificial Sequence
<220> FEATURE:
<223> OTHER INFORMATION: Oligonucleotide Primer umc1051 Forward

<400> SEQUENCE: 73
aatgatcgaa atgccattat ttgt                                          24

<210> SEQ ID NO 74
<211> LENGTH: 24
<212> TYPE: DNA
<213> ORGANISM: Artificial Sequence
<220> FEATURE:
<223> OTHER INFORMATION: Oligonucleotide Primer umc1051 Reverse

<400> SEQUENCE: 74
ctgatctgac taaggccatc aaac                                          24

<210> SEQ ID NO 75
<211> LENGTH: 24
<212> TYPE: DNA
<213> ORGANISM: Artificial Sequence
<220> FEATURE:
<223> OTHER INFORMATION: Oligonucleotide Primer umc2187 Forward

<400> SEQUENCE: 75
acccaacaag tcttaatcgg gttt                                          24

<210> SEQ ID NO 76
<211> LENGTH: 24
<212> TYPE: DNA
<213> ORGANISM: Artificial Sequence
<220> FEATURE:
<223> OTHER INFORMATION: Oligonucleotide Primer umc2187 Reverse

<400> SEQUENCE: 76
gtccacccta cctctcaaca aaca                                          24

<210> SEQ ID NO 77
<211> LENGTH: 23
<212> TYPE: DNA
<213> ORGANISM: Artificial Sequence
<220> FEATURE:
<223> OTHER INFORMATION: Oligonucleotide Primer umc1371 Forward

<400> SEQUENCE: 77
catgtgaatg gaagtgtccc ttt                                           23

<210> SEQ ID NO 78
<211> LENGTH: 24
<212> TYPE: DNA
<213> ORGANISM: Artificial Sequence
<220> FEATURE:
<223> OTHER INFORMATION: Oligonucleotide Primer umc1371 Reverse

<400> SEQUENCE: 78 gcatccttttt cgtttcaaat atgc                                         24

<210> SEQ ID NO 79
<211> LENGTH: 24
<212> TYPE: DNA
<213> ORGANISM: Artificial Sequence
<220> FEATURE:
<223> OTHER INFORMATION: Oligonucleotide Primer umc1856 Forward

<400> SEQUENCE: 79
```
agatctgttt tgctttgctc tgct                                        24

<210> SEQ ID NO 80
<211> LENGTH: 24
<212> TYPE: DNA
<213> ORGANISM: Artificial Sequence
<220> FEATURE:
<223> OTHER INFORMATION: Oligonucleotide Primer umc1856 Reverse

<400> SEQUENCE: 80
catgccttta ttctcacaca aacg                                        24

<210> SEQ ID NO 81
<211> LENGTH: 21
<212> TYPE: DNA
<213> ORGANISM: Artificial Sequence
<220> FEATURE:
<223> OTHER INFORMATION: Oligonucleotide Primer MZA1215 External Nested
      Forward Primer

<400> SEQUENCE: 81
agcccaattc tgtagatcca a                                           21

<210> SEQ ID NO 82
<211> LENGTH: 19
<212> TYPE: DNA
<213> ORGANISM: Artificial Sequence
<220> FEATURE:
<223> OTHER INFORMATION: Oligonucleotide Primer MZA1215 External Nested
      Reverse Primer

<400> SEQUENCE: 82
tgcatgcacc ggatccttc                                              19

<210> SEQ ID NO 83
<211> LENGTH: 20
<212> TYPE: DNA
<213> ORGANISM: Artificial Sequence
<220> FEATURE:
<223> OTHER INFORMATION: Oligonucleotide Primer MZA1215 Internal Nested
      Forward Primer

<400> SEQUENCE: 83
agcagcagac gatgcaaaga                                             20

<210> SEQ ID NO 84
<211> LENGTH: 19
<212> TYPE: DNA
<213> ORGANISM: Artificial Sequence
<220> FEATURE:
<223> OTHER INFORMATION: Oligonucleotide Primer MZA1215 Internal Nested
      Reverse Primer

<400> SEQUENCE: 84
aggctggcgg tggacttga                                              19

<210> SEQ ID NO 85
<211> LENGTH: 20
<212> TYPE: DNA
<213> ORGANISM: Artificial Sequence
<220> FEATURE:
<223> OTHER INFORMATION: Oligonucleotide Primer MZA1216 External Nested
      Forward Primer

<400> SEQUENCE: 85
ccggcctacg gcaacaagaa                                             20

```
<210> SEQ ID NO 86
<211> LENGTH: 19
<212> TYPE: DNA
<213> ORGANISM: Artificial Sequence
<220> FEATURE:
<223> OTHER INFORMATION: Oligonucleotide Primer MZA1216 External Nested
      Reverse Primer

<400> SEQUENCE: 86
agggtacggt gacccgaag                                                    19

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide Primer MZA1216 Internal Nested
      Forward Primer

<400> SEQUENCE: 87
ttcgagacgc tgtcgtacct                                                   20

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide Primer MZA1216 Internal Nested
      Reverse Primer

<400> SEQUENCE: 88
acgacgcatg gcactagcta                                                   20

<210> SEQ ID NO 89
<211> LENGTH: 18
<212> TYPE: DNA
<213> ORGANISM: Artificial Sequence
<220> FEATURE:
<223> OTHER INFORMATION: Oligonucleotide Primer MZA3434 External Nested
      Forward Primer

<400> SEQUENCE: 89
tgtaccgcga gaactcca                                                     18

<210> SEQ ID NO 90
<211> LENGTH: 21
<212> TYPE: DNA
<213> ORGANISM: Artificial Sequence
<220> FEATURE:
<223> OTHER INFORMATION: Oligonucleotide Primer MZA3434 External Nested
      Reverse Primer

<400> SEQUENCE: 90
ttgcattcac atgttcctca c                                                 21

<210> SEQ ID NO 91
<211> LENGTH: 18
<212> TYPE: DNA
<213> ORGANISM: Artificial Sequence
<220> FEATURE:
<223> OTHER INFORMATION: Oligonucleotide Primer MZA3434 Internal Nested
      Forward Primer

<400> SEQUENCE: 91
ctactacgac ggccgcta                                                     18
```

<210> SEQ ID NO 92
<211> LENGTH: 21
<212> TYPE: DNA
<213> ORGANISM: Artificial Sequence
<220> FEATURE:
<223> OTHER INFORMATION: Oligonucleotide Primer MZA3434 Internal Nested
      Reverse Primer

<400> SEQUENCE: 92
ttgcagtagt tttgtagcag g                                          21

<210> SEQ ID NO 93
<211> LENGTH: 22
<212> TYPE: DNA
<213> ORGANISM: Artificial Sequence
<220> FEATURE:
<223> OTHER INFORMATION: Oligonucleotide Primer MZA2591 External Nested
      Forward Primer

<400> SEQUENCE: 93
agtaaataac agcattgacc tc                                         22

<210> SEQ ID NO 94
<211> LENGTH: 18
<212> TYPE: DNA
<213> ORGANISM: Artificial Sequence
<220> FEATURE:
<223> OTHER INFORMATION: Oligonucleotide Primer MZA2591 External Nested
      Reverse Primer

<400> SEQUENCE: 94
tccaacggcg gtcactcc                                              18

<210> SEQ ID NO 95
<211> LENGTH: 21
<212> TYPE: DNA
<213> ORGANISM: Artificial Sequence
<220> FEATURE:
<223> OTHER INFORMATION: Oligonucleotide Primer MZA2591 Internal Nested
      Forward Primer

<400> SEQUENCE: 95
ctatataaca gggccctgga a                                          21

<210> SEQ ID NO 96
<211> LENGTH: 20
<212> TYPE: DNA
<213> ORGANISM: Artificial Sequence
<220> FEATURE:
<223> OTHER INFORMATION: Oligonucleotide Primer MZA2591 Internal Nested
      Reverse Primer

<400> SEQUENCE: 96
cacaaagccc acaagctaag                                            20

<210> SEQ ID NO 97
<211> LENGTH: 21
<212> TYPE: DNA
<213> ORGANISM: Artificial Sequence
<220> FEATURE:
<223> OTHER INFORMATION: Oligonucleotide Primer MZA11123 External Nested
      Forward Primer

<400> SEQUENCE: 97
accacaatct gaagcaagta g                                          21

<210> SEQ ID NO 98

```
<211> LENGTH: 20
<212> TYPE: DNA
<213> ORGANISM: Artificial Sequence
<220> FEATURE:
<223> OTHER INFORMATION: Oligonucleotide Primer MZA11123 External Nested
      Reverse Primer

<400> SEQUENCE: 98
cacagaaaca tctggtgctg                                                      20

<210> SEQ ID NO 99
<211> LENGTH: 21
<212> TYPE: DNA
<213> ORGANISM: Artificial Sequence
<220> FEATURE:
<223> OTHER INFORMATION: Oligonucleotide Primer MZA11123 Internal Nested
      Forward Primer

<400> SEQUENCE: 99
aaagaccaag aaatgcagtc c                                                    21

<210> SEQ ID NO 100
<211> LENGTH: 21
<212> TYPE: DNA
<213> ORGANISM: Artificial Sequence
<220> FEATURE:
<223> OTHER INFORMATION: Oligonucleotide Primer MZA11123 Internal Nested
      Reverse Primer

<400> SEQUENCE: 100
agacatcacg taacagtttc c                                                    21

<210> SEQ ID NO 101
<211> LENGTH: 20
<212> TYPE: DNA
<213> ORGANISM: Artificial Sequence
<220> FEATURE:
<223> OTHER INFORMATION: Oligonucleotide Primer MZA15842 External Nested
      Forward Primer

<400> SEQUENCE: 101
ctcgattggc atacgcgata                                                      20

<210> SEQ ID NO 102
<211> LENGTH: 20
<212> TYPE: DNA
<213> ORGANISM: Artificial Sequence
<220> FEATURE:
<223> OTHER INFORMATION: Oligonucleotide Primer MZA15842 External Nested
      Reverse Primer

<400> SEQUENCE: 102
ttccttctcc acgcagttca                                                      20

<210> SEQ ID NO 103
<211> LENGTH: 22
<212> TYPE: DNA
<213> ORGANISM: Artificial Sequence
<220> FEATURE:
<223> OTHER INFORMATION: Oligonucleotide Primer MZA15842 Internal Nested
      Forward Primer

<400> SEQUENCE: 103
agaaggtatt tgccatggct ta                                                   22

<210> SEQ ID NO 104
<211> LENGTH: 22
```

```
<212> TYPE: DNA
<213> ORGANISM: Artificial Sequence
<220> FEATURE:
<223> OTHER INFORMATION: Oligonucleotide Primer MZA15842 Internal Nested
      Reverse Primer

<400> SEQUENCE: 104
gtttcacttg ctgaaggcag tc                                               22

<210> SEQ ID NO 105
<211> LENGTH: 21
<212> TYPE: DNA
<213> ORGANISM: Artificial Sequence
<220> FEATURE:
<223> OTHER INFORMATION: Oligonucleotide Primer MZA11455 External Nested
      Forward Primer

<400> SEQUENCE: 105
gaccgatgaa ggcaattgtg a                                                21

<210> SEQ ID NO 106
<211> LENGTH: 22
<212> TYPE: DNA
<213> ORGANISM: Artificial Sequence
<220> FEATURE:
<223> OTHER INFORMATION: Oligonucleotide Primer MZA11455 External Nested
      Reverse Primer

<400> SEQUENCE: 106
accaaatagt cctagataat gg                                               22

<210> SEQ ID NO 107
<211> LENGTH: 22
<212> TYPE: DNA
<213> ORGANISM: Artificial Sequence
<220> FEATURE:
<223> OTHER INFORMATION: Oligonucleotide Primer MZA11455 Internal Nested
      Forward Primer

<400> SEQUENCE: 107
ttcaaccttc tgactgacac at                                               22

<210> SEQ ID NO 108
<211> LENGTH: 22
<212> TYPE: DNA
<213> ORGANISM: Artificial Sequence
<220> FEATURE:
<223> OTHER INFORMATION: Oligonucleotide Primer MZA11455 Internal Nested
      Reverse Primer

<400> SEQUENCE: 108
taaacatagt cataaaaatt ac                                               22

<210> SEQ ID NO 109
<211> LENGTH: 22
<212> TYPE: DNA
<213> ORGANISM: Artificial Sequence
<220> FEATURE:
<223> OTHER INFORMATION: Oligonucleotide Primer MZA6064 External Nested
      Forward Primer

<400> SEQUENCE: 109
tcgaatgtat tttttaatgc gg                                               22

<210> SEQ ID NO 110
<211> LENGTH: 20
<212> TYPE: DNA
```

```
<213> ORGANISM: Artificial Sequence
<220> FEATURE:
<223> OTHER INFORMATION: Oligonucleotide Primer MZA6064 External Nested
      Reverse Primer

<400> SEQUENCE: 110
atccacaatg gcacttgggt                                                   20

<210> SEQ ID NO 111
<211> LENGTH: 22
<212> TYPE: DNA
<213> ORGANISM: Artificial Sequence
<220> FEATURE:
<223> OTHER INFORMATION: Oligonucleotide Primer MZA6064 Internal Nested
      Forward Primer

<400> SEQUENCE: 111
cagctatttt tgtcttcttc ct                                                22

<210> SEQ ID NO 112
<211> LENGTH: 20
<212> TYPE: DNA
<213> ORGANISM: Artificial Sequence
<220> FEATURE:
<223> OTHER INFORMATION: Oligonucleotide Primer MZA6064 Internal Nested
      Reverse Primer

<400> SEQUENCE: 112
ggtcagattc caattcggac                                                   20

<210> SEQ ID NO 113
<211> LENGTH: 20
<212> TYPE: DNA
<213> ORGANISM: Artificial Sequence
<220> FEATURE:
<223> OTHER INFORMATION: Oligonucleotide Primer MZA11394 External Nested
      Forward Primer

<400> SEQUENCE: 113
tcgtcctaac agcctgtgtt                                                   20

<210> SEQ ID NO 114
<211> LENGTH: 20
<212> TYPE: DNA
<213> ORGANISM: Artificial Sequence
<220> FEATURE:
<223> OTHER INFORMATION: Oligonucleotide Primer MZA11394 External Nested
      Reverse Primer

<400> SEQUENCE: 114
gtccggatca aatggatcgt                                                   20

<210> SEQ ID NO 115
<211> LENGTH: 22
<212> TYPE: DNA
<213> ORGANISM: Artificial Sequence
<220> FEATURE:
<223> OTHER INFORMATION: Oligonucleotide Primer MZA11394 Internal Nested
      Forward Primer

<400> SEQUENCE: 115
aacagcctgt gttgaataag gt                                                22

<210> SEQ ID NO 116
<211> LENGTH: 19
<212> TYPE: DNA
<213> ORGANISM: Artificial Sequence
```

-continued

```
<220> FEATURE:
<223> OTHER INFORMATION: Oligonucleotide Primer MZA11394 Internal Nested
      Reverse Primer

<400> SEQUENCE: 116
cgtgttccgt cgagggagt                                                    19

<210> SEQ ID NO 117
<211> LENGTH: 22
<212> TYPE: DNA
<213> ORGANISM: Artificial Sequence
<220> FEATURE:
<223> OTHER INFORMATION: Oligonucleotide Primer MZA8761 External Nested
      Forward Primer

<400> SEQUENCE: 117
ttctttgatt ctactcttga gc                                                22

<210> SEQ ID NO 118
<211> LENGTH: 20
<212> TYPE: DNA
<213> ORGANISM: Artificial Sequence
<220> FEATURE:
<223> OTHER INFORMATION: Oligonucleotide Primer MZA8761 External Nested
      Reverse Primer

<400> SEQUENCE: 118
cttcatggac gcctgagatt                                                   20

<210> SEQ ID NO 119
<211> LENGTH: 22
<212> TYPE: DNA
<213> ORGANISM: Artificial Sequence
<220> FEATURE:
<223> OTHER INFORMATION: Oligonucleotide Primer MZA8761 Internal Nested
      Forward Primer

<400> SEQUENCE: 119
tagagctttc tgaactgata gc                                                22

<210> SEQ ID NO 120
<211> LENGTH: 21
<212> TYPE: DNA
<213> ORGANISM: Artificial Sequence
<220> FEATURE:
<223> OTHER INFORMATION: Oligonucleotide Primer MZA8761 Internal Nested
      Reverse Primer

<400> SEQUENCE: 120
ttggcattta gcttctctcc a                                                 21

<210> SEQ ID NO 121
<211> LENGTH: 22
<212> TYPE: DNA
<213> ORGANISM: Artificial Sequence
<220> FEATURE:
<223> OTHER INFORMATION: Oligonucleotide Primer MZA1851 External Nested
      Forward Primer

<400> SEQUENCE: 121
atatattgca ccacttaaag cc                                                22

<210> SEQ ID NO 122
<211> LENGTH: 22
<212> TYPE: DNA
<213> ORGANISM: Artificial Sequence
<220> FEATURE:
```

<223> OTHER INFORMATION: Oligonucleotide Primer MZA1851 External Nested
      Reverse Primer

<400> SEQUENCE: 122
gggtgttatc acttgttcta ta                                          22

<210> SEQ ID NO 123
<211> LENGTH: 20
<212> TYPE: DNA
<213> ORGANISM: Artificial Sequence
<220> FEATURE:
<223> OTHER INFORMATION: Oligonucleotide Primer MZA1851 Internal Nested
      Forward Primer

<400> SEQUENCE: 123
tggagtcctt gaccatttgc                                             20

<210> SEQ ID NO 124
<211> LENGTH: 22
<212> TYPE: DNA
<213> ORGANISM: Artificial Sequence
<220> FEATURE:
<223> OTHER INFORMATION: Oligonucleotide Primer MZA1851 Internal Nested
      Reverse Primer

<400> SEQUENCE: 124
tatatgcact tctagcgagt at                                          22

<210> SEQ ID NO 125
<211> LENGTH: 32
<212> TYPE: DNA
<213> ORGANISM: Artificial Sequence
<220> FEATURE:
<223> OTHER INFORMATION: Degenerate oligonucleotide consensus primer
      designed from the terminal inverted repeats (TIR)
      from the Mutator element sequence

<400> SEQUENCE: 125
agagaagcca acgccawcgc ctcyatttcg tc                               32

<210> SEQ ID NO 126
<211> LENGTH: 18
<212> TYPE: DNA
<213> ORGANISM: Artificial Sequence
<220> FEATURE:
<223> OTHER INFORMATION: Oligonucleotide primer used linked in
      combination with MZA internal primers in order to sequence PCR
      products

<400> SEQUENCE: 126
tgtaaaacga cggccagt                                               18

<210> SEQ ID NO 127
<211> LENGTH: 19
<212> TYPE: DNA
<213> ORGANISM: Artificial Sequence
<220> FEATURE:
<223> OTHER INFORMATION: Oligonucleotide primer used linked in
      combination with MZA internal primers in order to sequence PCR
      products

<400> SEQUENCE: 127
ggaaacagct atgaccatg                                              19

<210> SEQ ID NO 128
<211> LENGTH: 1698
<212> TYPE: DNA

<213> ORGANISM: Artificial Sequence
<220> FEATURE:
<223> OTHER INFORMATION: Rcg1 promoter with 14 bp of cloning
      oligonucleotide sequence added at 5' end

<400> SEQUENCE: 128

| | | | | | |
|---|---|---|---|---|---|
| gaggctcggg | ggctactgtc | ggggaccata | attaggggta | ccctcaagac | gcctaattct | 60 |
| cagctggtaa | cccccatcag | cataaagctg | caaaggcctg | atgggcacga | ttaagtcagg | 120 |
| gatcagtcca | cacgagtgac | tcgatcgcgc | ttcacccgag | cctagcctcg | gccgaaggca | 180 |
| gccgacctcg | agagacttcc | gtctcgcccg | aggcccccct | ttttatggcg | gacacatcac | 240 |
| cggcttgccc | aaggccttgg | cttcgctcag | aagcaacctt | gactaaatca | ccacaccgac | 300 |
| tgaccaaatt | gcaggggcat | ttaacgcaaa | ggtggcctga | cacctctatc | ctgacacgcg | 360 |
| cccccggcag | agccgaggtg | accgccgtca | ctccaccgct | ccactggcca | gtctgacaga | 420 |
| aggacagcgc | cgcctgcgcc | actccgactg | cagtgccact | cgacagagtg | agtctgacag | 480 |
| gcaactaggc | cttgccgaag | gcgccacggc | gaactccgct | ccgcccgacc | cagggctcg  | 540 |
| gactcgggct | aagacccgga | agacggcgaa | ctccgctccg | cccgacccca | gggctcggac | 600 |
| tcgggctaag | acccggaaga | cggcgaactc | cgctccgccc | gacccaggg  | ctcggactcg | 660 |
| ggctaagacc | cggaagacgg | cgaactccgc | tccgcccgac | cccagggctc | ggactcgggc | 720 |
| taagacccgg | aagacggcga | actccgctcc | gccgacccc  | agggctcgga | ctcgggctaa | 780 |
| gacccggaag | acggcgaact | ccgctccgcc | cgaccccagg | gctcagactc | aggctaagac | 840 |
| ccggaagacg | acgaaactcc | gcctcgcccg | accccagggc | tcggactccg | ccctggcctc | 900 |
| ggccggacga | cttccgcctc | gcccgacccc | ctggctcggg | ctcggccaca | gcaactgaag | 960 |
| gcaagactca | acctcggctt | cggaggaaac | cccacgtcgc | cctgcctaga | gcacagaccg | 1020 |
| ccacgtcaac | aggaaacgtc | atcatcaccc | taccccgaat | cgactcgggt | cacggagaac | 1080 |
| aagaccggcg | tctcgtccgg | ccagctccgc | cagaggggca | atgatggcgc | tccacgagct | 1140 |
| ctatgacgac | ggcggccccc | agctctctta | cggcagcagg | acaacgtcag | cagggactcg | 1200 |
| accgctccaa | cagctgtccc | tccatcaggc | tccgccgcac | caccgatagc | cacgacatca | 1260 |
| cgccagcagg | atgcccagat | ctctccggct | gccacatcgg | catgtaccta | gggcactagc | 1320 |
| tctccctccg | ctagacacgt | agcactctgc | tacatcccca | ttgtacacct | gggtcctctc | 1380 |
| cttacgacta | taaaaggaag | gaccagggtc | ttctcagaga | aggttggccg | cgcgggaccg | 1440 |
| aggacgggac | aggcgctctc | ttggggccgc | tcgcttccct | cacccgcgtg | gacgcttgta | 1500 |
| accccctac  | tgcaagcgca | cctgacctgg | gcgcgggacg | aacacgaagg | ccgcgggact | 1560 |
| tccacctctc | tcacgctcgg | ctccggccgc | ctcgcctctc | cccctccgc  | gctcgcccac | 1620 |
| gcgctcgacc | catctgggct | ggggcacgca | gcacactcac | tcgtcggctt | agggaccccc | 1680 |
| tgtctcgaaa | cgccgaca   |            |            |            |            | 1698 |

<210> SEQ ID NO 129
<211> LENGTH: 20
<212> TYPE: DNA
<213> ORGANISM: Artificial Sequence
<220> FEATURE:
<223> OTHER INFORMATION: Oligonucleotide Primer MZA16510 External Nested
      Forward Primer

<400> SEQUENCE: 129
aacaacaagg cgacggtgat                                                  20

```
<210> SEQ ID NO 130
<211> LENGTH: 20
<212> TYPE: DNA
<213> ORGANISM: Artificial Sequence
<220> FEATURE:
<223> OTHER INFORMATION: Oligonucleotide Primer MZA16510 External Nested
      Reverse Primer

<400> SEQUENCE: 130
tcatcttcgt cgtcctcatc                                                   20

<210> SEQ ID NO 131
<211> LENGTH: 18
<212> TYPE: DNA
<213> ORGANISM: Artificial Sequence
<220> FEATURE:
<223> OTHER INFORMATION: Oligonucleotide Primer MZA16510 Internal Nested
      Forward Primer

<400> SEQUENCE: 131
gatcatcctg ccggagtt                                                     18

<210> SEQ ID NO 132
<211> LENGTH: 18
<212> TYPE: DNA
<213> ORGANISM: Artificial Sequence
<220> FEATURE:
<223> OTHER INFORMATION: Oligonucleotide Primer MZA16510 Internal Nested
      Reverse Primer

<400> SEQUENCE: 132
aaccgaaaac acaccctc                                                     18

<210> SEQ ID NO 133
<211> LENGTH: 21
<212> TYPE: DNA
<213> ORGANISM: Artificial Sequence
<220> FEATURE:
<223> OTHER INFORMATION: Oligonucleotide Primer MZA1719 External Nested
      Forward Primer

<400> SEQUENCE: 133
ccagcggtag attatataca g                                                 21

<210> SEQ ID NO 134
<211> LENGTH: 19
<212> TYPE: DNA
<213> ORGANISM: Artificial Sequence
<220> FEATURE:
<223> OTHER INFORMATION: Oligonucleotide Primer MZA1719 External Nested
      Reverse Primer

<400> SEQUENCE: 134
cggtttggtc tgatgaggc                                                    19

<210> SEQ ID NO 135
<211> LENGTH: 19
<212> TYPE: DNA
<213> ORGANISM: Artificial Sequence
<220> FEATURE:
<223> OTHER INFORMATION: Oligonucleotide Primer MZA1719 Internal Nested
      Forward Primer

<400> SEQUENCE: 135
ctcgggaacc ttgttggga                                                    19

<210> SEQ ID NO 136
```

```
<211> LENGTH: 21
<212> TYPE: DNA
<213> ORGANISM: Artificial Sequence
<220> FEATURE:
<223> OTHER INFORMATION: Oligonucleotide Primer MZA1719 Internal Nested
      Reverse Primer

<400> SEQUENCE: 136
tgaaatccag aacctccttt g                                                21

<210> SEQ ID NO 137
<211> LENGTH: 50330
<212> TYPE: DNA
<213> ORGANISM: zea mays
<220> FEATURE:
<221> NAME/KEY: misc_feature
<222> LOCATION: (0)...(0)
<223> OTHER INFORMATION: Non-colinear sequence
<221> NAME/KEY: repeat_region
<222> LOCATION: (537)...(7229)
<223> OTHER INFORMATION: Highly repetitive region
<221> NAME/KEY: repeat_region
<222> LOCATION: (7536)...(11292)
<223> OTHER INFORMATION: Highly repetitive region
<221> NAME/KEY: repeat_region
<222> LOCATION: (12554)...(25411)
<223> OTHER INFORMATION: Highly repetitive region
<221> NAME/KEY: repeat_region
<222> LOCATION: (29087)...(43016)
<223> OTHER INFORMATION: Highly repetitive region
<221> NAME/KEY: misc_feature
<222> LOCATION: (1)...(50330)
<223> OTHER INFORMATION: n = A, T, C or G

<400> SEQUENCE: 137
taaaaacttg atttagaaac tcagctagtg cttttggcaa ccaaacccca cagccaaaca      60
gctgcatgtc tagaggtaga ggagtagact cctcacaccg ggtaagtcta gctgagtatt     120
agtatactca gccttgcttg tggcataatt tttacaggtt ctctggagga aatggttgct     180
ggagtgactt ggccgtccat cttgccaccg ggttggactg tcgagtggga ccctgccttg     240
gctgaggagg agcatgagga gtgatgggac aggcttcccc atctctctat ttatttaccg     300
ttagtttatt tccgctgcac ttcgaacaat gatggttact tttgcaaaaa ctccgaggat     360
gatgatgatg gtgatgtaat aatttaatac tctgacatgt atggttttat gctttattgt     420
atttgctctg tgactcacct tcgagtgaga ttgtggtact tgatcctgtc agtgccgtg     480 tcggactaga tccgagggat tgacgggtta ttcccaatta agtgtggtct agcctctaag     540
gcggggctta ggcacttaag ttggaataat tcgggcagtt ccgccacaaa tagagtgctc     600
ggatgaaata gcaattttc ctaacccttt caccttgcct tggttcccat cactgaatat     660
gattgaatct tggggatcct tgttcttgac gtaggaagag aacatcctct tttccccgt     720 catgtggttt gtgcatccgc tgtcgataat ccagcttgag cccccggatg cataaacctg     780
caaggcaaat ttaggcttgg gtcttaggta cccaactcat gttgggtcct acaaggttag     840
ttacaatagt cttagagacc caaatgcaag tcttgtctcc cttacatttg gcccctaatt     900
tcctagcaat taccttctta tcctttctac aaatagcaaa ggaagcattg caagcataat     960
aaattgtaca aggttcattc attactttcc tagggacatg aacaatatttt attctaggca    1020 tatgatgaac aacatttttc ctagcaaatt tttatcatgc ataatagaag aactagaagc    1080
aatcatggca tgagaatcaa aagcatcata acttctatac acattcctag aatgtctcct    1140
atcatgatac atgaaagcac ggttcttttg agcactacta gccataggg ccttcccttt    1200 ctccttggcg gagatggaag ccttatggct tgttaagttc ttgacttccc tcttgaagcc    1260
```

```
aagaccatcc ttaattgagg ggtgtctacc aatcgtgtag gcatcccttg caaattttag    1320
tttgtcaaat tcactcttgc tagtcttaag ttgagcatta agactagcca cttcatcatt    1380
caatttagaa attgaaacta ggcgttcact acaagcatca acattaaaat ctttacacct    1440
attgcaaact acaacatgtt ctacacaaga tgttgattta ttagctattt ctaacttagc    1500
actcaaatca tcatttatgc tctttaagct agaaatagag tcatgacatg tagacaattc    1560
acaagaaagc atttcattcc ttttaatttc taaagcaagg gattttgtg cctctacaaa     1620 cttatcatgt tcttcataca aaagatcctc ttgcttttct aataacctgt ttctatcatt    1680
caaggcatca attaattcat taatcttatc aactttagtt ctatctaggc ccttgaataa    1740
acatgaatag tctatttcat catcgctaga ttcttcatca cttgaggaag cgtaagtact    1800
agtatcacga gtgcttacct tcttttccct tgccatgagg caggtgtgat gctcattggg    1860
gaagagggac gatttgttga aggcggtggc ggcgagtcct tgttgtcgg agtcggacga     1920 cgaacaatcc gagtcccact ccttgccaag gtgtgcctcg cccttagcct tcttgtaagt    1980
cttcttcttt tccctcttgt tcccttgttc ctggtcacta tcattatcgg gacaattagc    2040
gataaaatga ccaatcttac cacatttgaa gcatgagcgt ttccccttg tcttgttctt     2100 gttgggatgc tccttacgac ccttttagcgc cgtcttgaaa cgcttgatga tgagggccat   2160
ttcttcatca ttaagcccgg ccgcctcaac ttgtgccacc ttgctaggta gcgcctcctt    2220
gctcctcgtt gctttgagag caatggtttg aggctcttgg attaggccat tcaatgcatc    2280
atcaacgtat ctagcctcct tgatcatcat ccgcccgctt acgaactttc caagtatctc    2340
ctcgggcgtc atcttggtgt acctaggatt ctcacgaata ttgttcacaa gatgtggatc    2400
aaggacagta aaagacttta gcattaggcg gacgacgtcg tggtccgtcc atcgcgtgct    2460
tccatagctc cttattttgt tgacgagggt cttgagccgg ttgtatgttt gggttggttc    2520 ttcgccctg atcattgcga atctcccaag ttctccctcc accaactcca tcttggtgag    2580
catggtgacg tcgtttccct catgagagat cttgagggtg tcccaaatct gcttggcatt    2640
atccaagccg ctcaccttat ggtattcatc cctgcacaat gaagctagaa gaaaagtagt    2700
agcttgtgca ttttgtgaa tttgctcatt aatgaacatg ggactatccg tactatcaaa     2760
gtgcattcca ttttctacta tctcccatat acttggatgg agagagaata agtggttgtg    2820
cattttgtga ctccaaaatc cgtagtcctc tccatcaaag tgggggggtt taccgagggg    2880
aatggaaagc aaatgagcat tgaaactttg cggaatatga gaataatcaa aggaaaagat    2940
tgaattaacc gtcttctttt tctcgtagtc gttgtcatcg tccttttggg aagaggaaga    3000
ttcgtcgctg tcgtagtaga ctatctcctt gatgcgcctt gttttcttct tcctcccgtc    3060
gtttcttttg tggcccgacc ccgagtcagt aggcttgtca tccttagat cattgacgaa     3120 ggactccttc tccttatcat tgaccaccat cccttgccc ttaggatcca tctcttcggg     3180
tgattagtcc ctttcttgaa gagaacggct ctgataccaa ttgagagcac tagaggggg     3240 gggtgaatag gtgatcctgt aaaacttgaa acttaatgcc acaaaacttg attagtagtt    3300
agcacgatta aagccaagtg gctagagagg agttcttgca agacccgata accacaagag    3360
gattaatcac atatagacac agtggtttat cccgtggttc ggccaagttc aacacttgcc    3420
tactccacgt tgtggcgtcc caacggacga gggttgcaat caacccctct caagtggtcc    3480
aaagacccac ttgaatacca cggtgttttg ctttgcttta ctatatcccg cttgcgagga    3540
atctccacaa cttggagcct ctcgccctta cactttgatg ttcacaaaga agcacggagt    3600
```

```
aagggaggga tgagcaacgc acacaagaca caaaattaga gtgacaatac gcacacaagt    3660
cacaacacga gctctcaaca caactcaaag agttctctac tcaaatggag ctctagttgc    3720
tatcacaaag aatcaaatgc gcggaatcga agtcttggtg cttagtaatg cttagagaat    3780
gcttggtgta ctcctccatg cgcctagggg tccctttat agccccaagg cagctatgaa     3840
ccgttgagat cattccaaga aggcaattct tgccttctgt cgcctggcgc accagacagt    3900
ccggtgcacc accggacact gtccggtgcg gatttcttt cttctttggc gaagccgacc    3960
gttggagatt cagagtcgtt ggcgcaccgg acactgtccg gtgcacaccg gacagtccgg    4020
tgcccccttc tgaccgttgg ctctgccacg cgtcgcgcgc gaattacgcg gccgaccgtt    4080
ggcccggctg actgttggct caccggacag tccggtgcac caccggacag tctggtgaat    4140
tatagccgta caccaccgtc aaagtcccga gagcagccat ttgacagacg ccagcctggc    4200
gcaccggaca ctgtccggtg caccaccgga cagtccggtg caccccgacg agcagccttt    4260
tggctgtaca cagccaactt ctccaaaatt gtttctccta tttctagcac ttagacacaa    4320
tacattagtc ttcaaaacaa tgtactaagt ctagaaacat acctttaatc ttgatttgca    4380
cttcttgagt ccatggcaca atttaacact tatgcacttg tgttggacac ttaatcacca    4440
aaatatttag aaatgcccca agggcacatt tccctttcac ctgcaatatc tccaccaagg    4500
agagctcccc ctcgacaaag ccgaagctcg gtgactggcg cggcgcgcca agtcgttcgt    4560
cttactgggc gatgaaaagg agctctacca ccgcatcccc tcaggcatcc tccaacgatg    4620
catatccatc gctgaaggac aggagctatt gcaagagata cactcgaggg cttgcggtca    4680
ccatgtagca cctcgagccc tcgttgggaa cgccttccga caaggcttct actggccgac    4740
cgcggtggcc gacgccacta ggattgtacg ctcctgccaa gggtgtcaat tctacgcaag    4800
acagacgcac ctgcccgctc agaccctgca gacaataccc atcacttggt catttgttgt    4860
gtggggtctg gacctcgtcg gtccattgca aaaggcacct ggggcttctc gcacctgctg    4920
gtcgccatcg acaaattctc caagtggatc gaggtccgac ccctaaccag catcaggtcc    4980
gagcaggcgg tggcgttctt caccaacatc gtccatcgct tcagggtccc gaactccatc    5040
atcaccgaca atggcaccca gttcactggc aagaggttcc tggacttctg cgaggaccac    5100
cacatccggg tggactgggc cgccgtggct cacccccatga caaatgggca agtggagcgt    5160
gccaacggta tgctcctgca aggactaaaa ccgaggatct acaacgacct caacaagttt    5220
ggcaagcaat ggatgaagga actaccctcg gtggtctgga gtctgaggac gacgccaagc    5280
tgagccacgg gcttctcacc gttctttcta gtctatgggg ccgaggctat cttgccata      5340 gacttagagt acggttcccc gaggatgagg gcgtacgacg accaaagcaa ctagaccagc    5400
cgagaagact cactgaccga gctggaggag gctcaggacg tggccttgct acacttggca    5460
cgatatcagc agtctcgacg ctaccacgcc cgaggtgttc ggccccgaga cctccaagtg    5520
ggagacttgg tgcttcggct gcggcaagac gctcgagggc gccacaagct tactcctccc    5580
tgggaggggc cattcatcat ctccaagatt ttgaagcccg aacttacaa gctggccaac     5640 aatcaaggcg aggtctacaa caacgcttgg aacatccgac aactacattg cttttaccct    5700
taagatgttt tcaagtcgtt catataccct attttctatt caaataaagt ctaaccgtta    5760
aggaagggtc agccttgcct cggcaaagcc cgaccctccc tcggggcta aaggggggga     5820 accccctctg cgtaaaaaat ttcctcggaa aaagtctttc tgccagaaca tctttcgcgc    5880 ttttgactt cttcgatagc gggatcctga aaacgacgga gtacacgtaa gcggcaaggc     5940
cgaccgagcc gagggactcc tacgcctccg ggatacggat acctcactca tcaccttctg    6000
```

```
tgataagtaa ctcacgctcg gataagcgat tttgctgacc gaacaagtgt taacgctcga   6060
aaacttttct gccagaacga ttttcgtgcc ttctcgacta tatcgataac agaatcctac   6120
ggacgagtaa gagtgcacgt aagcggcgag gccgaccgag ccgaggaact cctatgcctc   6180
cgggatacgg atacctcact catcaccttc tgtgaaaagt aactctcgct cggataaacg   6240
attctgttac cgacgaacaa gtccagatac tcgaaataag aggaaaggaa acgcagcttt   6300
acaacacaac aatgatatgt ttgggcctca gcggccgcga aaaacatacg cacactacag   6360
acaaactctc cctgcaggtt cagacatcag cagagggagc agcagcaccc tcgacgtcgt   6420
ctccaccttc ggcggaatct ggcccggcct tggacggcga cgtgggcgga aggatctcca   6480
cctcgaagat ggaagccaac accaagctcg ggccatcata gccaaggtct ccgtaagggt   6540
cccgccccgg gcaaacgcct cgaccggccg ctccgtagcc tcagccagct gtcccccgag   6600
gacatcagcc cgactcatgg cctcgacagc ctgactccgg ggttggtccc gccagcggac   6660
gacctggcca ggttccagcc gccgctgttg cacctcctcg accagggagg ccaagtgctc   6720
ctaggccaac gaagcttctt ctcgagccga tcagcctct gtccacactg acaccgctgc   6780
ctccggctcc ggctcatcgc agagcggccg agggttcttt aactgagcaa gagaagcctt   6840
gggtggcaag gccgaccgag ccgagggact cctacgcctc cgggatatgg atacctcact   6900
cgtcaccttc cgcagtgggc aactcacact tggttaagcg gttcagctag ccgacaggcg   6960
agtcctggtg ctcgaaatga ggaagaaaca tggtattgca ctcaaatacc tagatgttca   7020
ggcctcgaca gccataatga acaaacaccg gcactcaagg tgccattaca aacggaactc   7080
cggttccact cccgcgggta tgaacaacct ccacatcgga gggcctgcgg gacgacaaac   7140
tctagttggc tcgccgccga ccgctccatc agcagcgaca acgacctccg ctccgggcgg   7200
ctgaacagca gcagcgatga cctcagggca gacgctgctg cgacaaggcc ctcgcccgca   7260
tccccactcg aggggcgagg acaagctatc aaagccgaag agccggaggt ccgaccgcag   7320
gtggcgccga gaaaccttct ctggctgcca ccacctcagc accgacgacg gcagccacct   7380
gcccaccaac acccgccggg ccgtgaccaa tgtgctcggt tggcactgtt gggtcatgcg   7440
cagggttgcc tcgagtcgcg gcaccggttc cgcagtcgag aaggcgcggg aggaggcgcg   7500
acggtcgata tagccaaaag cgggccagca gtaatggcga cagcaggcga gcggaagcag   7560
cagtcaagtt gtctgcaggc tcacgtcccc tacctggcgc gccaactgtc ggcgtttcga   7620
ccccagggg tccctggacc aacgagtaaa ttgtcgctgc gtgccccagc ccagatgggt   7680
tggcgcgaga cggaacacag agggggggaa accgcggct tcgtgttgtc ctgcgccaga   7740
gtggatgcgc ttgcagtagg gggttacaag cgtccacgag ggagagaaag agagagtgcc   7800
tgttcgtcgg cccgtcctcc cgcgcgacca ccctcccgta tgagggccct ggaccttcct   7860
tttatagatg taagaagagg gtccaggtgt acaatggggg tgtagcaata tgctaacgtg   7920
tctggcagag aggagccaga gccctatgta catgccaacg tggctgtcgg agaggtgcta   7980
gagccctgtg catgcgatgt cgtggccgtc ggaggagcac ttgagccctg tagaagcaca   8040
actgttgggg ctgtcgggac cttgctgacg tctccttact tccgtaaggg gctgagagcc   8100
gccgtcgtca tggccgcacg cggggagcca tcattacttg ttaccggggc gagcctggat   8160
gggacaccga tcttgttccc tgtagcctga gctagctagg ggtagggtaa tgatgatccc   8220
ccctgtggcg tggtcggtcc gagcccaagg tcgggcgagg cggaaactcc tcctgaggcc   8280
gaggtcgggg ttgggtgagg acgcgattcc ttctgaggtc ggggccgagg tcgagccctg   8340
```

```
gggtcgggcg aggcggagac catcctccga ggtcgaggtc gaggctgagc cctggggtca    8400
ggcgaggcgg agtccatctt ccgaggccga ggcgagggcc gagccctagg gtcgggcaag    8460
gcggagactt ctcctgaggc cgaggcctaa ggtcgggcga ggcggagctt cctgtggcgc    8520
ctgaggctgg actcagctgc tgtcagcctc atcttggcag gtggcacagc agtcggagcg    8580
gggcaggcgg cgctgttttc ttgtcaggtc agtcagtgga ggggcgacgt gactgcggtc    8640
actttggccc taccgactga ggaacgtgcg tcaggataag gtgtcaggcg atccttgcat    8700
tgaatgctcc tgcgatacag tcggttggtg aggcgatctg gccaaggttg cttcactgcg    8760
aagcctgccc gagctgggcc tcgggcgagt cggggtgcg ctcgtttctt tgaggaggcc    8820
ctcgggcgag gcgtgaatcc gcctgggtct actgttcctg cccgaggctg ggctcgagcg    8880
aggcgagatc gcgtcccttg tcacacccgg atttcagggc accaagaccc gggcgcgaac    8940
ataatcacca ggtgtgctgg gaccaagtct cacacatatg atgattcatg gcacaggatc    9000
gaatgtcaca tctttactac ataacaggag ttctatacaa aataaataag taattacatt    9060
ataaggagac aacggtccag caacccaaag ttgactggga gacgacgacc tagatctctc    9120
tcacgaactc atcgcagcat cctccatgcg cctcatcctg cggtacttgt tcttgacctg    9180
tgggggggt gagacagcaa gagtgagctc acatacgttc atcgctcaac aagttgtggg    9240
gaataatgtg catgatctcg ccaaaggtgg gagctcacgt gaagtgtaag gcttaccaaa    9300
gaggatggtt agagctgagc attgctttta aagttggtca aaattttatt agcaattact    9360
aagtataagt aaataccaac ccaattaagt agtagaacaa agtaacaac atcacctgcg    9420
atgcaatgca tatgacaaat tgagtttaag ttccataatt taatcatcag agagtcctga    9480
gctgctcatg accgtgagct cggctagtat accagttta cactctgcag aggttgtacc    9540
ctttacccac aagtcatgtt acccatttgc gaagggatcg cgacttccca tacacctcta    9600
ccaaggaggc gaggcagggt aacactacga ggcctttaca aagttccact agcttcagaa    9660
aacccgctac agtttatagg aagctccaat gcagggttct tgcctgaccg ccatcgcagc    9720
aaaatcaacc aaggacctcc ctacactgac cactcccta ctgcccttgc ccctttcggg    9780
taaggtagtc ctccactggc tttcctaatt aatcagccaa gagcgtccat aaacccttgt    9840
ggtggcacgt gtttctcaag ttaagctcta tgttccaatt aacattaatg atcttgacat    9900
gaacataaat agaataacaa aataactgga acatagatat gataattaat tatcccaaat    9960
ccatgtaaag caatagcaaa ctacccaagt gattcagggg taaacaaggt aatgagataa   10020
acaatctagg gtaacctatt gggtcccatc aaaattaacc tatgcatgaa tagtgataat   10080
aacgaatatt attgggtaac agaagtgatc aagggcacaa cttgccttta atgagcacct   10140
gctcagctac ttcaacctgc tgctcaccag gatcctcatt cacgggctct tctactcgcc   10200
acaatacaaa caagcacaat atatagagaa atcaacatca caccaaacat gtaaacaaac   10260
tacacagtaa taatctatgc attaaaataa aatcctagga acagaaatca taattttcgg   10320
agttatagat tttaagttat ggattttcaa aggttttatg tgtttaaaat agattaagtg   10380
aggaattaaa tttcttactg ttttcatgac aaaacagagg ctctaagtga tagagaatta   10440
aattacaaaa atttagaaag tggaatggag taatttgggg ttcatataca ttttctatga   10500
attattgaag ttctagcaat tattttccta ttaaaaatcc cttttccaat ttatttactc   10560
aatttcaaac agctctggat cgagcctcaa ttaccgaaaa gtgcaggggc ttctgcgcat   10620
aattttctaa gactcagaat actatgcagt ggacggcggg tttattcctc ggttttccag   10680
ggtttctctt acaaaactga cccgcgaagg ggtatcagcc gatctcggcc gcaggatgtg   10740
```

```
aagtggacgg cccagattaa ttcatacaac ttaacaaatc ggtatgcacc caaggcccac   10800
ggatacgaaa tccatgaccg agagagttcc acgtcattga cctaacctaa ccatcggatc   10860
tataaccagt ggctcagatt tcatctgcga aggaggtatg ctgtatataa tctcgctcgt   10920
ccattcagat cgaacgatcc acatctagtt tgaacccgat ctaatctaga tcgttcgtac   10980
acagatcaaa ggcccacggc aagcgcttct cttcccccct cggccacccg tgcggccagg   11040
gacagggcac cgcggcggcg ccatcgccgg caacacggtc ggtcggcccc tacagcctta   11100
acccgagcga taaatggtgc aaacgggaga ggaagagatg caaaaccaaa tgggagcgat   11160
tttaccgtga atcgagtagc aggactcgcc gcccacggag acacgcaggt tcacagcaag   11220
agttgatgcc cgacgaggaa tttcccggcc atggctcgcc cagtcgactg gagagcgcct   11280
agcccgcgtt cgggtatccc tcacgaacac cccaaaccac atgccgaggc tgtagagtcg   11340
ccccagggtt gaatcgaccg aggcggtcat ttctcccctg accacggcga agagcggcac   11400
ggtgcgcaac tggttttcct gatagtgggc accggcgtga aattaggccg ccaactcgcg   11460
ccccgatgca ccgacccaca atcgccaagg cttctgctgc gcaaacgagt tccccgctgt   11520
gatggccgaa gcacagcaca gcaggtggac ggcagcggac cagtcgcggc ggcgcacaga   11580
ttggggcgag caggaggag aagaggaaca gcggcttcgg gtgttatagg cgcagggtaa   11640
aggaggggac gaacaggtca cgctggcgcg atgccgcacc tatatgacga gtccgggctg   11700
aggacgttaa ccgggcggcg ctagaatcct ggggcttcgg cagaggccgt tgcgggagta   11760
gcggcgggca ggtgtgccgc cagcgctgta cgcggggtcg gggcacggag gttgttgcgc   11820 tagggtccg cgatttccgt gaatcgggca cgagctcacc agcgccaccg gttttgcgca   11880
cgaagcggag gaaatgtagg gagggagaag aagaccactg ccggctgggt ggataagtta   11940
gctgggtgac cctggaatgt ggggcccgcc tggcggcgac gcgaaggcca cacgagcgag   12000
tgaggggcgt tgggtcgtgc ggtatcggaa aaaaagaat gggccgaaag tgaggattcg   12060
gcccaagtag tgttttattg ttttttcttt tcttattttt tttcaaattc aactttaaat   12120
tcccatttaa attcaaattt agtggtggat ctatcttcac attaatttcc caacttaaac   12180
atggcatggg tgaacttatt tatttcaat atttattta ttaaaactag tgctatgttt   12240
ctccaaatta gagtttaaat gctatgtgtc ccttaatata ttaatatatg ggtactaaca   12300
catttatttt actatccaca aatgcacaat caagtaaaaa ctcagcatga tgcataattt   12360
atttgagtgt cttctattaa ttatttattg tatagatgag gtgtccacat gaaatggtaa   12420
ataggataaa cccacacaca tgtaaaggaa tataatctct cctttagat ttttcttaca   12480 aagtgggtgt tacatccctt gagtggacgg agccttgacc tgaattgcgc ccaacagcct   12540
ctgcagtttg cgctgatggt gattaccagc cgagtttagg agtcttgggg gtaccctaa   12600 ttatggtacc cgacaactgg tatggacgag tctggtgtgg tatgacaatt agagattttc   12660
tataacctcc gtgaacaggg aaatgtgtgt gtaagtgcat actgaaaaag aaacaaggc   12720 cacgggagcg ggaagctcag tggtggttga gtattttgtt acttttaagt ctttgggaaa   12780
accttacagc aattgccttt ctctaagaaa atgaagagtg acttcaactc caccaaataa   12840
agcatgtatg atataggtct cttttctcttt acgggagcgc ggtgggcttg cggaataccc   12900
agtgtattca cccatatta tttatgtttt tcagcagccg aagacttctt ttctgctatg   12960
cttgattgag agggctgtgt ctgcacccag ttctgcctgt ggcttgggct agtatatttt   13020
tctactgcgc ttcatcttct ggctctctcg agcttgtacc cccgtattgt aataactctt   13080
```

```
atttaaactc tgtactattt gaagaaagga atgtgtttac tagcctcatg ggactactaa    13140
ttgtatcaca tttgagtccc aaaggatcgg gacgcttcag aaaatgtcgg ggaccataat    13200 tagggtacc ctcaagacgc ctaattctca gctggtaacc cccatcagca taaagctgca     13260
aaggcctgat gggtacgatt aagtcaggga tcagtccaca cgagtgactc gatcacgctt    13320
cgcccgagcc tagcctcggc caagggcagc cgacctcgag agacttccgt ctcgcccgag    13380
gccccctttt gtaatggcgg acacacctcc ggctcgcccg aggccctggc ttcgcttaga    13440
agcaaccctg actaaatcgc cgtgccgact gaccaggttg caggagcatt taacgcaaag    13500
gtggcctgac acctttatcc tgacacgcgc ccccggcag agccgaagtg accgccgtca     13560
ctccaccgct ctactgacca gtctgacaga aggacagcgc cgcctgcgcc actccgactg    13620
cagtgccact cgacagagtg agtctgacag gcaatcaggc cttgccaaag cgccataggg   13680
gaactccgct ccgcccgacc ccagggctcg gactcgggct aagacccgga agacggcgaa    13740
ctccgctccg cccgacccag ggctcggact cgggctaaga cccggaagac ggcgaactcc    13800
gctccgcccg accccagggc tcggactcgg gctaagaccc ggaagacggc gaactccgct   13860
ccgcccgacc ccagggctcg gactcgggct aagacccgga agacggcgaa ctccgctccg    13920
cccgacccag ggctcggact cgggctcagc ccagaagac gacgaaactc cgcctcgccc     13980
gacccagggc tcggactccg ccctggcctc ggccgaacga cctccgcctc gcccgaccca    14040
atggctcgga ctcggcctcg gcaacagaag acagactcaa cctcggcttc ggaggagccc    14100
ccacgtcgcc cgacctaggg cgcaggcccg ccacgtcaac aaggagcgcc atcatcatcc    14160 tacccccgagc cgactcgggt cacggagaac aagactggcg tcccatctgg ccagctccgc   14220
cagatggaca atgatggcgc cccacaagct ctgtgacgac ggcggctctc agctctctta    14280
cggaagcagg gcaacgtcag caaggactcg accgctccaa cagctgtccc tccgccaggc    14340
tccgtcgctc ctccgacagc cacgacatca cgccagcaag gtgccaagac ctctccggct    14400
gccacattgg catgtaccta gggcgctagc tctctctccg ctagacacgt agcactctgc    14460 tacaccccc attgtacacc tggatcctct ccttacgact ataaaaggaa ggaccagggc    14520
cttcttagag gaggttggcc gcgcgggac gaggacgaga catgcgctct cttggggccg     14580
ctcgcttccc tcaccgcgt ggacgcttgt aaccccccta ctgcaagcgc acccgacctg     14640
ggcgcgggac gaacacgaag gccgcgggat ctccacctct ctcacgcccg tctcaggcca    14700
cctcgcctct cccccttcg cgctcgaccc atctgggctg gggcacgcag cacactcact     14760
cgtcggctcg gggacccccc ggtctcgaaa cgccgacagt tggcgcgcca ggtaggggcc    14820
tgctgcgtgc tgacgaacag cttcccgtca agctccagat gggcagtctc cagaaacctc    14880
tccgccccgg gacggtgctc cgtttcggga gtctcgagtt catgtccttc aacggcagct    14940
acgacatgat actccttcct ccgccgcgcg acaacgacaa tggcggccga caacccgccc    15000
gccggcggcg gaatcggcga catcttcccc gcgtggcgga agaacaacat tcgagctcgc    15060
tccgtcctct cccccgccga cggaggagga ggcgaggcaa ccaaggccaa gcgggaggcc    15120
gcgcttcgtc ggctgtcgag cgaatcgacg tccccagcgc cccgacggaa ggcacgccgg    15180
gcgtcgacct cgcgttcgag atggaggcag gcgccgtccc ccgcgacac gctgatcccg     15240 agcaagaaga cgacgccagc gcgctcgcgg gaagcctgca ggacgtcgcc ctcgtacctg    15300
ggatgacggt gcaaccagtc cccgatgtga ctacgtcgct cctcgtcgac caaaaggtac    15360
cgactaactc ccatcttacg tcatttcgac tcggcctcaa cccgccaagc gacctcgctt    15420
tggcgggcgc tctcgttgag gcaagtgcaa ccccactggg gtttcgtatg cggtcgcctt    15480
```

```
gggaccggtt gacggacgtc tcaacctacg ggccctccga gtccgaggaa gatgacgatc    15540
ccagcatcta ttgggatttc tctggacttg caaccccag tgccatgcgg gacttcatga     15600
ccgcatgcga ctactgcctc tccgactgtt ccgacggaag tcgcagcctt gacgatgagg    15660
gctgcgcccc aagccgcgaa tgtttccacg ttgagctggg ggatccctcc gaaggcaacc    15720
atcttggcat gccggaggac ggtgattttc ctaggcccgt gcctcgcgcc gacatcccgc    15780
gggagctagc tgtggtcctc gttccggcgg ggggtcacga cccacagctc gagcgagtcc    15840
gcggggcgca ggctaggctc gacgagggaa caggagcgct tgagacgatc cgccgagacg    15900
tagggcaggt atgggcgggc caaccccgg gccggagaaa tacgtcacct gccccagggt      15960
ctccagcacc gcgtcgccaa cgatgtcagg gtcaggccgc cgcccgcatc cagcggggtt    16020
ggtcagaacc tggcagccgc agcgatgctc tccgcgcga tgccggagcc atcaaccacc     16080
gagggtcggc gaatccaggg agagctcaag aatcttctgg aaggcgctgc ggcctgacgg    16140
gccgagagca ctgcctcccg aaggtaggga tatccctcgg aacctcatgc cgcgacttcc    16200
cgattcatgc gggaagcctc ggtctacacc gggcgcacgc gtaacaccgc gcctgcggcc    16260
ccgggccacc tcggcaacga gcaccatcga cgcgaccgtc gggcccacct cgacgaaagg    16320
gtgcgccgag gctaccaccc caggcgtggg ggacgctacg acagcgggga ggatcggagt    16380
ccctcgcccg aaccaccgg cccgcaggcc ttcagtcggg ccatccgacg ggcgccgttc     16440
ccgacccggt tccgaccccc gactactatc gcgaagtact cggggaaac gagaccggaa     16500
ctgtggctcg cggactaccg cctggcctgc caactgggtg gaacgacga cgacaacctc      16560
atcatccgta acctccccct gttcctctcc gacactgctc gcgcctggtt ggagcacctg    16620
cctccggggc agatctccaa ctgggacgac ttggtccaag ccttcgctgg caatttccag    16680
ggcacatacg tgcgccccgg gaattcttgg gaccttcgaa gctgccggca acagccggga    16740
gagtctctcc gggactacat ccggcgattc tcgaagcagc gcaccgagct gcccaacatc    16800
accgactcgg atgtcatcgg cgcgttcctc gccggcacca cttgccgcga cctggtgagc    16860
aagctgggtc gcaagacccc caccagggcg agcgagctga tggacatcgc caccaagttc    16920
gcctctggcc aggaggcggt tgaggctatc ttccgaaagg acaagcagcc ccagggccgc    16980
ccgtcggaag aggctcccga ggcgtctact ccgcgcggcg ccaagaagaa aggcaagaag    17040
aagtcgcaat cgaaacgcgg caccgctgat gcggaccttg tcgccgccgc cgagtacaag    17100
aaccctcgga agccccccgg aggtgctaac ctcttcgaca agatgctcaa ggagccgtgc    17160
ccctaccatc agggacccat caagcacacc ctcgaggagt cgtcatgct tcggcgtcac    17220
ttccacaggg ccgggccacc cgccgagggt ggcagggctc gcaacgacga caaaaacgaa    17280
gatcaccaag caggagagtt ccccgaggtc cgcgactgct tcatgatcta cggtgggcat    17340
gcggcgaacg cctcggcttg gcaccacaag caagagcgcc gggaggtctg ctcggtgaag    17400
gtggcggcgc cagtctacct agactggtcc gacaagccca tccacttcga ccaggccgac    17460
caccccgacc acgtgccgag cccggggaaa tacccgctcg tcgtcgaccc cgtcatcggc    17520
gacgtcaggc tcaccaaggt cctgatggat ggggcagct gcctcaacat catctatgcc      17580
gagaccctca agctcctgcg cgtcgatcag tcctccgtcc gggcaggcgc tgcgccattc    17640
cacgggatcg tccctgggaa gcgcgtccag cccttcggac gactcgacct ccccgtctgc    17700
ttcggaacgc cctccaactt ccgaagggag accctgacgt tcgaggtggt cgggttccga    17760
ggaacctacc acgcggtact ggggaggcca tgctacgcga agttcatggc cgtccccaac    17820
```

-continued

```
tacacctact tgaagctcaa gatgccgggc cccaacgggg tcatcaccgt cggcccacg    17880 tacaaacacg cgttcgaatg cgacgtggag tgcgtggagt acgccgaggc cctcgccgag    17940
tccgaggccc tcatcgccga cctggagaac ctctccaagg aggtgccagc cgtgaagcgt    18000
cacgccggca acttcgagcc agcggagacg gttaaggccg tccctctcga ccccagtggc    18060
gacacctccg agcagatccg gattgggtcc gggctcgacc ccaaatagga agcagtgctc    18120
gtcgactttc tccgcgcaaa cgccgatgtc tttgcatgga gtccctcgga catgcctggc    18180
ataccgaggg atgtcgtcga acactcgctg gatactcgga cctgagtctg atccgtcagg    18240
cagcctctgc gcctcggtca tcaaggaagg gtcggccttg cctcggcaga gcccgaccct    18300
ccctcggggg ctaaaagggg ggaacccctc tgcgtcgaga ttgggcatac ttctccgcat    18360
cgaaaatttt caatcaaaaa agggggcctct tgcgttctcc tggctatgtc agaagcaggg    18420
tttcaaggag cgaacatggg tacatgtaaa tggcaaggcc gactgagccg agggactcct    18480
gtgcctccgg gttagggata cctcactcat cacctgccac gaagaatgac ccaactcgag    18540
aagccaccct attattgaca agctaggacg aaacacgcaga tggaaagaaa ggagggtacg    18600
acttcatgca agaaagacaa agtgttcagg cctcagcggc cacggtgaga cgcgcatcca    18660
acaagaaatt gttcaaacaa gaattaggcg ccgccttggg aaggagccgc gccctcagct    18720
tcgtccccgc cgtcggtgag gtccatctcg gcctccggtg atggcgcagg gggaaggatc    18780
tccgcctcaa aggtggtcgc cagcaccgtg ctcggacccg cggcgaccgc gtcaagccgc    18840
tggacctctg ccagggcagc atcgtcttcg tcaggaagac agtacccctc actaacccgc    18900
tccaggtcca cgacgtagtg ggaagcgagc acggcgaagg cccgcctgac gccgtggtgt    18960
agcgcctcgc ggactctgcc gcgcgtgtga tcacccaagg ctcgaaggcg ctttgaggg    19020 gagcttcctg aagggacgtc gccagagccg aggatacgat aaaagtccga gacggcctcg    19080
gacatggccg cgaggtcagc ttccctctgc tcggcagctc cggcaagcgc ctcggcgagc    19140
gccttggcgg actcatcaag ggcggactca agctctgcga gcaaccagga gaaataccctc    19200 aagcacaagc aaaggaaacg gacaagaaca agaaccaggg aggaccaaga catacctccg    19260
gctcggacac gatgctccga ggccgcgacc tgggccgcgg ctaggtcggc cgcgagggtc    19320
tcagctcggc tttcggcctc ggcagcccgg ccccgagatt ggtcccgctc ctcgacgacc    19380
tgggcgagct ccgatcgctg ccgttgcgcc tccgcacgcg ctgctgccgc ctcggccctc    19440
aggtcggcgc agagcagctg gaggtccgct accttggcat cctgctgaga aaggcgcgcg    19500
gtagccccgg cgagcgagga cctcagggat cgcagcgagc cctagacgtc gacctcgcgg    19560
cggatgaacg acgacttggc ggcgctccgg tctgacagat cctggggaaa ggaaacaggg    19620
cgtcacgacg agtgcctcgc tcacagaagg aaaaaggtat gcctgaaacc gctacctgga    19680
ggattttggg gacgtctctg cagaaaacct ccagcgatga ccggagcgac cccaccgttg    19740
cctcagcaca ctcgcggagc tcatcccagg actggtcctc ctgctcatcg tcgagaacga    19800
agacagggtc cgaggcctcg ccggtccgga atcgagcaa cgggcgccgg gctcggggc    19860 ttcgccacac agcgatgagg ctgtcacccg gctggacgga tcgcgcgtcc acgcccacct    19920
cttctgaggc cttgggcgcc gacgcatcag ccatcccgac actggcggca actggtcgct    19980
ctccgacagg gacggcgaca acctcggcgg tggcgggcgc cggcatggcc ggcacgacag    20040
gcgggctcag ggccacgttg gcgtcagccg cctcctcaac cacgatggcc gcctcggcag    20100
aagagccggc ctcgggagcc cgcttctcag agaccgggcga cgcccgagcc cctgcggtgt    20160
aagtaccccg cgaaagggtt ggctgaatga caaggcccgg ggcggcgctg gccacacagt    20220
```

```
ccggcgccgt cttgagggcc ttccggggtg ccaggtcggt ctggccatga ctttgcttgc   20280
tggatataaa aaagaggag gaaagaaaga tcacggccga gacatatgaa tgggaagcca    20340
agacgaagac gtcccgggat actcacccac ttcgggccat tatccaccgc gcctgggggg   20400
aggtctcttg gatcccggct cccaaggcgg ccgccgaggt ccgcttcgcc ggcattttcg   20460
gcgccaccct cgccgtggac gcccgggaag aagattgccc gggcgcggtt gcgacgacct   20520
gagggtcacc cccatgcgcc accggtgcga gcggcggccc ctcgggagcg gacgccctga   20580
cctggccctc cggagccacc tcagctcctc cggccgaggg aacaggtgac acctcgggtc   20640
gcccccgtgc ctcggactgg gaccccgacg ccccaactcc ggggactgat ggtgtcggcc   20700
cgcgcggggg ctggctcgac gactcctggc cgcaccccga gccggggccg aggccgagac   20760
gggcggccat gtcgtcctcc tcctcatcat cgtcgtcatc gtcgtcgtcg ggcgtctccg   20820
gcgacggctc cctcgggagt ccttccctct cctgctggcg acggcgcttc tccaaggcgt   20880
cccgagcccg cctccgctcg cgggcccggg ccttctccgc gtccttcttt ttcttcttct   20940
cctccgcggc gactcgccgc gctgcacggt ccaccgcatc ctccgggacc cgtggcaggg   21000
agggcttgtg ccaccccaca tcctaaaagg aggggagaaa ggaacccgat cataaggacc   21060
cggaacgacc caatgtacga agaaggaagg agcgaacact caccaaagtt acgcacccct   21120
ggtcggggcg catccgaagc tgggagtatg cgtgggggtc cggcttcccc atcgcagccg   21180
acacccgcca ttggagggcg ttgaagggaa gaggatcagg ggacattcgc gagccctccc   21240
agtcagcctc tggggtcatc tcctagagcg acagccgccg ctccgccaat ggaagcaccc   21300
tccgacggtg gatggcagcg atcactcccg cagcggtgag tccccctcc cgcaactcct    21360 tcagggcctg gagaagggc tcgaggttct tctgtctctc gtgcggggtc ctgtggcgcc    21420
aggcgtcggt ggcagcagta actactctct gggagaacgg tgggagcaac tcaccgtcat   21480
tccggaggta gaaccaccgg cgctgccacc ccttgttcga ggacgcaaga atggcaggaa   21540
tgtactgtga cgcccgcgac tgcctcagca aaagagtgca gccgccggcc cgcaccgctg   21600
cacggaccct cctctcctcc gtcgacaagg cgaaaagctc ggcgaggaag agatgagtcc   21660
gcaaatccca atgggggcg atccccaagt acccttcgca taccgctacg aagatagcgg   21720
cctgcgagat ggagttgggg gagaggttat gcaattccac cccgtagtgg aacaggatag   21780
ctcgcataaa gcggcccgtc ggcacaccga atccccgctc gtggaaggag acgaagctca   21840
cgacgtaccc cagcggtggg gacggagcgg ctccacccac gggaggaatc cactctggcc   21900
gctgcttatc ggtgaggggg cggagcaaac cctcgccgac cagctcctcc agatcgctcg   21960
ctgtcaccgt ggaaaaaggc cacggatcac gcgggggat tatggtcact cgatccgcca    22020
tcaccaaaat ggaagagatg gcggcgcggg gggcaggag ggcggttttt tctcttctcc    22080
gactaaagtt tcccggttg cgaaaaccta aagggaaagg aaggaagaag agcaaagaac    22140
cgtcaccgga ccccctctcg agtatatgaa ggcagggcg aaaccgtttc cagcgctcca   22200
cccggaccgg acgcgggatt cgaaaaacgc gaggcgaaac agccgttcct cgaacggctc   22260
gcgcacgcgc aacggccgcc ccgccaacca ctcgccccgt cgcattaact ccgcggcggg   22320
acaggcggcg cctctggcag gagaagcgga cgacgcttcg ccttcgccgt aataaccgcg   22380
tcaaaaaagg tacgccacgt cgttcgattt cgtatccttt tttcctcttt ctctatctct   22440
tgcaacagga accgggaaag ggggataccc cgaaaaggat ccttctctgt gaaggaaccg   22500
ggctccgagc cccctactg atcagaggtt cgaaggctgg ccctccgagg ggttcaacag   22560
```

```
tcgcctcaga tcgcgtgggc ccgacaccca ctactggtca ggggttcgaa ggccggcccc    22620
ccgaagggct ccatggccgc ctcaggctac tcgggctccg cacccattac tgatcagggg    22680
ttcgaaggct ggcccccgaa gggttcacag tcgcctcaga cgccgagcga gggatgacca    22740
ggggtacgtt cgatacataa ccgaggctcg ggctgcgctc ccgaggtacc ctaggacatt    22800
tccgagacca gcgggaacga tcttgtaacg gaatcccatc ggagggaggc atcgagccct    22860
cggaccccgt cgccagggga ccgggtccgg caaatcaccc gcaggtactt ttgggcgtgc    22920
ctctgggccc ctagccgacc cccaacgaac ggggcacgga cgtccactcg gattacccgc    22980
ttgcagctca ccggagacac catgttcggt gcccatcgag ggtaacatgg cgctctcccc    23040
cctcctcctt gcggaaaggc gacgtagggg cgtatgtaaa aaagccgagt ctgtccctga    23100
tcgtcctctc gccctgtgca gaggctcggg ggctgctctc gcaaacccgg ctccggccaa    23160
accgttgaca gcgtcaacat accagcccga gagcttgggc cctgaccgtg cacccgggct    23220
acggccagtt cgcatgaggg aacaaccaga ccagccgaag cattacgcaa ggcattaaga    23280
cctcgaagga gtgtaaccac tcctccgagg cctcggggcg tacacccggc gggtgcgctc    23340
gcgcgcaccc accggaacaa aatgcaaccg agaaaggctg gtccccttgc aaaaaagtgc    23400
gacgaaagcc tccaagcgag tgctaacact cccttcgagg ctcgggggct actgtcgggg    23460
accataatta ggggtaccct caagacgcct aattctcagc tggtaacccc catcagcata    23520
aagctgcaaa ggcctgatgg gtacgattaa gtcaggatc agtccacacg agtgactcga    23580
tcacgcttcg cccgagccta gcctcagcca agggcagccg acctcgagag acttccgtct    23640
cggccgaggc ccccctttgt aacggcggac acacctccgg ctcgcccgag gccctggctt    23700
tgcttagaag caaccctgac taaatcgccg tgccgactga ccaggttgca ggagcattta    23760
acgcaaaggt ggtctgacac ctttatcctg acacgcgccc ccggcagag ccgaagtgac    23820 cgccgtcact ccaccgctct actgaccagt ctgacagaag gacagcgccg tctgcgccac    23880
tccgactgca gtgccactcg acagagtgag tctgacaggc agtcaggcct taccaaaggc    23940
gccataggga actccgctcc gcccgacccc agggctcgga ctcgggctat gacccggaag    24000
acggcgaact ccgctccgcc cgacccaggg ctcggactcg ggctaagacc cggaagacgg    24060
cgaactccgc tccgcccgac cccagggctc ggactcgggc taagacccgg aagacggcga    24120
actccgctcc gcccgacccc agggctcgga ctcgggctaa gacccggaag acggcgaact    24180
ccgctccgcc cgacccagg gctcggactc gggctaagac ccggaagacg gcgaactccg    24240
ctccgcccga cccagggctc ggactcgggc tcagccccag aagacgacga aactccgcct    24300
cgcccgaccc agggctcgga ctccgccctg gcctcggccg aatgacctcc gcctcgcccg    24360
acccagggct cggactcggg ctaagacccg gaagacggcg aactccgctc cgcccgaccc    24420
cagggctcgg actcggcta agacccggaa gacggcgaac tccgctccgc ccgacccatg    24480
gctcggactc gggcttagcc ccagaagacg acgaaactcc gcctcgcccg acccagggct    24540
cggactccgc cctggcctcg gccgaacgac ctccgcctcg cccgacccaa tggctcggcc    24600
tcggcctcgg caacagaaga cagactcaac ctcggcttcg gaggagcccc cacgtcgccc    24660
gacctagggc gcaggcccgc cacgtcaaca aggagcgcca tcatcatcct accccgagcc    24720
gactcgggtc acggagaaca agaccggcgt cccatctggc cagctccgcc agatggacaa    24780
tgatggcgcc ccacaagctc tgtgacgacg gcggctctca gctctcttac ggaagcaggg    24840
cgacgtcagc aaggactcga ccgctccaac agctgtccct ccgccaggct ccgtcgctcc    24900
tccgacagcc acgacatcac gccagcaagg tgccaagacc tctccggctg ccacattggc    24960
```

```
atgtacctag ggcgctagct ctctctccgc tagacacgta gcactctgct acacccccca   25020
ttgtacacct ggatcctctc cttacgacta taaaaggaag gaccagggcc ttcttagagg   25080
aggttggccg cgcggggacg aggacgagac atgcgctctc ttggggccgc tcgcttccct   25140
cacccgcgtg gacgcttgta accccctac tgcaagcgca cccgacctgg gcgcgggacg    25200
aacacgaagg ctgcgggatc tccacctctc tcacgcccgt ctccggccac ctcgcctctc   25260
cccccttcgc gctcgcccac acgctcgacc catctgggct ggggcacgca gcacactcac   25320
tcgtcggctc ggggaccccc cggtctcgaa acgccgacag aaaataaggc catattttcg   25380
gcggctaggg tctagccgcc gaaagtagct tattttcggc ggccacaagt cagtcgccga   25440
aaattacctg ttcttttcgg tgggcctctg acggccgccg aaaataacaa gtgccgaaaa   25500
tagtatttaa aaatacaaaa aataacagaa aattcataca ataacagaaa attcatactt   25560
gagtccacaa cataaaactt aagtccatac aaacataaag tccacaaata gtccatacaa   25620
acataaagtc cacaaatagt ccattacaaa gcacaatgcc gcacaaagct aactccatca   25680
catatcgggg tcgttggagt tgtgtccact accttcagaa gcgaaaaact cgttgacgaa   25740
gtcgtgtaac gggtttagat tctaaagaaa aagaagaca ttaataacga tattagttac    25800
atgtatgacc actattcaaa caaattgttt ctcaaactaa cctctcatgg agtagctccc   25860
tcccctgcat atgctcctcc tggtgctggt atgagcggtg gtggcgtgtt gtggcccatg   25920
accccggatc cctacaaaat caagtttagt aaagatttga aattagattg atacaaacga   25980
caagtcttaa ctaaattgaa gcacctgagg tggaggtggc ggagcatgta atccccactg   26040
aggcatcgac ggctgaaact gagggaaaac aaatggttgt tgttgtgcct gctgtggaaa   26100
ccaagaccgt tgcaaatata atatgttagt tatagaacca atatcgagcg tgttgagaag   26160
aaataagaca ctcacgttca ttgcttgttg ggcctgtgcg ttgtaagcag ccatgtactc   26220
tgattgctct ttgaggaatg ccatttgttg ttgccgcagc tcttcacgaa acttttttg    26280 ctactccctc atagcctcct ccatgctaga tacagagcgg caactacgcc tgctactaca   26340
acaacccgcc tgcgcgcggg cggtcggcgg cgcgcaggcg tgggcggcgg acagcgcgcg   26400
ggcgtgggtg gctgatttgg gagaggagag agagagagga aaaacaaaga agaagaaggg   26460
cgtcggtttt aaaaagacta ttttcggcgg cccctggca cagccgccga aaatagcgtt     26520
actttcggtg gccctctgac acagccgccg aaagtagcct tatttccggc ggctgtgtga   26580
gaggccaccg aaaatagcct tatttccggc ggttgtggca ggccgccaaa aatagcagat   26640
aattttcggc ggctataggt gggccatcga aaattacatt ggccgccgaa aatgttcaac   26700
agtgttgttg tgatagcaac caacaggtat gagccacaat actacacatt gcaacttggg   26760
aaagtaattt actggtcacc atatttccga atagctggtt atgatatgat atttacaaat   26820
cttccaattc attccttcag cttaaatgaa tctcattaat tcatctagga aacatctggg   26880
ctgaaacgtc agaacaacag tgttttctac tgttaacatg atccgtttat cttgtaaaaa   26940
acaaggtttt gtaaatggat ttatttttat gctcaaactt aaattgaaca attcaatcac   27000
gcacaattgc tatgctgaca gaagtttatg acaagtttga gcataatgtt gtaataataa   27060 tgagacccctt catgatcttg ttgttattcc acatttccat ctctcctcga agcatagcag   27120
tgcccaccat tttctaccga gtcagcaaca ataatctagg ctgaaagaac aatggacaac   27180
agcttcgtgt gttgtccatc tagtagtcct ttgaataaca gtataatatg cttatgagaa   27240
tcaatattat tttcatggca cacttgtttt tttcatgaat agtttcattt ttgtagataa   27300
```

```
ttttcagttc tctgtcacag gtacaatatt tgcctatggt gttacaagga gtggaaagat    27360
acatacgatg catgtgggaa aacttattac aatattttc ctttaataag ttttaccttt     27420
gtagagtgta tgtttctagt cataggcttt gaagtatgcc tcatgctacc aattaacatg    27480
caaaaacttg gactaatctt actgatacta agatctaaca tagttgtcaa cctccttggt    27540
tggacatttt agttgctttt gttgtattaa gcttttaatt ctctacaggc tgaggatgat    27600
gatggcactg atcttttcgg gacgaaaccg aagaggacaa gaaggctgct gatgagcatg    27660
tccctaccaa ggtctcttat agaaagtctc tttatcgaag aggacaagaa gtgctaacct    27720
acattatttc agttagggc atgcctttga gaagtctctt tacaatgcaa cgggcaaaat     27780
gcccccgaag caaccctagg gatgatgccg gatccaagtg agacagggca tatagtggga    27840
ggggaagcaa tggggcata cctgacgacg ttagagagaa agagggcgag gactttggcg     27900
acgaagccgg gtagcaggtt gacaatatta atgtacttga cgcagagact cgagacgggt    27960
gcgacgtcgt agctgtgcag tgcctcaacg atctccaccg gcttcatcag cgggaaggag    28020
agctcgccct cccctccgtc gcaggcacca caggtaaact gctgcattga cgacttcctg    28080
gcgatggctt cctctgtcac tcaaagccgc ggccgccgcg cgctcggcgc atatccttgg    28140
ccgggctggt gtgaggaggt ctaggatggt ggccgggttc cgtcgtacga tctcattccc    28200
aacgcctagg tcctcgacgc cgccaacggg aggcgcgggg cccagcgctg ccaacaagta    28260
tggggcctac cgcgcgtggt tgatgagcct gccatgccgg ttccacctgc gggagctggt    28320
aggccgcctt gcgtcgaaag cctccgtgga ggccatgacc gagggtgcgg catggcgggg    28380
ccgcgtggtc ttgtcactct ccgagctgct gcaccagccg ctgcgccggc tcggcccgtc    28440
cctgtagggt cgcgtcgtcg ggcgggggg gattggattt gtggtggggt gcgtgggcgg     28500
gcatcacgcg tggcgatggc actggaagca cggggaacag ggcaggtgta gggtgggggc    28560
aggcgatgga atggcgcggc atgcttgcgg ccgattgtcc ttgcgtggat ggagggatt     28620
gcgggctcga ggatgaggat ggcgggatgc gcgcgccttt cgtcgatcga acgtgggcac    28680
gggacgagga ttgcattgcg cggccacgcg ggggcgagat tggcgtcgtc ggtgggatgt    28740
aggcttcgat gactgtcagc ggggtgggac gtgaatcacg ggggcgaaac aattgctatt    28800
ttagcccttc taacgtgggc tctctgctat tatgtgaccc tctgtctatg acttgtgtga    28860
ccatttgtgt ctatgatttg tgggactggt ggtaaaatag agaagttcac aactgagagt    28920
gacaaaatag caaattctcc cacgggggcg ggggcacgac gcaccagtgt ggacgtccac    28980
actatagcct tatagagtag tggagattat tttttttaat taaactatac ttaatatttc    29040
tacttaacat aatatttgat gtaacatgga cgactaaact tttccctcaa gccggtatta    29100
caaggacacc gggacacgtg ctgtgcggtg acaaaactgt cggggaccat aattagggt     29160
accctcaaga cgcctaattc tcagctggta accccatca gcataaagct gcaaaggcct     29220
gatgggcacg attaagtcag ggatcagtcc acacgagtga ctcgatcgcg cttcacccga    29280
gcctagcctc ggccgaaggc agccgacctc gagagacttc cgtctcgccc gaggccccc    29340
tttttatggc ggacacatca ccggcttgcc caaggccttg gcttcgctca gaagcaacct    29400
tgactaaatc accacaccga ctgaccaaat tgcagggca tttaacgcaa aggtggcctg     29460
acacctctat cctgacacgc gccccggca gagccgaggt gaccgccgtc actccaccgc     29520
tccactggcc agtctgacag aaggacagcg ccgcctgcgc cactccgact gcagtgccac    29580
tcgacagagt gagtctgaca ggcaactagg ccttgccgaa ggcgccacgg cgaactccgg    29640
tccgcccgac cccagggctc ggactcgggc taagacccgg aagacggcga actccgctcc    29700
```

```
gcccgacccc agggctcgga ctcgggctaa gacccggaag acggcgaact ccgctccgcc   29760
cgacccccagg gctcggactc gggctaagac ccggaagacg gcgaactccg ctccgcccga   29820
ccccagggct cggactcggg ctaagacccg gaagacggcg aactccgctc cgcccgaccc   29880
cagggctcgg actcgggcta agacccggaa gacggcgaac tccgctccgc ccgaccccag   29940
ggctcagact caggctaaga cccggaagac gacgaaactc cgcctcgccc gaccccaggg   30000
ctcggactcc gccctggcct cggcggacg acttctgcct cgcccgaccc cctggctcgg   30060
gctcggccac ggcaactgaa ggcaagactc aacctcggct tcggaggaaa ccccacgtcg   30120
ccctgcctag agcacagacc gccacgtcaa taggaaacgt catcatcacc ctaccccgaa   30180
tcgactcggg tcacggagaa caagaccggc gtctcgtccg gccagctccg ctagaggggc   30240
aatgatggcg ctccacgagc tctatgacga cggcggcccc cagctctctt acggcagcag   30300
gacaacgtca gcaggactc gaccgctcca acagctgtcc ctccatcagg ctccgccgca   30360
ccaccgatag ccacgacatc acgccagcag gatgcccaga tctctccggc tgccacatcg   30420
tcatgtacct agggcactag ctctcccctcc gctagacacg tagcactctg ctacatcccc   30480
attgtacacc tgggtcctct ccttacgact ataaaaggaa ggaccagggc cttctcagag   30540
aaggttggcc gcgcgggacc gaggacggga caggcgctct cttggggccg ctcgcttccc   30600
tcacccgcgt ggacgcttgt aaccccccta ctgcaagcgc acctgacctg ggcgcgggac   30660
gaacacgaag gccgcgggac ttccacctct ctcacgctcg gctccggccg cctcgcctct   30720
ccccctccg cgctcgccca cgcgctcgac ccatctgggc tggggcacgc agcacactca   30780
ctcgtcggct tagggacccc cctgtctcga aacgccgaca gttggcgcgc caggtagggg   30840
cacgctgcgt gctgacgaat agctccccgt caagctccag atgggcagtc tccagcaacc   30900
tctccggccc gggacggtgc ttcgtttcgg ggctctcgag ttcatgtcct tcgacggcag   30960
ctacgacatg atacttcttc caccgccgtg cgaccacgac aatggcgcc gacaacccgc   31020
ccgccggcgg cggaatcgac gacgtctacc ccgcgtggtg gaaaagcaac attcgggctc   31080
gctccgttct ctccccccgcc aacgaggag gaggcggggc cgtcaaggcc agacgggaga   31140
ccgcgcttcg ccggccgtcg agcgaatcga cgccccccgac gccccgacgg aaggcacgcc   31200
ggacaccgac ctcgcgttca agacggaggc aagcgccgtc ccccccgcggc acgacgaccc   31260
cgagcaagaa gacgacgccg gcgcgctcgc ggaaagcctg caggacgtcg ccctcgaacc   31320
agagatgacg gcgcaaccag tccccgatgt gactacgtcg ctcctcgtcg accaaaaggt   31380
aacgactaac tcccatcttg cgtcatttcg actcggcctc aacccgccaa acgacctcgt   31440
tttggcgggc gccctcattg aggcgagtgc aacccccactg aggttctgta tgcgatcgcc   31500
ttgggaccga ctgacggacg tctcgaccta cgggccctct gggtccgagg aagatgacga   31560
ccccagcatc ggttgggatt tctccggact tggcaacccc agtgtcgtgc cggacttcat   31620
ggccgcatgt gactactgtc tgtccgactg ttccgatgca agccgcagcc ttggcgacga   31680
gagctgcggc ccaagccgcg aatgtttcca catcgagcta gggaatccca ccgaaggcaa   31740
ccatcttggc atgccggagg atggtgatct ccctaggccg gtgcctcgcg ccgacatccc   31800
acgggagcta gctgtggtcc ccgctccggc gggggttac gacccacaac tcgagcaagt   31860
ccgcgaggcg caggccaggc tcaacgaggg aacgggagcg cttgagccga tccgtcggga   31920
cgtcggacag gcatgggtgg gccaaccccct ggccggagaa atacgtcatc tgccccaagg   31980
tctccagcac cgcgtcgcca acgacatcag gatcaggccg ccgcccgcat ccagcggggt   32040
```

```
cggtcagaac ctggcaaccg cagcaatgct catccgcgcg atgccggagc cgtcaaccac    32100
cgagggtcgg cggatccagg gagaactcaa gaatctcctg gaaggcgccg cggcccggcg    32160
ggccgagagc actgcatccc gaaggcaagg atatccctcg gaacctcatg ccgcgacttc    32220
ccgattcatg cggaagcct cggtctacac cgggcgcacg cgcaacaccg cgcctgcggc    32280
cccgggccac ctcggcaacg agcaccatcg acacgaccgt cgggctcacc tcgacgaaag    32340
ggtgcgccga ggctatcacc ccaggcgtgg gggacgttac gacagcgggg aggatcggag    32400
tccttcgccc gaaccacccg gtccgcaggc tttcagtcgg gccatccgac gggcgccatt    32460
cccgacccgt ttccgacccc cgactactat cgtaaagtac tcgggggaaa cgagaccgga    32520
gctgtggctc gcggactacc gccttgcctg ccaactgggt ggaacggacg acgacaacct    32580
catcatccgc aacctccccc tgttcctctc cgacactgct cgtgcctggt tggagcacct    32640
gcctccgggg cagatttcca actgggacga cttggtccaa gccttcgctg gcaatttcca    32700
gggcacatac gtgcgccccg ggaattcctg ggaccttcga agctgccggc aacagccggg    32760
ggagtcgctc cgggactaca tccagcgatt ctcgaagcag cacaccgagc tgcccaacat    32820
caccgactcg gatgtcatcg gcgcgttcct cgccggcacc acttgccgcg acctggtgag    32880
caagctgggt cgcaaaaccc ccaccagggc cagcgagctg atggacatcg ccaccaagtt    32940
cgcctccggc caggaggcgg tcgaggctat cttccgaaag gacaagcagc cccagggccg    33000
cccgtcggaa gaagctcccg agacgtctgc tccgcgcggc gccaagaaga aaggcaagaa    33060
gaagtcgcaa tcgaaacgcg acgccgccga cgcggacctt gtcgccgccg ccgagtataa    33120
gaaccctcgg aagcccccca gaggtgcaaa cctcttcgac aagatgctca aggagccgtg    33180
cccctaccat cagaggcccg tcaagcacac cctcgaggag tgcgttatgc ttcggcgtca    33240
tttccacagg gccgggccac ccgccgaggg tggcagggcc cacgacgaca acaagaacga    33300 agaatacccca gcaggggggt tccccgaggt ccgcgactgc ttcatgatct acggagggca    33360
tgcggcgaat gcctcggctc ggcaccgcaa gcaagagcgc cggggaggtct gctcgttgaa    33420 ggtggcggcg ccagtctacc tagactggtc cgacaagccc atcactttcg accgagccga    33480
ccaccccgac catgtgccga gccgggggaa atacccgctc gtcgtcgacc ccgttgtcgg    33540
cgatgtcagg ctcaccaagg tcctgatgga cggggggcagc tgcctcaaca tcatcctacgc    33600 cgagaccctc aagctcctgc gcgtcgatcc gtccaccgtc cgagcaggcg ctgcgcctt    33660 ccacgggatc atcctgggga agcgcgtcca gcccctcggg cgactcgacc tcccagtctg    33720
cttcgggaca ccctccaact tccgaaggaa gaccctgacg ttcgaagtgg tcgggttccg    33780
aggaacctac cacgccgtgt tagggaggcc atgctacgcg aagttcatgg ccgtcccaa    33840 ctacacctac ctgaagctca agatgccggg ccccaacggg gtcatcaccg tcggccccac    33900
gtacaaacac gcgttcgaat gcgacgtgga gtgcgtggag tacgccgagg ccctcgccga    33960
gtccgaggcc ctcatcgccg acctggagaa cctctccaag gaggtcccag acgtgaagcg    34020
ccatgccggc aacttcgagc cagcggagac ggtcaaggcc gtcccctcg acccagcgg    34080 cgacaccacc aagcagatcc ggatcggttc cgggctcgac cccaaatagg aagcagtgct    34140
cgtcgacttt ctccgcgcaa cgccgacgt ctttgcgtgg agtccctcgg acatgccgg    34200 cataccgagg gatgtcgccg agcactcgct ggatattcgg gccggagccc gacccgtcag    34260
acagcctctg cgccgattcg acgaggagaa gcgcagagcg attggcgaag agatccacaa    34320
gctaatggcg gcagggttca tcaaagaggt attccatccc aaatggcttg ccaaccctgt    34380
gcttgtgagg aagaaagggg ggaaatggcg gatgtgtgta gactacactg gtctcaacaa    34440
```

```
agcatgtccg aaggttccct accctctgcc tcgcatcgac caaatcgtgg attccactgc   34500
tgggtgcgaa accctgtcct tcctcgatgc ctactcgggg tatcaccaga tccggatgaa   34560
agagtccgac cagctcgcga cctctttcat cacgccgttc ggcatgtact gctacgtcac   34620
catgccgttc ggcctgagga atgcaggcgc gacgtaccag cggtgcatga accatgtgtt   34680
cggcgaacac atcggtcgca cagtcgaggc ctacgtcgat gacatcgtag tcaagacacg   34740
gaaggctccc aacctcctct ccgaccttga agtgacattc cggtgtctca aggcgaaagg   34800
agtcaagctt aatcctgaga agtgtgtctt cggggtgccc cgaggcatgc tcctagggtt   34860
catcgtctct gagcgaggca tcgaggccaa cccggagaag atcgcggcca tcaccagcat   34920
ggggcccatc aaggacttaa aagggtaca gagggtcatg ggatgcctcg cggccctgag   34980
ccgcttcatc tcacgcctcg gcgaaagagg tctgcccctg taccgccttt taaggaaagc   35040
cgagtgtttc gtttggaccc ctgaggccga ggaagccctc ggcaacctaa aggcgctcct   35100
tacaaaggcg ccagtcttgg tgccgccggc ggacggagaa accctcttgg tctacgtcgc   35160
cgcgaccact caggtggtta gcgccgcgat tgtggtcgaa aggcaggagg aagggcatac   35220
attgcccgtt cagaggccgg tttacttcat cagcgaagtg ctgtccgaga ctaagatccg   35280
ctacccacaa gttcaaaagc tgctgtatgc tgtgatcctg acgaggcgga agctacgaca   35340
ctacttcgag tcccatccgg tgactgtggt gtcatccttc ccctggggg agatcatcca   35400
gtgccgagag gcctcgggca ggatcgcaaa gtgggcagtg gagatcatgg gcgaaacgat   35460
ctcgttcgcc cctcggaagg ccatcaagtc ccaagtgttg gcggatttcg tggctgaatg   35520
ggtcgacacc caactaccaa cgactccgat ccaaccggag ctctggacca tgtttttcga   35580
cgggtcgctg atgaagacgg gggccggtgc gggcctgctc ttcatctcgc ccctcggaaa   35640
gcacttgcgc tacgtgctgc gcctccactt cccggcgtcc aacaatgtgg ccgagtacga   35700
agctctggtc aacggattgc ggatcgccat cgagctaggg gtcagacgcc tcgacgcccg   35760
tggtgattcg cagctcgtca tcgaccaagt catgaagaac tcccactgcc gcgacccgaa   35820
gatggaggcc tactgcgacg aggttcggcg cctggaagac aagttcttcg ggctcgagct   35880
caaccatatc gctcggcgct acaacgaaac cgcagacgag ctggcgaaga tagcctcggg   35940
gcgaacgaca gtccccccgg acgtcttctc ccgggatctg catcaaccct ccgtcaagct   36000
cgacgacgcg cccgagcccg aggtatcctc ggctcagccc gaggtaccct cggctcagcc   36060
cgaggtaccc tcggttcagc ccgaggcacc ctcggcccag cccgaggtac tctcggcccc   36120
cgagggcagg gcattgaacg tcgaggaagg gcagagcggg gccacgccag accaggattg   36180
gcaggccccg tacctgcaat atctccgtcg aggagagcta cccctcgacc aagtcgaggc   36240
tcggcgggta gcgcgacgcg ccaagtcatt cgtcttgctg ggcgacgaag aggagctcta   36300
ccatcgcagc ccctcgggca tcctccagcg atgcatctcc atcgccgaag gtcgggaact   36360
gctgcaagaa gtacactcgg gggcttgcgg ccaccacgca gcaccccgag cccttgttgg   36420
aaatgctttc cggcaaggct tctactggcc aacggcggtg gctgacgcca ctagaattgt   36480
ccgcacctgc gaagggtgcc aattctatgc gaagcggaca cacctgcccg ctcaggctct   36540
gcagacaata cccatcacct ggcccttcgc tgtatgggt ctggacctcg tcggtccctt   36600
gcaaaaggcg cccggggggct acacgcacct gctggtcgcc atcgacaaat tctccaagtg   36660
gatcgaggtc cgacctctga acagcatcag gtccgagcag gcggtggcat tcttcaccaa   36720
catcatccat cgcttcgggg tcccgaactc catcatcacc gacaacggca cccagttcac   36780
```

```
cggcaaaaaa ttcttggatt tttgcgagga tcatcatatc cgggtggact gggccgccgt    36840
ggctcatccc atgtcgaatg ggcaagtaga gcgtgccaac ggcatgattc tacaagggct    36900
caagcctcgg atctacaacg acctcaacaa gttcggcagg cgatggatga aggaactccc    36960
ctcggtggtc tggagcctaa ggacgacgcc gagtcgtgcc acgggcttca cgccgttttt    37020
cctggtctat ggggctgaag ctatcctgcc cactgacctg gaatacggct ccccaagggc    37080
gagggcctac accgagcaaa gcaaccaagc cagccgagag gaatcgctgg accagttgga    37140
ggaagctcgg gacagggcct tactacactc ggcgcggtac caacagtccc tgcgacgtta    37200
ccacgcccga ggggtccggt cccgagaact ccaggtgggc gacctggtgc ttcggctgcg    37260
acaagacgcc cgagggaggc acaagctcac gccccctgg aaagggccgt tcgtcatcgc    37320
caaagttctg aagcccggaa catacaagct ggccaacaat caaggcgaga tctacggcaa    37380
cgcttggaac atcaaacagc tacgtcgctt ctacccttaa gatgttttca agttgttcac    37440
atacctcgca cctacgcaaa gtttagttgt caaggaaggg tcggcctagc ctcggcaaag    37500
cccgaccctc cctcggggc taaaaggggg gagaccccct ctgcgtcgaa tttttttcctc    37560
gaaaaaggac ctcttttag caggatttct tccgtgcttc ttgactactt tggaaagcgg    37620
atcctggaaa cgacgaggta cacgtaagca gccaaggctg accaagccga gggactccta    37680
cgcctccggg atacggatac ctcactcgtc cccttctgcg ataagtaact tgcgctcgga    37740
taaagcgact ccgtgaccg aacgagtcat cacgttcgga agctctcctg ccgaagcagt    37800
ccttcaagct ttctcgacta atcggggac agggcctcat ggacgggtga agtacgcgt    37860
aagcggcaag gccgaccgag ccgagggatt cccacgcctc tgggatacgg atacctcact    37920
cgtcccttcc gcgaaaagca actctcgctc acacaaacat ccctattacc gacagagtcc    37980
agatgctcga aacaagagga aaaaaggacg cagcttcgca agcgcggcga gggcgtgttc    38040
ttctggcctc ggcggccgca gaaagcgcac gctacaagat gatctgatcc tgcaggctcg    38100
ggtcttcacg ccgaagggag ccgtagcacc ctcggcatcg acgacgtcta cagcaaagcc    38160
cgacccagcc tcgggcggcg ccgaggtcca ggggctcctc caggaatccg gcccgagcag    38220
gcggctcaac cggttacccc tgggccctcg ggcaaccggc ttccaagggc gctagcccga    38280
tccaaggcct cgactgaccg acttgggcgt cggcaccgct gacgggcgac acggctaggc    38340
tccgccaac caggttcccc attctcgagc caactccgcc tctgttcaca ctgatatcgc    38400
tacccccggc ctcgatccac caaagggcgg ccgagggggtc ccttcaacta agctagaaga    38460
gcctcacgta acaaggccga acgggccgag ggattcctac gcctccggga tacggatacc    38520
tcacccgtca ccttgacacg gggcaactca tgcttggtaa agcggtttag ataataaaac    38580
aggcgagact tagtgctcgg aaatgaggaa aaaacacggc tccgtgccaa aattacatac    38640
atgttcaggc ctcgacagcc acaatgaacg aactcactgg cattcgaagt gccattacaa    38700
acggaactcc ggttcccct ccgcaggtac gaacaacccc actccgaggg ggaaggcctg    38760
cggagcaacg gaagaccgac gaacggcgcg ccgtcacctg ctccagcagt ggcgacgacg    38820
gcgacttctg ctccgggggg ccgaacagcg gcaacgctga cctcagggtg gatgccgctg    38880
tcaggaggcc cccgcccgtg ccaaaactcg tgaggcaagg acgggcagaa ggccgtagaa    38940
gatggaggtc agcccgtggc cggtcccggc cgccgcgccg gcggaagaac ctcttccggc    39000
tgccgtggca gacgccgacg ccgcaagggg ccccgaagcc actcgcggct gaagaacagg    39060
cacgctgcag ctgccggacg ccacgggcaa tgccgcttc tccccccatc actgagtgaa    39120
ggagcgggcc accgcccacg caggggctga ccccaactcg gcactctccc ctccccagcc    39180
```

-continued

```
ttggtgatga aaatccttga ggctgaggaa ggggcagagg ccacagcccg gctcgctttc    39240
ccccaccatc aagctggagg tcgccatctc gggtgaccgc cggtgaaggg gtgcgaccgg    39300
gctgcgtggt gaaaatcctt gaagccgaac gatggctgag aggtaccaac tcccatggag    39360
ttgcgttcct ccaacgagga ggcggaaagg cggcggatat cccccatccg ggggcttgga    39420
agacgggaag acccggcgct taagggagga agaagacatg gtcgccttac gaaaggagcc    39480
tccctccttt taaaggcaac tccctacgt gcgccccag gcgccgcggg ccgagtcttc    39540
tccaacacgc tccaaggccc tccctgcga ctcggggct gggtcccgca tgtcatgcaa    39600
gccggctcag ggcagaagaa gccaaaccgc gcgcatggt gcgcacgacc gtccagcggt    39660
tacaggcgac ccccatttc cgcccagacc aacaggcaga aggggcgagc agccatgcag    39720
gcggcatgca accgcgccag atggacgcgc ttctccaact tctgacacgc cagcctgggg    39780
cccaggccca cgcgtcgagc aactggcacg ccagttgctg catgcaagca accgcaccgc    39840
cacttgtgcc accgtcgcgc tcttcggtt gcgaagccta tgccacgact cgaggcgacc    39900
caacagcgcc agactggcgc gtcggtcaaa gcgaccgaaa gtgggccggc agtaatagcg    39960
gtggcaggcg ggcgggcgca gcggtcacgt cgtcagccag gctcacgtcc catcctgaga    40020
cagcaagaga gcctcctctc acggcgtgaa gacggtgcac ccgtgacccg ttcctcgaac    40080
ggatcacccg cgcgcaacgg ccgccccgcc aaccactcgc cccgtcgcat taactccgcg    40140
gcgggacacg cggcgcttct ggcaggagga gcgcgcgacg cttcacctcc gccttaataa    40200
ccgcgtcaga aaaggtacgc cacgtcgtct gatttcgtat ccttttccgt tttcctcttt    40260
ctctatctct tgcatcaggg accggggaag ggggataccc cgagagggat ccttctccgc    40320
gaaggaaccg ggctccgcgc cccccattac tgatcagggg ttcgaaggct ggccccccga    40380
gggttcaaca gccgcctcag atcgcgtggg cccgacaccc actactggtc aggggttcga    40440
aggccggccc tccgaagggc tccacggccg cctcaggcta ctcgggctcc gcgcccatta    40500
ctgatcaggg gttcgaaggc tggcccccga agggttcaca gtcgcctcag acaccgagcg    40560
agggatgacc aggggtacgt tcgatacata accgaggctc gggctgcgct cccgaggtac    40620
cctaggacat atccgagacc agcgggaacg atcttgtaac ggaatcccat cggagggagg    40680
catcgagccc tcggaccccg tcgccagggg accgggtccg gcaagtcacc cgcatgtact    40740
tttgggcgtg cctctgggcc cctagccgac ccccaacgaa cggggcacgg acgtccactc    40800
ggattacccg cttgcagctc accggagaca ccatgttcgg tgcccatcga gggtaacatg    40860
gcgcactccc ccctcctcct tgcggaaagg cgacgtaggg gcgtatgtaa aaagccgagt    40920
ctgtccctga tcgtcctctc gccctgtgca gaggctcggg ggctgctctc gcaaaaccg    40980 gctccggcca aatcgttgac agcgtcaaca taccagcccg agagcttggg ccccgaccgt    41040
gcacccgggc tacggccagt tcgcatgagg gaacgaccag accagccgaa gcgctaagcg    41100
aagtattaag acctcgaagg agtgtaacca ctcctccgag gcctcggggg ctacacccgg    41160
cgggtgcgct cgcgcgcacc caccggaacg aaatgcaacc gagaaaggct ggtcccctg    41220 caaaaagtg cgacaaaagc ctccaagcga gtgctaacac tcccttcgag gctcgggggc    41280
tactgtcggg gaccataatt aggggtaccc tcaagacgcc taattctcag ctggtaaccc    41340
ccatcagcat aaagctgcaa aggcctgatg ggcacgatta agtcagggat cagtccacac    41400
gagtgactcg atcgcgcttc acccgagcct agcctcggcc gaaggcagcc gacctcgaga    41460
gacttccgtc tcgcctgagg ccccccttt tatggcggac acatcaccgg cttgcccaag    41520
```

```
gccttggctt cgctcagaag caaccttgac taaatcacca caccgactga ccaaattgca    41580
ggggcattta acgcaaaggt ggcctgacac ctctatcctg acacgcgccc ccggcagagc    41640
cgaggtgacc gccgtcactc caccgctcca ctggccagtc tgacagaagg acagcgccgc    41700
ctgcgccact ccgactgcag tgccactcga cagagtgagt ctgacaggca actaggcctt    41760
gccgaaggcg ccacggcgaa ctccgctccg cccgacccca gggctcggac tcgggctaag    41820
acccggaaga cggcgaactc cgctccgccc gaccccaggg ctcggactcg gctaagacc     41880 cggaagacgg cgaactccgc tccgcccgac cccagggctc ggactcgggc taagacccgg    41940
aagacgcgca actccgctcc gcccgacccc agggctcgga ctcgggctaa gacccggaag    42000
acggcgaact ccgctccgcc cgaccccagg gctcggactc gggctaagac ccggaagacg    42060
gcgaactccg ctccgcccga ccccagggct cagactcagg ctaagacccg gaagacgacg    42120
aaactccgcc tcgcccgacc ccagggctcg gactccgccc tggcctcggc cggacgactt    42180
ccgcctcgcc cgaccccctg gctcgggctc ggccacagca actgaaggca agactcaacc    42240
tcggcttcgg aggaaacccc acgtcgccct gcctagagca cagaccgcca cgtcaacagg    42300
aaacgtcatc atcaccctac cccgaatcga ctcgggtcac ggagaacaag accggcgtct    42360
cgtccggcca gctccgccag aggggcaatg atggcgctcc acgagctcta tgacgacggc    42420
ggcccccagc tctcttacgg cagcaggaca acgtcagcag ggactcgacc gctccaacag    42480
ctgtccctcc atcaggctcc gccgcaccac cgatagccac gacatcacgc cagcaggatg    42540
cccagatctc tccggctgcc acatcggcat gtacctaggg cactagctct ccctccgcta    42600
gacacgtagc actctgctac atccccattg tacacctggg tcctctcctt acgactataa    42660
aaggaaggac cagggtcttc tcagagaagg ttggccgcgc gggaccgagg acgggacagg    42720
cgctctcttg gggccgctcg cttccctcac ccgcgtggac gcttgtaacc ccctactgc     42780 aagcgcacct gacctgggcg cgggacgaac acgaaggccg cgggacttcc acctctctca    42840
cgctcggctc cggccgcctc gcctctcccc cctccgcgct cgcccacgcg ctcgacccat    42900
ctgggctggg gcacgcagca cactcactcg tcggcttagg accccctgt ctcgaaacgc     42960 cgacaaaaac cctcaccaca ttttcctcaa ccacatgatg gagattgggg ctactagata    43020
ctatgcctgg tggtagactg gtagctgatg tctttggacc agtagttggt gctagatttg    43080
tgaactctac caaggtgaga aacggagatg gaggctgccc tgctgagcgg gttcatcaaa    43140
accatcctgc caaggctctt ctcactggta caagggagat acaagctgca caagggcctc    43200
aagagcgaca tcaaatcgct ggagaaagag ctccatatga tcgctgttac aatcgatgaa    43260
caaatctcgc tggggaggaa ggatcaggga gctgtgctga gcctctcaat tgatgagctg    43320
catgaactgg ctcaccaaat cgaggactcc atagatcgct tcttgtacca tgtgaccagg    43380
gagcagcaag catccttttt tcgtcggact gtacggtcgc cgaagactct gttgtcacgt    43440
cagcggctgg ctgccgaggt tcagttcctg aagaagatac cggaggaggc gcaccagcga    43500
gagaagaggt acagggtctt cgccggcctt tcttcctcta cccggcacac tgaatcgtct    43560
tcctgttcgt ctgtatctga tccgcacaca cttaaggccg acgtcgtcgg catcgacggt    43620
cccagggacg agcttgtgca gcagttaacc gaagaggcag agggcctaac aaagcagctc    43680
aaggtgatct ccatcgtcgg gatccatggc tccggcaaga ccgtccttgc cagagaggta    43740
tacgagagcg acgtcggccg gcagttcagt ctccgggcat gggtttctgc tactgacaga    43800
ggtccgagag aggtgctcat ggagatcctc cgaaattttg gtaggccagt ggtggatagc    43860
tctagtattg accagcttac ggtagatctc aggaaacact tgggtgagaa aaggtgaaaa    43920
```

```
aaacctcttc tttatgttat ttattattta tgaagtttct tcaactacgg gttttcatgt    43980
tcaaattgcc tctctgaact tcgaaaacgt ttaataccaa ttgaattgag gatcttagct    44040
ttggaaaagc ggtagtgttt tgacgttttg catacatttc tcaccgttat tttattcatt    44100
tataatttag agtttaagca gtatattcat tttgaaattt atgagatttc tgtctgcacg    44160
cttacttcca tgcccaaaac atgtccgatt gagaacagaa ggtaattttg tttgatcttt    44220
gagatcagac acactgattg agtagtaaca ggaaacaagt gctcaccaat caccaagtca    44280
cttacaaaga atttcatgct tacaaaacac actgattgtt aaggatagag actatgtttg    44340
atctgcatag tttgaatttt gattatgtca tcgtcgattg ttatcattaa ctttttgttgg   44400 aaatttctct tgtagctatt tcattgtaat cgatggcatg caaacagatc agtggagcac    44460
cattgaaact gccttcccag aaaacaatgt tgttagcagc agagtaattg ttacaacaac    44520
aatccggtca gtagctaatt cttgcagctc ttctaacggt tatgtgcaca aaatgaaaag    44580
acttagtgac gaacactcag agcaattgtt tatcaagaaa gcttgcccaa caaaatattc    44640
aggttatact cgaccggaat caaaagaagt tctgaagaaa tgtgatggtc aaccacttgc    44700
tcttgttact atgggccaat tcttgaggaa aaatggttgg cccacaggac ccaactgcga    44760
aaatgtgtgt agagatctta gacgacatct ggagcaggat gatacattgg agagaatgcg    44820
aagggtgctt atccacagct tatctagtct tcctagccat gttcccaaag cctgcctttt    44880
gtattttggt atgtttccat gtgatcatcc cataaagagg aagagcctga tgaggcgatg    44940
gttagcagag ggatttgtac aaacacagcc ttcatctagt gaaaacttca acaccctcat    45000
agaccggaat attattgagc ccatcggcat atgtaacgat gatcaggtaa agacatgcaa    45060
aacatatggc atgatgcacg agttcatttt gttaatgtcc acctcccatg acttcattac    45120
cctgctttgt aataataaag ttgaacacaa atatgtgcgt cggctttctc tccatcatca    45180
tagtgctaca agtggcagtt tttcggtcat cgacttatct cttgttagat ctctgatggt    45240
ttttggggag gctggcaaaa ctattttgag tttccgaaag tacgagctat tgagagtctt    45300
ggatcttgaa caatgtaccg acttggaaga tgatcacctc aaagacatat gcaacctttt    45360
tcttatgaaa tatctaagcc tcggagaaac tattagaagt cttccaaagg agatagaaaa    45420
actgaagctc ttggagacac ttgacttgag gagaacaaag gtgaaaacac tacctataga    45480
ggtcctcctg ctcccctgtt tactccatct gtttgggaag ttccaatttt ctgataaaat    45540
caagataaca agtgacatgc agaagttttt cttaactgga cagagtaact tagagacact    45600
ttcaggattt atcacagatg ggtctcaagg attgccacag atgatgaatt acatgaattt    45660
aagaaagctt aagatatggt ttgagaggag taagagaagc accaacttca ccgatcttgt    45720
gaatgctgtc caaaagttca tccatgatga caaagagagc aatgatccac gttctctatc    45780
acttcatttc gatgacggca ctgaaaacat cctgaactct ttgaaggctc cttgttacct    45840
taggtcattg aagttaaaag ggaatttgct ggaacttccc cagtttgtca tatcaatgcg    45900
gggtctccgg gagatatgcc tttcatcaac aaaattgaca tcgggcctcc ttgcaacact    45960
cgctaacttg aaaggcttgc agcatctcaa gctgattgca gatgtccttg aagattttat    46020
cattgaaggt caggcattcc tggggctgct acacctatgt tttgtcctag aacgtgccac    46080
cttaccaata attgaaggag gagctttgcc gtacctcatc tcacttaagc taatctgcaa    46140
agatctagtt ggcctcggtg acatcaaaat caaccgcctc aaatgtctta aggaagtcag    46200
tctagatcat agagtcgctt cggaaacaag agaaatctgg gaaaaagctg ccgagaagca    46260
```

```
tccaaaccgg ccgaaagtat tgttggtcaa ctcatctgat gaaagcgaaa ttaaggctgt   46320
agactgttct gttgcttcaa gaccagctgt gagtgaggct aatggaactt ctcccatgtc   46380
agaggttgat gtacgagagg atgacattca gatgatactt aaccaggggc tctctgccgc   46440
tgctgagaaa cagatgaatt gtgcagttca gccaagttca aaagctgaac tgaactctga   46500
tttcaataat attagtttcc cagaggttgc gcttggttta accgagctgt gaattgcttg   46560
gaattgaaat gtgtcttcat acacctattg atccttgatt gtccatggtc agtttcgttg   46620
cacttgcagc atattactat gaggctagta tcatgtaaat tacaaatctt ttgttgttaa   46680
ggccataaat tgcatattat agcacaacaa gctggtatgt ctcaacaatg gcattaattt   46740
tttttctgct tgaatctaca aatttcatca ttattttgca atttcgcttt tatacagata   46800
tggtgatgcc atgtcatttt gactttgcag catatatgca agcaacggtt tgagttgctg   46860
gagttgctag aatattgata caacttcagt ttactcgaag gctacaggga tctcataact   46920
aggatggttg aagataattt gcgattgttt ccttcagtgt cactgaaaag acttttgtaa   46980
caataaagca tacctttgct tcctactttt ttgaagttac ttcagatgct aagttcgcag   47040
ttgggcctgg actttatcat gtttatccag ctgtttattt gtttcatgta caataatacc   47100
ggtgattgct gttgttatat aatctatatt tatactatag ttaaagtatc agtttcaacg   47160
gttgtcccgc gccatctttt tacaaataat ccatcacaaa tatttcaaat taacccgatg   47220
cacgcctata gatggccaaa cggcggtccg gcacgggcca gatgccttcg ggccacaact   47280
ctggcccagg cacgtcatgc cgggtcagct cattagcccg ttcgattaaa tcagcgtaaa   47340
atgttaaaaa acagtgtaag agttggagtt tgaacccatg ccctgattaa agaagggcaa   47400
aagacacttg gtgaagctat ctaaccaata gaacatcatg ctcaaatatt ttaatattga   47460
atataaattg tatatatgta tatacatttt tttataaaat ttaaaaaatt ataatcgtgt   47520
cgggctgtgc cagcactacg gactgaggct acagcccaag cacggcacga cgttcttggc   47580
tcttgcaagc attagattgt ttctgagact acattggcgc aatggactcg atggtgtttg   47640
aggttgctga attggatgaa gcaacaatga tttgtcacac taacagtaaa atgaaaggtt   47700
atttgttatt tttaaacgtt agttattgct acgaagtagc ataatttata tgaagtacat   47760
ccagttttta ttgatgcctg actttaacaa tcacttcata ttttgatata tcttttttat   47820
aagtttgagt tcagtgactt atttttagaaa tttgagctca caaactttct cttatttggt   47880
ctctgtatgg tggaattatg tcattttata attttttgttc gttcagccag tcgttgtgaa   47940 cttcttcta actgctcact tcattggccg tattgtacca agacatattg gatgtagtaa   48000
accataacat cagatagtta aatcaaaaaa atattatacg gagagcggag acaataaata   48060
aaaaatcttg aaattttttg gtggatagtt tatataggta ttgttgtaag ccgtcgcaac   48120
gcacgtgtaa ccgactagta ctaagtgaat tccccacttg tgggaattgt gagattgttt   48180
ttatatgaac gaatattgta ggtaaatgag taacataata ttccttttgt taacaccttg   48240
atctggtacg tcaaaaccac gtatgtacca tatgttttaa cttttgtatc tggtagaatg   48300
gactgaagta aagaatctca tccatcgact gctgctaata tatgcagctt cccagatcag   48360
aggtcccaaa catgtcacca cttaccaatt aaatctctta tttacttggc cttcccatga   48420
aactagcaaa agttgctgtc tccacaaact gcaggtcaat tcgtttcttt agcgccttat   48480
ttcagaaacc gtggtagcat tgacatttta ctcatctgga tagttcggc ttgaatacgt   48540 agcgtcttgt acatttattc tctcacagta acagctaact cctgtgcaaa gatgcggctt   48600
attccattgg agaatagcgg acttttttgtt ttatttagtt tcagctctct ggttgcaact   48660
```

```
tgcaattagc cactctgccc ttttgcgtta cctacattct atctagcaag gcagccaatg    48720
tttctcattg ccaggtcact tgtttttgaa ggctgtgcgg aagaaacatt tctacaaaca    48780
aacaattaga actgacatta ccgaagaaac agttaagtca aaagcttgtt ggttggatnn    48840
nnnnnnnnnn nnnnnnnnnn nnnnnnnnnn nnnnnnnngt tcnttcttgc gttccgttgn    48900
ttnnnnnnnn gnnngnnggn aatnnnannn taaannagnn actnaatnnn aagnttatac    48960
cnntagttta atttgtttac cctcccagga atattgcacg cctcgatgta ggcctccact    49020
cagactttat ttgggtactt tagtattggg gttttatag tggtgccctc ggttttgctg    49080
gtgtgctcat ttttatcctt ggttccgctt tattttgctc agttttgccc ttccagtgct    49140
atagaacaga agggcaaaag tgagcaaaaa aaaacacaac taaggataaa aatgagcaca    49200
ccagcaaaac cgagggcacc actataaaaa ccccaatact aaagtaccca aataaagtct    49260
gagtggaggc ctaaatagag gcttgctaat tattagacct ttataactac attaaataag    49320
ataaaatatc cactgaaatt agaaaattga gtgaggtctg tgcccccgct aagccgtcca    49380
atgagggttc gtccgtcttc caacctgatt aaataagata aatatccac taaaattaga    49440 aaaattgagt gcggtctgtg cccccgctaa gccgcccaac ccaaccttga tgaatttcct    49500
ggttcacaca tatgtggtgt gattgaaggg ttacacgaaa aacctcacaa ccccgatggc    49560
ctgtcttcgc tgaagtgtca ttcagtggtg atcaggaaca aatccatcc caaactcaag    49620 cagagaacat tacaagttaa cataactgaa gttgaaccag atggtggtca gaatgagaag    49680
gcctgcaaca gtcaatttgt tctgattcct tttgtgcagg ctgctacagg ttgttctcct    49740
gacgagaaaa gcagttctaa gccggttgaa ttcgtgcagg atgcatacaa cagaaccatg    49800
cagactgaac ctcattgtgg atggcaatat ttttttcaat ctctgatact agtaccaagt    49860
cagcatgttt tgtccatccc catggcaatg gcatagagat agaactttct ataaatagtc    49920
ttgaggatca ggggacaagt caatcttgtg aaatcctaag taatacggag tacaagtttg    49980
tctgaaatat cacatcgagc gattgtgtgt gcgcgcctac tagctcatga aagtcctggt    50040
actgaagttt tcattttctct caagtcataa attatgcagg atgttataac tccacagagg    50100
gttatggagg ggacaaatag agcaaaatgt ggatggaaac atagaacaca gcaggctgcg    50160
gaaaaggaaa cataatctgt tcatccgctg acacaaaagc aagaacctct atttgagtgg    50220
aacctacaac ccattgtcac cgttgctcta ttgggtcttc agaagaaatt ttgactgaaa    50280
tgttctaggc ggatggcgac ggcgattagg catcgtttct ccttcatgaa               50330

<210> SEQ ID NO 138
<211> LENGTH: 507
<212> TYPE: DNA
<213> ORGANISM: Artificial Sequence
<220> FEATURE:
<223> OTHER INFORMATION: MZA3434 Processed consensus sequence

<400> SEQUENCE: 138
gtcatgtccc ccctcattag aggcgctact ggacatgtgg aagctgccat gttcggctgc       60
aacgacgcca cccaggtgta caaggagctg caggaggcca tcaaatccta cccggacgcc      120
ttccaccgcg tcatcggctt cgacaacatc aagcagacgc agtgcgtcag cttcatcgcc      180
tacaagcccc cgggcagcga ctagaccgcg cccgccggcc gcccccgcc ggctagctag      240 ctagctagct cctgcgtgag ctagtagcta gctagtgcca tgcgtcgtct ctgtcgttcg      300
gttttgcttc ggggtcaccg tgtacccttt gcttgcttgg tttcttcttt ccttttttcc      360
```

```
tttttttttt cttcttttcc ccggccatgg ttcctttgct ttccagcagt tctctgctgg    420
atgtaatgta tccattgttg caagcatggc cttgcattgg ctacctctat acctgctaaa    480
aaactactgc aaatggtcat agctgtc                                        507

<210> SEQ ID NO 139
<211> LENGTH: 650
<212> TYPE: DNA
<213> ORGANISM: Artificial Sequence
<220> FEATURE:
<223> OTHER INFORMATION: MZA2591 Processed consensus sequence

<400> SEQUENCE: 139
asggtaccaa ctaaaagggc ctggaatcat ggaagcccac ataaccagg agcgagctac     60 ctgcgaagcc acatctctcc ttcctcttca tcgatagtac tcatctccat attcaggtaa   120
ataacatcgt ctgcatgccg cgcgcccta atagcatctc gatcacattt ttgtgttctt   180
gacttctcct cggaagcctt cttgtttaac aaacttatat tagtcgttgg tcgatctttg   240
gacccacatg taaatcttgg ttcgcgtccg ccgtgcagtg cagaggcaca agctaagcca   300
tgagcaacgg tggtaaccgc agcaggggcg gcgcgaggtt cgagctgcag ctgcacctgt   360
cgccgccgcc gcccgtggct aggagggtgt aggtttactg cgtatgctac tgcagcgact   420
cgtcttcttc cccgagctcg tgcgtgtcgt ctgactgcat tccagggagc aattcgccga   480
ttgtaatcgg cgcctgcacg cggtgcatga tgtactgcat ggtgtccaag aatgacttcc   540
ccacctgcat caactgcaag cagccctgcc tcgtgtacct cctccactgc tcttggcccc   600
tgctgcagcg gcaccggcaa ggccaattaa aakgacttca acctttcgta              650

<210> SEQ ID NO 140
<211> LENGTH: 731
<212> TYPE: DNA
<213> ORGANISM: Artificial Sequence
<220> FEATURE:
<223> OTHER INFORMATION: MZA11123 Processed consensus sequence

<400> SEQUENCE: 140
tcaaatcctg gggggaaacc ttccgggtgg gtcattgcaa aatgggcagt ttatgggctc     60
cttaatgatg gggggtcacg gttcgggggt ttttcggcc gggaccatgt ttcggtctct   120
tcttaatata ataccgggag gcagtttttc ctcctccccg gccgcgtttt ttagtgtaaa   180
tatgcaaatg taccatcttg attggcttct atgatctaca ttttagtgta ggctgcaagt   240
ccacgagctt tgaaaagtta cacaatctgg attatttgca agtcgtaaac acttatagga   300
ctcagtgact agattggacc agcctgttgc attcatgcaa ttgttaggct aattgtcatt   360
tcaccttcag tctacaatga aatggttaac atagtgcatg gatttcttcc attggtacat   420
caataataat atccaacagc gctaatgaga tgtacgtctt gtttccagat gttacagatc   480
caactgcaaa tggtgcagcg tggcgctgct gggccgccca gtaacgagaa tactgagcac   540
acagaagaat gactgaatct gtgaacagac acttctgcat cgtggtgtaa taataaggag   600
aatactgatg agcacacacg ctgaagaatc tgtaaatagg cggcgatgag gatgggacaa   660
aagaaagcca aggattggcg atacctgggc tggggaaact gtacgggtaa aaacttaata   720 aggggggttta a                                                        731

<210> SEQ ID NO 141
<211> LENGTH: 704
<212> TYPE: DNA
<213> ORGANISM: Artificial Sequence
```

<220> FEATURE:
<223> OTHER INFORMATION: MZA15842 Processed consensus sequence

<400> SEQUENCE: 141

| | | |
|---|---|---|
| taaccacccg cctggctaat tgttccgacc attttatag cctgcatggc ttacattgtc | 60 |
| ttcacgaggg tcaacaggat attcagattg cgcatttgga cttaaaacca gcaaatatat | 120 |
| tacttgacag tgacatggtt cctaaacttg ctgattttgg tatgtcaagg ctcttcagtc | 180 |
| tcgaacaagt ttatatcctt gcttccaagc ctatgggaac aatgtaagct cattaagttt | 240 |
| actgaatgtg ctttcttgat cttatatggc ttgcaacacc tttgaaactt atttggttta | 300 |
| aaagacacat ttaattttcc ttcattagta catgtgtcct gaagtataag gaaaccttag | 360 |
| ttcgttaact caaaagattt ctatttggct aagtttatag agaagagtat tagcatatac | 420 |
| catattaaaa agctagctat gaaaatatat ttcatagtgg gtttaatgat gatcatttga | 480 |
| tactccctct gccccaattt ataatccgtt taactttttt actctaagtt tgatcgactc | 540 |
| gtcttattca aaactatgc gagaaaatgg aaaattcaaa gccatactta agcatatta | 600 |
| tatgctaaat gacatcacag taaaaattaa taacaattat gatttttta ataggacgaa | 660 |
| ttggtcaaag ttagggtaaa aaagtcaaac aaattataaa ttgg | 704 |

<210> SEQ ID NO 142
<211> LENGTH: 665
<212> TYPE: DNA
<213> ORGANISM: Artificial Sequence
<220> FEATURE:
<223> OTHER INFORMATION: MZA1851 Processed consensus sequence

<400> SEQUENCE: 142

| | | |
|---|---|---|
| aaaaaggaaa tttttttttt taaaaaaaac ggaggctcta acagggctct gggtagtggc | 60 |
| ccaaactgtg ccaatatgga taatggaaga ttcttggggc agagtattaa gggaagttgc | 120 |
| ttttttcttc ttcttttggt tggtcttttt aagctgaatg gatgacatga ttgcctatgt | 180 |
| tatgtattgg gtaattttag ttgtcaaaat atatctttac agctatacgc tatcgctgtg | 240 |
| ctctgagcac ctcaaaacat ccaggtgatg acatctacac atggggttgg ggaggcgcca | 300 |
| atgggacttt tttcgaagag ggccattctt ccggtggaca gctggtgagt tgcttttcaga | 360 |
| ccacaactgt ttccgcttga tggcaacaat gtgcggcatg cataatcccc acaggacacc | 420 |
| attcatatgg atatggtcga actgacttgc tacttgcagg gacatggaaa cgacgtagac | 480 |
| tattttgagc ctatgatggt tcccttggc acgaatgcca gagccgtcca tgtatcgtgt | 540 |
| ggcttcaatc atactggtgc aatttacgag tgctccgagg actttgactg acgtgagact | 600 |
| tgcagacagc agatccgcat gtcttggaga cttaggttag ttatcaaata tactcgctga | 660 |
| ggaaa | 665 |

<210> SEQ ID NO 143
<211> LENGTH: 698
<212> TYPE: DNA
<213> ORGANISM: Artificial Sequence
<220> FEATURE:
<223> OTHER INFORMATION: MZA8761 Processed consensus sequence

<400> SEQUENCE: 143

| | | |
|---|---|---|
| tgccaaaggg ggaacagtta aggctttata gaagggraag atttggttca ggtaactggg | 60 |
| ctcacatttg ttactatttg gaatcatagg ggttcaagca tttaaaaaga actgggatcc | 120 |
| ctaccaccag tttggagtgt tccacaaata cactttatg tccttgggca tcgccaaggg | 180 |

```
ctgctttttt ttctttgggt attcctgtta actcagatgc tcaaaaattg ggacaatatt      240
gacatgccct cttgattaga agtgtttgta gtttgtaatt tgcatcttat actttcatga      300
gtactcgagc cattgttgtg ttctcagttg atgtaatttc attatttaaa cttcttgttg      360
ggttgtctaa tggaatgcaa aaaaaatact tgaaaaatga cagatagcag atccagcagc      420
aattgaggca atggtagata agtaattgc tgataatcca aagcaacttg agcagtaccg       480
```

(correction line 480):
```
aattgaggca atggtagata agtaattgc tgataatcca aagcaacttg agcagtaccg       480
```

```
tgctggaaaa actaagctac aaggatttt tgctggccag gtttgtcaat tgatgactag       540
cactgtttgt cccttcagct aggatgtatt atcagtgatc atatttgttt caattgatta      600
taggtgatga aagcatcgaa gggaaggcca acccagtttt gttgaataaa attcttgaaa      660
aattcttgga gagaagtttt tgctaaattt tatataaa                              698

<210> SEQ ID NO 144
<211> LENGTH: 521
<212> TYPE: DNA
<213> ORGANISM: Artificial Sequence
<220> FEATURE:
<223> OTHER INFORMATION: MZA11455 Processed consensus sequence

<400> SEQUENCE: 144
ttgaggcaat ttaaataagc attgcaggga aggcccagta caaacgttca accttctgac       60
tgacacatgt tgtggaacta accctcagca taggagcaag agaaaaatga ctgggaagag      120
aatgactggg aagagagatt gtttgcatgc acgtagcaga tatctgagag ctacagagga      180
aagctgggaa atagaagaag ctctaaaaca aggagtgttt ctggaaattc tttagttttc      240
aaaaaacact ttctgaaaat gtgtgtacaa gaaaattcca ggaaggtgaa attgcttcgt      300
tgactgcagt gggaagggga aagagagaag ctagaatctc atgtcgagta atccagtaca      360
atgtgttctt ttgtctggtc taaattcttg taacagctct tcctatgatg gaagaatcca      420
ttcaacaatt ccacctatga ttactggatt gagtatgttg aataggttgg ttgaggctat      480
ctagtaattt tatgactatt taatttattt ataactattt a                          521

<210> SEQ ID NO 145
<211> LENGTH: 18
<212> TYPE: DNA
<213> ORGANISM: Artificial Sequence
<220> FEATURE:
<223> OTHER INFORMATION: Oligonucleotide primer C00060-01-F1

<400> SEQUENCE: 145
ggtcttcgcc ggccttc                                                     18

<210> SEQ ID NO 146
<211> LENGTH: 25
<212> TYPE: DNA
<213> ORGANISM: Artificial Sequence
<220> FEATURE:
<223> OTHER INFORMATION: Oligonucleotide primer C00060-02-F1

<400> SEQUENCE: 146
ggtcagtagc taattcttgc agctc                                            25

<210> SEQ ID NO 147
<211> LENGTH: 17
<212> TYPE: DNA
<213> ORGANISM: Artificial Sequence
<220> FEATURE:
<223> OTHER INFORMATION: Oligonucleotide primer C00060-01-F-Taq

<400> SEQUENCE: 147
```
tcttcgccgg cctttct                                                          17

<210> SEQ ID NO 148
<211> LENGTH: 26
<212> TYPE: DNA
<213> ORGANISM: Artificial Sequence
<220> FEATURE:
<223> OTHER INFORMATION: Oligonucleotide primer C00060-02-F-Taq

<400> SEQUENCE: 148
cagagcaatt gtttatcaag aaagct                                                26

<210> SEQ ID NO 149
<211> LENGTH: 18
<212> TYPE: DNA
<213> ORGANISM: Artificial Sequence
<220> FEATURE:
<223> OTHER INFORMATION: Oligonucleotide primer C00060-01-R1

<400> SEQUENCE: 149
gggaccgtcg atgccgac                                                         18

<210> SEQ ID NO 150
<211> LENGTH: 29
<212> TYPE: DNA
<213> ORGANISM: Artificial Sequence
<220> FEATURE:
<223> OTHER INFORMATION: Oligonucleotide primer C00060-02-R1

<400> SEQUENCE: 150
tttcctcaag aattggccca tagtaacaa                                             29

<210> SEQ ID NO 151
<211> LENGTH: 22
<212> TYPE: DNA
<213> ORGANISM: Artificial Sequence
<220> FEATURE:
<223> OTHER INFORMATION: Oligonucleotide primer C00060-01-R-Taq

<400> SEQUENCE: 151
gcggatcaga tacagacgaa ca                                                    22

<210> SEQ ID NO 152
<211> LENGTH: 24
<212> TYPE: DNA
<213> ORGANISM: Artificial Sequence
<220> FEATURE:
<223> OTHER INFORMATION: Oligonucleotide primer C00060-02-R-Taq

<400> SEQUENCE: 152
ggttgaccat cacatttctt caga                                                  24

<210> SEQ ID NO 153
<211> LENGTH: 25
<212> TYPE: DNA
<213> ORGANISM: Artificial Sequence
<220> FEATURE:
<223> OTHER INFORMATION: Oligonucleotide primer FLP111RB

<400> SEQUENCE: 153
caggttatac tcgaccggaa tcaaa                                                 25

<210> SEQ ID NO 154
<211> LENGTH: 30
<212> TYPE: DNA

```
<213> ORGANISM: Artificial Sequence
<220> FEATURE:
<223> OTHER INFORMATION: Oligonucleotide probe C00060-01-PCA

<400> SEQUENCE: 154
acggacgcgg aggaacagga agacgattca                                         30

<210> SEQ ID NO 155
<211> LENGTH: 29
<212> TYPE: DNA
<213> ORGANISM: Artificial Sequence
<220> FEATURE:
<223> OTHER INFORMATION: Oligonucleotide probe C00060-02-PCA

<400> SEQUENCE: 155
acggacgcgg agctcgaccg gaatcaaaa                                          29

<210> SEQ ID NO 156
<211> LENGTH: 26
<212> TYPE: DNA
<213> ORGANISM: Artificial Sequence
<220> FEATURE:
<223> OTHER INFORMATION: Oligonucleotide probe C00060-01-P-Taq

<400> SEQUENCE: 156
cctctacccg gcacactgaa tcgtct                                             26

<210> SEQ ID NO 157
<211> LENGTH: 32
<212> TYPE: DNA
<213> ORGANISM: Artificial Sequence
<220> FEATURE:
<223> OTHER INFORMATION: Oligonucleotide probe C00060-02-P-Taq

<400> SEQUENCE: 157
cccaacaaaa tattcaggtt atactcgacc gg                                      32

<210> SEQ ID NO 158
<211> LENGTH: 259
<212> TYPE: DNA
<213> ORGANISM: Artificial Sequence
<220> FEATURE:
<223> OTHER INFORMATION: SNP Sequence for Marker PHD0001-01

<400> SEQUENCE: 158
tttagaaact cagctagtgc ttttggcaac caaacccccac agccaaacag ctgcatgtct       60
agaggtagag gagtagactc ctcacaccgg gtaagtctag ctgagtatta gtatactcag      120
ccttgcttgt ggcataaattt ttacaggttc tctggaggaa atggttgctg gagtgacttg     180
gccgtccatc ttgccaccgg gttggactgt cgagtgggac cctgccttgg ctgaggagga     240
gcatgaggag tgatgggac                                                   259

<210> SEQ ID NO 159
<211> LENGTH: 34
<212> TYPE: DNA
<213> ORGANISM: Artificial Sequence
<220> FEATURE:
<223> OTHER INFORMATION: Invader Oligo for Marker PHD0001-01

<400> SEQUENCE: 159
tgccacaagc aaggctgagt atactaatac tcat                                    34

<210> SEQ ID NO 160
<211> LENGTH: 26
```

```
<212> TYPE: DNA
<213> ORGANISM: Artificial Sequence
<220> FEATURE:
<223> OTHER INFORMATION: Invader Probe for Marker PHD0001-01

<400> SEQUENCE: 160
cgcgccgagg gctagactta cccggt                                          26

<210> SEQ ID NO 161
<211> LENGTH: 22
<212> TYPE: DNA
<213> ORGANISM: Artificial Sequence
<220> FEATURE:
<223> OTHER INFORMATION: Forward Oligonucleotide Primer for Marker
      PHD0001-01

<400> SEQUENCE: 161
tagtgctttt ggcaaccaaa cc                                              22

<210> SEQ ID NO 162
<211> LENGTH: 22
<212> TYPE: DNA
<213> ORGANISM: Artificial Sequence
<220> FEATURE:
<223> OTHER INFORMATION: Reverse Oligonucleotide Primer for Marker
      PHD0001-01

<400> SEQUENCE: 162
ccatttcctc cagagaacct gt                                              22

<210> SEQ ID NO 163
<211> LENGTH: 259
<212> TYPE: DNA
<213> ORGANISM: Artificial Sequence
<220> FEATURE:
<223> OTHER INFORMATION: SNP Sequence for Marker PHD0002-01

<400> SEQUENCE: 163
ggcttcccca tctctctatt tatttaccgt tagtttattt ccgctgcact tcgaacaatg     60
atggttactt ttgcaaaaac tccgaggatg atgatgatgg tgatgtaata atttaatact    120
ctgacatgta tggtttttatg ctttattgta tttgctctgt gactcacctt cgagtgagat   180
tgtggtactt gatcctgtca gtggccgtgt cggactagat ccgagggatt gacgggttat    240
tcccaattaa gtgtggtct                                                  259

<210> SEQ ID NO 164
<211> LENGTH: 36
<212> TYPE: DNA
<213> ORGANISM: Artificial Sequence
<220> FEATURE:
<223> OTHER INFORMATION: Invader Oligo for Marker PHD0002-01

<400> SEQUENCE: 164
ggccactgac aggatcaagt accacaatct cactct                               36

<210> SEQ ID NO 165
<211> LENGTH: 27
<212> TYPE: DNA
<213> ORGANISM: Artificial Sequence
<220> FEATURE:
<223> OTHER INFORMATION: Invader Probe for Marker PHD0002-01

<400> SEQUENCE: 165
cgcgccgagg gaaggtgagt cacagag                                         27
```

```
<210> SEQ ID NO 166
<211> LENGTH: 23
<212> TYPE: DNA
<213> ORGANISM: Artificial Sequence
<220> FEATURE:
<223> OTHER INFORMATION: Forward Oligonucleotide Primer for Marker
      PHD0002-01

<400> SEQUENCE: 166
ggatgatgat gatggtgatg taa                                              23

<210> SEQ ID NO 167
<211> LENGTH: 22
<212> TYPE: DNA
<213> ORGANISM: Artificial Sequence
<220> FEATURE:
<223> OTHER INFORMATION: Reverse Oligonucleotide Primer for Marker
      PHD0002-01

<400> SEQUENCE: 167
ccgtcaatcc ctcggatcta gt                                               22

<210> SEQ ID NO 168
<211> LENGTH: 269
<212> TYPE: DNA
<213> ORGANISM: Artificial Sequence
<220> FEATURE:
<223> OTHER INFORMATION: SNP Sequence for Marker PHD0003-01

<400> SEQUENCE: 168
acgctgctgc gacaaggccc tcgcccgcat ccccactcga ggggcgagga caagctatca      60
aagccgaaga gccggaggtc cgaccgcagg tggcgccgag aaaccttctc tggctgccac     120
cacctcagca ccgacgacgg cagccacctg cccaccaaca cccgccgggc cgtgaccaat     180
gtgctcggtt ggcactgttg ggtcatgcgc agggttgcct cgagtcgcgg caccggttcc     240
gcagtcgaga aggcgcggga ggaggcgcg                                       269

<210> SEQ ID NO 169
<211> LENGTH: 21
<212> TYPE: DNA
<213> ORGANISM: Artificial Sequence
<220> FEATURE:
<223> OTHER INFORMATION: Invader Oligo for Marker PHD0003-01

<400> SEQUENCE: 169
tggctgccgt cgtcggtgct t                                                21

<210> SEQ ID NO 170
<211> LENGTH: 24
<212> TYPE: DNA
<213> ORGANISM: Artificial Sequence
<220> FEATURE:
<223> OTHER INFORMATION: Invader Probe for Marker PHD0003-01

<400> SEQUENCE: 170
cgcgccgagg gaggtggtgg cagc                                             24

<210> SEQ ID NO 171
<211> LENGTH: 22
<212> TYPE: DNA
<213> ORGANISM: Artificial Sequence
<220> FEATURE:
<223> OTHER INFORMATION: Forward Oligonucleotide Primer for Marker
      PHD0003-01
```

-continued

<400> SEQUENCE: 171
ggacaagcta tcaaagccga ag                                             22

<210> SEQ ID NO 172
<211> LENGTH: 20
<212> TYPE: DNA
<213> ORGANISM: Artificial Sequence
<220> FEATURE:
<223> OTHER INFORMATION: Reverse Oligonucleotide Primer for Marker
      PHD0003-01

<400> SEQUENCE: 172
caaccgagca cattggtcac                                                20

<210> SEQ ID NO 173
<211> LENGTH: 279
<212> TYPE: DNA
<213> ORGANISM: Artificial Sequence
<220> FEATURE:
<223> OTHER INFORMATION: SNP Sequence for marker PHD0004-01

<400> SEQUENCE: 173
cacgaacacc ccaaaccaca tgccgaggct gtagagtcgc cccagggttg aatcgaccga     60
ggcggtcatt tctcccctga ccacggcgaa gagcggcacg gtgcgcaact ggttttcctg   120
atagtgggca ccggcgtgaa attaggccgc caactcgcgc cccgatgcac cgacccacaa   180
tcgccaaggc ttctgctgcg caaacgagtt ccccgctgtg atggccgaag cacagcacag   240
caggtggacg gcagcggacc agtcgcggcg gcgcacaga                          279

<210> SEQ ID NO 174
<211> LENGTH: 24
<212> TYPE: DNA
<213> ORGANISM: Artificial Sequence
<220> FEATURE:
<223> OTHER INFORMATION: Invader Oligo for marker PHD0004-01

<400> SEQUENCE: 174
tggcggccta atttcacgcc ggtt                                           24

<210> SEQ ID NO 175
<211> LENGTH: 28
<212> TYPE: DNA
<213> ORGANISM: Artificial Sequence
<220> FEATURE:
<223> OTHER INFORMATION: Invader Probe for marker PHD0004-01

<400> SEQUENCE: 175
cgcgccgagg gcccactatc aggaaaac                                       28

<210> SEQ ID NO 176
<211> LENGTH: 21
<212> TYPE: DNA
<213> ORGANISM: Artificial Sequence
<220> FEATURE:
<223> OTHER INFORMATION: Forward oligonucleotide primer for marker
      PHD0004-01

<400> SEQUENCE: 176
ggtcatttct cccctgacca c                                              21

<210> SEQ ID NO 177
<211> LENGTH: 19
<212> TYPE: DNA
<213> ORGANISM: Artificial Sequence

```
<220> FEATURE:
<223> OTHER INFORMATION: Reverse oligonucleotide primer for marker
      PHD0004-01

<400> SEQUENCE: 177
agcagaagcc ttggcgatt                                               19

<210> SEQ ID NO 178
<211> LENGTH: 300
<212> TYPE: DNA
<213> ORGANISM: Artificial Sequence
<220> FEATURE:
<223> OTHER INFORMATION: SNP Sequence for marker PHD0005-01

<400> SEQUENCE: 178
ttggggcgag cagggaggag aagaggaaca gcggcttcgg gtgttatagg cgcagggtaa    60
aggaggggac gaacaggtca cgctggcgcg atgccgcacc tatatgacga gtccgggctg   120
aggacgttaa ccgggcggcg ctagaatcct ggggcttcgg cagaggccgt tgcgggagta   180
gcggcgggca ggtgtgccgc cagcgctgta cgcggggtcg gggcacggag gttgttgcgc   240
taggggtccg cgatttccgt gaatcgggca cgagctcacc agcgccaccg gttttgcgca   300

<210> SEQ ID NO 179
<211> LENGTH: 23
<212> TYPE: DNA
<213> ORGANISM: Artificial Sequence
<220> FEATURE:
<223> OTHER INFORMATION: Invader Oligo for marker PHD0005-01

<400> SEQUENCE: 179
cgctactccc gcaacggcct ctt                                          23

<210> SEQ ID NO 180
<211> LENGTH: 22
<212> TYPE: DNA
<213> ORGANISM: Artificial Sequence
<220> FEATURE:
<223> OTHER INFORMATION: Invader Probe for marker PHD0005-01

<400> SEQUENCE: 180
cgcgccgagg gccgaagccc ca                                           22

<210> SEQ ID NO 181
<211> LENGTH: 22
<212> TYPE: DNA
<213> ORGANISM: Artificial Sequence
<220> FEATURE:
<223> OTHER INFORMATION: Forward oligonucleotide primer for marker
      PHD0005-01

<400> SEQUENCE: 181
ctatatgacg agtccgggct ga                                           22

<210> SEQ ID NO 182
<211> LENGTH: 19
<212> TYPE: DNA
<213> ORGANISM: Artificial Sequence
<220> FEATURE:
<223> OTHER INFORMATION: Reverse oligonucleotide primer for marker
      PHD0005-01

<400> SEQUENCE: 182
acccctagcg caacaacct                                               19
```

-continued

<210> SEQ ID NO 183
<211> LENGTH: 290
<212> TYPE: DNA
<213> ORGANISM: Artificial Sequence
<220> FEATURE:
<223> OTHER INFORMATION: SNP sequence for marker PHD0006-01

<400> SEQUENCE: 183

```
cgaagcggag gaaatgtagg gagggagaag aagaccactg ccggctgggt ggataagtta        60
gctgggtgac cctggaatgt ggggcccgcc tggcggcgac gcgaaggcca cacgagcgag       120 tgagggcgt tgggtcgtgc ggtatcggaa aaaaagaat gggccgaaag tgaggattcg        180
gcccaagtag tgttttattg ttttctttt tcttatttt tttcaaattc aactttaaat        240
tcccatttaa attcaaattt agtggtggat ctatcttcac attaatttcc                  290
```

<210> SEQ ID NO 184
<211> LENGTH: 23
<212> TYPE: DNA
<213> ORGANISM: Artificial Sequence
<220> FEATURE:
<223> OTHER INFORMATION: Invader oligo for marker PHD0006-01

<400> SEQUENCE: 184

```
tcgctcgtgt ggccttcgcg tct                                                23
```

<210> SEQ ID NO 185
<211> LENGTH: 21
<212> TYPE: DNA
<213> ORGANISM: Artificial Sequence
<220> FEATURE:
<223> OTHER INFORMATION: Invader probe for marker PHD0006-01

<400> SEQUENCE: 185

```
cgcgccgagg gccgccaggc g                                                  21
```

<210> SEQ ID NO 186
<211> LENGTH: 22
<212> TYPE: DNA
<213> ORGANISM: Artificial Sequence
<220> FEATURE:
<223> OTHER INFORMATION: Forward oligonucleotide primer for marker
      PHD0006-01

<400> SEQUENCE: 186

```
ggctgggtgg ataagttagc tg                                                 22
```

<210> SEQ ID NO 187
<211> LENGTH: 21
<212> TYPE: DNA
<213> ORGANISM: Artificial Sequence
<220> FEATURE:
<223> OTHER INFORMATION: Reverse oligonucleotide primer for marker
      PHD0006-01

<400> SEQUENCE: 187

```
cactttcggc ccattctttt t                                                  21
```

<210> SEQ ID NO 188
<211> LENGTH: 300
<212> TYPE: DNA
<213> ORGANISM: Artificial Sequence
<220> FEATURE:
<223> OTHER INFORMATION: SNP Sequence for marker PHD0007-01

<400> SEQUENCE: 188

```
caacttaaac atggcatggg tgaacttatt tattttcaat atttattta ttaaaactag    60 tgctatgttt ctccaaatta gagtttaaat gctatgtgtc ccttaatata ttaatatatg   120
ggtactaaca catttatttt actatccaca aatgcacaat caagtaaaaa ctcagcatga   180
tgcataattt atttgagtgt cttctattaa ttatttattg tatagatgag gtgtccacat   240
gaaatggtaa atagggataa cccacacaca tgtaaaggaa tataatctct ccttttagat   300

<210> SEQ ID NO 189
<211> LENGTH: 58
<212> TYPE: DNA
<213> ORGANISM: Artificial Sequence
<220> FEATURE:
<223> OTHER INFORMATION: Invader oligo for marker PHD0007-01

<400> SEQUENCE: 189
tttctccaaa ttagagttta aatgctatgt gtcccttaat atattaatat atgggtat     58

<210> SEQ ID NO 190
<211> LENGTH: 36
<212> TYPE: DNA
<213> ORGANISM: Artificial Sequence
<220> FEATURE:
<223> OTHER INFORMATION: Invader probe for marker PHD0007-01

<400> SEQUENCE: 190
cgcgccgagg ctaacacatt tattttacta tccaca                              36

<210> SEQ ID NO 191
<211> LENGTH: 22
<212> TYPE: DNA
<213> ORGANISM: Artificial Sequence
<220> FEATURE:
<223> OTHER INFORMATION: Forward oligonucleotide primer for marker
      PHD0007-01

<400> SEQUENCE: 191
ttaaacatgg catgggtgaa ct                                             22

<210> SEQ ID NO 192
<211> LENGTH: 24
<212> TYPE: DNA
<213> ORGANISM: Artificial Sequence
<220> FEATURE:
<223> OTHER INFORMATION: Reverse oligonucleotide primer for marker
      PHD0007-01

<400> SEQUENCE: 192
tgcatcatgc tgagtttta cttg                                            24

<210> SEQ ID NO 193
<211> LENGTH: 274
<212> TYPE: DNA
<213> ORGANISM: Artificial Sequence
<220> FEATURE:
<223> OTHER INFORMATION: SNP Sequence for marker PHD0008-01

<400> SEQUENCE: 193
cggcggccac aagtcagtcg ccgaaaatta cctgttcttt tcggtgggcc tctgacggcc    60
gccgaaaata acaagtgccg aaaatagtat ttaaaaatac aaaaaataac agaaaattca   120
tacaataaca gaaaattcat acttgagtcc acaacataaa acttaagtcc atacaaacat   180
aaagtccaca aatagtccat acaaacataa agtccacaa tagtccatta caaagcacaa   240
tgccgcacaa agctaactcc atcacatatc gggg                               274
```

<210> SEQ ID NO 194
<211> LENGTH: 51
<212> TYPE: DNA
<213> ORGANISM: Artificial Sequence
<220> FEATURE:
<223> OTHER INFORMATION: Invader oligo for marker PHD0008-01

<400> SEQUENCE: 194
tttgtatgga ctatttgtgg actttatgtt tgtatggact taagttttat t    51

<210> SEQ ID NO 195
<211> LENGTH: 29
<212> TYPE: DNA
<213> ORGANISM: Artificial Sequence
<220> FEATURE:
<223> OTHER INFORMATION: Invader probe for marker PHD0008-01

<400> SEQUENCE: 195
cgcgccgagg gttgtggact caagtatga    29

<210> SEQ ID NO 196
<211> LENGTH: 22
<212> TYPE: DNA
<213> ORGANISM: Artificial Sequence
<220> FEATURE:
<223> OTHER INFORMATION: Forward oligonucleotide primer for marker
      PHD0008-01

<400> SEQUENCE: 196
cgaaaataac aagtgccgaa aa    22

<210> SEQ ID NO 197
<211> LENGTH: 23
<212> TYPE: DNA
<213> ORGANISM: Artificial Sequence
<220> FEATURE:
<223> OTHER INFORMATION: Reverse oligonucleotide primer for marker
      PHD0008-01

<400> SEQUENCE: 197
ggcattgtgc tttgtaatgg act    23

<210> SEQ ID NO 198
<211> LENGTH: 259
<212> TYPE: DNA
<213> ORGANISM: Artificial Sequence
<220> FEATURE:
<223> OTHER INFORMATION: SNP sequence for marker PHD0009-01

<400> SEQUENCE: 198
cgttggagtt gtgtccacta ccttcagaag cgaaaaactc gttgacgaag tcgtgtaacg    60
ggtttagatt ctaaagaaaa aagaagacat taataacgat attagttaca tgtatgacca   120
ctattcaaac aaattgtttc tcaaactaac ctctcatgga gtagctccct ccctgcata    180 tgctcctcct ggtgctggta tgagcggtgg tggcgtgttg tggcccatga ccccggatcc   240
ctacaaaatc aagtttagt                                                259

<210> SEQ ID NO 199
<211> LENGTH: 49
<212> TYPE: DNA
<213> ORGANISM: Artificial Sequence
<220> FEATURE:
<223> OTHER INFORMATION: Invader oligo for marker PHD0009-01

<400> SEQUENCE: 199
gggagctact ccatgagagg ttagtttgag aaacaatttg tttgaatat          49

<210> SEQ ID NO 200
<211> LENGTH: 34
<212> TYPE: DNA
<213> ORGANISM: Artificial Sequence
<220> FEATURE:
<223> OTHER INFORMATION: Invader probe for marker PHD0009-01

<400> SEQUENCE: 200
cgcgccgagg gtggtcatac atgtaactaa tatc                          34

<210> SEQ ID NO 201
<211> LENGTH: 24
<212> TYPE: DNA
<213> ORGANISM: Artificial Sequence
<220> FEATURE:
<223> OTHER INFORMATION: Forward oligonucleotide primer for marker
      PHD0009-01

<400> SEQUENCE: 201
aagtcgtgta acgggtttag attc                                     24

<210> SEQ ID NO 202
<211> LENGTH: 19
<212> TYPE: DNA
<213> ORGANISM: Artificial Sequence
<220> FEATURE:
<223> OTHER INFORMATION: Reverse oligonucleotide primer for marker
      PHD0009-01

<400> SEQUENCE: 202
cagcaccagg aggagcata                                           19

<210> SEQ ID NO 203
<211> LENGTH: 250
<212> TYPE: DNA
<213> ORGANISM: Artificial Sequence
<220> FEATURE:
<223> OTHER INFORMATION: SNP sequence for marker PHD0010-01

<400> SEQUENCE: 203
aaagatttga aattagattg atacaaacga caagtcttaa ctaaattgaa gcacctgagg     60
tggaggtggc ggagcatgta atccccactg aggcatcgac ggctgaaact gagggaaaac   120
aaatggttgt tgttgtgcct gctgtggaaa ccaagaccgt tgcaaatata atatgttagt   180
tatagaacca atatcgagcg tgttgagaag aaataagaca ctcacgttca ttgcttgttg   240
ggcctgtgcg                                                         250

<210> SEQ ID NO 204
<211> LENGTH: 34
<212> TYPE: DNA
<213> ORGANISM: Artificial Sequence
<220> FEATURE:
<223> OTHER INFORMATION: Invader oligo for marker PHD0010-01

<400> SEQUENCE: 204
gcaggcacaa caacaaccat ttgttttccc tcat                          34

<210> SEQ ID NO 205
<211> LENGTH: 26
<212> TYPE: DNA
<213> ORGANISM: Artificial Sequence

```
<220> FEATURE:
<223> OTHER INFORMATION: Invader probe for marker PHD0010-01

<400> SEQUENCE: 205
cgcgccgagg gtttcagccg tcgatg                                          26

<210> SEQ ID NO 206
<211> LENGTH: 22
<212> TYPE: DNA
<213> ORGANISM: Artificial Sequence
<220> FEATURE:
<223> OTHER INFORMATION: Forward oligonucleotide primer for marker
      PHD0010-01

<400> SEQUENCE: 206
ggagcatgta atccccactg ag                                              22

<210> SEQ ID NO 207
<211> LENGTH: 22
<212> TYPE: DNA
<213> ORGANISM: Artificial Sequence
<220> FEATURE:
<223> OTHER INFORMATION: Reverse oligonucleotide primer for marker
      PHD0010-01

<400> SEQUENCE: 207
tctcaacacg ctcgatattg gt                                              22

<210> SEQ ID NO 208
<211> LENGTH: 259
<212> TYPE: DNA
<213> ORGANISM: Artificial Sequence
<220> FEATURE:
<223> OTHER INFORMATION: SNP sequence for marker PHD0011-01

<400> SEQUENCE: 208
atttccggcg gttgtggcag gccgccaaaa atagcagata attttcggcg gctataggtg     60
ggccatcgaa aattacattg gccgccgaaa atgttcaaca gtgttgttgt gatagcaacc    120
aacaggtatg agccacaata ctacacattg caacttggga aagtaattta ctggtcacca    180
tatttccgaa tagctggtta tgatatgata tttacaaatc ttccaattca ttccttcagc    240
ttaaatgaat ctcattaat                                                 259

<210> SEQ ID NO 209
<211> LENGTH: 40
<212> TYPE: DNA
<213> ORGANISM: Artificial Sequence
<220> FEATURE:
<223> OTHER INFORMATION: Invader oligo for marker PHD0011-01

<400> SEQUENCE: 209
agttgcaatg tgtagtattg tggctcatac ctgttggttt                           40

<210> SEQ ID NO 210
<211> LENGTH: 29
<212> TYPE: DNA
<213> ORGANISM: Artificial Sequence
<220> FEATURE:
<223> OTHER INFORMATION: Invader probe for marker PHD0011-01

<400> SEQUENCE: 210
cgcgccgagg gctatcacaa caacactgt                                       29

<210> SEQ ID NO 211
```

```
<211> LENGTH: 22
<212> TYPE: DNA
<213> ORGANISM: Artificial Sequence
<220> FEATURE:
<223> OTHER INFORMATION: Forward oligonucleotide primer for marker
      PHD0011-01

<400> SEQUENCE: 211
taggtgggcc atcgaaaatt ac                                              22

<210> SEQ ID NO 212
<211> LENGTH: 24
<212> TYPE: DNA
<213> ORGANISM: Artificial Sequence
<220> FEATURE:
<223> OTHER INFORMATION: Reverse oligonucleotide primer for marker
      PHD0011-01

<400> SEQUENCE: 212
ttcggaaata tggtgaccag taaa                                            24

<210> SEQ ID NO 213
<211> LENGTH: 269
<212> TYPE: DNA
<213> ORGANISM: Artificial Sequence
<220> FEATURE:
<223> OTHER INFORMATION: SNP sequence for marker PHD0012-01

<400> SEQUENCE: 213
ttgtaaaaaa caaggttttg taaatggatt tatttttatg ctcaaactta aattgaacaa     60
ttcaatcacg cacaattgct atgctgacag aagtttatga caagtttgag cataatgttg    120
taataataat gagacccttc atgatcttgt tgttattcca catttccatc tctcctcgaa    180
gcatagcagt gcccaccatt ttctaccgag tcagcaacaa taatctaggc tgaaagaaca    240
atggacaaca gcttcgtgtg ttgtccatc                                     269

<210> SEQ ID NO 214
<211> LENGTH: 51
<212> TYPE: DNA
<213> ORGANISM: Artificial Sequence
<220> FEATURE:
<223> OTHER INFORMATION: Invader oligo for marker PHD0012-01

<400> SEQUENCE: 214
gtggaataac aacaagatca tgaagggtct cattattatt acaacattat t              51

<210> SEQ ID NO 215
<211> LENGTH: 31
<212> TYPE: DNA
<213> ORGANISM: Artificial Sequence
<220> FEATURE:
<223> OTHER INFORMATION: Invader probe for marker PHD0012-01

<400> SEQUENCE: 215
cgcgccgagg gctcaaactt gtcataaact t                                    31

<210> SEQ ID NO 216
<211> LENGTH: 22
<212> TYPE: DNA
<213> ORGANISM: Artificial Sequence
<220> FEATURE:
<223> OTHER INFORMATION: Forward oligonucleotide primer for marker
      PHD0012-01

<400> SEQUENCE: 216
```

-continued

```
tcaatcacgc acaattgcta tg                                              22

<210> SEQ ID NO 217
<211> LENGTH: 22
<212> TYPE: DNA
<213> ORGANISM: Artificial Sequence
<220> FEATURE:
<223> OTHER INFORMATION: Reverse oligonucleotide primer for marker
      PHD0012-01

<400> SEQUENCE: 217
agaaaatggt gggcactgct at                                              22

<210> SEQ ID NO 218
<211> LENGTH: 259
<212> TYPE: DNA
<213> ORGANISM: Artificial Sequence
<220> FEATURE:
<223> OTHER INFORMATION: SNP sequence for marker PHD0013-01

<400> SEQUENCE: 218
tacaatattt gcctatggtg ttacaaggag tggaaagata catacgatgc atgtgggaaa     60
acttattaca atattttcc tttaataagt tttacctttg tagagtgtat gtttctagtc    120
ataggctttg aagtatgcct catgctacca attaacatgc aaaaacttgg actaatctta   180
ctgatactaa gatctaacat agttgtcaac ctccttggtt ggacatttta gttgcttttg   240
ttgtattaag cttttaatt                                                 259

<210> SEQ ID NO 219
<211> LENGTH: 45
<212> TYPE: DNA
<213> ORGANISM: Artificial Sequence
<220> FEATURE:
<223> OTHER INFORMATION: Invader oligo for marker PHD0013-01

<400> SEQUENCE: 219
ccaagttttt gcatgttaat tggtagcatg aggcatactt caaat                     45

<210> SEQ ID NO 220
<211> LENGTH: 31
<212> TYPE: DNA
<213> ORGANISM: Artificial Sequence
<220> FEATURE:
<223> OTHER INFORMATION: Invader probe for marker PHD0013-01

<400> SEQUENCE: 220
cgcgccgagg gcctatgact agaaacatac a                                    31

<210> SEQ ID NO 221
<211> LENGTH: 22
<212> TYPE: DNA
<213> ORGANISM: Artificial Sequence
<220> FEATURE:
<223> OTHER INFORMATION: Forward oligonucleotide primer for marker
      PHD0013-01

<400> SEQUENCE: 221
acatacgatg catgtgggaa aa                                              22

<210> SEQ ID NO 222
<211> LENGTH: 22
<212> TYPE: DNA
<213> ORGANISM: Artificial Sequence
<220> FEATURE:
<223> OTHER INFORMATION: Reverse oligonucleotide primer for marker
```

```
        PHD0013-01

<400> SEQUENCE: 222
aatgtccaac caaggaggtt ga                                              22

<210> SEQ ID NO 223
<211> LENGTH: 269
<212> TYPE: DNA
<213> ORGANISM: Artificial Sequence
<220> FEATURE:
<223> OTHER INFORMATION: SNP sequence for marker PHD0014-01

<400> SEQUENCE: 223
attggatttg tggtggggtg cgtgggcggg catcacgcgt ggcgatggca ctggaagcac     60
ggggaacagg gcaggtgtag ggtgggggca ggcgatggaa tggcgcggca tgcttgcggc    120
cgattgtcct tgcgtggatg gagggattg cgggctcgag gatgaggatg gcgggatgcg    180
cgcgcctttc gtcgatcgaa cgtgggcacg ggacgaggat tgcattgcgc ggccacgcgg    240
gggcgagatt ggcgtcgtcg gtgggatgt                                      269

<210> SEQ ID NO 224
<211> LENGTH: 24
<212> TYPE: DNA
<213> ORGANISM: Artificial Sequence
<220> FEATURE:
<223> OTHER INFORMATION: Invader oligo for marker PHD0014-01

<400> SEQUENCE: 224
ccgccatcct catcctcgag ccct                                            24

<210> SEQ ID NO 225
<211> LENGTH: 25
<212> TYPE: DNA
<213> ORGANISM: Artificial Sequence
<220> FEATURE:
<223> OTHER INFORMATION: Invader probe for marker PHD0014-01

<400> SEQUENCE: 225
cgcgccgagg gcaatcccct ccatc                                           25

<210> SEQ ID NO 226
<211> LENGTH: 18
<212> TYPE: DNA
<213> ORGANISM: Artificial Sequence
<220> FEATURE:
<223> OTHER INFORMATION: Forward oligonucleotide primer for marker
      PHD0014-01

<400> SEQUENCE: 226
cttgcggccg attgtcct                                                   18

<210> SEQ ID NO 227
<211> LENGTH: 18
<212> TYPE: DNA
<213> ORGANISM: Artificial Sequence
<220> FEATURE:
<223> OTHER INFORMATION: Reverse oligonucleotide primer for marker
      PHD0014-01

<400> SEQUENCE: 227
accgacgacg ccaatctc                                                   18

<210> SEQ ID NO 228
<211> LENGTH: 210
```

```
<212> TYPE: DNA
<213> ORGANISM: Artificial Sequence
<220> FEATURE:
<223> OTHER INFORMATION: SNP sequence for marker PHD0015-01

<400> SEQUENCE: 228
aattgctatt ttagcccttc taacgtgggc tctctgctat tatgtgaccc tctgtctatg      60
acttgtgtga ccatttgtgt ctatgatttg tgggactggt ggtaaaatag agaagttcac     120
aactgagagt gacaaaatag caaattctcc cacgggggcg ggggcacgac gcaccagtgt     180
ggacgtccac actatagcct tatagagtag                                       210

<210> SEQ ID NO 229
<211> LENGTH: 39
<212> TYPE: DNA
<213> ORGANISM: Artificial Sequence
<220> FEATURE:
<223> OTHER INFORMATION: Invader oligo for marker PHD0015-01

<400> SEQUENCE: 229
cccgtgggag aatttgctat tttgtcactc tcagttgtt                              39

<210> SEQ ID NO 230
<211> LENGTH: 32
<212> TYPE: DNA
<213> ORGANISM: Artificial Sequence
<220> FEATURE:
<223> OTHER INFORMATION: Invader probe for marker PHD0015-01

<400> SEQUENCE: 230
cgcgccgagg gaacttctct attttaccac ca                                     32

<210> SEQ ID NO 231
<211> LENGTH: 24
<212> TYPE: DNA
<213> ORGANISM: Artificial Sequence
<220> FEATURE:
<223> OTHER INFORMATION: Forward oligonucleotide primer for marker
      PHD0015-01

<400> SEQUENCE: 231
tgacttgtgt gaccatttgt gtct                                              24

<210> SEQ ID NO 232
<211> LENGTH: 19
<212> TYPE: DNA
<213> ORGANISM: Artificial Sequence
<220> FEATURE:
<223> OTHER INFORMATION: Reverse oligonucleotide primer for marker
      PHD0015-01

<400> SEQUENCE: 232
gtccacactg gtgcgtcgt                                                    19
```

POLYNUCLEOTIDES AND METHODS FOR MAKING PLANTS RESISTANT TO FUNGAL PATHOGENS

CROSS REFERENCE TO RELATED APPLICATIONS

This application is a continuation of Ser. No. 13/270,722 filed Oct. 11, 2011 now granted as U.S. Pat. No. 8,884,126, which is a continuation of U.S. application Ser. No. 11/774,121 filed Jul. 6, 2007, now granted as U.S. Pat. No. 8,084,671, which is a continuation of U.S. application Ser. No. 11/397,247 filed Apr. 4, 2006 and also claims priority to and the benefit of U.S. Provisional Application Nos. 60/668,241 and 60/675,664, filed on Apr. 4, 2005 and Apr. 28, 2005 respectively, which are herein incorporated by reference in their entirety.

THE NAMES OF THE PARTIES TO A JOINT RESEARCH AGREEMENT

A joint Research Project Agreement was executed on Feb. 18, 2002 for map-based cloning and gene expression studies of a maize gene(s) that confer(s) resistance to ASR. The names of the parties executing the joint Research Project Agreement are the University of Delaware and E.I. du Pont de Nemours and Company.

FIELD OF THE INVENTION

This invention relates to compositions and methods useful in creating or enhancing pathogen-resistance in plants. Additionally, the invention relates to plants that have been genetically transformed with the compositions of the invention.

BACKGROUND OF THE INVENTION

*Colletotrichum graminicola* (Ces.) (Cg), more commonly known as anthracnose, is the causative agent of anthracnose leaf blight, anthracnose stalk rot (ASR) and top dieback that affects *Zea mays* (L.), also known as maize or corn. It is the only known common stalk rot that also causes a leaf blight (Bergstrom, et al., (1999), *Plant Disease*, 83:596-608, White, D. G. (1998), *Compendium of Corn Diseases*, pp. 1-78). It has been known to occur in the United States since 1855 and has been reported in the Americas, Europe, Africa, Asia, and Australia (McGee, D. C. (1988), *Maize Diseases: A Reference Source for Seed Technologists*, APS Press, St. Paul, Minn.; White, (1998) supra; White, et al., (1979) *Proc. Annu. Corn Sorghum Res Conf* (34$^{th}$), 1-15). In the United States alone, over 37.5 million acres are infested annually with average yield losses of 6.6% nationwide (See FIG. 1). The yield losses are due both to low kernel weight in infected plants and "lodging," that is, the falling over of the plants due to weakness in the stalks caused by the infection (Dodd, J., (1980), *Plant Disease*, 64:533-537). Lodged plants are more difficult to harvest and are susceptible to other diseases. After infection, typically the upper portion of the stalk dies first while the lower stalk is still green. Externally, infection can be recognized by blotchy black patches on the outer rind of the stalk, while internally the pith tissue is discolored or black in appearance. Inoculation occurs in a number of ways. Roots may grow through stalk debris and become infected. This will become an increasing problem as "no till" methods of agriculture are more widely adopted due to their environmental benefits. The fungus may also infect the stalks through insect damage and other wounds (White (1998) supra). Stalk infection may be preceded by leaf infection causing leaf blight and providing inoculum for stalk infection. There is controversy in the technical literature as to the number of different varieties or races of Cg present in nature. The pathogen is transmitted by wind or contaminated seed lots. Spores remain viable for up to 2 years (McGee (1988) supra; Nicholson, et al., (1980), *Phytopathology*, 70:255-261; Warren, H. L. (1977), *Phytopathology*, 67:160-162; Warren, et al., (1975), *Phytopathology*, 65:620-623).

Farmers may combat infection by corn fungal diseases such as anthracnose through the use of fungicides, but these have environmental side effects, and require monitoring of fields and diagnostic techniques to determine which fungus is causing the infection so that the correct fungicide can be used. Particularly with large field crops such as corn, this is difficult. The use of corn lines that carry genetic or transgenic sources of resistance is more practical if the genes responsible for resistance can be incorporated into elite, high yielding germplasm without reducing yield. Genetic sources of resistance to Cg have been described. There have been several maize lines identified that carry some level of resistance to Cg (White, et al. (1979) supra). These included A556, MP305, H21, SP288, CI88A, and FR16. A reciprocal translocation testcross analysis using A556 indicated that genes controlling resistance to ASR lie on the long arms of chromosomes 1, 4, and 8 as well as both arms of chromosome 6 (Carson, M. L. (1981), *Sources of inheritance of resistance to anthracnose stalk rot of corn*. Ph.D. Thesis, University of Illinois, Urbana-Champaign). Introgression of resistance derived from such lines is complex. Another inbred, LB31, was reported to carry a single dominant gene controlling resistance to ASR but appears to be unstable, especially in the presence of European corn borer infestation (Badu-Apraku et al., (1987) *Phytopathology* 77: 957-959). The line MP305 was found to carry two dominant genes for resistance, one with a major effect and one with a minor effect (Carson (1981) supra). MP305 has been made available by the University of Mississippi through the National Plant Germplasm System (GRIN ID: NSL 250298) operated by the United States Department of Agriculture. See Compilation of North American Maize Breeding Germplasm, J. T. Gerdes et al., Crop Science Society of America, 1993. Seed of MP305 can be obtained through W. Paul Williams, Supervisory Research Geneticist USDA-ARS, Corn Host Plant Resistance Research Unit, Box 9555, 340 Dorman Hall, Mississippi State, Miss. 39762.

It has been reported that there are two genes linked on the long arm of chromosome 4 that confer resistance to Cg (Toman, et al., (1993), *Phytopathology*, 83:981-986; Cowen, N et al. (1991) Maize Genetics Conference Abstracts 33). A significant resistance quantitative trait locus (QTL) on chromosome 4 has also been reported (Jung, et al., (1994), *Theoretical and Applied Genetics*, 89:413-418). Jung et al. (supra) reported that UMC15 could be used to select for the QTL on chromosome 4 in MP305, and suggested that the QTL is on a 12cM region of chromosome 4 between UMC15 and UMC66. In fact, as discussed in more detail below, the region between UMC15 and UMC66 as reported on the IBM2 neighbors 4 genetic map is approximately 129 cM, and selection for the QTL in the manner suggested by Jung et al. (1994, supra) would at best select a large chromosomal interval with considerable linkage drag and negative phenotypic effect, and at worst, a double recombination could occur between the two markers resulting in a false positive selection for the Rcg1 locus.

Much work has been done on the mechanisms of disease resistance in plants in general. Some mechanisms of resistance are non-pathogen specific in nature, or so-called "non-host resistance." These may be based on cell wall structure or similar protective mechanisms. However, while plants lack an immune system with circulating antibodies and the other attributes of a mammalian immune system, they do have other mechanisms to specifically protect against pathogens. The most important and best studied of these are the plant disease resistance genes, or "R" genes. One of very many reviews of this resistance mechanism and the R genes can be found in Bekhadir et al., (2004), *Current Opinion in Plant Biology* 7:391-399. There are 5 recognized classes of R genes: intracellular proteins with a nucleotide-binding site (NBS) and a leucine-rich repeat (LRR); transmembrane proteins with an extracellular LRR domain (TM-LRR); transmembrane and extracellular LRR with a cytoplasmic kinase domain (TM-CK-LRR); membrane signal anchored protein with a coiled-coil cytoplasmic domain (MSAP-CC); and membrane associated kinases with an N-terminal myristylation site (MAK-N) (See, for example: Cohn, et al., (2001), *Immunology*, 13:55-62; Dangl, et al. (2001), *Nature*, 411:826-833).

The resistance gene of the embodiments of the present invention encodes a novel R gene related to the NBS-LRR type. While multiple NBS-LRR genes have been described, they differ widely in their response to different pathogens and exact action. To Applicants' knowledge, the novel R gene described in this disclosure is the only one demonstrated to provide resistance to Cg.

SUMMARY OF THE INVENTION

Embodiments of this invention are based on the fine mapping, cloning and characterization of the gene responsible for the major portion of the resistance phenotype from the line MP305, the introgression of a truncated chromosomal interval with the MP305 resistance locus into other lines with little or no linkage drag, the demonstration of the use of that gene as a transgene and the use of molecular markers to move the gene or transgene into elite lines using breeding techniques.

Embodiments include an isolated polynucleotide comprising a nucleotide sequence encoding a polypeptide capable of conferring resistance to *Colletotrichum*, wherein the polypeptide has an amino acid sequence of at least 50%, at least 75%, at least 80%, at least 85%, at least 90%, and at least 95% identity, when compared to SEQ ID NO:3 or the sequences deposited with the Agricultural Research Service (ARS) Culture Collection on Feb. 22, 2006 as Patent Deposit No. NRRL B-30895, based on the Needleman-Wunsch alignment algorithm, or a complement of the nucleotide sequence, wherein the complement and the nucleotide sequence consist of the same number of nucleotides and are 100% complementary.

Additional embodiments of the present invention include a vector comprising the polynucleotide of an embodiment of the present invention, such as SEQ ID NO: 3, or the sequences of the plasmid deposited as Patent Deposit No. NRRL-30895, and a recombinant DNA construct comprising the polynucleotide of an embodiment of the present invention operably linked to at least one regulatory sequence. A plant cell, as well as a plant, each comprising the recombinant DNA construct of an embodiment of the present invention, and a seed comprising the recombinant DNA construct are also embodied by the present invention.

The methods embodied by the present invention include 1) a method for transforming a host cell, including a plant cell, comprising transforming the host cell with the polynucleotide of an embodiment of the present invention, 2) a method for producing a plant comprising transforming a plant cell with the recombinant DNA construct of an embodiment of the present invention and regenerating a plant from the transformed plant cell, and 3) methods of conferring or enhancing resistance to *Colletotrichum* and/or stalk rot, comprising transforming a plant with the recombinant DNA construct of an embodiment of the present invention, thereby conferring and/or enhancing resistance to *Colletotrichum* or stalk rot.

Additional embodiments include methods of determining the presence or absence of the polynucleotides of an embodiment of the present invention, or the Rcg1 locus, in a corn plant, comprising at least one of (a) isolating nucleic acid molecules from the corn plant and determining if an Rcg1 gene is present or absent by amplifying sequences homologous to the polynucleotide, (b) isolating nucleic acid molecules from the corn plant and performing a Southern hybridization, (c) isolating proteins from the corn plant and performing a western blot using antibodies to the Rcg1 protein, (d) isolating proteins from the corn plant and performing an ELISA assay using antibodies to the Rcg1 protein, or (e) demonstrating the presence of mRNA sequences derived from the Rcg1 mRNA transcript and unique to Rcg1, thereby determining the presence of the polynucleotide or the Rcg1 locus in the corn plant.

Methods of altering the level of expression of a protein capable of conferring resistance to *Colletotrichum* or stalk rot in a plant or plant cell comprising (a) transforming a plant cell with the recombinant DNA construct of an embodiment of the present invention and (b) growing the transformed plant cell under conditions that are suitable for expression of the recombinant DNA construct wherein expression of the recombinant DNA construct results in production of altered levels of a protein capable of conferring resistance to *Colletotrichum* or stalk rot in the transformed host are also embodied by the present invention.

An additional method embodied by the present invention is a method of conferring or enhancing resistance to *Colletotrichum* and/or stalk rot in a corn plant, comprising (a) crossing a first corn plant lacking the Rcg1 locus with a second corn plant containing the Rcg1 locus to produce a segregating population, (b) screening the segregating population for a member containing the Rcg1 locus with a first nucleic acid, not including UMC15a or UMC66, capable of hybridizing with a second nucleic acid linked to or located within the Rcg1 locus, and (c) selecting the member for further crossing and selection.

Methods of enhancing resistance to *Colletotrichum* and/or stalk rot, or introgressing *Colletotrichum* and/or stalk rot resistance into a corn plant, comprising performing marker assisted selection of the corn plant with a nucleic acid marker, wherein the nucleic acid marker specifically hybridizes with a nucleic acid molecule having a first nucleic acid sequence that is linked to a second nucleic acid sequence that is located on the Rcg1 locus of MP305 and selecting the corn plant based on the marker assisted selection are also embodiments of the present invention. Specific FLP, MZA and Rcg1 specific SNP markers disclosed herein are further aspects of the invention.

Additional embodiments are an improved donor source of germplasm for introgressing resistance or enhancing resistance to *Colletotrichum* or stalk rot into a corn plant, said germplasm comprising DE811ASR (BC5) and progeny derived therefrom. Said progeny can be further characterized as containing the DE811ASR (BC5) Rcg1 sequences disclosed herein, molecular markers in or genetically linked to Rcg1, resistance or enhanced resistance to *Colletotrichum*, or any combinations thereof.

Further embodiments include processes for identifying corn plants that display newly conferred or enhanced resistance to *Colletotrichum* by detecting alleles of at least 2 markers in the corn plant, wherein at least one of the markers is on or within the chromosomal interval below UMC2041 and above the Rcg1 gene, and at least one of the markers is on or within the interval below the Rcg1 gene and above UMC2200. Similar embodiments encompassed by this process include at least one of the markers being on or within the chromosomal interval below UMC1086 and above the Rcg1 gene, on or within the chromosomal interval below UMC2285 and above the Rcg1 gene, and at least one of the markers is on or within the interval below the Rcg1 gene and above UMC2200, on or within the interval below the Rcg1 gene and above UMC2187, or on or within the interval below the Rcg1 gene and above UMC15a. Further embodiments related to the same process include those in which at least one of the markers is capable of detecting a polymorphism located at a position corresponding to nucleotides 7230 and 7535 of SEQ ID NO: 137, nucleotides 11293 and 12553 of SEQ ID NO: 173, nucleotides 25412 and 29086 of SEQ ID NO: 137, or nucleotides 43017 and 50330 of SEQ ID NO: 137.

Further embodiments include processes for identifying corn plants that display newly conferred or enhanced resistance to *Colletotrichum* by detecting alleles of at least 2 markers in the corn plant, wherein at least one of the markers on or within the chromosomal interval below UMC2041 and above the Rcg1 gene is selected from the markers listed in Table 16, and at least one of the markers on or within the interval below the Rcg1 gene and above UMC2200 is also selected from the markers listed in Table 16. Embodiments include processes for identifying corn plants that display newly conferred or enhanced resistance to *Colletotrichum* by selecting for at least four markers or at least six, wherein at least two or three of the markers are on or within the chromosomal interval below UMC2041 and above the Rcg1 gene, and at least two or three of the markers are on or within the interval below the Rcg1 gene and above UMC2200. Additional embodiments include this same process when the two or three markers on or within the chromosomal interval below UMC2041 and above the Rcg1 gene, as well as the two or three markers on or within the interval below the Rcg1 gene and above UMC2200, are selected from those listed in Table 16. Another embodiment of this process includes detecting allele 7 at MZA1112, detecting allele 2 at MZA2591, or detecting allele 8 at MZA3434. Corn plants and seeds produced by the embodied processes are also embodiments of the invention, including those corn plants which do not comprise the same alleles as MP305 at or above UMC2041, or at or below UMC2200 at the loci shown in Table 16.

Other embodiments include processes for identifying corn plants that display newly conferred or enhanced resistance to *Colletotrichum* by detecting alleles of at least 2 markers in the corn plant, wherein at least one of the markers is on or within the chromosomal interval below UMC2041 and above the Rcg1 gene, and at least one of the markers is on or within the interval below the Rcg1 gene and above UMC2200, and where the process detects the presence or absence of at least one marker located within the Rcg1 gene. A further such embodiment includes a modification of this process in which four markers are selected for, in which two of the markers are within the chromosomal interval below UMC2285 and above the Rcg1 gene, and at least two of the markers are within the interval below the Rcg1 gene and above UMC15a. A further embodiment of this process includes the Rcg1 gene having been introgressed from a donor corn plant, including MP305 or DE811ASR(BC5), into a recipient corn plant to produce an introgressed corn plant. This process also includes the instance when the introgressed corn plant is selected for a recombination event below the Rcg1 gene and above UMC15a, so that the introgressed corn plant retains a first MP305 derived chromosomal interval below the Rcg1 gene and above UMC15a, and does not retain a second MP305 derived chromosomal interval at and below UMC15a. Corn plants and seeds produced by these processes are also embodiments of the invention. Introgressed corn plants embodied by the invention include those that are Rcg1 locus conversions of PH705, PH5W4, PH51K or PH87P, or progeny thereof.

A further embodiment of the invention is a process of identifying a corn plant that displays enhanced resistance to *Colletotrichum* infection, by detecting in the corn plant the presence or absence of at least one marker at the Rcg1 locus, and selecting the corn plant in which the at least one marker is present. Embodiments include when at least one marker is on or within SEQ ID NO: 137, and also when the at least one marker is capable of detecting a polymorphism located at a position in SEQ ID NO: 137 corresponding to the position between nucleotides 1 and 536, between nucleotides 7230 and 7535, between nucleotides 11293 and 12553, between nucleotides 25412 and 29086; and between nucleotides 43017 and 50330, and also when at least one marker is on or within the Rcg1 coding sequence, or located on or within the polynucleotide set forth in SEQ ID NO: 1. Another embodiment includes when the process detects a single nucleotide polymorphism at a position in SEQ ID NO: 1 corresponding to one or more of position 413, 958, 971, 1099, 1154, 1235, 1250, 1308, 1607, 2001, 2598, and 3342. Markers included by the processes in these embodiments include SNP markers C00060-01 and C00060-02, markers that detect an mRNA sequence derived from the Rcg1 mRNA transcript and unique to Rcg1, and FLP markers on an amplicon generated by a primer pair set forth in this disclosure, such as those of SEQ ID NOs: 35-42, and their complements. Another embodiment includes when the process detects the presence or absence of at least two markers within the Rcg1 locus, including C00060-01 and C00060-02. Corn plants and seeds produced by these processes are also embodiments of the invention. Introgressed corn plants embodied by the invention include those that are Rcg1 locus conversions of PH705, PH5W4, PH51K or PH87P, or progeny thereof. Such embodiments include corn seed comprising a first MP305 derived chromosomal interval defined by BNLG2162 and UMC1051, and not comprising a second MP305 derived chromosomal interval above UMC2041 or below UMC1051, and when the corn seed comprises the Rcg1 gene and, when grown, produces a corn plant that exhibits resistance to *Colletotrichum* infection. Seed of the embodiments also includes corn seed comprising a first MP305 derived chromosomal interval between, but not including, UMC2285 and UMC15a, and not comprising a second MP305 derived chromosomal interval at or above UMC2285 or at or below UMC15a, and furthermore such corn seed which comprises the Rcg1 gene and, when grown, produces a corn plant that exhibits resistance to *Colletotri*-

*chum* infection. Corn plants and plant cells produced from this seed are also included in the embodiments of the invention.

Additional embodiments include seed of a corn variety designated DE811ASR(BC5), or the corn seed deposited as ATCC accession number PTA-7434, or a progeny seed derived from that variety, that comprises the Rcg1 gene, that when grown, produces a plant that exhibits enhanced or newly conferred resistance to *Colletotrichum* infection. Plants and plant cells grown from this seed are also embodiments, as well as progeny seed that retain a first MP305 or DE811ASR(BC5) derived chromosomal interval within, but not including, UMC2285 and UMC15a, and progeny seed that do not comprise a second MP305 derived chromosomal interval at or above UMC2285 or at or below UMC15a. Plants and plant cells of the above seed are included as embodiments. Progeny seed that is an Rcg1 locus conversion of PH705, PH5W4, PH51K or PH87P, or a progeny thereof is also embodied in the invention, as are progeny seed that comprise at least two or more of allele 7 at MZA11123, allele 2 at MZA2591, or allele 8 at MZA3434. Further embodiments include progeny seed which comprise a cytosine nucleotide at MZA2591.32, a thymine nucleotide at MZA2591.35, and a cytosine nucleotide at MZA3434.17.

Additional embodiments include a computer system for identifying a corn plant that displays newly conferred or enhanced resistance to *Colletotrichum* infection comprising a database comprising an allele score information for one or more corn plants for four or more marker loci closely linked to or within the Rcg1 locus, and instructions that examine said database to determine inheritance of the chromosomal interval or portions thereof defined by the four or more marker loci and compute whether or not the one or more corn plants comprise the Rcg1 gene. Further embodiments include a computer system for identifying a corn plant that displays newly conferred or enhanced resistance to *Colletotrichum* infection comprising a database comprising allele score information for one or more corn plants for one or more marker loci within the Rcg1 locus, and instructions that examine said database to determine inheritance of the Rcg1 locus. The allele score information for one or more corn plants for such computer systems may further comprise two, three, or more marker loci within the Rcg1 locus.

Embodiments also include genetic markers on or within SEQ ID NOs: 140 through 146 for MZA3434, MZA2591, MZA11123, MZA15842, MZA1851, MZA8761 and MZA11455, respectively. Other embodiments include genetic markers located on or in the Rcg1 locus or the Rcg1 gene, including those located on SEQ ID NO: 137, for example those located on regions corresponding to nucleotides between 1 and 536, between 7230 and 7535, between 11293 and 12553, between 25412 and 29086, and the region between nucleotides 43017 and 50330. Embodied markers also include those located on SEQ ID NO: 1, such as those located on or within nucleotide positions 550-658 of SEQ ID NO: 1, or those located on or within nucleotide positions 1562-1767 of SEQ ID NO: 1. Markers of the embodiments include those on markers located on amplicons generated by a primer pair wherein the first primer is an odd-numbered sequence from SEQ ID NO: 23 to 41, and wherein the second primer is an even-numbered sequence from SEQ ID NO: 24 to 42.

Further embodiments include corn plants obtainable by a method comprising: crossing MP305 or DE811ASR(BC5) [Deposit No. PTO-7434] as a first parent plant, with a different plant that lacks an Rcg1 locus as a second parent plant, thereby to obtain progeny comprising the Rcg1 locus of the first parent; and optionally further comprising one or more further breeding steps to obtain progeny of one or more further generations comprising the Rcg1 locus of the first parent. Such embodied corn plants include both inbred and hybrid plants. Seeds of such plants, including those seeds which are homozygous and heterozygous for the Rcg1 locus, and methods of obtaining corn products resulting from the processing of those seeds are embodied in the invention. Using such seed in food or feed or the production of a corn product, such as corn flour, corn meal and corn oil is also an embodiment of the invention.

BRIEF DESCRIPTION OF THE DRAWINGS

FIG. 2 (*a, b, c*) is an alignment of a polypeptide sequence of the embodiments (SEQ ID NO: 3) comparing it to other known NBS-LRR polypeptides.

FIG. 9(*a*) shows the alignment of the non-colinear region from DE811ASR (BC5) relative to B73 and Mo17. The BAC sizes in FIG. 9(*a*) are estimates. FIG. 9(*b*) shows a portion of the non-colinear region as set forth in SEQ ID NO: 137 on which Rcg1 resides, including the repetitive regions therein, as well as the Rcg1 exons 1 and 2.

FIG. 10(a-b) show distributions of average leaf lesion size in different individual plants at 15 days after inoculation with Cg in the DE811ASR(BC5) and DE811 lines, respectively.

DETAILED DESCRIPTION OF THE INVENTION

Embodiments of the present invention provide compositions and methods (or processes) directed to inducing pathogen resistance, particularly fungal resistance, in plants. The compositions are novel nucleotide and amino acid sequences that confer or enhance resistance to plant fungal pathogens. Specifically, certain embodiments provide polypeptides having the amino acid sequence set forth in SEQ ID NO: 3, and variants and fragments thereof. Isolated nucleic acid molecules, and variants and fragments thereof, comprising nucleotide sequences that encode the amino acid sequence shown in SEQ ID NO: 3 are further provided.

Nucleotide sequences that encode the polypeptide of SEQ ID NO: 3 are set forth in SEQ ID NOs: 1 and 4. Plants, plant cells, seeds, and microorganisms comprising a nucleotide sequence that encodes a polypeptide of the embodiments are also disclosed herein.

A deposit of the Rcg1 nucleic acid molecule was made on Feb. 22, 2006 with the Agricultural Research Service (ARS) Culture Collection, housed in the Microbial Genomics and Bioprocessing Research Unit of the National Center for Agricultural Utilization Research (NCAUR), under the Budapest Treaty provisions. The deposit was given the following accession number: NRRL B-30895. The address of NCAUR is 1815 N. University Street, Peoria, Ill., 61604. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112. The deposit will irrevocably and without restriction or condition be available to the public upon issuance of a patent. However, it should be understood that the availability of a deposit does not constitute a license to practice the subject invention in derogation of patent rights granted by government action.

A sample of 2500 seeds of DE811ASR (BC5) were deposited in the American Type Culture Collection (ATCC), 10801 University Blvd., Manassas, Va. 20110-2209, USA on Mar. 13, 2006 and assigned Deposit No. PTO-7434. Access to this deposit will be available during the pendency of the application to the Commissioner of Patents and Trademarks, persons determined by the Commissioner to be entitled thereto upon request, and corresponding officials in foreign patent offices in which this patent application is filed. This deposit will be maintained under the terms of the Budapest Treaty on the International Recognition of the Deposit of Microorganisms for the Purposes of Patent Procedure. The deposit will irrevocably and without restriction or condition be available to the public upon issuance of a patent. However, it should be understood that the availability of the deposit does not constitute a license to practice the subject invention or methods in derogation of patent rights.

Figure 1:
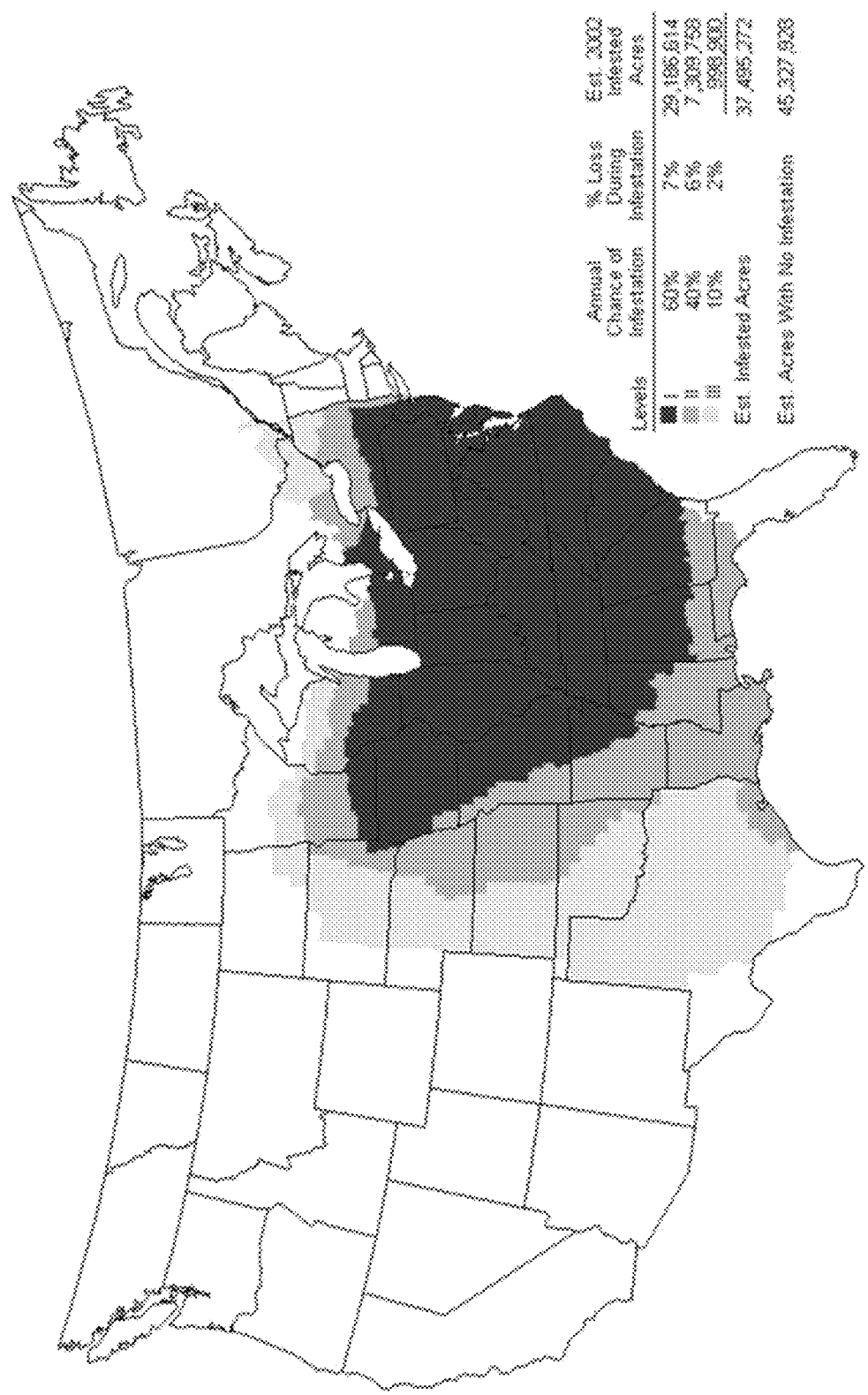
FIG. 1 is a map of the United States showing the severity of anthracnose stalk rot infestation by county for 2002.

The full length polypeptide of the embodiments (SEQ ID NO: 3) shares varying degrees of homology with known polypeptides of the NBS-LRR family. In particular, the novel polypeptide of the embodiments shares homology with NBS-LRR proteins isolated from *Oryza sativa* (Accession Nos. NP_910480 (SEQ ID NO: 14), NP_910482 (SEQ ID NO: 16), NP_921091 (SEQ ID NO: 17) and NP_910483 (SEQ ID NO: 15)) and *Hordeum vulgare* (Accession No. AAG37354 (SEQ ID NO: 18); Zhou et al., (2001) Plant Cell 13:337-350). FIG. 1 provides an alignment of the amino acid sequence set forth in SEQ ID NO: 3 with the *O. sativa* and *H. vulgare* antifungal proteins (SEQ ID NOs: 14-18).

Amino acid alignments using the GAP program indicate that SEQ ID NO:3 shares approximately 42.3% sequence similarity with the *O. sativa* antifungal protein NP_910480 (SEQ ID NO: 14), 41.7% sequence similarity with the *O. sativa* protein NP_910482 (SEQ ID NO: 16), 56.9% similarity with the *O. sativa* protein NP_921091 (SEQ ID NO: 17) and 42.1% sequence similarity with the *O. sativa* protein NP_910483 (SEQ ID NO: 15). Furthermore, SEQ ID NO: 3 shares approximately 42.8% sequence similarity with the *H. vulgare* protein AAG37354 (SEQ ID NO: 18).

The NBS-LRR group of R-genes is the largest class of R-genes discovered to date. In *Arabidopsis thaliana*, over 150 are predicted to be present in the genome (Meyers, et al., (2003), *Plant Cell,* 15:809-834; Monosi, et al., (2004), *Theoretical and Applied Genetics,* 109:1434-1447), while in rice, approximately 500 NBS-LRR genes have been predicted (Monosi, (2004) supra). The NBS-LRR class of R genes is comprised of two subclasses. Class 1 NBS-LRR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) *Genome Research,* 12:1871-1884; Monosi, (2004) supra; Pan, et al., (2000), *Journal of Molecular Evolution,* 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), *Current Biology: CB,* 8:R226-R227). The LRR region appears to be the region that interacts with the pathogen AVR products (Michelmore, et al., (1998), *Genome Res.,* 8:1113-1130; Meyers, (2003) supra). This LRR region in comparison with the NBS domain is under a much greater selection pressure to diversify (Michelmore, (1998) supra; Meyers, (2003) supra; Palomino, et al., (2002), *Genome Research,* 12:1305-1315). LRR domains are found in other contexts as well; these 20-29-residue motifs are present in tandem arrays in a number of proteins with diverse functions, such as hormone-receptor interactions, enzyme inhibition, cell adhesion and cellular trafficking. A number of recent studies revealed the involvement of LRR proteins in early mammalian development, neural development, cell polarization, regulation of gene expression and apoptosis signaling.

The gene of the embodiments is clearly related to the NBS-LRR of the class 2 family, but does not completely fit the classical mold. The amino end has homology to so-called nucleotide binding sites (NBS). There is a leucine rich region as well, located, as expected, downstream of the NBS. However, unlike previously studied NBS-LRR proteins, the leucine rich region lacks the systematic repetitive nature found in more classical LRR domains, much less consistently following the typical Lxx repeat pattern and in particular having no instances of the consensus sequences described by Wang et al. ((1999) *Plant J.* 19:55-64; see especially, FIG. 5) or Bryan et al. ((2000), Plant Cell 12:2033-2045; see especially, FIG. 3).

As the LRR region is the receptor portion of an NBS-LRR, when a new LRR such as that of this disclosure is found, the range of its activity, that is, the range of pathogens to which it will respond, is not immediately obvious from the sequence. The gene of the embodiments was isolated on the basis of the Cg resistance phenotype, and therefore the novel LRR responds to Cg. However, it is not excluded that it responds to other pathogens not tested in the work done heretofore.

The nucleic acids and polypeptides of the embodiments find use in methods for conferring or enhancing fungal resistance to a plant. Accordingly, the compositions and methods disclosed herein are useful in protecting plants from fungal pathogens. "Pathogen resistance," "fungal resistance," and "disease resistance" are intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss. One of skill in the art will appreciate that the compositions and methods disclosed herein can be used with other compositions and methods available in the art for protecting plants from pathogen attack.

Figure 20:
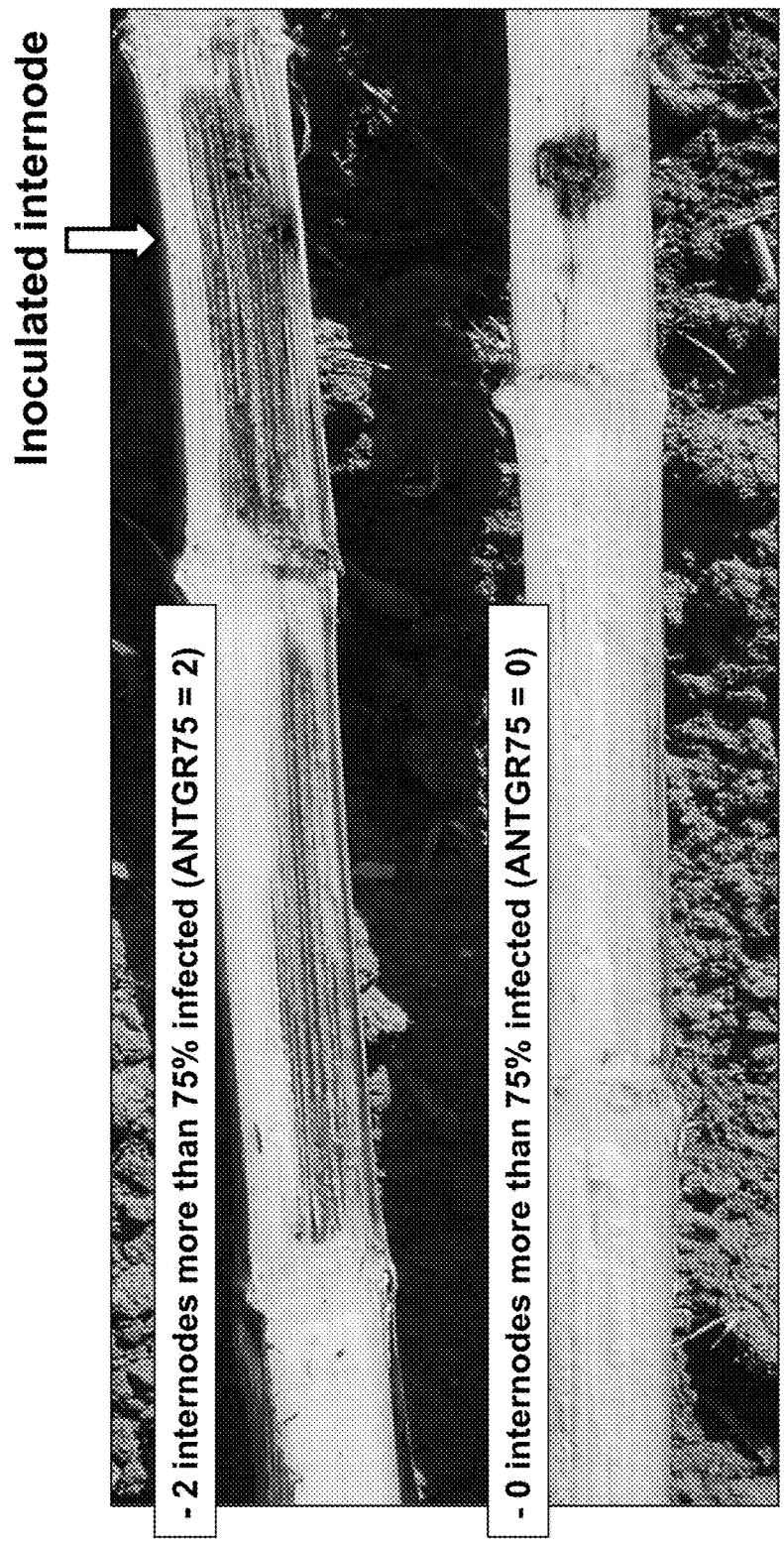
FIG. 20 shows the method of scoring for disease severity in corn stalks. The stalks are given a score, designated antgr75, which represents the number of internodes (up to 5, including the inoculated internode) that are more than 75% discolored. This results in a score ranging from 0 to 5, with 0 indicating less than 75% discoloration in the inoculated internode, and 5 indicating 75% or more discoloration of the first five internodes, including the inoculated internode.

Hence, the methods of the embodiments can be utilized to protect plants from disease, particularly those diseases that are caused by plant fungal pathogens. As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens constitutes "enhanced" or improved fungal resistance. The embodiments of the invention also will enhance or improve fungal plant pathogen resistance, such that the resistance of the plant to a fungal pathogen or pathogens will increase. The term "enhance" refers to improve, increase, amplify, multiply, elevate, raise, and the like. Herein, plants of the invention are described as being resistant to infection by Cg or having 'enhanced resistance' to infection by Cg as a result of the Rcg1 locus of the invention. Accordingly, they typically exhibit increased resistance to the disease when compared to equivalent plants that are susceptible to infection by Cg because they lack the Rcg1 locus. For example, using the scoring system described in Example 11 (also see FIG. 20), they typically exhibit a one point, two point or three point or more decrease in the infection score, or even a reduction of the score to 1 or 0, when compared to equivalent plants that are susceptible to infection by Cg because they lack the Rcg1 locus In particular aspects, methods for conferring or enhancing fungal resistance in a plant comprise introducing into a plant at least one expression cassette, wherein the expression cassette comprises a nucleotide sequence encoding an antifungal polypeptide of the embodiments operably linked to a promoter that drives expression in the plant. The plant expresses the polypeptide, thereby conferring fungal resistance upon the plant, or improving the plant's inherent level of resistance. In particular embodiments, the gene confers resistance to the fungal pathogen, Cg.

Expression of an antifungal polypeptide of the embodiments may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the embodiments can be produced either from a nucleic acid disclosed herein, or by the use of standard molecular biology techniques. For example, a truncated protein of the embodiments can be produced by expression of a recombinant nucleic acid of the embodiments in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The embodiments of the invention encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques (e.g. PCR amplification), or substantially free of chemical precursors or other chemicals when chemically synthesized. Optimally, an "isolated" polynucleotide is free of sequences (for example, protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof, is recombinantly produced, optimally culture medium represents less than about 30%, about 20%, about 10%, about 5%, or about 1% (by dry weight) of chemical precursors or non-protein-of-interest chemicals.

Fragments and variants of the disclosed nucleotide sequences and proteins encoded thereby are also encompassed by the embodiments. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have the ability to confer fungal resistance upon a plant. Alternatively, fragments of a nucleotide sequence that are useful as hybridization probes do not necessarily encode fragment proteins retaining biological activity. Thus, fragments of a nucleotide sequence may range from at least about 15 nucleotides, about 50 nucleotides, about 100 nucleotides, and up to the full-length nucleotide sequence encoding the polypeptides of the embodiments.

A fragment of a nucleotide sequence that encodes a biologically active portion of a polypeptide of the embodiments will encode at least about 15, about 25, about 30, about 40, or about 50 contiguous amino acids, or up to the total number of amino acids present in a full-length polypeptide of the embodiments (for example, 980 amino acids for the peptide encoded by SEQ ID NO:1). Fragments of a nucleotide sequence that are useful as hybridization probes or PCR primers generally need not encode a biologically active portion of a protein.

As used herein, "full-length sequence," in reference to a specified polynucleotide, means having the entire nucleic acid sequence of a native sequence. "Native sequence" is intended to mean an endogenous sequence, i.e., a non-engineered sequence found in an organism's genome.

Thus, a fragment of a nucleotide sequence of the embodiments may encode a biologically active portion of a polypeptide, or it may be a fragment that can be used as a hybridization probe or PCR primer using methods disclosed below. A biologically active portion of an antipathogenic polypeptide can be prepared by isolating a portion of one of the nucleotide sequences of the embodiments, expressing the encoded portion of the protein and assessing the ability of the encoded portion of the protein to confer or enhance fungal resistance in a plant. Nucleic acid molecules that are fragments of a nucleotide sequence of the embodiments comprise at least about 15, about 20, about 50, about 75, about 100, or about 150 nucleotides, or up to the number of nucleotides present in a full-length nucleotide sequence disclosed herein (for example, 4212 nucleotides for SEQ ID NO: 1).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a protein of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 3 are disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, the ability to confer or enhance plant fungal pathogen resistance as described herein. Such variants may result, for example, from genetic polymorphism or from human manipulation. Biologically active variants of a native protein of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs and parameters described elsewhere herein. A biologically active variant of a protein of the embodiments may differ from that protein by as few as about 1-15 amino acid residues, as few as about 1-10, such as about 6-10, as few as about 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the embodiments include both naturally occurring sequences as well as mutant forms. Likewise, the proteins of the embodiments encompass both naturally occurring proteins as well as variations and modified forms thereof. Such variants will continue to possess the desired ability to confer or enhance plant fungal pathogen resistance. Obviously, the mutations that will be made in the DNA encoding the variant must not place the sequence out of reading frame and optimally will not create complementary regions that could produce secondary mRNA structure. See, EP Patent No. 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by screening transgenic plants which have been transformed with the variant protein to ascertain the effect on the ability of the plant to resist fungal pathogenic attack.

Variant polynucleotides and proteins also encompass sequences and proteins derived from mutagenic or recombinogenic procedures, including and not limited to procedures such as DNA shuffling. One of skill in the art could envision modifications that would alter the range of pathogens to which the protein responds. With such a procedure, one or more different protein coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the protein gene of the embodiments and other known protein genes to obtain a new gene coding for a protein with an improved property of interest, such as increased ability to confer or enhance plant fungal pathogen resistance. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al.

(1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. Thus, isolated polynucleotides that encode for a protein that confers or enhances fungal plant pathogen resistance and that hybridize under stringent conditions to the sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, and are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the embodiments. Methods for preparation of probes for hybridization and for construction of cDNA and genomic libraries are generally known in the art and are disclosed in Sambrook et al. (1989) supra.

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique and are optimally at least about 10 nucleotides in length, at least about 15 nucleotides in length, or at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) supra.

Various procedures can be used to check for the presence or absence of a particular sequence of DNA, RNA, or a protein. These include, for example, Southern blots, northern blots, western blots, and ELISA analysis. Techniques such as these are well known to those of skill in the art and many references exist which provide detailed protocols. Such references include Sambrook et al. (1989) supra, and Crowther, J. R. (2001), *The ELISA Guidebook*, Humana Press, Totowa, N.J., USA.

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least about 20 contiguous nucleotides in length, and optionally can be about 30, about 40, about 50, about 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, and are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: identity and % similarity for a nucleotide sequence using Gap Weight of 50 and Length Weight of 3, and the nwsgapdna.cmp scoring matrix; % identity and % similarity for an amino acid sequence using Gap Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, and no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the embodiments to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, and not limited to, single-stranded forms, double-stranded forms, and the like.

Isolated polynucleotides of the embodiments can be incorporated into recombinant DNA constructs capable of introduction into and replication in a host cell. A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., *Cloning Vectors: A Laboratory Manual*, 1985, supp. 1987; Weissbach and Weissbach, *Methods for Plant Molecular Biology*, Academic Press, 1989; and Flevin et al., *Plant Molecular Biology Manual, Kluwer Academic Publishers,* 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The terms "recombinant construct," "expression cassette," "expression construct," "chimeric construct," "construct," "recombinant DNA construct" and "recombinant DNA fragment" are used interchangeably herein and are nucleic acid fragments. A recombinant construct comprises an artificial combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the embodiments. Screening to obtain lines displaying the desired expression level and pattern of the polynucleotides or of the Rcg1 locus may be accomplished by amplification, Southern analysis of DNA, northern analysis of mRNA expression, immunoblotting analysis of protein expression, phenotypic analysis, and the like.

The term "recombinant DNA construct" refers to a DNA construct assembled from nucleic acid fragments obtained from different sources. The types and origins of the nucleic acid fragments may be very diverse.

In some embodiments, expression cassettes comprising a promoter operably linked to a heterologous nucleotide sequence of the embodiments are further provided. The expression cassettes of the embodiments find use in generating transformed plants, plant cells, and microorganisms and in practicing the methods for inducing plant fungal pathogen resistance disclosed herein. The expression cassette will include 5' and 3' regulatory sequences operably linked to a polynucleotide of the embodiments. "Operably linked" is intended to mean a functional linkage between two or more elements. "Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences. For example, an operable linkage between a polynucleotide of interest and a regulatory sequence (a promoter, for example) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the embodiments, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

A number of promoters can be used in the practice of the embodiments, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

It may sometimes be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the embodiments. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, and are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the polypeptides of the embodiments within a particular plant tissue. For example, a tissue-preferred promoter may be used to express a polypeptide in a plant tissue where disease resistance is particularly important, such as, for example, the roots, the stalk or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, and are not limited to, the *Prunus serotina* prunasin hydrolase gene promoter (see, e.g., International Publication No. WO 03/006651), and also those found in U.S. patent application Ser. No. 10/109,488.

Stalk-preferred promoters may be used to drive expression of a polypeptide of the embodiments. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and roID root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and roIB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, and are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is a preferred endosperm-specific promoter. Glob-1 is a preferred embryo-specific promoter. For dicots, seed-specific promoters include, and are not limited to, bean β-phaseolin, napin, β-conglycinin, soybean lectin, cruciferin, and the like. For monocots, seed-specific promoters include, and are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology, Vol. 78* (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the embodiments.

The gene of the embodiments can be expressed as a transgene in order to make plants resistant to Cg. Using the different promoters described elsewhere in this disclosure, this will allow its expression in a modulated form in different circumstances. For example, one might desire higher levels of expression in stalks to enhance resistance to Cg-caused stalk rot. In environments where Cg-caused leaf blight is more of a problem, lines with higher expression levels in leaves could be used. However, one can also insert the entire gene, both native promoter and coding sequence, as a transgene. Finally, using the gene of the embodiments as a transgene will allow quick combination with other traits, such as insect or herbicide resistance.

In certain embodiments the nucleic acid sequences of the embodiments can be stacked with any combination of polynucleotide sequences of interest in order to create plants with a desired phenotype. This stacking may be accomplished by a combination of genes within the DNA construct, or by crossing Rcg1 with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AG- Pase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The methods of the embodiments may involve, and are not limited to, introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the embodiments do not depend on a particular method for introducing a sequence into a plant, only that the polynucleotide gains access to the interior of at least one cell of the plant. Methods for introducing polynucleotides into plants are known in the art including, and not limited to, stable transformation methods, transient transformation methods, and virus-mediated methods.

"Transformation" refers to the transfer of a nucleic acid fragment into the genome of a host organism, resulting in genetically stable inheritance. Host organisms containing the transformed nucleic acid fragments are referred to as "transgenic" organisms. "Host cell" refers the cell into which transformation of the recombinant DNA construct takes place and may include a yeast cell, a bacterial cell, and a plant cell. Examples of methods of plant transformation include *Agrobacterium*-mediated transformation (De Blaere et al., 1987, *Meth. Enzymol.* 143:277) and particle-accelerated or "gene gun" transformation technology (Klein et al., 1987, *Nature* (London) 327:70-73; U.S. Pat. No. 4,945,050), among others.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Led transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provides transformed seed (also referred to as "transgenic seed") having a nucleotide construct of the embodiments, for example, an expression cassette of the embodiments, stably incorporated into their genome.

As used herein, the term "plant" can be a whole plant, any part thereof, or a cell or tissue culture derived from a plant. Thus, the term "plant" can refer to any of: whole plants, plant components or organs (including but not limited to embryos, pollen, ovules, seeds, leaves, flowers, branches, fruit, kernels, ears, cobs, husks, stalks, roots, root tips, anthers, and the like), plant tissues, plant cells, plant protoplasts, plant cell tissue cultures from which maize plant can be regenerated, plant calli, plant clumps, and plant seeds. A plant cell is a cell of a plant, either taken directly from a seed or plant, or derived through culture from a cell taken from a plant. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides.

The embodiments of the invention may be used to confer or enhance fungal plant pathogen resistance or protect from fungal pathogen attack in plants, especially corn (*Zea mays*). It will protect different parts of the plant from attack by pathogens, including and not limited to stalks, ears, leaves, roots and tassels. Other plant species may also be of interest in practicing the embodiments of the invention, including, and not limited to, other monocot crop plants.

There appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

The embodiments of the present invention may be effective against a variety of plant pathogens, particularly fungal pathogens, such as, for example, *Colletotrichum*, including Cg. The embodiments of the present invention may also be effective against maize stalk rot, including anthracnose stalk rot, wherein the causative agent is *Colletotrichum*. Other plant pathogenic fungi and oomycetes (many of the latter of which have been historically been considered fungi although modern taxonomists have now classified them separately) include, and are not limited to, the following: Soybeans: *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticta sojicola*, *Alternaria alternata*, *Microsphaera diffusa*, *Fusarium semitectum*, *Phialophora gregata*, *Glomerella glycines*, *Phakopsora pachyrhizi*, *Pythium aphanidermatum*, *Pythium ultimum*, *Pythium debaryanum*, *Fusarium solani*; Canola: *Albugo candida*, *Alternaria brassicae*, *Leptosphaeria maculans*, *Rhizoctonia solani*, *Sclerotinia sclerotiorum*, *Mycosphaerella brassicola*, *Pythium ultimum*, *Peronospora parasitica*, *Fusarium roseum*, *Alternaria alternata*; Alfalfa: *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium oxysporum*, *Verticillium albo-atrum*, *Aphanomyces euteiches*, *Stemphylium herbarum*, *Stemphylium alfalfae*, *Colletotrichum trifolii*, *Leptosphaerulina briosiana*, *Uromyces striatus*, *Sclerotinia trifoliorum*, *Stagnospora meliloti*, *Stemphylium botryosum*, *Leptotrochila medicaginis*; Wheat: *Urocystis agropyri*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, *Claviceps purpurea*, *Tilletia tritici*, *Tilletia laevis*, *Ustilago tritici*, *Tilletia indica*, *Rhizoctonia solani*, *Pythium arrhenomanes*, *Pythium gramicola*, *Pythium aphanidermatum*; Sunflower: *Plasmophora halstedii*, *Sclerotinia sclerotiorum*, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* pv. *carotovora*, *Cephalosporium acremonium*, *Phytophthora cryptogea*, *Albugo tragopogonis*; Corn: *Fusarium moniliforme* var. *subglutinans*, *Erwinia stewartii*, *Fusarium moniliforme*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Trichoderma viride*, *Claviceps sorghi*, *Erwinia chrysanthemi* pv. *zea*, *Erwinia carotovora*, *Diplodia macrospora*, *Sclerophthora macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporium maydis*, *Cephalosporium acremonium*; Sorghum: *Exserohilum turcicum*, *Colletotrichum graminicola* (*Glomerella graminicola*), *Cercospora sorghi*, *Gloeocercospora sorghi*, *Ascochyta sorghina*, *Puccinia purpurea*, *Macrophomina phaseolina*, *Perconia circinata*, *Fusarium moniliforme*, *Alternaria alternata*, *Bipolaris sorghicola*,

*Helminthosporium sorghicola, Curvularia lunata, Phoma insidiosa, Ramulispora sorghi, Ramulispora sorghicola, Phyllachara sacchari, Sporisorium reilianum (Sphacelotheca reiliana), Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

The term "allele" refers to one of two or more different nucleotide sequences that occur at a specific locus. A first allele is found on one chromosome, while a second allele occurs at the same position on the homologue of that chromosome, e.g., as occurs for different chromosomes of a heterozygous individual, or between different homozygous or heterozygous individuals in a population. A "favorable allele" is the allele at a particular locus that confers, or contributes to, an agronomically desirable phenotype, e.g., resistance to Cg infection. A favorable allele of a marker is a marker allele that segregates with the favorable phenotype. A favorable allelic form of a chromosome segment is a chromosome segment that includes a nucleotide sequence that contributes to superior agronomic performance at one or more genetic loci physically located on the chromosome segment. "Allele frequency" refers to the frequency (proportion or percentage) of an allele within a population, or a population of lines. One can estimate the allele frequency within a population by averaging the allele frequencies of a sample of individuals from that population.

An allele "positively" correlates with a trait when it is linked to it and when presence of the allele is an indicator that the desired trait or trait form will occur in a plant comprising the allele. An allele negatively correlates with a trait when it is linked to it and when presence of the allele is an indicator that a desired trait or trait form will not occur in a plant comprising the allele.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). A special case of a heterozygous situation is where one chromosome has an allele of a gene and the other chromosome lacks that gene, locus or region completely—in other words, has a deletion relative to the first chromosome. This situation is referred to as "hemizygous." The term "homogeneity" indicates that members of a group have the same genotype at one or more specific loci. In contrast, the term "heterogeneity" is used to indicate that individuals within the group differ in genotype at one or more specific loci.

The embodiments provide not only a gene and its functional variants for use in transgenic applications, but sequences and processes that allow the Rcg1 resistance gene to be moved between corn lines using marker assisted breeding. The embodiments also relate to plants produced by these processes that retain a truncated chromosomal interval comprising the Rcg1 resistance gene.

A genetic map is a graphical representation of a genome (or a portion of a genome such as a single chromosome) where the distances between landmarks on a chromosome are measured by the recombination frequencies between the landmarks. Recombinations between genetic landmarks can be detected using a variety of molecular genetic markers (also called molecular markers) that are described in more detail herein.

For markers to be useful at detecting recombinations, they need to detect differences, or polymorphisms, within the population being monitored. For molecular markers, this means differences at the DNA level due to polynucleotide sequence differences (eg SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs). ESTs are generally well conserved within a species, while other regions of DNA (typically non-coding) tend to accumulate polymorphism, and therefore, can be more variable between individuals of the same species. A large number of corn molecular markers are known in the art, and are published or available from various sources, such as the Maize GDB internet resource and the Arizona Genomics Institute internet resource run by the University of Arizona.

Molecular markers can be used in a variety of plant breeding applications (eg see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in the plants development, e.g. kernel characteristics. Since DNA marker assays are less laborious, and take up less physical space, than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination can not occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, as in the case of the Rcg1 locus being introgressed from MP305, an exotic source, into elite inbreds, these flanking regions carry additional genes that may code for agronomically undesirable traits. This "linkage drag" may also result in reduced yield or other negative agronomic characteristics even after multiple cycles of backcrossing into the elite corn line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, a series of flanking markers surrounding the gene can be utilized to select for recombinations in different population sizes. For example, in smaller population sizes recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors 4 map [online], [retrieved on 2006 Mar. 21]. Retrieved from the Internet:<URL: http://www.maizegdb.org/cgi-bin/displaymaprecord.cgi?id=871214>

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The three types of markers described in this disclosure can be used in marker assisted selection protocols; simple sequence repeat (SSR, also known as microsatellite) markers, single nucleotide polymorphism (SNP) markers and fragment length polymorphic (FLP) markers. SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics*, 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. pp 75-135).

For example, an SSR marker profile of MP305 is provided in Example 5 herein. This marker profile was generated by gel electrophoresis of the amplification products generated by the primer pairs for these markers. Scoring of marker genotype is based on the size of the amplified fragment, which in this case was measured by the base pair weight of the fragment. While variation in the primer used or in laboratory procedures can affect the reported base pair weight, relative values will remain constant regardless of the specific primer or laboratory used. Thus, when comparing lines, the SSR profiles being compared should be obtained from the same lab, so that the same primers and equipment is used. For this reason, when comparing plants or lines vis a vis specific markers, it is preferable to state that such plants or lines have the same (or different) alleles at specified loci (e.g. one can say that if a plant does not comprise the MP305 derived chromosomal interval at or below UMC15a, it will not comprise the same alleles as MP305 at all of the loci at or below UMC15a listed on Table 6 in Example 5). An SSR service for corn is available to the public on a contractual basis by DNA Landmarks in Saint-Jean-sur-Richelieu, Quebec, Canada.

Various types of FLP markers can be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). Plant Mol Biol 48, 539-547; Rafalski (2002b), supra). The term "indel" refers to an insertion or deletion, wherein one line may be referred to as having an insertion relative to a second line, or the second line may be referred to as having a deletion relative to the first line. The MZA markers disclosed herein are examples of amplified FLP markers that have been selected because they are in close proximity to the Rcg1 gene.

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), supra). Haplotypes can be more informative than single SNPs and can be more descriptive of any particular genotype. For example, a single SNP may be allele 'T' for MP305, but the allele 'T' might also occur in the maize breeding population being utilized for recurrent parents. In this case, a haplotype, e.g. a series of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

As described herein, many of the primers listed in Tables 1 and 2 can readily be used as FLP markers to select for the Rcg1 locus. These primers can also be used to convert these markers to SNP or other structurally similar or functionally equivalent markers (SSRs, CAPs, indels, etc), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs as described above, other types of molecular markers are also widely used, including but not limited to expressed sequence tags (ESTs) and SSR markers derived from EST sequences, and randomly amplified polymorphic DNA (RAPD). As used herein, the term "Genetic Marker" shall refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, Trends in Genetics 9:275-280), Amplified Fragment Length Polymorphism (AFLP) (Vos et al., 1995, Nucleic Acids Res. 23:4407-4414), Single Nucleotide Polymorphism (SNP) (Brookes, 1999, Gene 234:177-186), Sequence Characterized Amplified Region (SCAR) (Paran and Michelmore, 1993, Theor. Appl. Genet. 85:985-993), Sequence Tagged Site (STS) (Onozaki et al., 2004, Euphytica 138:255-262), Single Stranded Conformation Polymorphism (SSCP) (Orita et al., 1989, Proc Natl Acad Sci USA 86:2766-2770), Inter-Simple Sequence Repeat (ISSR) (Blair et al., 1999, Theor. Appl. Genet. 98:780-792), Inter-Retrotransposon Amplified Polymorphism (IRAP), Retrotransposon-Microsatellite Amplified Polymorphism (REMAP) (Kalendar et al., 1999, Theor. Appl. Genet. 98:704-711), an RNA cleavage product (such as a Lynx tag) and the like.

More generically, the term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST.

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like).

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers.

For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

Figure 9A:
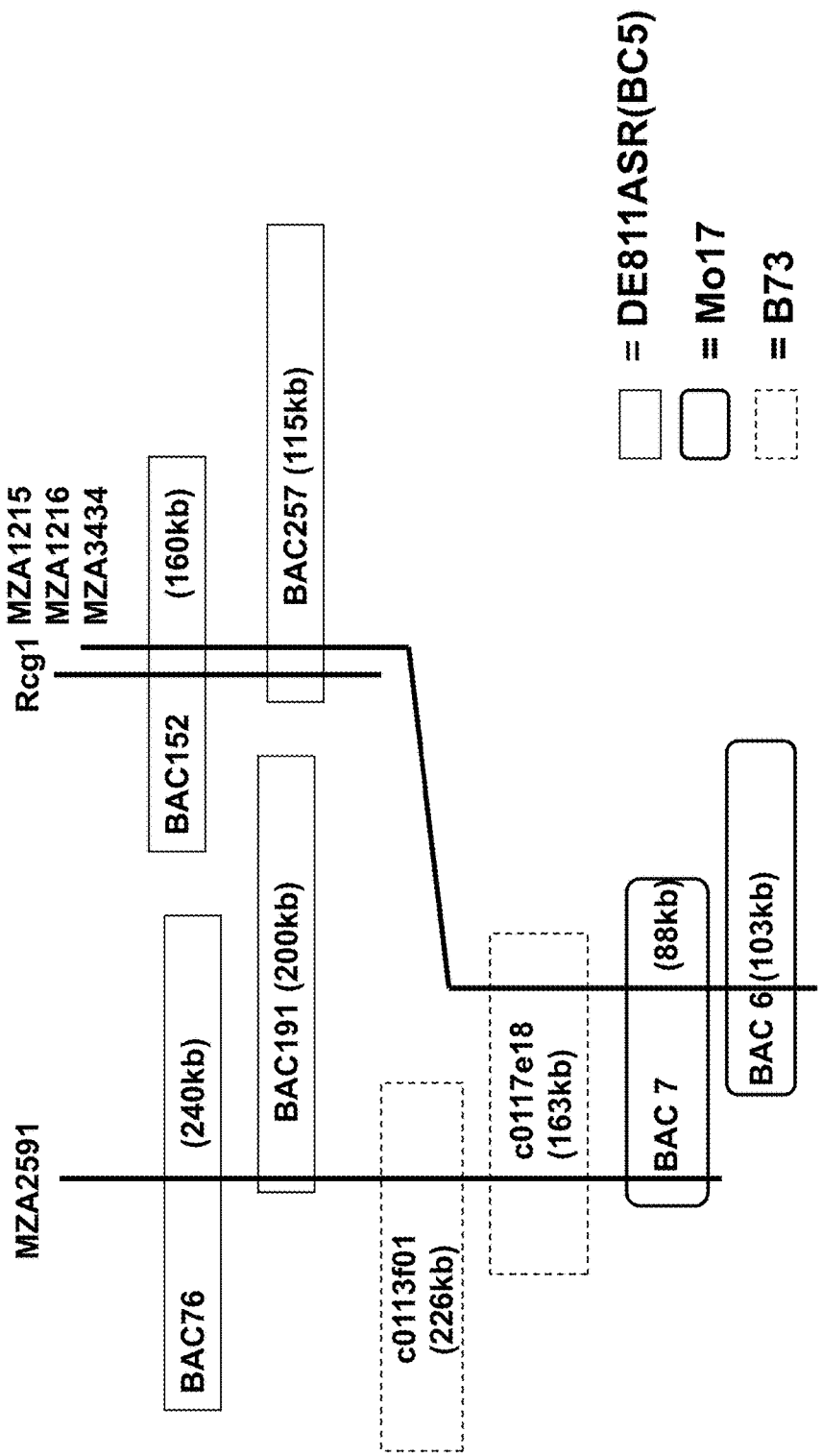
FIGS. 9(*a-b*).

As noted in Example 2, by using common sequences from the region flanking the Rcg1 locus that hybridized to BACs in the Mo17 and the B73 BAC libraries, the BACs from both libraries were lined up with BACs from the DE811ASR (BC5) homologous region flanking the Rcg1 locus in a tiling path as shown in FIG. 9(a). The public B73 BACs, c0113f01 and c0117e18 were identified as directly north and south, respectively, of the Rcg1 locus.

With this information, an extended non-contiguous tiling path of B73 BACs between genetic markers UMC2285 and UMC15a, UMC2285 and UMC2187, UMC1086 and UMC2200, or UMC2041 and UMC2200, can be created by aligning genetic markers within this region with the physical map of the B73 BAC. Alignment information of the genetic and physical maps of B73 is obtained from the maize genome database of the Arizona Genomics Institute on the world wide web, accessed by entering the following web address prefixed by "www.": genome.arizona.edu/fpc/maize/#webagcol. In the WebChrom view, one can select the genetic markers in the vicinity of the Rcg1 gene and get a link to the physical contig where these genetic markers are located. By aligning the physical map in such way with the genetic map one can find a plethora of B73 BACs in the region between the chromosomal intervals defined by genetic markers UMC2285 and UMC15a, UMC2285 and UMC2187, UMC1086 and UMC2200, or UMC2041 and UMC2200. The BACs can be used by one of ordinary skill in the art to develop new markers for introgression of the Rcg1 locus into maize germplasm. In particular, such genetic markers would be useful for tracking the Rcg1 locus in any lines into which the Rcg1 locus or Rcg1 gene has been introgressed, and for selecting for recurrent parent genome in a backcrossing program.

Figure 21:
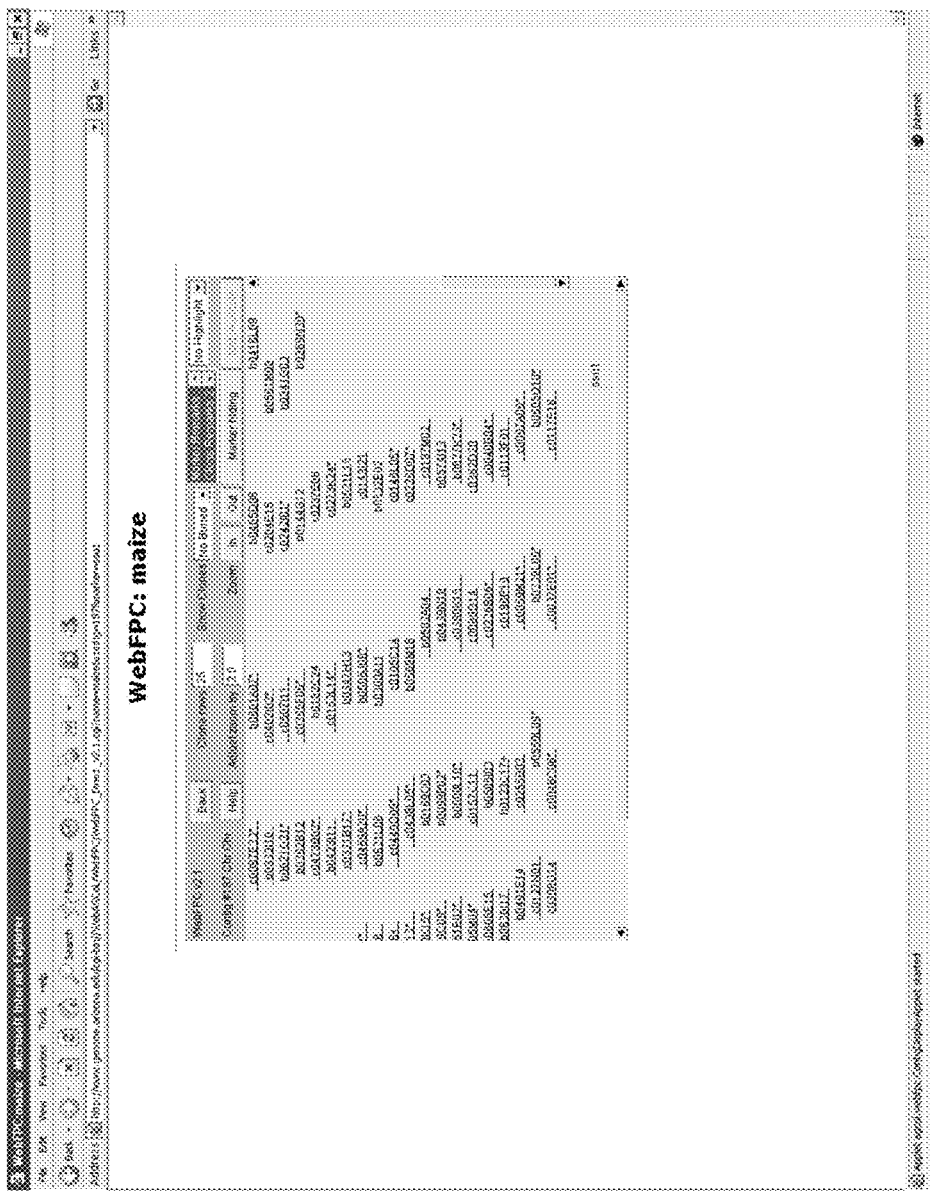
FIG. 21 shows a contig on the B73 physical map that is homologous to the region into which the Rcg1 non-colinear region containing DE811ASR (BC5) is inserted, which demonstrates that many B73 derived bacterial artificial chromosomes (BACs) are available in the region of interest from which sequence information can be obtained.

For example, in order to design polymorphic markers that will be useful for introgression and selection of the Rcg1 gene or locus in other maize germplasm, sequence information of the region surrounding the Rcg1 locus can be used. There are many B73 derived bacterial artificial chromosomes (BACs) available in the region of interest from which sequence information can be obtained. An example of BACs in the region of interest is shown in FIG. 21, which shows a contig on the B73 physical map that is homologous to the Rcg1 region in DE811ASR (BC5) [FIG. 21 retrieved 2006 Mar. 10]. Retrieved from the Internet <URL: http://www.genome.arizona.edu/cgi-bin/WebAGCoL/WebFPC/WebFPC_Direct_v2.1.cgi?name=maize&contig=187&marker=ssu1>. Sequence information is obtained either through information that is already publicly available (e.g. BAC end-sequence, sequence of Expressed Sequence Tags (ESTs) that hybridize to BACs in this region, overgo probes that often relate to these ESTs, etc.) or by obtaining new sequence by directly sequencing BAC clones in this region. From this sequence one can determine which regions are most unique using several different methods known to one of ordinary skill in the art. For example, by using gene prediction software or by blasting the sequence against all available maize sequence, one can select for non-repetitive sequence. Low copy sequence can be used to develop a wide array of nucleic acid based markers. These markers are used to screen the plant material in which the Rcg1 locus is present and the plant material in which the Rcg1 locus is absent. If a marker outside of the Rcg1 locus is desired, then the markers are used to screen the plant material in which the Rcg1 locus is present and the plant material in which the Rcg1 locus is absent to determine if the marker is polymorphic in such germplasm. Polymorphic markers are then used for marker assisted introgression and selection of the Rcg1 region and optimally also recurrent parent genome selection, in other maize germplasm. Thus, with the location of the Rcg1 locus identified and its association with resistance to *Colletotrichum* established, one of ordinary skill in the art can utilize any number of existing markers, or readily develop new markers, that can be used introgress or identify the presence or absence of the Rcg1 locus in germplasm, and to select for recurrent parent genome in a backcrossing program.

On a genetic map, linkage of one molecular marker to a gene or another molecular marker is measured as a recombination frequency. In general, the closer two loci (e.g., two SSR markers) are on the genetic map, the closer they lie to each other on the physical map. A relative genetic distance (determined by crossing over frequencies, measured in centimorgans; cM) can be proportional to the physical distance (measured in base pairs, e.g., kilobase pairs [kb] or megabasepairs [Mbp]) that two linked loci are separated from each other on a chromosome. A lack of precise proportionality between cM and physical distance can result from variation in recombination frequencies for different chromosomal regions, e.g., some chromosomal regions are recombination "hot spots," while others regions do not show any recombination, or only demonstrate rare recombination events. Some of the introgression data and mapping information suggest that the region around the Rcg1 locus is one that does have a high amount of recombination.

In general, the closer one marker is to another marker, whether measured in terms of recombination or physical distance, the more strongly they are linked. The closer a molecular marker is to a gene that encodes a polypeptide that imparts a particular phenotype (disease resistance), whether measured in terms of recombination or physical distance, the better that marker serves to tag the desired phenotypic trait. If possible, the best marker is one within the gene itself, since it will always remain linked with the gene causing the desired phenotype.

Genetic mapping variability can also be observed between different populations of the same crop species, including maize. In spite of this variability in the genetic map that may occur between populations, genetic map and marker information derived from one population generally remains useful across multiple populations in identification of plants with desired traits, counter-selection of plants with undesirable traits and in guiding MAS.

To locate equivalent markers across genetic maps, a mapping population may be used to confirm whether any such equivalent marker is within the region described herein and therefore useful for selection of Rcg1. Using this method, the equivalent marker, along with the markers listed herein, are mapped on such mapping population. Any equivalent marker that falls within the same region can be used to select for Rcg1. Mapping populations known in the art and that may be used for this purpose include, but are not limited to, the IBM populations and T218×GT119 IF$_2$ population described in Sharopova, N. et al. (2002) *Plant Mol Biol* 48(5):463-481 and Lee, M. et al. (1999): *Tools for high resolution genetic mapping in maize—status report*. Proc. Plant Animal Genome VII, Jan. 17-21, 1999, San Diego, USA, P. 146; the UMC 98 population, described in Davis, G. L. et al. (1999) *Genetics* 152(3):1137-72 and in Davis, M. D. et al., (1998) The 1998 UMC Maize Genetic Map: ESTs, Sequenced Core Markers, and Nonmaize Probes as a Foundation for Gene Discovery, *Maize Genetics Conference Abstracts* 40.

As used herein, "introgression" or "introgressing" shall refer to moving a gene or locus from one line to another by: (1) crossing individuals of each line to create a population; and (2) selecting individuals carrying the desired gene or locus. After each cross, the selection process is repeated. For example, the gene of the embodiments, or the locus containing it, may be introgressed into a recurrent parent that is not resistant or only partially resistant, meaning that it is sensitive or susceptible or partially so, to Cg. The recurrent parent line with the introgressed gene or locus then has enhanced or newly conferred resistance to Cg. This line into which the Rcg1 locus has been introgressed is referred to herein as an Rcg1 locus conversion.

The process of introgressing is often referred to as "backcrossing" when the process is repeated two or more times. In introgressing or backcrossing, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires (Les Colloques, Vol. 72, pp. 45-56 and Openshaw et al., (1994) Marker-assisted Selection in Backcross Breeding, Analysis of Molecular Marker Data, pp. 41-43. The initial cross gives rise to the F1 generation; the term "BC1" then refers to the second use of the recurrent parent, "BC2" refers to the third use of the recurrent parent, and so on.

In the case of Rcg1, where the sequence of the gene and very nearby regions are available, DNA markers based on the gene itself or closely linked sequences can be developed for direct selection of the donor gene in the recurrent parent background. While any polymorphic DNA sequence from the chromosomal region carrying the gene could be used, the sequences provided in the embodiments allow the use of DNA markers within or close to the gene, minimizing false positive selection for the gene. Flanking markers limit the size of the donor genome fragments introduced into the recipient background, thus minimizing so called "linkage drag," meaning the introduction of undesirable sequences from the donor line that could impact plant performance in otherwise elite germplasm. The embodiments provide multiple examples of DNA markers that could be so used, and the person skilled in the art will be able to use the genomic sequences provided to create even more markers. An example is to use markers that hybridize (in the case of RFLP assays) or anneal (in the case of PCR assays) specifically (exclusively) to sequences closely linked, including within, the locus. In principle, sequences that also hybridize or anneal elsewhere in the genome could be used if several such markers are used in combination. When PCR reactions are used, in practice the length of the primers used in the amplification reaction should be at least about 15 nucleotides, but depending on the sequences and hybridization conditions, any length that provides specific annealing can be used, such as about 16, about 17, about 18, about 19, about 20, about 21, about 22, about 23, about 24, about 25, about 26, about 27, about 28 or longer. For PCR reactions the term "anneal" is commonly used, and as used herein it shall be understood to have the same meaning as "hybridize."

Thus, by using the markers and processes described herein, one may produce a plant comprising a truncated chromosomal interval comprising the Rcg1 locus and/or the Rcg1 gene. The term "chromosomal interval" or "chromosomal segment" refers to a contiguous linear span of genomic DNA that resides in planta on a single chromosome, usually defined with reference to two markers defining the end points of the chromosomal interval. The specified interval may include the markers at the end points (e.g. one or more markers on or within the chromosomal interval defined by marker A and marker B) or may exclude the markers at the end points of the interval (e.g. one or more markers within the chromosomal interval defined by marker A and marker B). A truncated chromosomal interval refers to a chromosomal interval that has been reduced in size by selecting for one or more recombination events that have reduced the size of the chromosomal interval. A "recombination event" refers to the occurrence of recombination between homologous chromosomes, and refers to a specific chromosomal location where such a recombination has occurred (e.g. a recombination of a chromosomal interval internal to the end points of the chromosome will have a recombination event at each end of the chromosomal interval). The truncated chromosomal interval may be defined with reference to one or both new markers at the end points of the segment. The length of two chromosomal segments may be measured by either centimorgans or base pairs. The genetic elements or genes located on a single chromosomal interval are physically linked. The size of a chromosomal interval is not particularly limited, but in the context of the embodiments of the present invention, generally the genetic elements located within a single chromosomal interval are also genetically linked.

By using the processes of the embodiments, it is possible to select for a plant that comprises a truncated chromosomal interval comprising the Rcg1 gene. Specifically, with respect to the invention described in more detail in the examples below, the chromosomal interval may be reduced to a length of 12cM or less, 10 cM or less, 8 cM or less, 6 cM or less, 4 cM or less, 3cM or less, 2.5 cM or less, 2 cM or less, 1.5 cM or less, 1 cM or less, 0.75 cM or less, 0.50 cM or less, or 0.25 cM or less, in each case as measured with respect to the map distances as shown on the IBM2 Neighbors 4 genetic map as in effect on Mar. 21, 2006. As measured in base pairs, the chromosomal interval may be reduced to a length of 15 mbp or less, 10 mbp or less, 5 mbp or less, 3 mbp or less, 1 mpb or less, 500 kbp or less, or 250 kbp or less. One of ordinary skill in the art would understand that it is undesirable to cause a break in the chromosomal region so proximal to the Rcg1 coding sequence (e.g. within 5 kpb or less, within 4 kbp or less, 3 kbp or less, 2 kbp or less, 1 kbp or less, or 0.5 kbp or less), such that the promoter and other upstream regulatory elements would be unlinked from the coding sequence.

The term "locus" generally refers to a genetically defined region of a chromosome carrying a gene or, possibly, two or more genes so closely linked that genetically they behave as a single locus responsible for a phenotype. When used herein with respect to Rcg1, the "Rcg1 locus" shall refer to the defined region of the chromosome carrying the Rcg1 gene including its associated regulatory sequences, plus the region surrounding the Rcg1 gene that is non-colinear with B73, or any smaller portion thereof that retains the Rcg1 gene and associated regulatory sequences. This locus has also been referred to elsewhere as the ASR locus, and will be referred to as the Rcg1 locus here.

A "gene" shall refer to a specific genetic coding region within a locus, including its associated regulatory sequences. The region encoding the Rcg1 primary transcript, referred to herein as the "Rcg1 coding sequence", will be used to define the position of the Rcg1 gene, and one of ordinary skill in the art would understand that the associated regulatory sequences will be within a distance of about 4 kb from the Rcg1 coding sequence, with the promoter located upstream. One embodiment of the present invention is the isolation of the Rcg1 gene and the demonstration that it is the gene responsible for the phenotype conferred by the presence of the locus.

As used herein, "linked" or "linkage" (as distinguished from the term "operably linked") shall refer to the genetic or physical linkage of loci or genes. Loci or genes are considered genetically linked if the recombination frequency between them is less than about 50% as determined on a single meiosis map. They are progressively more linked if the recombination frequency is about 40%, about 30%, about 20%, about 10% or less, as determined on a single meiosis map. Two or more genes are physically linked (or syntenic) if they have been demonstrated to be on a single piece of DNA, such as a chromosome. Genetically linked genes will in practice be physically linked (or syntenic), but the exact physical distance (number of nucleotides) may not have been demonstrated yet. As used herein, the term "closely linked" refers to genetically linked markers within 15 cM or less, including without limitation 12 cM or less, 10 cM or less, 8 cM or less, 7 cM or less, 6 cM or less, 5 cM or less, 4 cM or less, 3 cM or less, 2 cM or less, 1 cM or less and 0.5 cM or less, as determined on the IBM2 neighbors 4 genetic map publicly available on the Maize GDB website previously referenced in this disclosure. A DNA sequence, such as a short oligonucleotide representing a sequence within a locus or one complementary to it, is also linked to that locus.

A "line" or "strain" is a group of individuals of identical parentage that are generally inbred to some degree and that are generally homozygous and homogeneous at most loci.

An "ancestral line" or "progenitor" is a parent line used as a source of genes, e.g., for the development of elite lines. "Progeny" are the descendents of the ancestral line, and may be separated from their ancestors by many generations of breeding. For example, many elite lines are the progeny of B73 or Mo17. A "pedigree structure" defines the relationship between a descendant and each ancestor that gave rise to that descendant. A pedigree structure can span one or more generations, describing relationships between the descendant and it's parents, grand parents, great-grand parents, etc.

An "elite line" or "elite variety" is an agronomically superior line or variety that has resulted from many cycles of breeding and selection for superior agronomic performance. An "elite inbred line" is an elite line that is an inbred, and that has been shown to be useful for producing sufficiently high yielding and agronomically fit hybrid varieties (an "elite hybrid variety"). Numerous elite lines and varieties are available and known to those of skill in the art of corn breeding. Similarly, "elite germplasm" is an agronomically superior germplasm, typically derived from and/or capable of giving rise to a plant with superior agronomic performance, such as an existing or newly developed elite line of corn.

In contrast, an "exotic corn line" or "exotic corn germplasm" is germplasm derived from corn not belonging to an available elite line, elite variety or elite germplasm. In the context of a cross between two corn plants, an exotic line or exotic germplasm is not closely related by descent to the elite line, elite variety or elite germplasm with which it is crossed. Most commonly, the exotic line or exotic germplasm is selected to introduce novel genetic elements (typically novel alleles) into a breeding program.

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

Figure 7A:
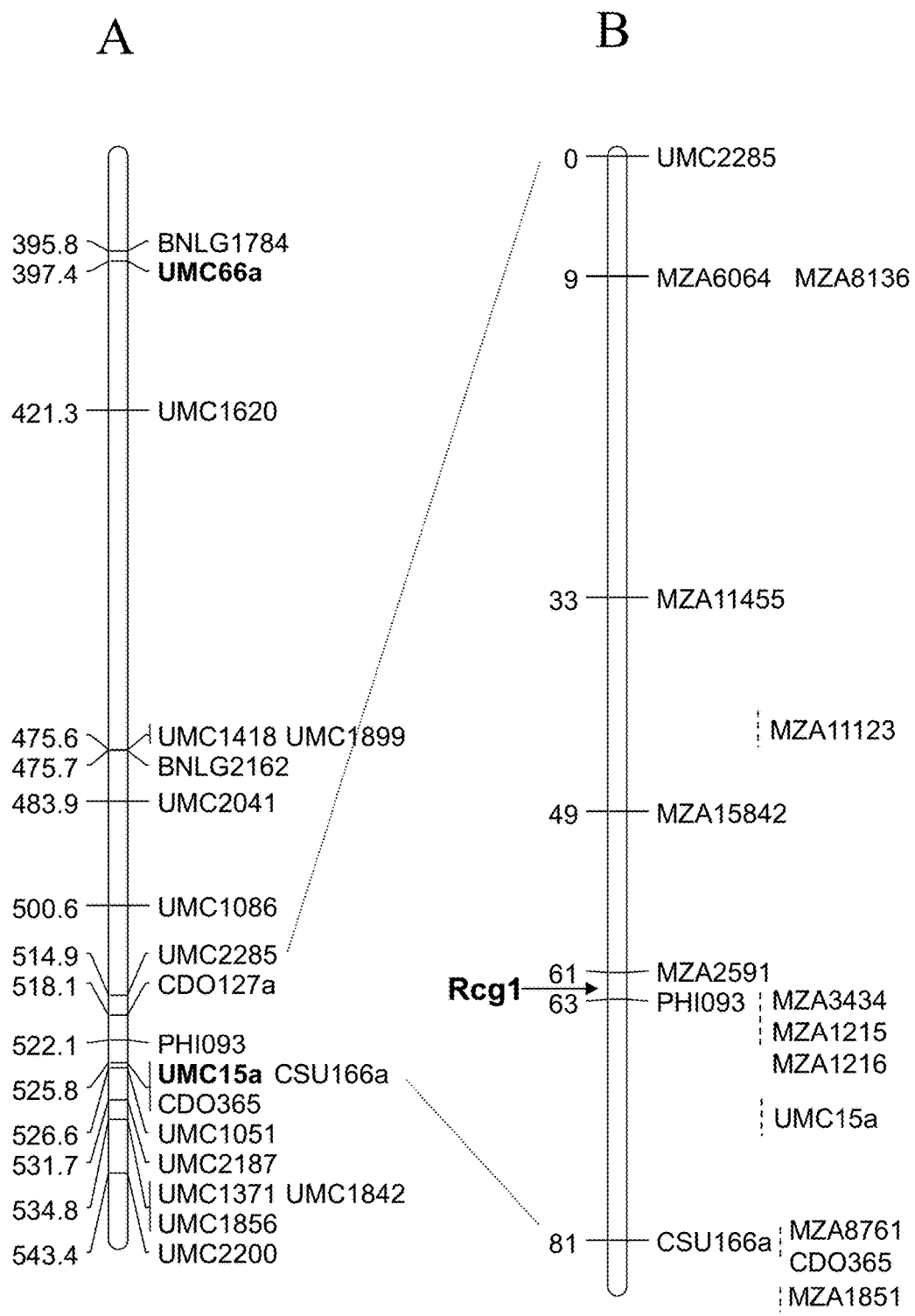
FIG. 7(*a-b*) is a series of genetic map images with increasing resolution of the map of the region near the Rcg1 gene. Map distances for 7(*a*) for the map labelled "A" are in cM and in relation to the IBM2 Neighbors 4 genetic map. Map distances for 7(*b*) for the map labelled "B" were developed using 184 individuals from the BC7 population, and map distances for 7(*b*) for the map labelled "C" were developed using 1060 individuals from the BC7 population. Genetic mapping in the BC7 population increased the map resolution greater than 10-fold, when compared with the published map. The location of the markers shown to the right of each map is based on extrapolation of their location on the physical map.
Figure 7B:
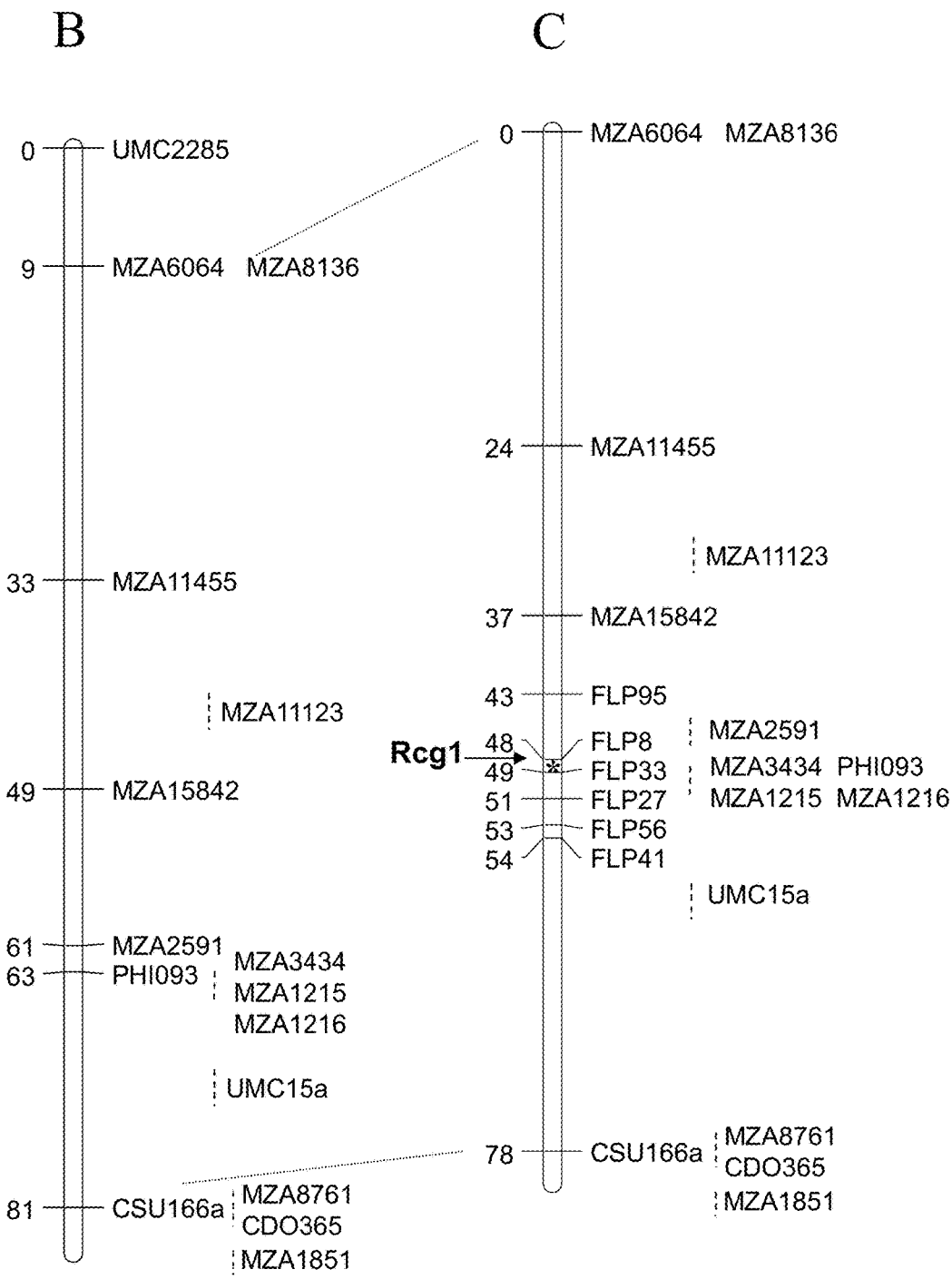
Figure 22:
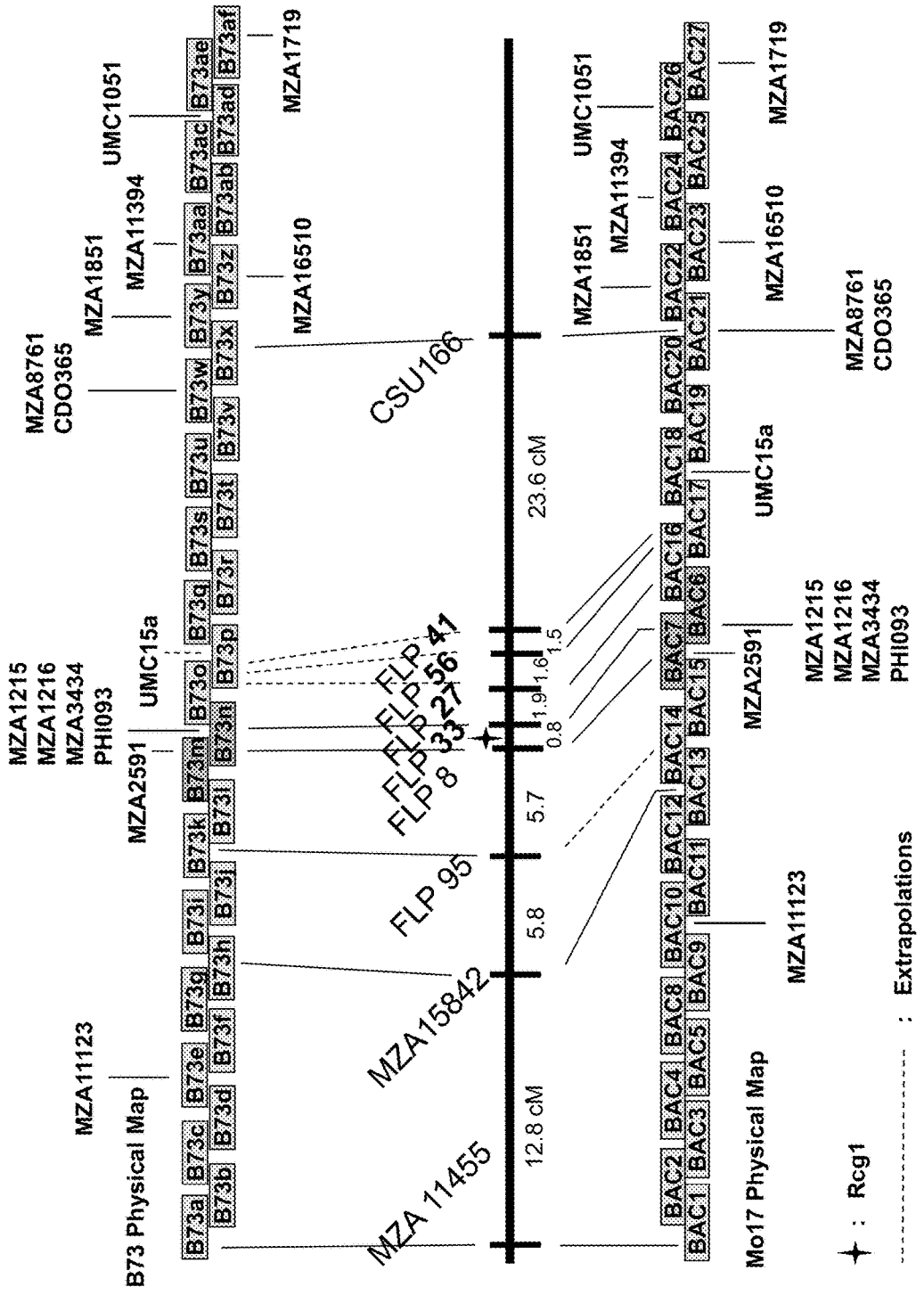
FIG. 22 shows the alignment of the genetic map containing MZA and public markers with the physical maps of Mo17 and B73. The genetic map distances were developed by using 1060 individuals from the BC7 mapping population. An analysis of a Mo17 BAC library also showed the Rcg1 locus to be non-colinear with the corresponding region of Mo17. The location of the markers shown by dotted lines to the B73 map are extrapolations from the Mo17 physical map location. The location of the markers shown by dotted lines to the Mo17 map are extrapolations from the B73 physical map location.
Figure 26:
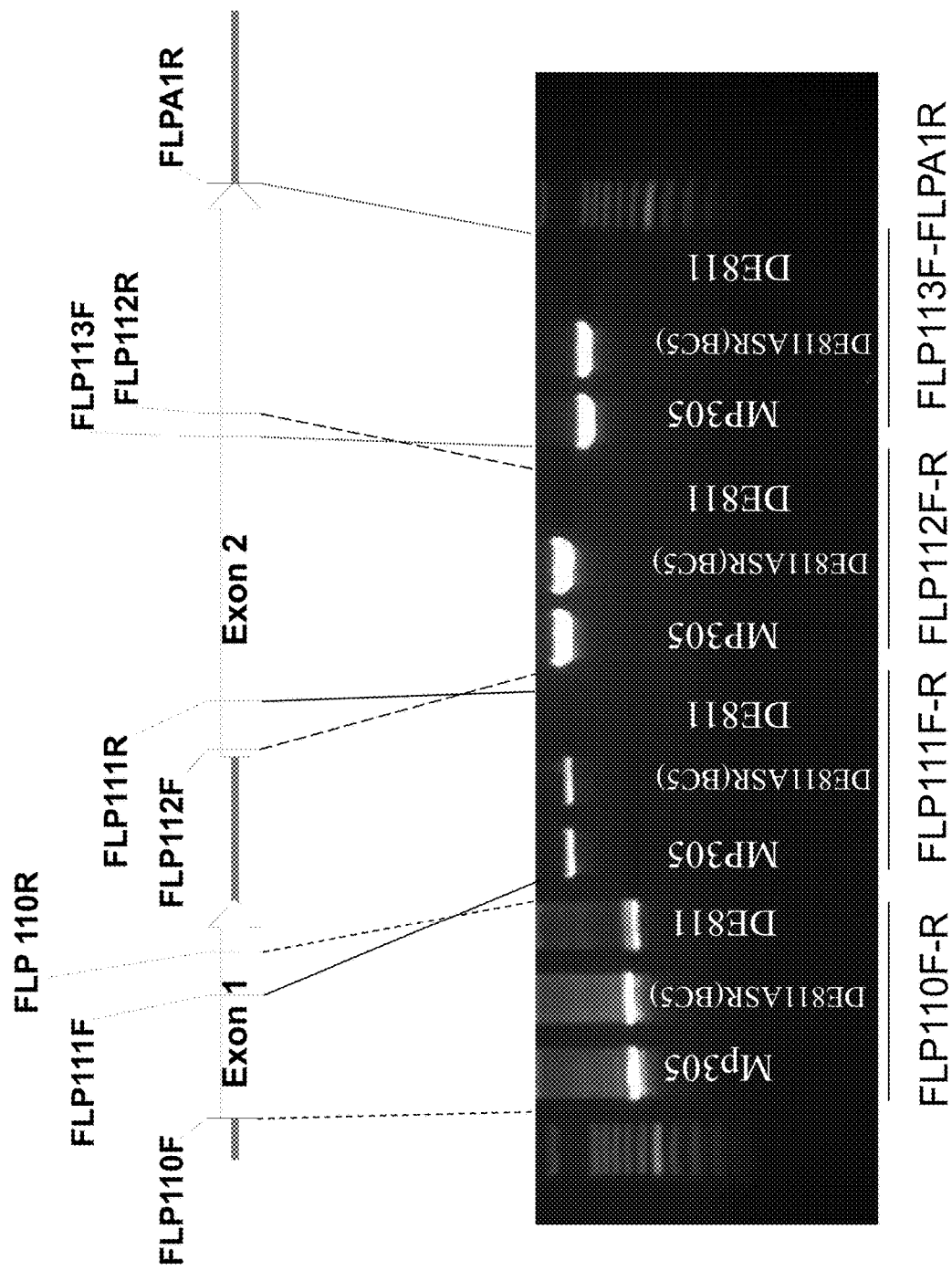
FIG. 26 shows that PCR amplification using Rcg1 specific primer pairs only amplifies in the resistant line DE811ASR (BC5) and donor parent MP305, but not in susceptible line DE811, with the exception of FLP110F-R, which amplifies the coiled coil-nucleotide binding site region, which is highly conserved, and thus amplifies a region elsewhere in the genome that is not Rcg1 in the DE811 line. A 100 bp ladder was used for fragment sizing.

With respect to map directions noted herein, instead of the terms 5' and 3', the terms "north" and "above" are used (e.g., a marker north of the Rcg1 gene refers to a marker above the Rcg1 gene, as determined with reference to the maps provided in a vertical orientation, such as FIGS. 7 and 8, and to the left of the Rcg1 gene, as determined with reference to maps provided in a horizontal orientation, such as FIG. 22). Likewise, the terms "south" and "below" are used (e.g. a marker south of the Rcg1 gene refers to a marker below the Rcg1 gene, as determined with reference to the vertically oriented maps provided herein, and to the right of the Rcg1 gene, as determined with reference to the horizontally oriented maps provided herein). More specifically, above the Rcg1 coding sequence refers to the chromosome above, or north of the primary transcript in SEQ ID NO: 1 (at about FLP110F), and below the Rcg1 coding sequence refers to the chromosome below or south of the primary transcript in SEQ ID NO: 1 (at about FLPA1R). See FIG. 26. The term "proximal" and "distal" are relative terms meaning, respectively, nearer and farther from a specified location (e.g., the Rcg1 gene) when used to compare two points on a map relative to the specified location.

The term "computer systems" refers generally to various automated systems used to perform some or all of the method steps described herein. The term "instructions" refers to computer code that instructs the computer system to perform some or all of the method steps. In addition to practicing some or all of the method steps, digital or analog systems, e.g., comprising a digital or analog computer, can also control a variety of other functions such as a user viewable display (e.g., to permit viewing of method results by a user) and/or control of output features (e.g., to assist in marker assisted selection or control of automated field equipment).

Certain of the methods described herein are optionally (and typically) implemented via a computer program or programs (e.g., that store and can be used to analyze molecular marker data). Thus, the embodiments provide digital systems, e.g., computers, computer readable media, and/or integrated systems comprising instructions (e.g., embodied in appropriate software) for performing the methods herein. The digital system will include information (data) corresponding to plant genotypes for a set of genetic markers, and optionally, phenotypic values and/or family relationships. The system can also aid a user in performing marker assisted selection for Rcg1 according to the methods herein, or can control field equipment which automates selection, harvesting, and/or breeding schemes.

Standard desktop applications such as word processing software (e.g., Microsoft Word™ or Corel WordPerfect™) and/or database software (e.g., spreadsheet software such as Microsoft Excel™, Corel Quattro Pro™, or database programs such as Microsoft Access™ or Paradox™) can be adapted to the embodiments by inputting data which is loaded into the memory of a digital system, and performing an operation as noted herein on the data. For example, systems can include the foregoing software having the appropriate genotypic data, and optionally pedigree data, used in conjunction with a user interface (e.g., a GUI in a standard operating system such as a Windows, Macintosh or LINUX system) to perform any analysis noted herein, or simply to acquire data (e.g., in a spreadsheet) to be used in the methods herein. The computer can be, e.g., a PC (Intel x86 or Pentium chip-compatible DOS™, OS2™, WINDOWS™, WINDOWS NT™, WINDOWS95™, WINDOWS98™, LINUX, Apple-compatible, MACINTOSH™ compatible, Power PC compatible, or a UNIX compatible (e.g., SUN™ work station) machine) or other commercially common computer which is known to one of skill. Software for performing association analysis and/or phenotypic value prediction can be constructed by one of skill using a standard programming language such as Visualbasic, Fortran, Basic, Java, or the like, according to the methods herein.

Any system controller or computer optionally includes a monitor which can include, e.g., a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of genetic marker genotype, phenotypic value, or the like in the relevant computer system.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to an appropriate language for instructing the system to carry out any desired operation. For example, a digital system can instruct selection of plants comprising certain markers, or control field machinery for harvesting, selecting, crossing or preserving crops according to the relevant method herein.

The invention can also be embodied within the circuitry of an application specific integrated circuit (ASIC) or programmable logic device (PLD). In such a case, the invention is embodied in a computer readable descriptor language that can be used to create an ASIC or PLD. The invention can also be embodied within the circuitry or logic processors of a variety of other digital apparatus, such as PDAs, laptop computer systems, displays, image editing equipment, etc.

EXAMPLES

The embodiments of the invention are further defined in the following examples, in which all parts and percentages are by weight and degrees are Celsius, unless otherwise stated. It should be understood that these examples, while indicating embodiments of the invention, are given by way of illustration only. From the above discussion and these examples, one skilled in the art can ascertain the essential characteristics of the embodiments of this invention, and without departing from the spirit and scope thereof, can make various changes and modifications to adapt it to various usages and conditions. Thus, various modifications of the embodiments of the invention in addition to those shown and described herein will be apparent to those skilled in the art from the foregoing description. Such modifications are also intended to fall within the scope of the appended claims. The disclosure of each reference set forth herein is incorporated by reference in its entirety. Examples 1-4 and 7-12 are actual. Examples 5, 6 and 13 are actual in part and prophetic in part.

Example 1

Fine Mapping of the Rcg1 Locus to a Specific Region of 4L

In order to map and clone the gene responsible for the resistance of corn line MP305 to Cg, lines had previously been created which differed as little as possible from each other genetically with the exception of the presence of the locus responsible for the resistant phenotype. Such lines are called near isogenic lines. To this end, DE811 had been crossed to MP305 and the progeny had been backcrossed to the sensitive line DE811 three times, at each backcross selecting for resistance to Cg and otherwise for characteristics of DE811 (Weldekidan and Hawk, (1993), *Maydica*, 38:189-192). The resulting line was designated DE811ASR (BC3) (Weldekidan and Hawk, (1993) supra). This line was used as the starting point for the fine mapping of the Rcg1 locus. It was first necessary to know roughly where in the maize genome it was located. Using standard genetic methods, Jung et al. ((1994) supra) had previously localized the locus on the long arm of chromosome 4.

Since the Rcg1 locus had previously been mapped to the long arm of maize chromosome 4, using the information on markers near the locus obtained by Jung et al. (1994) supra, all available public and private simple sequence repeat (SSR) markers located in the region of the chromosome designated 4.06-4.08 were analyzed to determine if these markers were polymorphic between the two near isogenic lines DE811 and DE811ASR (BC5). The DE811ASR (BC5) line was derived from the DE811ASR (BC3) line described by Weldekidan and Hawk (1993), supra through two backcrosses to DE811 under selection for resistance to Cg, followed by 5 generations of selfing and selection to obtain the BC5 line. The BC5 line was backcrossed twice more to DE811 to create the BC7 segregating population used for fine mapping. In order to be able to conduct phenotypic evaluation on a family basis, BC7 individuals were selfed to create BC7S1 families.

From this analysis two SSR markers, PH1093 and UMC2041, were discovered to be polymorphic. Using the publicly available inter-mated (Coe et al. (2002) *Plant Physiol.* 128:9-12; Gardiner, et al., (2004), *Plant Physiol.*, 134:1317-1326; Yim et al., (2002) *Plant Physiol.* 130:1686-1696) B73×Mo17 (IBM) neighbors map (Lee et al. (2002) *Plant Mol Biol* 48:453-61; Sharopova et al., (2002) *Plant Mol Biol* 48:463-81), the sequences of three nearby Restriction Fragment Length Polymorphism (RFLP) markers, CDO365, CSU166 and CDO127, were used to create fragment length polymorphic markers (hereafter designated FLPs). FLPs are markers that can be assayed using gel electrophoresis or any similar high-resolution fragment separation method following a PCR reaction using primers of a defined sequence. All three markers were found to be polymorphic. The FLPs used in mapping the Rcg1 locus are summarized in Table 1. Any primers for the MZA FLPs shown on Table 1, which also have the same MZA markers names shown on Table 2, will amplify a region of the FLP internal to the internal sequence shown on Table 2. The annealing temperature for all the primers listed in Table 1 is 60° C.

Figure 3:
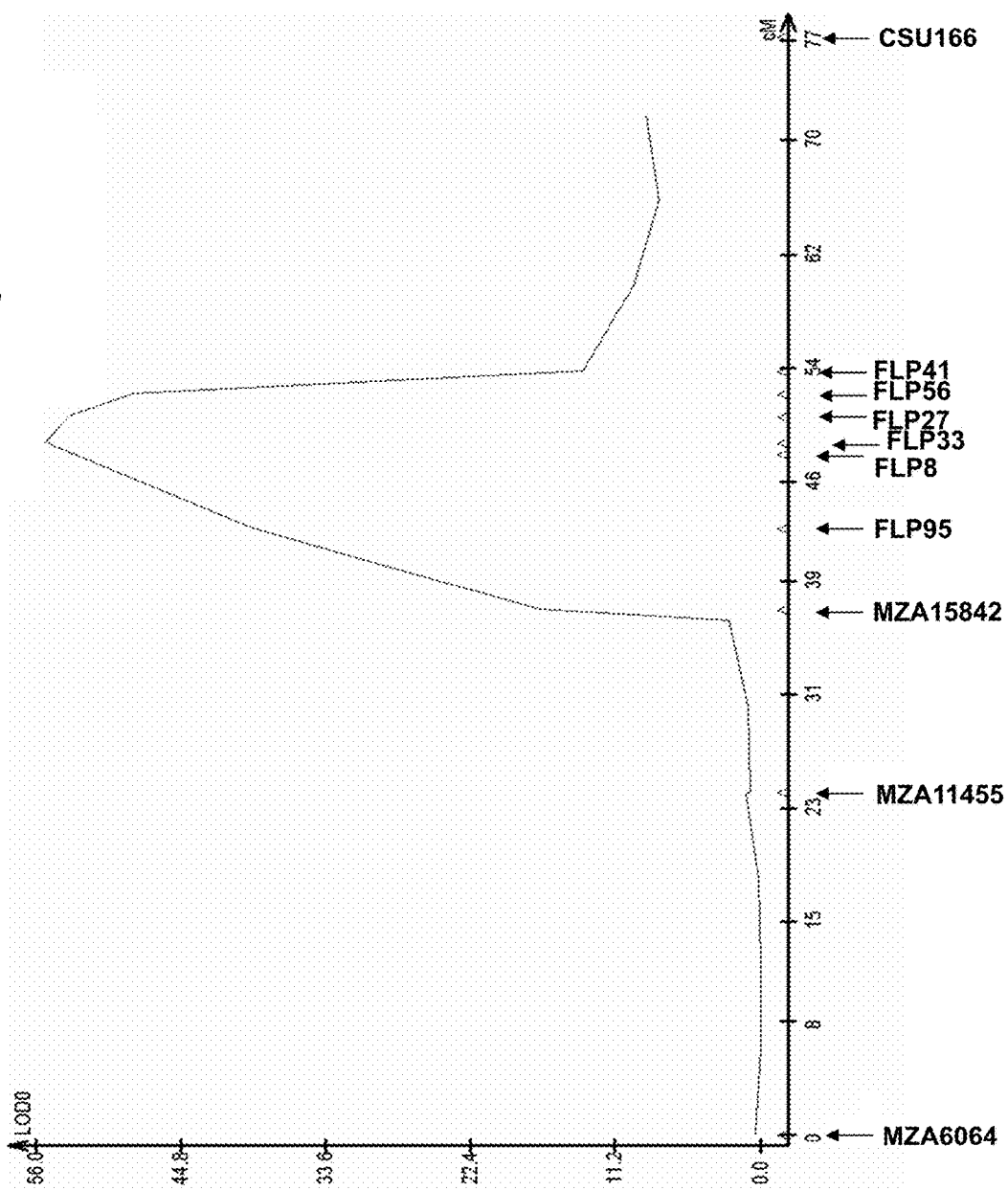
FIG. 3 is a graph produced by Windows QTL Cartographer software showing a statistical analysis of the chance (Y axis) that the locus responsible for the Cg resistance phenotype is located at a particular position along the chromosome (X axis) as defined by FLP markers.

In order to determine whether the presence of these three polymorphic FLPs and two polymorphic SSRs was associated with the resistant phenotype, indicating that the region carrying the Rcg1 locus was located on a chromosomal segment containing these three markers, a table was created in which the phenotypic status of 4784 individuals determined by field observation and the genotypic status relative to each of the five markers, determined by fragment size analysis, were entered. This data was submitted sequentially to the software programs Joinmap (Van Ooijen, et al., (2001), *Plant Research International, Wageningen, the Netherlands*) and Windows QTL Cartographer (Wang, et al., (2004), (online, version 2.0 retrieved on 2004 Jun. 14 and version 2.5 retrieved on 2005 Feb. 22); retrieved from the North Carolina State University Statistical Genetics and Bioinformatics website on the Internet <URL: http://statgen.ncsu.edu/qticart/WQTLCart.htm>. The former program determines the order of the markers along the chromosomal region. The latter determines if a particular allele of a marker (a particular form of the two polymorphic forms of the marker) is significantly associated with the presence of the phenotype. Markers for which the presence of one or the other allele is more significantly associated with the resistant phenotype are more likely to be closer to the gene responsible for the resistant phenotype. FIG. 3 depicts a graph produced by Windows QTL Cartographer showing a statistical analysis of the chance (Y axis) that the locus responsible for the Cg resistance phenotype is located at a particular position along the chromosome (X axis) as defined by FLP markers.

From the integrated physical and genetic map as described by Fengler, et al., ((2004) Plant and Animal Genome XII Abstract Book, Page 192 (Poster number P487), January 10-14, San Diego, Calif.) and Gardiner, (2004) supra, it was possible to identify two bacterial artificial chromosome (BAC) contigs, derived from a Mo17 BAC library, harboring the above mentioned genetic markers.

However, the two BAC contigs containing the markers flanking the region of interest contained a gap of unknown size. In order to identify further BACs to bridge this gap, a dense genetic map containing markers (Fengler, (2004) supra) with known positions on the physical map was used to find additional markers genetically linked to markers previously identified on the two BAC contigs. These additional markers in Table 2, were used to identify BAC contigs from a B73 BAC library which closed the physical gap between the previously found Mo17-derived BAC contigs (Coe et al. (2002) supra; Gardiner (2004) supra; Yim et al. (2002) supra. Four markers, MZA11455, MZA6064, MZA2591 and MZA15842, were used for mapping purposes. In Table 2, "E" stands for "external" and "I" stands for "internal," which respectively refer to the outer and inner primers used during nested PCR. The external set is used in the first round of PCR, after which the internal sequences are used for a second round of PCR on the products of the first round. This increases the specificity of the reaction. Upper case letters indicate portions of the primer based on vector sequences, which are later used to sequence the PCR product. They are not maize sequences. For the forward internal nested MZA primers, the upper case portion of the sequence is SEQ ID NO: 126, and for the reverse internal nested MZA primers, the upper case portion is SEQ ID NO: 127. The sequences shown in Table 2 for the internal forward MZA nested primers are therefore a combination of SEQ ID NO: 126 plus the SEQ ID NO: for each respective primer. Similarly, the sequences shown in Table 2 for the internal reverse MZA nested primers are a combination of SEQ ID NO: 127 plus the SEQ ID NO: for each respective primer. These combinations are indicated in the SEQ ID NO: column of Table 2. The annealing temperature for all the primers listed in Table 2 is 55° C. All markers set forth in Table 2 have shown polymorphism within a diverse panel of corn germplasm, including MP305 and the corn lines shown on Table 18.

The sequences of the ends of several of these BACs, as well as ESTs known to be located on these BACs, were used in order to identify new markers with which to further narrow the range in which the locus was located. The further markers used for this purpose are designated FLP8, FLP27, FLP33, FLP41, FLP56 and FLP95 in Table 1. In a manner similar to that described above, phenotype and genotypic correlations were made. It was determined that the locus was most likely located between FLP 8 and FLP 27 (See FIG. 3).

TABLE 1

Markers and primer pairs used in Examples 1, 4 and 5

| Used in Example | Name | Forward | SEQ ID NO: | Reverse | SEQ ID NO: |
|---|---|---|---|---|---|
| 1,4 | FLP8 | CATGGAAGCCCCACAATAAC | 24 | ACATGGGTCCAAAGATCGAC | 23 |
| 1,4 | FLP27 | AGCCCTATTTCCTGCTCCTG | 26 | GCATGCCCCATCTGGTATAG | 25 |
| 1,4 | FLP33 | CTGTCGTTCGGTTTTGCTTC | 28 | GCATTCACATGTTCCTCACC | 27 |
| 1,4 | FLP41 | TGTGTTCGCATCAAAGGTGT | 30 | CTGTAAGGCACCCGATGTTT | 29 |
| 1,4 | FLP56 | GGTCTGGGAATGCTAAAGAGG | 32 | TGTCCAGGGTTACAGAAAACG | 31 |
| 1,4 | FLP95 | ATTTCGACGGAGGGTTCTTC | 33 | GCAGCAGGAGGAGCTCATAG | 34 |
| 4 | FLP110 | ATGGAGGCTGCCCTGCTGAG | 35 | CGTATACCTCTCTGGCAAGGACGG | 36 |
| 4 | FLP111 | TTCCTGTTCGTCTGTATCTGATCCG | 37 | TTTGATTCCGGTCGAGTATAACCTG | 38 |

TABLE 1-continued

Markers and primer pairs used in Examples 1, 4 and 5

| Used in Example | Name | Forward | SEQ ID NO: | Reverse | SEQ ID NO: |
|---|---|---|---|---|---|
| 4 | FLP112 | GAAACTGCCTTCCCAGAAAACAATG | 39 | CAAGATCGGTGAAGTTGGTGCTTC | 40 |
| 4 | FLP113F | ATCACAGATGGGTCTCAAGGATTGC | 41 | | |
| 4 | FLPA1R | | | TTCCAAGCAATTCACAGCTC | 42 |
| 1,5 | UMC1612 | AGGTCCAGGTTACAGAGCAAGAGA | 43 | GCTAGTAGGTGCATGGTGGTTTCT | 44 |
| 1,4,5 | UMC2041 | CTACACAAGCATAGAGGCCTGGAG | 45 | CAGTACGAGACGATGGAGGACAT | 46 |
| 1,4 | CDO127 | TGCTGTTGTTACTCGGGTTG | 47 | CTCTGCCTCAGCACAAATTC | 48 |
| 1,4,5 | PHI093 | AGTGCGTCAGCTTCATCGCCTACAAG | 49 | AGGCCATGCATGCTTGCAACAATGGATACA | 50 |
| 1,4 | CDO365 | CTTCCAGAGGCAAAGCGTAG | 51 | TGTCACCCATGATCCAGTTG | 52 |
| 1,4,5 | CSU166 | TATTGTGCACGTCACCTTGG | 53 | GGGCAGACTTACTGCTGGAG | 54 |
| 1,4 | UMC2285 | ATCTGCCTCCTTTTCCTTGG | 55 | AAGTAGCTGGGCTTGGAGGG | 56 |
| 1,4 | MZA11455 | ACGAAGCAATTTCACCTTCC | 57 | TGTGGAACTAACCCTCAGCATAG | 58 |
| 1 | MZA6064 | CGAGAACCGGAGAAGAAGG | 59 | TTGGGCTGCTGTATTTTGTG | 60 |
| 1,4 | MZA15842 | GACGCAGCTGTGAAGTTGG | 61 | CACCGGAATACCTTGACCAC | 62 |
| 1,5 | UMC1086 | CATGAAAGTTTTCCTGTGCAGATT | 63 | GGGCAACTTTAGAGGTCGATTTATT | 64 |
| 5 | UMC1466 | GATCCACTAGGGTTTCGGGGT | 65 | CGAATAGTGGTCTCGCGTCTATCT | 66 |
| 5 | UMC1418 | GAGCCAAGAGCCAGAGCAAAG | 67 | TCACACACACTACACTCGCAAT | 68 |
| 5 | BNLG2162 | CACCGGCATTCGATATCTTT | 69 | GTCTGCTGCTAGTGGTGGTG | 70 |
| 5 | CSU166 | AAATATCGGCTTTGGTCACG | 71 | TCGTCCTTCCTCAATTCGAC | 72 |
| 5 | UMC1051 | AATGATCGAAATGCCATTATTTGT | 73 | CTGATCTGACTAAGGCCATCAAAC | 74 |
| 5 | UMC2187 | ACCCAACAAGTCTTAATCGGGTTT | 75 | GTCCACCCTACCTCTCAACAAACA | 76 |
| 5 | UMC1371 | CATGTGAATGGAAGTGTCCCTTT | 77 | GCATCCTTTTCGTTTCAAATATGC | 78 |
| 5 | UMC1856 | AGATCTGTTTTGCTTTGCTCTGCT | 79 | CATGCCTTTATTCTCACACAAACG | 80 |

TABLE 2

Nested MZA Primer Pairs Used in Example 1

| Name | Forward | SEQ ID NOs: | Reverse | SEQ ID NOs: |
|---|---|---|---|---|
| MZA1215 E | Agcccaattctgtagatccaa | 81 | Tgcatgcaccggatccttc | 82 |
| MZA1215 I | TGTAAAACGACGGCCAGTagcagcagacgatgcaaaga | 126 + 83 | GGAAACAGCTATGACCATGagctggcggtggacttga | 127 + 84 |
| MZA1216 E | Ccggcctacggcaacaagaa | 85 | agggtacggtgacccgaag | 86 |
| MZA1216 I | TGTAAAACGACGGCCAGTttcgagacgctgtcgtacct | 126 + 87 | GGAAACAGCTATGACCATGacgacgcatggcactagcta | 127 + 88 |
| MZA3434 E | Tgtaccgcgagaactcca | 89 | ttgcattcacatgttcctcac | 90 |
| MZA3434 I | TGTAAAACGACGGCCAGTctactacgacggccgcta | 126 + 91 | GGAAACAGCTATGACCATGttgcagtagttttgtagcagg | 127 + 92 |
| MZA2591 E | Agtaaataacagcattgacctc | 93 | tccaacggcggtcactcc | 94 |
| MZA2591 I | TGTAAAACGACGGCCAGTctatataacagggccctggaa | 126 + 95 | GGAAACAGCTATGACCATGcacaaagcccacaagctaag | 127 + 96 |
| MZA11123 E | Accacaatctgaagcaagtag | 97 | cacagaaacatctggtgctg | 98 |

TABLE 2-continued

Nested MZA Primer Pairs Used in Example 1

| Name | Forward | SEQ ID NOs: | Reverse | SEQ ID NOs: |
|---|---|---|---|---|
| MZA11123 I | TGTAAAACGACGGCCAGTaaa gaccaagaaatgcagtcc | 126 + 99 | GGAAACAGCTATGACCATGa gacatcacgtaacagtttcc | 127 + 100 |
| MZA15842 E | Ctcgattggcatacgcgata | 101 | ttccttctccacgcagttca | 102 |
| MZA15842 I | TGTAAAACGACGGCCAGTag aaggtatttgccatggctta | 126 + 103 | GGAAACAGCTATGACCATGgt ttcacttgctgaaggcagtc | 127 + 104 |
| MZA11455 E | Gaccgatgaaggcaattgtga | 105 | accaaatagtcctagataatgg | 106 |
| MZA11455I I | TGTAAAACGACGGCCAGTtt caaccttctgactgacacat | 126 + 107 | GGAAACAGCTATGACCATGta aacatagtcataaaaattac | 127 + 108 |
| MZA6064 E | Tcgaatgtattttttaatgcgg | 109 | atccacaatggcacttgggt | 110 |
| MZA6064 I | TGTAAAACGACGGCCAGTcagc tattttgtcttcttcct | 126 + 111 | GGAAACAGCTATGACCATGg gtcagattccaattcggac | 127 + 112 |
| MZA11394 E | Tcgtcctaacagcctgtgtt | 113 | gtccggatcaaatggatcgt | 114 |
| MZA11394 I | TGTAAAACGACGGCCAGTaac agcctgtgttgaataaggt | 126 + 115 | GGAAACAGCTATGACCATGc gtgttccgtcgagggagt | 127 + 116 |
| MZA8761 E | Ttctttgattctactcttgagc | 117 | cttcatggacgcctgagatt | 118 |
| MZA8761 I | TGTAAAACGACGGCCAGTag agctttctgaactgatagc | 126 + 119 | GGAAACAGCTATGACCATGtt ggcatttagcttctctcca | 127 + 120 |
| MZA1851 E | Atatattgcaccacttaaagcc | 121 | gggtgttatcacttgttctata | 122 |
| MZA1851 I | TGTAAAACGACGGCCAGTg gagtccttgaccatttgc | 126 + 123 | GGAAACAGCTATGACCATGta tatgcacttctagcgagtat | 127 + 124 |
| MZA16510 E | Aacaacaaggcgacggtgat | 127 | Tcatcttcgtcgtcctcatc | 130 |
| MZA16510 I | TGTAAAACGACGGCCAGTgat catcctgccggagtt | 126 + 131 | GGAAACAGCTATGACCATG aaccgaaaacacaccctc | 127 + 132 |
| MZA1719 E | ccagcggtagattatatacag | 133 | cggtttggtctgatgaggc | 134 |
| MZA1719 I | TGTAAAACGACGGCCAGTct cgggaaccttgttggga | 126 + 135 | GGAAACAGCTATGACCATGt gaaatccagaacctcctttg | 127 + 136 |

Example 2

Isolation of BAC Clones from the Resistant Lines and Identification of Candidate Genes in the Region of the Rcg1 Locus In order to isolate the gene responsible for the phenotype conferred by the Rcg1 locus, BACs containing the region between the FLP 8 and FLP 27 markers were isolated from a BAC library prepared from the resistant line DE811ASR (BC5). This library was prepared using standard techniques for the preparation of genomic DNA (Zhang et al. (1995) *Plant Journal* 7:175-184) followed by partial digestion with HindII and ligation of size selected fragments into a modified form of the commercially available vector pCC1BAC™ (Epicentre, Madison, USA). After transformation into EPI300™ *E. coli* cells following the vendors instructions (Epicentre, Madison, USA), 125, 184 recombinant clones were arrayed into 326 384-well microtiter dishes. These clones were then gridded onto nylon filters (Hybond N+, Amersham Biosciences, Piscataway, USA).

The library was probed with overlapping oligonucleotide probes (overgo probes; Ross et al. (1999) *Screening large-insert libraries by hybridization*, p. 5.6.1-5.6.52, In A. Boyl, ed. Current Protocols in Human Genetics. Wiley, N.Y.) designed on the basis of sequences found in the BAC sequences shown in the previous example to be present between FLP8 and FLP27. BLAST search analyses were done to screen out repeated sequences and identify unique sequences for probe design. The position and interspacing of the probes along the contig was verified by PCR. For each probe two 24-mer oligos self-complementary over 8 bp were designed. Their annealing resulted in a 40 bp overgo, whose two 16 bp overhangs were filled in. The probes used in this way are presented in Table 4. Note that some of these probes were based on markers also used in Example 1 and Table 1, but the exact sequences are different as they were to be used as overgo probes rather than just PCR primers. Probes for hybridization were prepared as described (Ross et al. (1999) supra), and the filters prepared by the gridding of the BAC library were hybridized and washed as described by (Ross et al. (1999) supra). Phosphorimager analysis was used for detection of hybridization signals. Thereafter, the membranes were stripped of probes by placing them in a just-boiled solution of 0.1×SSC and 0.1% SDS and allowing them to cool to room temperature in the solution overnight.

BACs that gave a positive signal were isolated from the plates. Restriction mapping, PCR experiments with primers corresponding to the markers previously used and sequences obtained from the ends of each BAC were used to determine the order of the BACs covering the region of interest. Four BACs that spanned the entire region were selected for sequencing. These BACs were sequenced using standard shotgun sequencing techniques and the sequences assembled using the Phred/Phrap/Consed software package (Ewing et al. (1998) *Genome Research*, 8:175-185).

After assembly, the sequences thought to be in the region closest to the locus on the basis of the mapping data were annotated, meaning that possible gene-encoding regions and regions representing repetitive elements were deduced. Gene encoding (genic) regions were sought using the fGenesH software package (Softberry, Mount Kisco, N.Y., USA). fGenesH predicted a portion of a protein, that when BLASTed (BLASTx/nr), displayed partial homology at the amino acid level to a portion of a rice protein that was annotated as encoding for a protein that confers disease resistance in rice. The portion of the maize sequence that displayed homology to this protein fell at the end of a contiguous stretch of BAC consensus sequence and appeared to be truncated. In order to obtain the full representation of the gene in the maize BAC, the rice amino acid sequence was used in a tBLASTn analysis against all other consensus sequences from the same maize BAC clone. This resulted in the identification of a consensus sequence representing the 3' end of the maize gene. However, the center portion of the gene was not represented in the sequences so obtained. PCR primers were designed based on the 5' and 3' regions of the putative gene and used in a PCR experiment with DNA from the original maize BAC as a template. The sequence of the resulting PCR product contained sequence bridging the 5' and 3' fragments previously isolated.

Figure 9B:
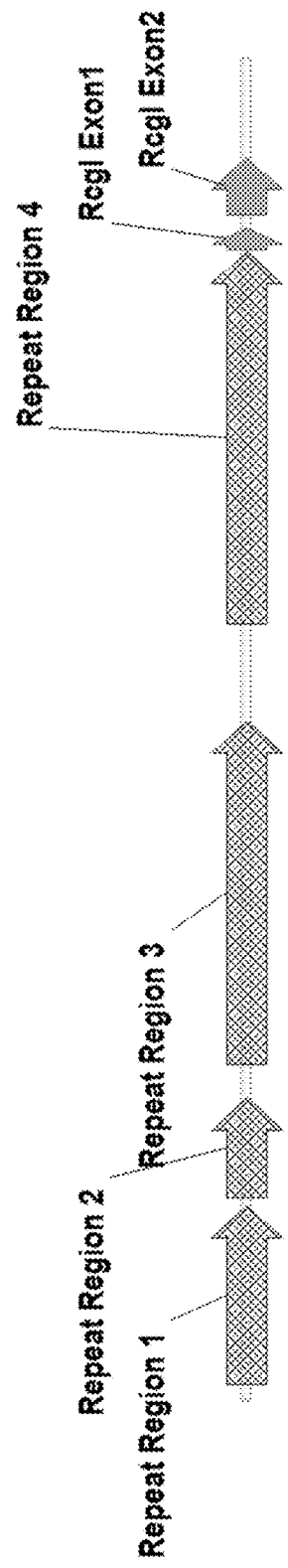
Figure 11:
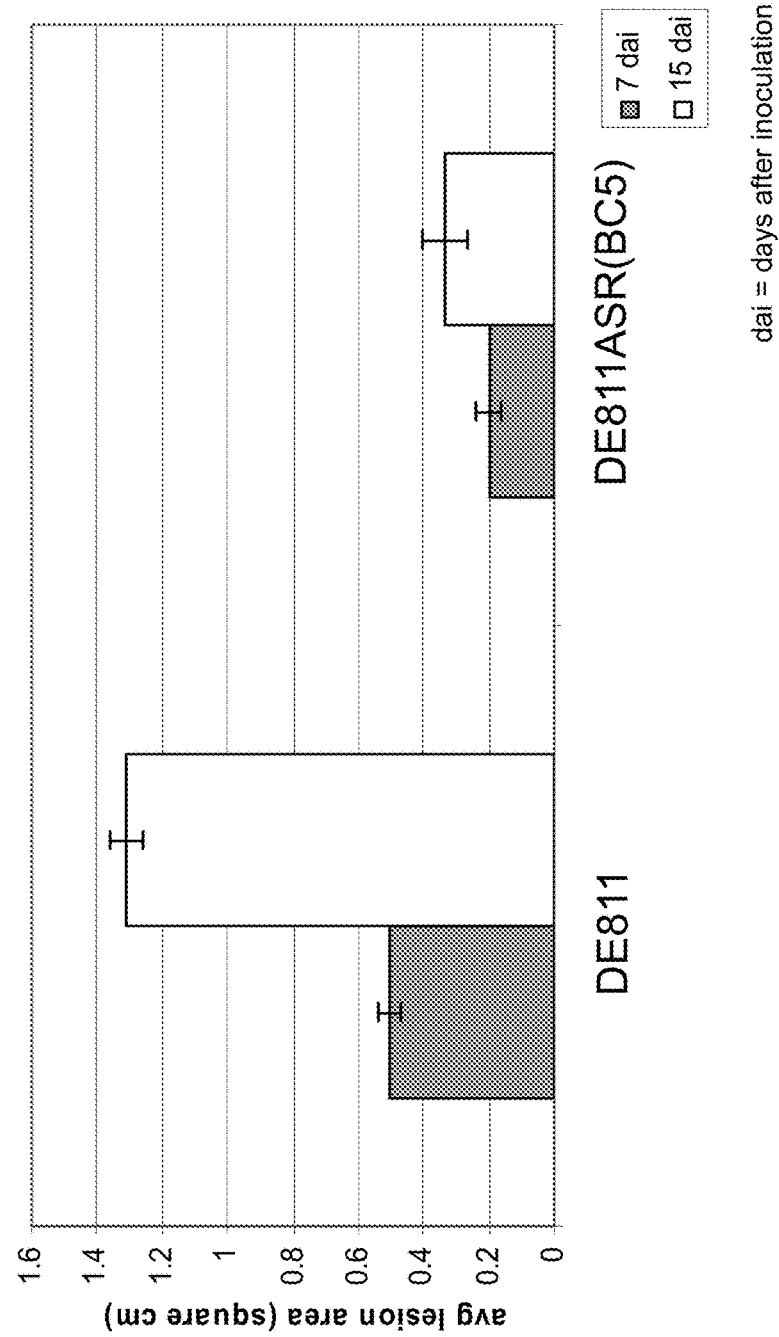
FIG. 11 shows a comparison of average leaf lesion size on plants of DE811 and DE811ASR(BC5) infected with Cg at 7 and 15 days after inoculation.
Figure 12:
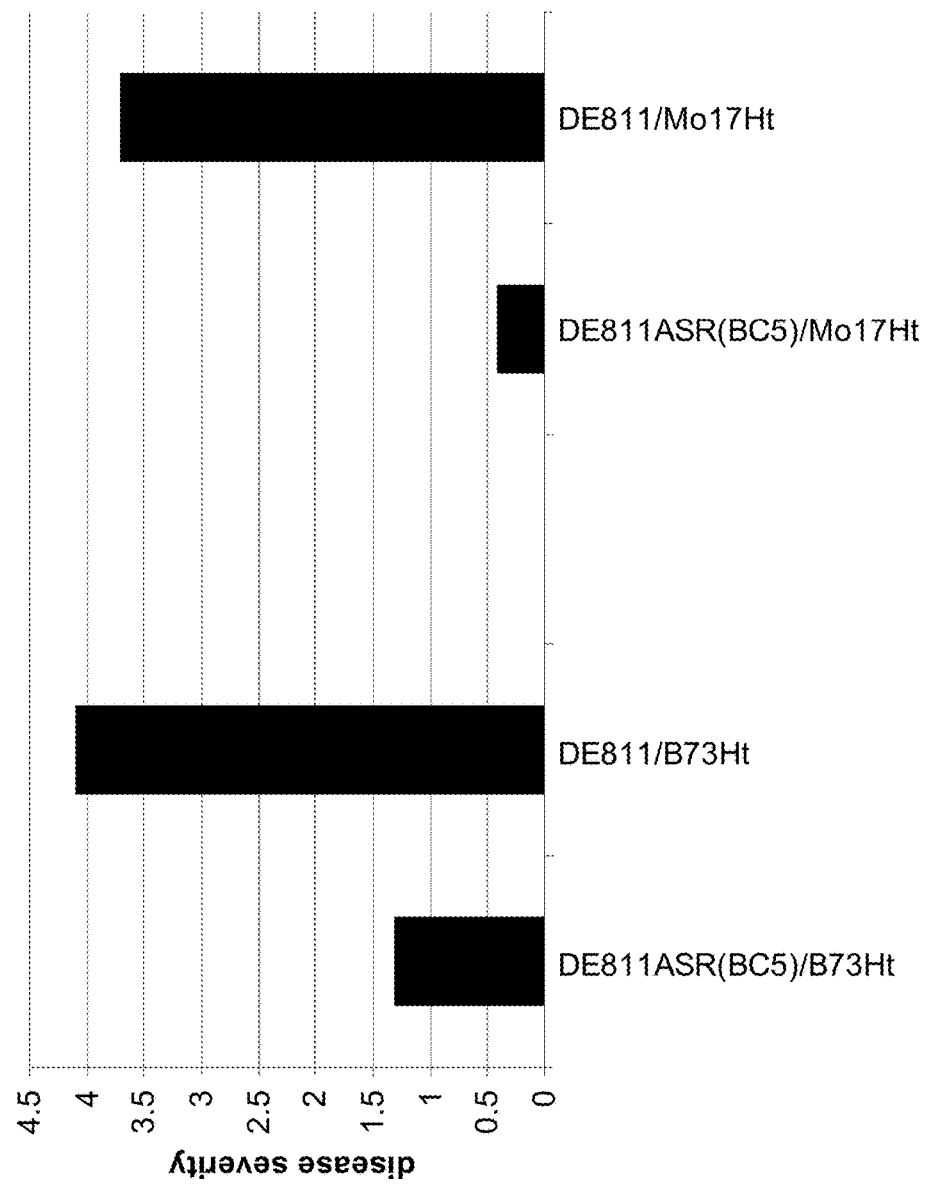
FIG. 12 shows the average severity of disease four to five weeks after inoculation with Cg in stalks of hybrids derived from crossing DE811ASR(BC5) and DE811 to the line indicated.
Figure 13:
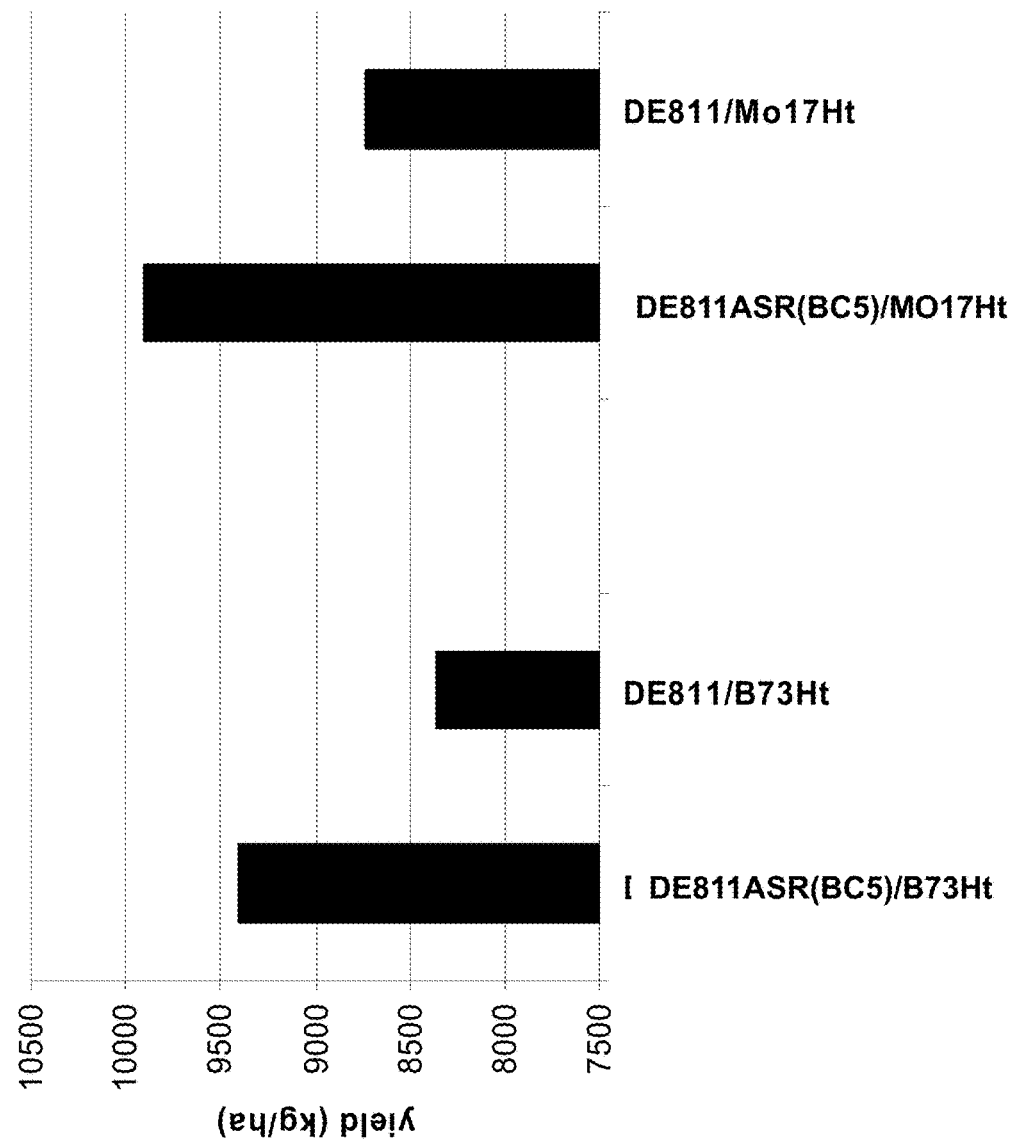
FIG. 13 shows the improvement in yield at maturity after inoculation with Cg in hybrids derived from crossing DE811ASR(BC5) to the line indicated when compared to the yield of hybrids derived from crossing DE811 to the line indicated.

DE811ASR (BC5) has been deposited with the ATCC, and the methods described herein may be used to obtain a BAC clone comprising the Rcg1 locus. As shown in FIG. 9(a), the DE811ASR (BC5) chromosomal interval with the Rcg1 locus is non-colinear with the corresponding region of B73 and Mo17 (See FIGS. 9 and 22), as determined by the analysis of BAC libraries.

Using common sequence that hybridize to BACs in the Mo17 and the B73 BAC libraries, the corresponding BACs from both libraries were lined up in a tiling path as shown in FIG. 22. The B73 BACs in FIG. 22 were given shorter names for the purposes of the figure. Table 3, below, shows the BAC ID for each BAC designation indicated on FIG. 22. The public B73 BACs, c0113f01 and c0117e18 are directly north and south, respectively, of the Rcg1 locus indel region, with the deletion occurring in B73. Information about these two BACs can be viewed on several websites including the maize GDB website (maizegdb.org), the Gramene website (gramene.org) and the maize genome database of the Arizona Genomics Institute (genome.arizona.edu). The Arizona Genomics Institute website also provides the Maize Agarose FPC Map, version Jul. 19, 2005, which identifies BACs contiguous with c0113f01 and c0117e18. By searching on those databases, a multitude of BACs were identified that form a contig of the regions flanking the Rcg1 locus. Thus, the precise location of the Rcg1 locus and Rcg1 gene have now been identified on both the maize genetic and physical map. See FIGS. 7(a,b) and 22.

TABLE 3

BAC designations in FIG. 22, which were part of either the 187 contig (B73a through B73p) or 188 contig (B73q through B73af) of B73as shown on the Arizona Genomics Institute website mentioned above.

| B73 BAC designation in FIG. 22 | B73 BAC ID |
| --- | --- |
| B73a | c0100m06 |
| B73b | b0050k15 |
| B73c | c0127n01 |
| B73d | c0449o09 |
| B73e | c0046c06 |
| B73f | c0212g06 |
| B73g | c0153l14 |
| B73h | c0105c14 |
| B73i | b0502a04 |
| B73j | b0239l06 |
| B73k | b0171g07 |
| B73l | c0273k24 |
| B73m | c0113f01 |
| B73n | c0117e18 |
| B73o | c0119n15 |
| B73p | b0369n20 |
| B73q | b0031c17 |
| B73r | c0081g12 |
| B73s | c0303g03 |
| B73t | c0222i18 |
| B73u | c0428j12 |
| B73v | c0314e18 |
| B73w | c0150j16 |
| B73x | b0085n01 |
| B73y | c0040c01 |
| B73z | c0018f13 |
| B73aa | c0091e23 |
| B73ab | b0100g11 |
| B73ac | c0177e03 |
| B73ad | b0264h08 |
| B73ae | c0410a17 |
| B73af | c0012f18 |

The complete sequence of the putative gene is set forth in SEQ ID NO: 1. The gene contains one intron, from nucleotide 950 to nucleotide 1452 of SEQ ID NO: 1. Reverse transcriptase-PCR using RNA prepared from DE811ASR (BC5) plants was used to determine the borders of the intron. The protein coding sequence of the gene is set forth in SEQ ID NO: 2, and the amino acid translation is set forth in SEQ ID NO 3. The predicted protein has a molecular weight of 110.76 kD.

The amino end from approximately amino acids 157 to 404 has homology to so-called nucleotide binding sites (NBS). There is a region with loose homology to LRR domains located approximately from amino acids 528 to 846. However, unlike previously studied NBS-LRR proteins, the leucine rich region lacks the systematic repetitive nature (Lxx) found in more classical LRR domains and in particular having no instances of the consensus sequences described by Wang et al. ((1999), *Plant J.* 19:55-64) or Bryan et al. ((2000), *Plant Cell* 12:2033-2045). The gene has loose homology with a family of rice genes and a barley gene as shown in FIG. 2 (*a, b* and *c*). Most of the homology is at the amino terminal end of the protein; the carboxyl end is quite distinct. This is demonstrated by the use of bold type, in FIG. 2 (*a, b* and *c*), which are amino acids identical to the gene of the embodiments, while those which are non-identical are not shown in bold type.

TABLE 4

Oligonucleotides annealed to synthesize overgo probes

| Associated Genetic marker | Forward oligonucleotide sequence | SEQ ID NO: | Reverse oligonucleotide sequence | SEQ ID NO: |
|---|---|---|---|---|
| FLP8 | cagggcctactt ggtttagtaata | 4 | gggtactacact agcctattacta | 5 |
| None | cggttacaaggt ctacccaatctg | 6 | gtcaaacagata gccgcagattgg | 7 |
| FLP33/ PHI93 | tacaaaactact gcaacgcctata | 8 | cctcaccccaag tatatataggcg | 9 |
| FLP27 | cattggacctct tccccactaaga | 10 | tccttgagtcca gtgctcttagtg | 11 |
| None | gaaactaggcgc gtcaggttttat | 12 | aaggcagccact gaaaataaaacc | 13 |

Example 3

Comparison of Genetic Structure in the Region of the Rcg1 Locus Between Resistant and Susceptible Lines and Expression Profiles of Candidate Genes Found in that Region Between Resistant and Susceptible Lines Having found a candidate gene in the region genetically defined to carry the locus responsible for the resistance to anthracnose phenotype, efforts were undertaken first to determine if there might be other genes present in the region and second to determine if the expression patterns of the candidate gene were consistent with its putative role. Fu and Dooner ((2002), *Proc Natl Acad Sci* 99:9573-9578) and Brunner et al. ((2005), *Plant Cell* 17:343-360) have demonstrated that different corn inbred lines may have significant rearrangements and lack of colinearity with respect to each other. Comparison of such genomes over larger regions can thus be complex. Such a comparison of the genomes of Mo17 (Missouri 17) and DE811ASR (BC5) revealed that in the region where the candidate gene is found in DE811ASR (BC5), a large insertion relative to Mo17 is present. Regions within and surrounding the insertion were sequenced and scanned for possible genes. A gene encoding a subunit of Ribulose bisphosphate carboxylase (Rubisco, a protein involved in carbon fixation after photosynthesis whose gene is present in multiple copies in the corn genome) was found in both the DE811ASR (BC5) and Mo17 genomes, just downstream of the position of the Rcg1 gene. A pseudogene (a gene rendered nonfunctional due to mutations disrupting the coding sequence) related to a vegetative storage protein was found, present only in the DE811ASR (BC5) genome some distance upstream of the Rcg1 gene. The only structurally intact gene likely to encode a protein with a function likely to be related to disease resistance was the Rcg1 gene isolated in the previous example. Other genes equally unlikely to be involved in disease resistance were located at a greater distance from the most likely position of the locus, as well as a large number of repetitive sequences.

In order to determine if and where the Rcg1 gene was transcribed, two techniques were used. First, the RNA profiles of resistant and susceptible plant materials were surveyed using Massively Parallel Signature Sequencing (MPSS; Lynx Therapeutics, Berkeley, USA). Briefly, cDNA libraries were constructed and immobilized on microbeads as described (Brenner, S. et al. (2000) *Nat. Biotechnol.* 18(6): 630-634). The construction of the library on a solid support allows the library to be arrayed in a monolayer and thousands of clones to be subjected to nucleotide sequence analysis in parallel. The analysis results in a "signature" 17-mer sequence whose frequency of occurrence is proportional to the abundance of that transcript in the plant tissue. cDNA derived from RNA prepared from DE811ASR(BC5) and from DE811 (control line, susceptible to Cg) was subjected to MPSS analysis. Bioinformatic inspection of the resulting signatures showed that a signature sequence, referred to herein as Lynx19, (SEQ ID NO: 19) was present at 43 parts per million (ppm) in RNA samples from DE811ASR (BC5) uninfected stalks and at 65 ppm in infected, resistant stalks 9 days post inoculation (DPI) with Cg. This signature sequence was not detected in cDNA libraries of uninfected or Cg-infected stalks of the susceptible corn line DE811. An analysis of the sequence of Rcg1 indicates that the 17-mer tag is present at nucleotides 3945 to 3961 of SEQ ID NO: 1 in the putative 3' untranslated region of the gene.

Figure 4:
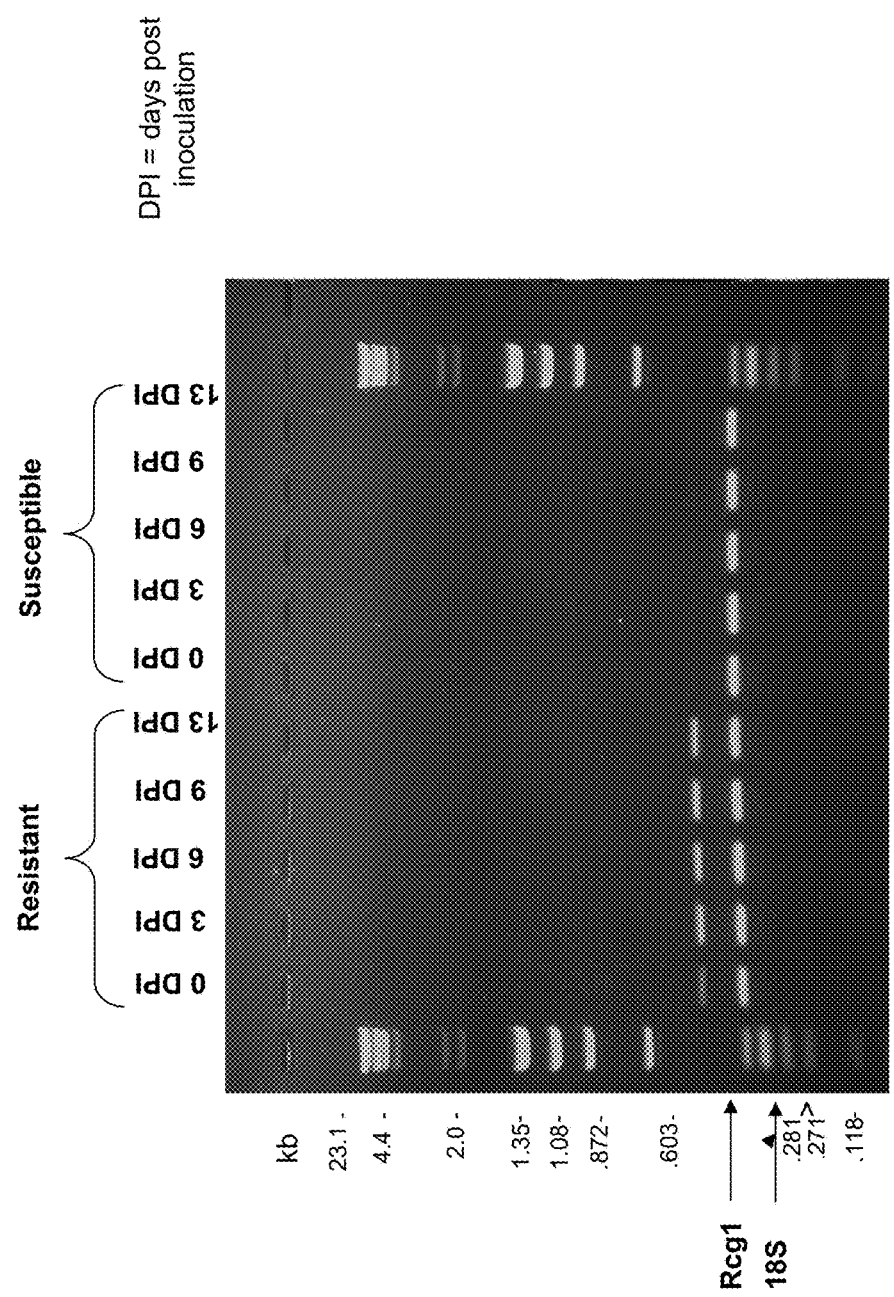
FIG. 4 is an electrophoresis gel blot of aliquots of RT-PCR reactions which reveals the presence of a 260 bp band present in the samples derived from both infected and uninfected resistant plants but absent from susceptible samples. RT-PCR fragments were obtained from 12.5 ng total RNA from DE811 and DE811ASR stalk tissue. cDNA obtained by reverse transcription was amplified using Rcg1 specific primers and 18S rRNA primers as an internal standard.

Further proof that Rcg1 is exclusively expressed in corn lines that are derived from MP305 and resistant to anthracnose stalk rot was obtained by RT-PCR experiments. Total RNA was isolated from uninfected and Cg-infected stalks of resistant (DE811ASR1 (BC5)) and susceptible (DE811) corn lines using RNA STAT-60™ (Iso-Tex Diagnostics, Friendswood, Tex., USA). Total RNA (250 ng) from 0, 3, 6, 9, and 13 DPI resistant and susceptible samples was copied into cDNA and amplified using a GeneAmp® RNA-PCR kit (Applied Biosystems, Foster City, Calif., USA). The cDNA synthesis reaction was assembled according to the kit protocol using random hexamers as primers and incubated at 42° C. for 45 minutes. For PCR, KEB131 (SEQ ID NO: 20) and KEB138 (SEQ ID NO: 21), both designed from the putative 3' untranslated sequence of Rcg1, were used as the upstream and downstream primers, respectively. The cDNA was amplified for 30 cycles consisting of 1 minute at 94° C., 2 minutes at 50° C. and 3 minutes at 72° C. followed by a 7 minute extension at 72° C. As shown in FIG. 4, agarose gel electrophoresis of an aliquot of the RT-PCRs revealed the presence of a 260 bp band present in the samples derived from both infected and uninfected resistant plants but absent from susceptible samples. DNA sequence analysis confirmed that this fragment corresponded to nt 3625 to 3884 of the Rcg1 sequence consistent with the amplification product predicted from primers KEB131 and KEB138.

Example 4

Isolation of Lines Containing Mu Insertions in the Candidate Gene

One method to determine if a gene is responsible for a phenotype is to disrupt the gene genetically through the insertion of a transposition element (so-called transposon tagging) and then determine if the relevant phenotype of the plant is altered, in this case from resistant to Cg to susceptible to Cg. In corn this can be done using the mutator (Mu) element (Walbot, V. (1992) *Annu. Rev. Plant Physiol. Plant Mol. Biol.* 43:49-82). The basic strategy, outlined in FIG. 5, was to introduce active mutator elements into lines carrying the resistance gene, isolating plants homozygous for the resistance gene by assaying associated DNA markers as well as resistance to Cg by inoculation with Cg, then crossing those homozygous plants with a susceptible "tester" line. If the resistance gene is dominant, in principle all the resulting progeny would be resistant but heterozygous for the gene. However, if a Mu element inserted into the resistance gene in a way that disrupted its function, that individual would be susceptible to Cg. The disrupted gene can then be isolated and characterized.

MP305 was crossed with fifteen diverse mutator stocks (lines carrying active mutator elements). The resulting F1s were inter-mated (crossed with each other) in all possible combinations. To track the chromosomal region 4 L on which the resistance locus was known to reside (see Example 1) a variety of DNA markers known to be in the vicinity of the locus from the work described in Example 1 were selected and used on the Mu-tagged materials. About 1500 progeny plants from the inter-mating process were examined for resistance to Cg and for the presence of these markers. Analysis of the markers was done using either Southern blots (Botstein et al., (1980) *Am. J. Hum. Gen.* 32:314-331) for RFLP markers or by PCR for FLP markers as described in Example 1. Plants that were homozygous for all the markers tested and resistant to Cg were selected and test crossed with susceptible tester lines (A63, EH6WA and EFO9B). About 16,000 test cross seeds generated from these homozygous and resistant plants were then planted and were used as female parents (meaning the pollen producing tassels were removed) and crossed with the susceptible tester lines used as males. All the female plants were screened for susceptibility to Cg. More than ten susceptible plants (putative knockout mutants) were identified. The open pollinated seed from each of these susceptible plants was harvested, along with eight resistant siblings as controls.

Figure 5:
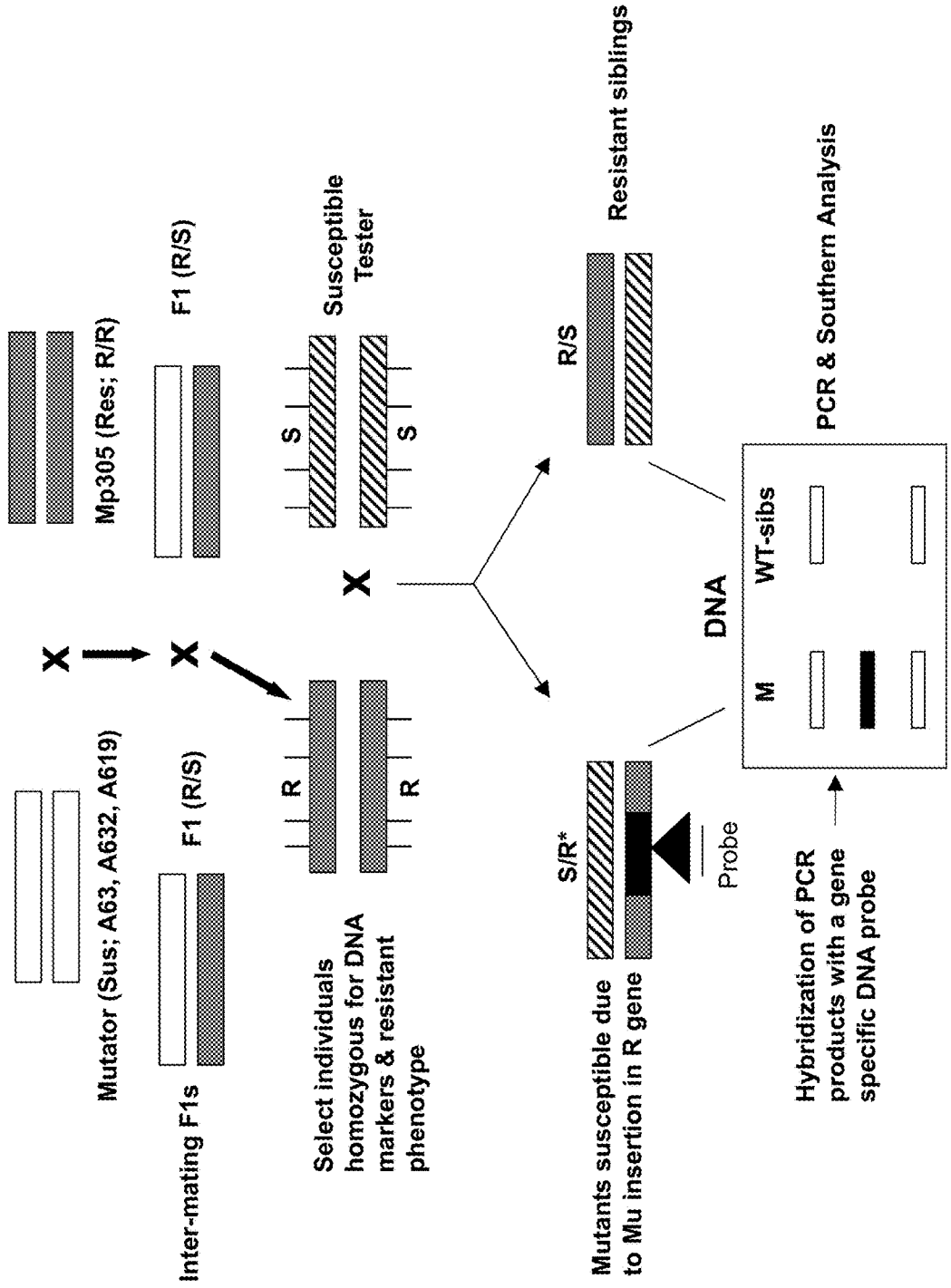
FIG. 5 is a schematic diagram of the Mu-tagging strategy used to validate the Rcg1 gene.
Figure 6:
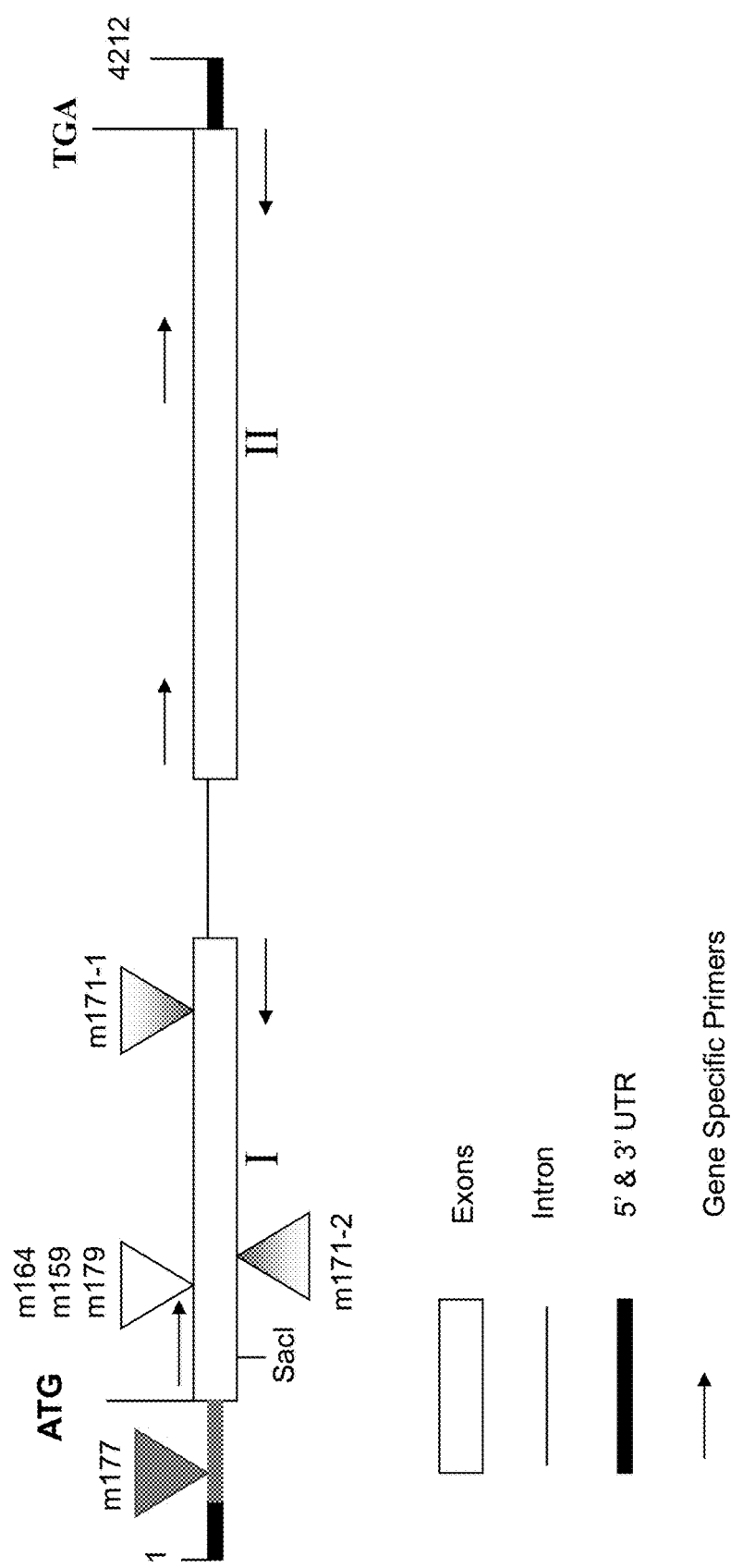
FIG. 6 is the gene structure of Rcg1 showing the location of four different mutator insertion sites.

DNA from a pool of 24 seedlings (grown in paper towels) from each of the putative knockouts and the control resistant siblings was extracted. This DNA was used as template for amplifying the flanking sequence from the site of Mu-insertion using gene-specific primers in combination with a consensus primer designed from the terminal inverted repeats (TIR) from the Mutator element sequence (SEQ ID NO: 125). In other words, PCR products would only be observed if a Mu element had inserted into the candidate gene isolated in Example 2. The primers FLP110F, FLP110R, FLP111F, FLP111R, FLP112F, FLP112R, FLP113F, and FLPA1R were used as the gene-specific primers (See Table 1). PCR amplified products were blotted onto nylon membranes and hybridized with a DNA probe from the candidate gene isolated in Example 2. PCR products that showed strong hybridization were excised from the gel, purified, cloned and sequenced. The resulting sequences were analyzed by aligning with sequences from the candidate gene and Mu-TIR. Mutator elements cause a direct 9 bp duplication at the site of insertion. Based on the flanking sequence information and a direct 9 bp duplication, four independent insertions were identified in exon 1 of the candidate gene (FIG. 5). One insertion (m177) was detected approximately 97 bp upstream of the initiation codon, in the 5' untranslated region of the gene. One common insertion event, 270 bp downstream of the initiation codon, was detected in three susceptible plants: m164, m159, and m179. The m171 susceptible plant was found to contain two Mu-insertions, 556 bp and 286 bp downstream of the initiation codon. When Southern blots were carried out using the exon1 region of the gene as a DNA probe, the modified hybridization pattern observed further confirmed these results.

This and the preceding examples may be summarized as follows. The earlier work cited in Example 1 showed that a previously observed locus conferring resistance to Cg was localized on the long arm of maize chromosome 4. The nature of this locus, its exact location or the gene(s) encoded by it were completely unknown. The work done in Example 1 demonstrates that the locus can be mapped to a very small region of the long arm of chromosome 4. Example 2 demonstrates that there is only one gene to be found in this chromosomal region likely to be such a resistance gene. It encodes a novel form of an NBS-LRR protein, a family of proteins known to be involved in resistance to pathogens but which vary widely in their sequence and specificity of resistance. Example 3 shows that this gene is present only in the resistant line, not the isogenic susceptible line, and that transcripts corresponding to this gene are found in the resistant line, indicating that the gene is expressed, and these transcripts are found only in the resistant line. Example 4 demonstrates that in four independently isolated Mu insertion events, when the gene is disrupted by insertion of a Mu element, the phenotype of these plants is changed from resistant to susceptible to Cg. Taken together, these data provide overwhelming evidence that the subject of the embodiments of this invention is a gene that can enhance or confer Cg resistance to corn plants.

Example 5

Backcrossing of the Rcg1 Locus into Susceptible Lines

An Rcg1 locus introgression of an inbred was made to confirm that the Rcg1 locus could be successfully backcrossed into inbreds, and that hybrids produced with the inbred line with the Rcg1 locus would have enhanced or conferred Cg resistance. DE811ASR (BC5) was also developed and used as an improved donor source for introgression of the Rcg1 locus. Next, several additional inbreds were utilized as recurrent parents in order to use the marker assisted breeding methods described herein to efficiently introgress the Rcg1 locus into a variety of inbred and hybrid genetic backgrounds, thereby enhancing or conferring resistance to Cg. Each of these examples are discussed in more detail below.

Proof of Concept (PH09B)

MP305 is a white kernel color inbred line with strong resistance to Cg, but its late flowering, poor yield and weak agronomic characteristics make it a poor donor parent in the absence of the use of the marker assisted breeding methods described herein. A molecular marker profile of MP305 is provided in Table 6. Primers used for the SSRs reported in the table can be constructed from publicly available sequences found in the Maize GDB on the World Wide Web at maizegdb.org (sponsored by the USDA Agricultural Research Service), in Sharopova et al. (Plant Mol. Biol. 48(5-6):463-481), and/or in Lee et al. (Plant Mol. Biol. 48(5-6); 453-461). UMC15a is an RFLP marker, and the score reported is based on EcoR1 restriction.

To demonstrate the phenotypic value of the Rcg1 locus, the locus was first introgressed into line PH09B (U.S. Pat. No. 5,859,354) through to the BC3 stage as follows. The F1 population derived from the cross between MP305 and line PH09B was backcrossed once more to line PH09B, resulting in a BC1 population. Seedlings were planted out and backcrossed again to line PH09B to develop a BC2 population. DNA was prepared from leaf punches of BC2 families. To determine which BC2 families to plant for further backcrosses, genotyping was carried out on DNA from BC2 families using primers for markers flanking the region of interest, UMC2041, PHI093 and CSU166 (See Table 1).

Seeds from BC2 families were planted and individual plants were genotyped again for the presence of the MP305 version of that region of the chromosome using the same three markers noted above. Positive plants were backcrossed to line PH09B once more to develop BC3 populations. Seed from these BC3 populations was planted and plants were selfed to obtain BC3S1 families segregating for the region of interest as well as BC3S1 families missing the region of interest. These families were used for phenotypic comparison (BC3S1 segregating versus BC3S1 without the region of interest).

In order to observe the performance of the Rcg1 gene in a heterozygous situation such as would be found in a commercial hybrid, appropriate testcrosses were made. Specifically, BC3S1 families segregating for the region of interest were planted and individual BC3S1 plants were genotyped. Plants homozygous for the Rcg1 gene as well as plants homozygous for the null allele (lacking the gene on both chromosomes) within each family were used to make testcrosses with inbreds PH2EJ (U.S. Pat. No. 6,333,453), PH2NO (U.S. Pat. No. 6,124,533), PH4CV (U.S. Pat. No. 6,897,363) and PH8CW (U.S. Pat. No. 6,784,349).

In the case of both the BC3S1 lines and the hybrids, the observed phenotypic differences indicated significant improvement for ASR resistance in lines and hybrids containing the region carrying Rcg1. The effect of the introgressed Rcg1 locus in the BC3S1 families and the derived testcross hybrids resulted in an improvement in terms of both the number of internodes infected and the number of internodes infected at more than 75%. The scores, using a visual scoring system commonly used by plant breeders, are shown in Table 5 below. The data clearly demonstrate that using crossing techniques to move the gene of the embodiments into other lines genetically competent to use the gene result in enhanced resistance to Cg.

TABLE 5

Effect of the introgressed Rcg1 region on degree of resistance to anthracnose stalk rot in BC3S1 families and derived test crosses.

| | Rcg1 | Number of internodes infected | Number of internodes >75% infected |
|---|---|---|---|
| BC3S1 | Absent | 3.1 | 2.4 |
| | Present | 2.3 | 1.5 |
| | Difference | 0.8 | 0.9 |
| PH2EJ | Absent | 2.6 | 1.5 |
| | Present | 2.1 | 0.9 |
| | Difference | 0.5 | 0.6 |
| PH2NO | Absent | 3.0 | 2.1 |
| | Present | 2.4 | 1.3 |
| | Difference | 0.6 | 0.8 |
| PH4CV | Absent | 2.8 | 1.8 |
| | Present | 2.2 | 1.0 |
| | Difference | 0.6 | 0.8 |
| PH8CW | Absent | 2.9 | 1.7 |
| | Present | 2.3 | 0.8 |
| | Difference | 0.6 | 0.9 |

TABLE 6

Molecular marker profile of MP305

| Marker Name | Base Pair Weight | Bin | Marker Name | Base Pair Weight | Bin |
|---|---|---|---|---|---|
| phi295450 | 191.1 | 4.01 | umc1667 | 154.65 | 4.08 |
| phi213984 | 302.23 | 4.01 | phi438301 | 212.76 | 4.05 |
| phi096 | 235.07 | 4.04 | umc1808 | 106.67 | 4.08 |
| mmc0471 | 241.6 | 4.04 | umc1043 | 199.6 | 4.07 |
| umc1969 | 65.01 | 4.05 | umc1871 | 148.48 | 4.08 |
| umc1662 | 116.14 | 4.05 | dupssr28 | 100.64 | 4.08 |
| umc2061 | 125.34 | 4.05 | umc1466 | 110.91 | 4.08 |
| phi079 | 185.76 | 4.05 | umc1418 | 153.12 | 4.08 |
| bnlg1937 | 235.87 | 4.05 | umc1899 | 111.81 | 4.08 |
| umc1382 | 153.7 | 4.05 | bnlg2162 | 144.98 | 4.08 |
| bnlg1217 | 194.36 | 4.05 | umc2041 | 165.17 | 4.08 |
| umc1390 | 133.46 | 4.05 | umc2285 | 156 | 4.08 |
| bnlg1265 | 221.83 | 4.05 | umc1086 | 95.57 | 4.08 |
| umc1303 | 127.2 | 4.05 | umc1612 | 108.54 | 4.08 |
| bnlg252 | 167.85 | 4.06 | umc15a | approx 10 kb with EcoRI restriction | 4.08 |
| umc1895 | 142 | 4.05 | cdo365 | 411.5 | 4.08 |
| umc1175 | 279.6 | 4.05 | umc1051 | 125.9 | 4.08 |
| umc1317 | 110.12 | 4.05 | umc2187 | 84.94 | 4.08 |
| umc1548 | 159.52 | 4.05 | umc1371 | 120.6 | 4.08 |
| umc1451 | 110.69 | 4.05 | umc1132 | 132.14 | 4.08 |
| umc1896 | 87.89 | 4.05 | umc1856 | 156.88 | 4.08 |
| umc1511 | 166.43 | 4.05 | umc2153 | 131.97 | 4.08 |
| umc1851 | 114.13 | 4.05 | umc2200 | 151 | 4.08 |
| umc1791 | 153.23 | 4.05 | phi066 | 160 | 4.08 |
| bnlg1755 | 216.93 | 4.05 | umc1039 | 222.7 | 4.08 |
| umc1702 | 94.8 | 4.05 | umc2139 | 134.2 | 4.09 |
| umc1346 | 96.39 | 4.05 | umc1559 | 141.09 | 4.09 |
| umc1142 | 146.98 | 4.05 | umc1999 | 131.55 | 4.09 |
| mmc0371 | 230.82 | 4.06 | umc1820 | 138.94 | 4.09 |
| umc1945 | 113.52 | 4.06 | umc1173 | 168.02 | 4.09 |
| umc1093 | 222.7 | 4.06 | umc1650 | 139.84 | 4.09 |
| umc2027 | 111 | 4.06 | umc1328 | 161.33 | 4.09 |
| bnlg1621 | 184.11 | 4.06 | umc1740 | 98.2 | 4.09 |
| umc1299 | 144.46 | 4.06 | umc1643 | 145.23 | 4.09 |
| umc1869 | 154.39 | 4.06 | umc1989 | 100.5 | 4.09 |
| bnlg2291 | 201.5 | 4.06 | umc1284 | 144.39 | 4.09 |
| bnlg1784 | 237.23 | 4.07 | umc1574 | 155.11 | 4.09 |
| dupssr34 | 326.01 | 4.07 | umc2137 | 158.1 | 4.08 |
| umc1651 | 99.59 | 4.07 | umc1101 | 160.12 | 4.09 |
| umc2038 | 122.19 | 4.07 | umc2046 | 115.82 | 4.09 |
| umc1847 | 160.17 | 4.07 | phi314704 | 143.54 | 4.09 |
| umc1620 | 148.2 | 4.07 | bnlg1890 | 251.68 | 4.11 |
| umc1194 | 162.29 | 4.07 | phi076 | 158.05 | 4.11 |

DE811ASR(BC5) as Most Improved Donor for Use in Backcrossing

Figure 8A:
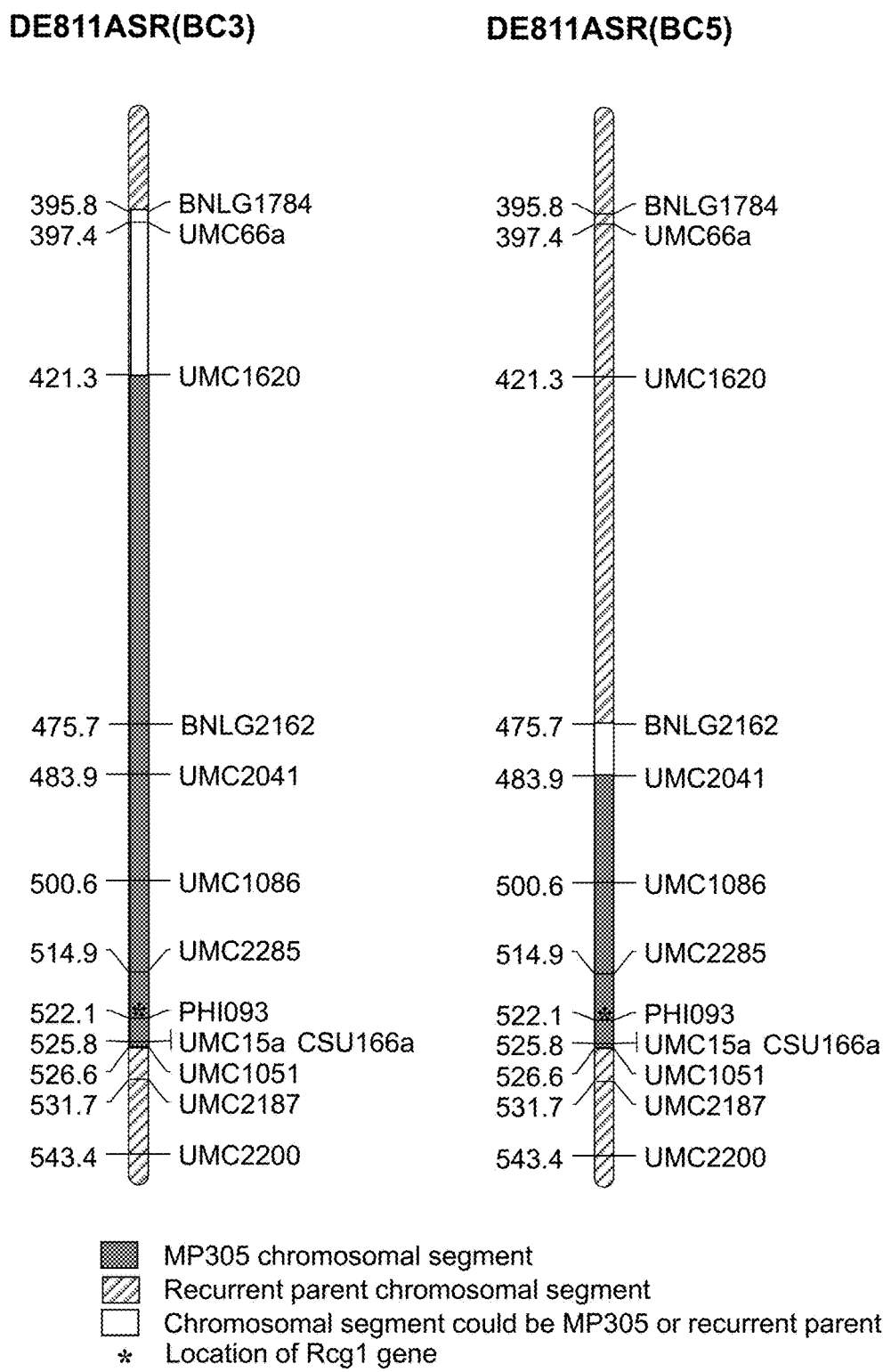
FIG. 8(*a-b*) is a genetic map image showing the chromosomal interval with the Rcg1 gene in DE811ASR (BC3), the reduced size of the chromosomal interval with the Rcg1 gene obtained in DE811ASR (BC5) and the further reduced size of the chromosomal interval in inbreds obtained by initially using DE811ASR (BC5) as a donor source. For all markers, the map distances shown were reported on the IBM2 neighbors map publicly available on the Maize GDB, apart from for MZA15842, FLP27 and FLP56 for which map positions were extrapolated using regression analysis relative to the high resolution maps in FIG. 7(*b*), maps B and C, using the positions of UMC2285, PHI093 and CSU166a which were common to both maps.

Although MP305 was utilized in the above experiment, as is illustrated in FIG. 8(a), DE811ASR(BC5) retains a smaller MP305 chromosomal interval with the Rcg1 locus than DE811ASR(BC3) (and of course MP305 as well), and therefore is particularly useful as a donor source for the Rcg1 gene. The shortened chromosomal interval from the DE811ASR(BC5) source has been shown to be associated with an improved agronomic phenotype. Twenty two plants from the DE811ASR(BC3) derived line, 20 plants from the DE811ASR(BC5) derived line, five DE811 plants and five MP305 plants were grown in a greenhouse from November 2005 through March 2006 and data were taken for plant height and ear height; dates when 50% of the plants shed pollen (midshed), when 50% of the plants had visual ear shoots (midves) and when 50% of the plants had silks protruding from the earshoots (midslk); and kernel color was observed. On average, the DE811ASR(BC5) line was shorter than DE811ASR(BC3) (293 cm vs 345 cm) and the location of the ear was lower in the DE811ASR(BC5) than in the DE811ASR(BC3) (146 cm vs 183 cm), both of which are positive traits in terms of elite variety development. DE811ASR(BC5) was earlier for midshed, midves and midslk compared to DE811ASR(BC3). Midshed was approximately 1 day earlier, midves was approximately 6 days earlier and midslk was approximately 3 days earlier for DE811ASR(BC5) compared to DE811ASR(BC3). Kernels of DE811ASR(BC5) had a yellowish-brown (bronze) color whereas kernels of DE811ASR(BC3) had a pale yellow cap. Dates for midshed, midves and midslk were similar for DE811ASR(BC5) and DE811, whereas MP305 was approximately 11 days later for midshed and did not produce 50% visual ear shoots, nor 50% silks during the growing period. While these data are based on only a few plants for DE811 and MP305, and ears were not produced on those few lines, these greenhouse results resemble observations of these lines in the field. These data indicate that DE811ASR (BC5) resembles the DE811 recurrent parent much more closely than DE811ASR(BC3). Thus, DE811ASR(BC5) is an excellent initial donor source for the Rcg1 locus and the Rcg1 gene, both genotypically and phenotypically. In addition, DE811ASR(BC5) is particularly useful when introgressing the Rcg1 locus into germplasm with similar adaptation to DE811.

DE811 was developed by J. Hawk (Hawk, J. A. (1985). *Crop Science Vol* 25: p716) and has been described as a yellow dent inbred line that originated from selfing and selection for six generations in a pedigree program out of a cross of B68 to an inbred derived from [B37 Htx(C103× Mp3204 double cross) sel]. DE811 silked 1 to 2 days later than B73 in tests in Delaware, but 4 days later than B73 at Missouri. Limited yield trials indicate that DE811 has satisfactory combining ability. It is a good silker (forms good silks, a component of the maize female flower important for fertility) and pollen shedder and can be crossed to earlier maturity germplasm for Northern US adaptation and to later maturity germplasm for Southern US adaptation. Thus, DE811ASR (BC5), in combination with the markers and breeding methods disclosed herein, is useful as an initial donor source for introgressing the Rcg1 gene into a wide variety of germplasm, including germplasm adapted to all of the regions in the US where Cg is present.

Creation of Inbred Rcg1 Locus Conversions

Following the tests for successful Rcg1 locus introgression in PH09B described above, additional Rcg1 locus conversions were carried out on other inbred lines. The first series had 5 backcrosses, with MP305 and DE811ASR (BC5) as donors. For the second series of backcrosses, molecular markers were used to reduce the chromosome interval in the BC5 conversions from the first series. These BC5 conversions were selected for crossovers below the Rcg1 gene. Those selected plants were then backcrossed to create the BC6 generation. Plants with crossovers above the gene were selected in the BC6 generation.

First Series of Backcrosses

In the first series, DE811ASR(BC5) was used as the primary donor source, but parallel introgressions were also made to the same inbreds using MP305 as a donor source. These data, described in more detail below, show that while DE811ASR(BC5) is the preferred donor in many situations, MP305 can also be effectively used with the marker assisted breeding methods of the embodiments taught herein.

Elite inbred lines primarily adapted to North American growing conditions were selected for use as recurrent parents. The inbreds lines initially selected for use as recurrent parents were lines PHOR8 (U.S. Pat. No. 6,717,036), PH7CH (U.S. Pat. No. 6,730,835), PH705 (U.S. Pat. No. 6,903,25), PH5W4 (U.S. Pat. No. 6,717,040), PH51K (U.S. Pat. No. 6,881,881) and PH87P (U.S. Pat. No. 6,888,051). Each of these lines was crossed with DE811ASR (BC5) as well as with MP305. The F1 generation derived from each of these crosses was backcrossed once more to the respective inbred line, resulting in a first backcross (the recurrent parent BC1) generation. Seedlings were planted out and DNA was prepared from leaf punches. PCR reactions were carried out using primers for markers flanking the region of interest; UMC1466, UMC1418, BNLG2162, UMC1086, UMC2041, UMC1612, CSU166, UMC1051, UMC2187, UMC1371, and UMC1856 were used in the early BC rounds (See Table 1) while in later BC rounds, UMC1418, BNLG2162, UMC1051, UMC2041, UMC2187, UMC1371 and UMC1856 were used. Seedlings whose PCR reactions gave a positive result (meaning that the MP305 derived Rcg1 locus was present) were then further backcrossed to the respective inbred lines to make a BC2. This procedure, called "genotyping", identifies the genetic composition of a plant at the site of a particular marker. These steps were repeated for the recurrent parent BC3, BC4 and BC5 development. Analysis shows that, after five backcrosses, these lines retained a significantly truncated chromosomal interval comprising the Rcg1 locus, and, based on visual observations, no indication of negative effects resulting from the presence of the Rcg1 locus was observed.

Recurrent parent selection was also carried out by selecting the plants most phenotypically like the recurrent parent. Using these genotypic and phenotypic methods, high quality conversions were selected with a high percentage of recurrent parent across the whole genome.

This example also illustrates that flanking markers are not used exclusively to select either for or away from the Rcg1 gene. Seedlings whose PCR reactions gave a positive result (meaning that the MP305 derived Rcg1 locus was present) were then further backcrossed to the respective inbred lines to make the final backcross (the recurrent parent BC5 generation) in this first series. Where the closest flanking polymorphic markers determined that the gene was present, the next set of double flanking polymorphic markers more distal to the gene were used for recurrent parent selection. Thus, the use of markers flanking the Rcg1 gene or Rcg1 locus serves to illuminate the recombination occurring in the region.

Second Series of Backcrossing

The inbred Rcg1 locus conversions made using the SSRs flanking the Rcg1 locus in the first series of backcrossing were then used as donors in a successive round of backcrossing. For this series of backcrossing, SNP markers were developed for the Rcg1 gene that enabled marker assisted selection in a high throughput manner, as described in Example 13, to select for the Rcg1 gene. SNP markers were also designed in the region around the Rcg1 locus, allowing flanking markers to be used to select away from the MP305 chromosomal interval surrounding the Rcg1 locus, and to select for the recurrent parent genotype, thereby greatly reducing linkage drag. It is only through physically mapping and cloning the gene that such precise marker-assisted recurrent parent selection is possible.

Figure 8B:
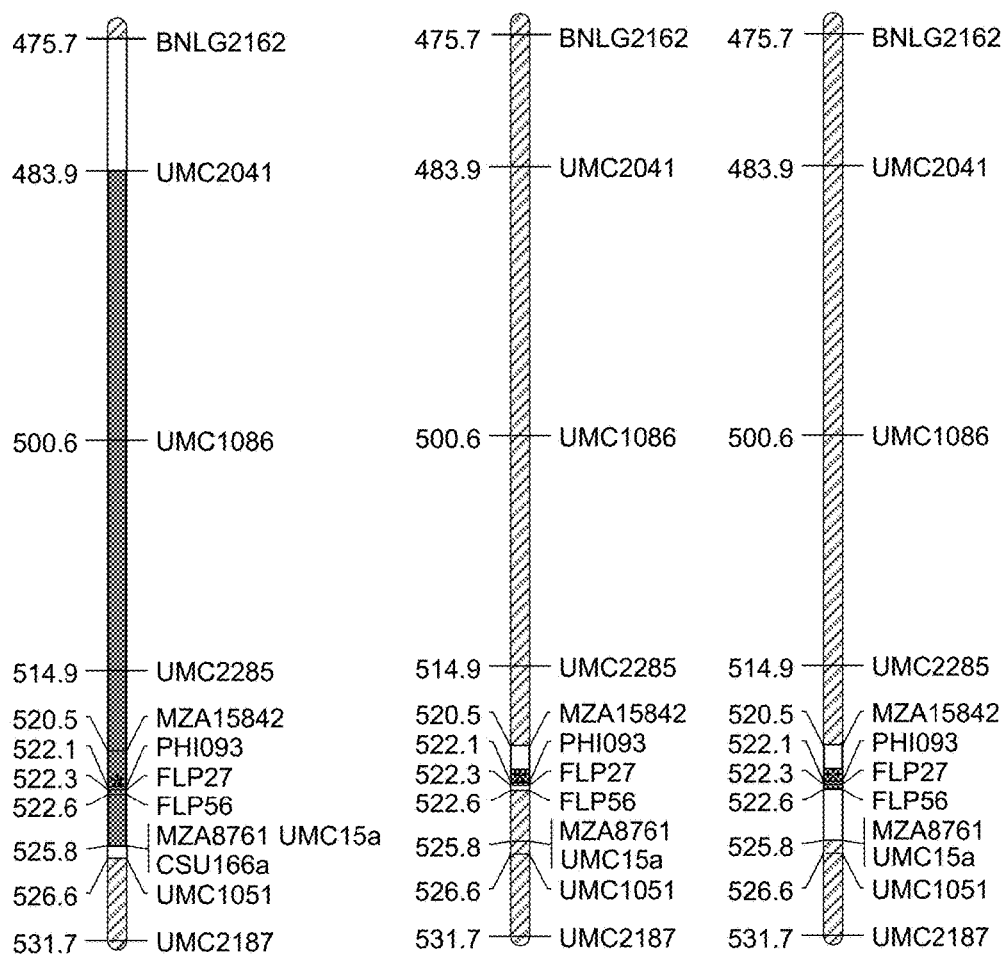

First, the recurrent parent BC5 plants resulting from the first series of backcrossing were re-screened with the more precise marker set, and recombination was selected for south of the Rcg1 gene. Flanking markers tightly linked to the Rcg1 gene (MZA8761, MZA1851, UMC1051, and UMC2187) were used to select for recurrent parent to the south of the gene in small population sizes of approximately 40 progeny. (See FIG. 8(*a-b*)). These progeny were then analyzed using the FLP markers disclosed herein, to more precisely determine the point of recombination. This data showed that some progeny were selected with recurrent parent genome less than 1 cM (based on IBM2 Neighbors genetic map distances) south of the Rcg1 gene, as shown in FIG. 8(b). Other progeny had recurrent parent genome less than 4 cM south of the Rcg1 gene. These marker-selected BC5 conversions were then used as donors, and crossed to near-isogenic counterparts of PH705, PH5W4, PH51K and PH87P as the recurrent parents to give a BC6 population. Markers in the Rcg1 gene were again used to select for Rcg1, with flanking markers to the north of Rcg1 this time being used to select for recurrent parent. In this round of selections, recombinations were detected in each population between Rcg1 and the marker MZA15842. The position of MZA15842 on the IBM2 Neighbors genetic map can be extrapolated from its position on the high resolution map shown in FIG. 7(b), map B, using regression relative to the flanking markers UMC2285 and PHI093. This placed MZA15842 at 520.5 cM on the IBM2 Neighbors genetic map. Therefore, as shown in FIG. 8(b), in two rounds of backcrossing, the donor genome was reduced to a segment of less than 6 cM in each population, or less than 0.8% of chromosome 4, based on the IBM2 Neighbors genetic map distances, and in some progeny the segment was less than 2.1 cM, or less than 0.25% of chromosome 4. For comparison, the MP305 chromosomal interval with the Rcg1 locus in DE811ASR (BC3) was 131 cM, or approximately 16% of chromosome 4, based on the IBM2 Neighbors genetic map distances. It is only through physically mapping and cloning the gene that such precise and efficient marker-assisted recurrent parent selection is possible.

Further Analysis

Therefore, as a result of fine mapping the location of the Rcg1 gene, one may utilize any two flanking markers that are genetically linked with the Rcg1 gene to select for a small chromosomal region with crossovers both north and south of the Rcg1 gene. This has the benefit of reducing linkage drag, which can be a confounding factor when trying to introgress a specific gene from non-adapted germplasm, such as MP305, into elite germplasm, such as the inbred lines noted above. FIGS. 7 and 22, and Table 16 show many combinations of markers flanking the Rcg1 gene and locus that may be used for this purpose. Some specific flanking markers that may be used for selecting truncated chromosomal intervals that include the Rcg1 gene or locus are UMC2285 and UMC15a, UMC2285 and UMC2187, UMC1086 and UMC2200, UMC2041 and UMC2200, UMC2041 and PHI093, MZA11455 and UMC15a, MZA11455 and MZA3434, MZA15842 and MZA3434, and FLP8 and FLP33. Optionally, on or within each of these chromosomal intervals, one could utilize at least 1, 2, 3, 4, 5, 6, 7, 8, 9, 10, 11, 12, 13, 14, 15, 16 or more markers in order to locate the recombination event and select for the Rcg1 gene or Rcg1 locus with the maximum amount of recurrent parent genotype. Further, one may have at least 2, 3, 4, 5, 6, 7, 8, 9, 10, 11, 12, 13, 14, 15, or more markers between the north end of such chromosomal interval and the top of the Rcg1 gene and/or between the south end of such chromosomal interval and the bottom of the Rcg1 gene.

It is advantageous to have closely linked flanking markers for selection of a gene, and highly advantageous to have markers within the gene itself. This is an improvement over the use of a single marker or distant flanking markers, since with a single marker or with distant flanking markers the linkage associated with Rcg1 may be broken, and by selecting for such markers one is more likely to inadvertently select for plants without the Rcg1 gene. Since marker assisted selection is often used instead of phenotypic selection once the marker-trait association has been confirmed, the unfortunate result of such a mistake would be to select plants that are not resistant to Cg and to discard plants that are resistant to Cg. In this regard, markers within the Rcg1 gene are particularly useful, since they will, by definition, remain linked with resistance to Cg as enhanced or conferred by the gene. Further, markers within the Rcg1 locus are just as useful for a similar reason. Due to their very close proximity to the Rcg1 gene they are highly likely to remain linked with the Rcg1 gene. Once introgressed with the Rcg1 gene, such elite inbreds may be used both for hybrid seed production and as a donor source for further introgression of the Rcg1 gene into other inbred lines.

Thus, the data clearly shows that inbred progeny converted by using DE811ASR(BC5) as a donor source retain the truncated MP305 chromosomal interval. The inbreds comprising the truncated MP305 chromosomal interval are very useful as donor sources themselves, and there is no need to revert to DE811ASR(BC5) as a donor source. By using marker assisted breeding as described herein, the truncated MP305 chromosomal interval can be further reduced in size as necessary without concern for losing the linkage between the markers and the Rcg1 gene. Phenotypically, a reduced chromosomal interval is associated with improved agronomic performance, as was demonstrated for DE811ASR(BC5) versus DE811ASR(BC3) described above.

Example 6

Use of Rcg1 as a Transgene to Create Resistant Corn Plants

The Rcg1 gene can be expressed as a transgene as well, allowing modulation of its expression in different circumstances. The following examples show how the Rcg1 gene could be expressed in different ways to combat different diseases or protect different portions of the plant, or simply to move the Rcg1 gene into different corn lines as a transgene, as an alternative to the method described in Example 5.

Example 6a

In this example, the Rcg1 gene is expressed using its own promoter. The upstream region of the Rcg1 gene was sequenced using the same BACs which in Example 2 provided the sequences of the protein-coding section of the gene. The sequence of 1684 bp 5' to the ATG is set forth in SEQ ID NO: 24.

In order to transform the complete Rcg1 gene, including the promoter and protein encoding region, a 5910 bp fragment extending from position 41268 through position 47176 in SEQ ID NO: 137 was amplified by PCR using BAC clone #24 (pk257m7) as template DNA. To enable cloning using the Gateway® Technology (Invitrogen, Carlsbad, USA), attB sites were incorporated into the PCR primers, and the amplified product was cloned into pDONR221 vector by Gateway® BP recombination reaction. The resulting fragment, flanked by attL sites, was moved by the Gateway® LR recombination reaction into a binary vector. The construct DNA was then used for corn transformation as described in Example 7.

Example 6b

In order to express the Rcg1 gene throughout the plant at a low level, the coding region of the gene and its terminator are placed behind the promoters of either a rice actin gene (U.S. Pat. No. 5,641,876 and U.S. Pat. No. 5,684,239) or the F3.7 gene (U.S. Pat. No. 5,850,018). To enable cloning using the Gateway® Technology (Invitrogen, Carlsbad, USA), attB sites are incorporated into PCR primers that are used to amplify the Rcg1 gene starting 35 bp upstream from its initiation codon. A NotI site is added to the attB1 primer. The amplified Rcg1 product is cloned into pDONR221 vector by Gateway® BP recombination reaction (Invitrogen, Carlsbad, USA). After cloning, the resulting Rcg1 gene is flanked by attL sites and has a unique NotI site at 35 bp upstream the initiation codon. Thereafter, promoter fragments are PCR amplified using primers that contain NotI sites. Each promoter is fused to the NotI site of Rcg1. In the final step, the chimeric gene construct is moved by Gateway® LR recombination reaction (Invitrogen, Carlsbad, USA) into the binary vector PHP20622. This is used for corn transformation as described in Example 7.

Example 6c

In order to express the Rcg1 gene throughout the plant at a high level, the coding region of the gene and its terminator were placed behind the promoter, 5' untranslated region and an intron of a maize ubiquitin gene (Christensen et al. (1989) *Plant Mol. Biol.* 12:619-632; Christensen et al. (1992) *Plant Mol. Biol.* 18:675-689). To enable cloning using the Gateway® Technology (Invitrogen, Carlsbad, USA), attB sites were incorporated into PCR primers that were used to amplify the Rcg1 gene starting at 142 bp upstream of the initiation codon. The amplified product was cloned into pDONR221 (Invitrogen, Carlsbad, USA) using a Gateway® BP recombination reaction (Invitrogen, Carlsbad, USA). After cloning, the resulting Rcg1 gene was flanked by attL sites. In the final step, the Rcg1 clone was moved by Gateway® LR recombination reaction (Invitrogen, Carlsbad, USA) into a vector which contained the maize ubiquitin promoter, 5' untranslated region and first intron of the ubiquitin gene as described by Christensen et al. (supra) followed by Gateway® ATTR1 and R2 sites for insertion of the Rcg1 gene, behind the ubiquitin expression cassette. The vector also contained a marker gene suitable for corn transformation, so the resulting plasmid, carrying the chimeric gene (maize ubiquitin promoter—ubiquitin 5' untranslated region—ubiquitin intron 1—Rcg1), was suitable for corn transformation as described in Example 7.

Example 6d

In order to express the Rcg1 gene at a stalk-preferred, low level of expression, the coding region of the gene and its terminator are placed behind the promoter of the Br2 gene (U.S. application Ser. No. 10/931,077). The fragment described in Example 6b containing the Rcg1 coding region flanked by attL sites and containing a unique NotI site 35 bp upstream of the Rcg1 initiation codon is used to enable cloning using the Gateway® Technology (Invitrogen, Carlsbad, USA). Promoter fragments of either Br2 or ZM-419 are PCR amplified using primers that contain NotI sites. Each promoter is fused to the NotI site of Rcg1. In the final step, the chimeric gene construct is moved by Gateway® LR recombination reaction (Invitrogen, Carlsbad, USA) into the binary vector PHP20622. This is used for corn transformation as described in Example 7.

Example 7

*Agrobacterium*-Mediated Transformation of Maize and Regeneration of Transgenic Plants The recombinant DNA constructs prepared in Example 6a and 6c were used to prepare transgenic maize plants as follows.

Maize was transformed with selected polynucleotide constructs described in Example 6a and 6c using the method of Zhao (U.S. Pat. No. 5,981,840, and PCT patent publication WO98/32326). Briefly, immature embryos were isolated from maize and the embryos contacted with a suspension of *Agrobacterium*, where the bacteria were capable of transferring the polynucleotide construct to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step was performed. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent, and growing transformed callus was recovered (step 4: the selection step). The callus was then regenerated into plants (step 5: the regeneration step), and calli grown on selective medium were cultured on solid medium to regenerate the plants.

Example 8: Transgenic Plant Evaluation

Transgenic plants were made as described in Example 7 using the constructs described in Examples 6a and 6c, respectively. For both the native Rcg1 gene and the ubiquitin Rcg1 gene constructs, 30 independent events and 10 vector only control events were generated.

Leaf discs of each native gene transgenic event were harvested for total RNA isolation. RT-PCR was performed using the gene specific primers FLP111F and FLP111R set forth in SEQ ID NOS: 37 and 38. In 30 out of 30 transgenic events, the expected 637 bp RT-PCR band was present indicating expression of the native gene construct. Disease assays were performed in the greenhouse on the same 30 native Rcg1 transgenic events to determine if the plants were resistant to Cg. To accomplish this, leaf blight assays were first carried out on 5 sibling plants of each event using the procedures described in Example 10. A single event was found to show a significant reduction in disease relative to control plants lacking the native Rcg1 gene construct. Plants that had been subjected to the leaf blight assay were allowed to develop two weeks post anthesis and were then further tested by Cg inoculation into the first elongated stalk internode. These stalk infection assays showed a single transgenic event expressing the native Rcg1 transgene to be more resistant to infection by Cg when compared to control plants.

However, this event differed from the positive event identified via the leaf infection assays.

Plants transformed with the ubiquitin Rcg1 construct described in Example 6c were analyzed in a similar fashion. RT-PCR analysis showed that 28 out of 30 transgenic events contained the expected transcript band, indicating expression of the ubiquitin Rcg1 construct. When leaf infection assays were performed on 5 plants from each of the 30 events, a single event was identified that showed a statistically significant reduction in disease compared to control plants. The transgenic plants were further analyzed by stalk infection assays. Three events were found to exhibit increased resistance to stalk rot when compared to control plants lacking the ubiquitin Rcg1 gene. These transgenic events did not include the former positive event identified in the leaf blight assays.

The results of these experiments were considered encouraging for the events that showed some resistance but overall inconclusive for several reasons. Positive events showing increased disease resistance by the leaf blight assay failed to correlate with those identified by the stalk infection assay. This is in contrast to the DE811ASR(BC5) positive control which shows a clear increase in resistance relative to DE811 in both leaf blight and stalk infection assays. In addition, assays of the primary transgenics showed a higher degree of variability than assays of DE811 or DE811ASR(BC5) controls. This was often seen within replicates as well as across negative control events. This latter observation may render discrimination of positive from negative events difficult. The possible causes for the inconclusive nature of the disease assay results include but are not limited to the following. It is well known to those skilled in the art that transgenic plants being tissue culture derived, exhibit greater plant to plant variability than control plants that are seed derived. Moreover, gene expression in primary transformants, that is, plants which have been through the transformation and regeneration process described in Example 7, is often unpredictable due to the stress of tissue culture procedures. If, in fact, the events are negative, which cannot be determined at this point, there are several technical reasons why this could be the case. The assays carried out also did not determine if the protein encoded by the Rcg1 gene is actually present in the transgenic lines—only the presence of a segment of the predicted mRNA was assayed using RT-PCR. It could be that artifacts were introduced into the gene cassette during transformation—extensive Southern blots or sequencing were not carried out to determine the integrity of the entire construct in the transgenic lines. In order to more carefully study these transgenic lines, plants of later generations will be grown in larger numbers under field conditions and assayed for disease resistance. It is anticipated that these future transgenic plants will more clearly exhibit increased resistance to Cg.

Example 9

Analysis of Rcg1 Gene Distribution Across Germplasm and Identification of Rcg1 Sequence Variants Following the identification, sequencing and fine mapping of Rcg1, other lines were screened for the Rcg1 gene. To determine the presence of the Rcg1 gene in other maize germplasm, gene specific primers combinations FLP111F and FLP111R as well as FLP113F and FLPA1R were used to amplify genomic DNA from a diverse panel of maize inbred lines, including those lines listed on Table 18 and F2834T, by polymerase chain reaction. In only 14 (including MP305) out of the panel of maize inbred lines an amplification product was detected, indicating that the Rcg1 gene is only present in a very small percentage of the inbred lines that were screened. Thus, in addition to using MP305 or DE811ASR (BC5) as the donor source, other sources containing the Rcg1 gene can also be used as a donor source. For example the public inbred lines TX601 (available under ID 'Ames 22763' from National Plant Germplasm System (NPGS)) and F2834T (available under ID 'Ames 27112' from NPGS) which contain the Rcg1 gene can be used as donor sources in crosses with other maize inbred lines not containing the Rcg1 gene, and selecting for the Rcg1 gene by using markers as described herein.

Variants of the Rcg1 gene were also identified and analyzed for single nucleotide polymorphisms (SNPs). SNPs were identified at positions on Sequence ID number 1 corresponding to one or more of position 413, 958, 971, 1099, 1154, 1235, 1250, 1308, 1607, 2001, 2598 and 3342. (See Table 7). Not all of the allelic variants of the Rcg1 gene indicated a resistant phenotype. Therefore, these SNPs can be used as markers to precisely identify and track the Rcg1 sequence in a plant breeding program, and to distinguish between resistant and susceptible allelic variants. Further, these SNPs indicate that there are variant sequences that show a resistant phenotype and can be used in the methods and products disclosed herein. Four other lines have also been found to contain an Rcg1 allele: BYD10, 7F11, CML261 and CML277. Testing of 10 plants did not provide sufficient data to conclusively determine whether line 7F11 is resistant. No data are available on the resistance of the BYD10, CML261 and CML277 lines, and sequencing of these alleles has not been completed.

TABLE 7

SNPs identified in allelic variants of the Rcg1 gene

| | Phenotype | # Plants Tested | \| | \| | \| | \| | Consensus position | | | | | | |
|---|---|---|---|---|---|---|---|---|---|---|---|---|---|---|
| | | | 413 | 958 | 971 | 1099 | 1154 | 1235 | 1250 | 1308 | 1607 | 2001 | 2598 | 3342 |
| SEQ ID NO: 1 from DE811ASR (BC5) | Resistant | Over 500 plants over 4-5 years | A | A | G | C | C | A | A | C | A | A | G | C |
| PHBTB | Resistant | 150-210, over 3 years | A | A | G | C | C | A | A | : | A | A | G | C |
| PH26T | Resistant | 50, over 1 year | A | A | G | C | C | A | A | : | A | A | G | C |
| TX601 | Insufficient data | 10, over 1 year | A | A | G | C | C | ? | A | : | A | A | G | C |

TABLE 7-continued

SNPs identified in allelic variants of the Rcg1 gene

| | | # Plants | Consensus position | | | | | | | | | | | |
|---|---|---|---|---|---|---|---|---|---|---|---|---|---|---|
| | Phenotype | Tested | 413 | 958 | 971 | 1099 | 1154 | 1235 | 1250 | 1308 | 1607 | 2001 | 2598 | 3342 |
| F2834T | No data | — | A | A | G | C | C | A | A | : | A | A | G | C |
| B54 | No data | — | C | C | C | T | A | A | T | : | G | G | A | A |
| PH0RC | Insufficient data | 19, over 1 year | C | C | C | T | A | A | T | : | G | G | A | A |
| PH277 | Insufficient data | 17, over 1 year | C | C | C | T | A | A | T | : | G | G | A | A |
| PHDGP | Susceptible | 150-210, over 3 years | C | C | C | T | A | A | T | : | G | G | A | A |
| PHDH7 | No data | — | C | C | C | T | A | A | T | : | G | G | A | A |
| MP305 (public) | Resistant | 50 | A | A | G | C | C | A | A | C | A | A | G | C |

Length of Consensus = 4212 nucleotides.
SEQ ID NO: 1 is the Rcg1 sequence.
For the remaining lines, the sequence available spanned from the "atg" start codon in the first exon to the "tga" stop codon in the second exon. The consensus position is based on SEQ ID NO: 1.

Example 10

Lines Containing the Rcg1 Gene are Resistant to Anthracnose-Induced Leaf Blight

Figure 14:
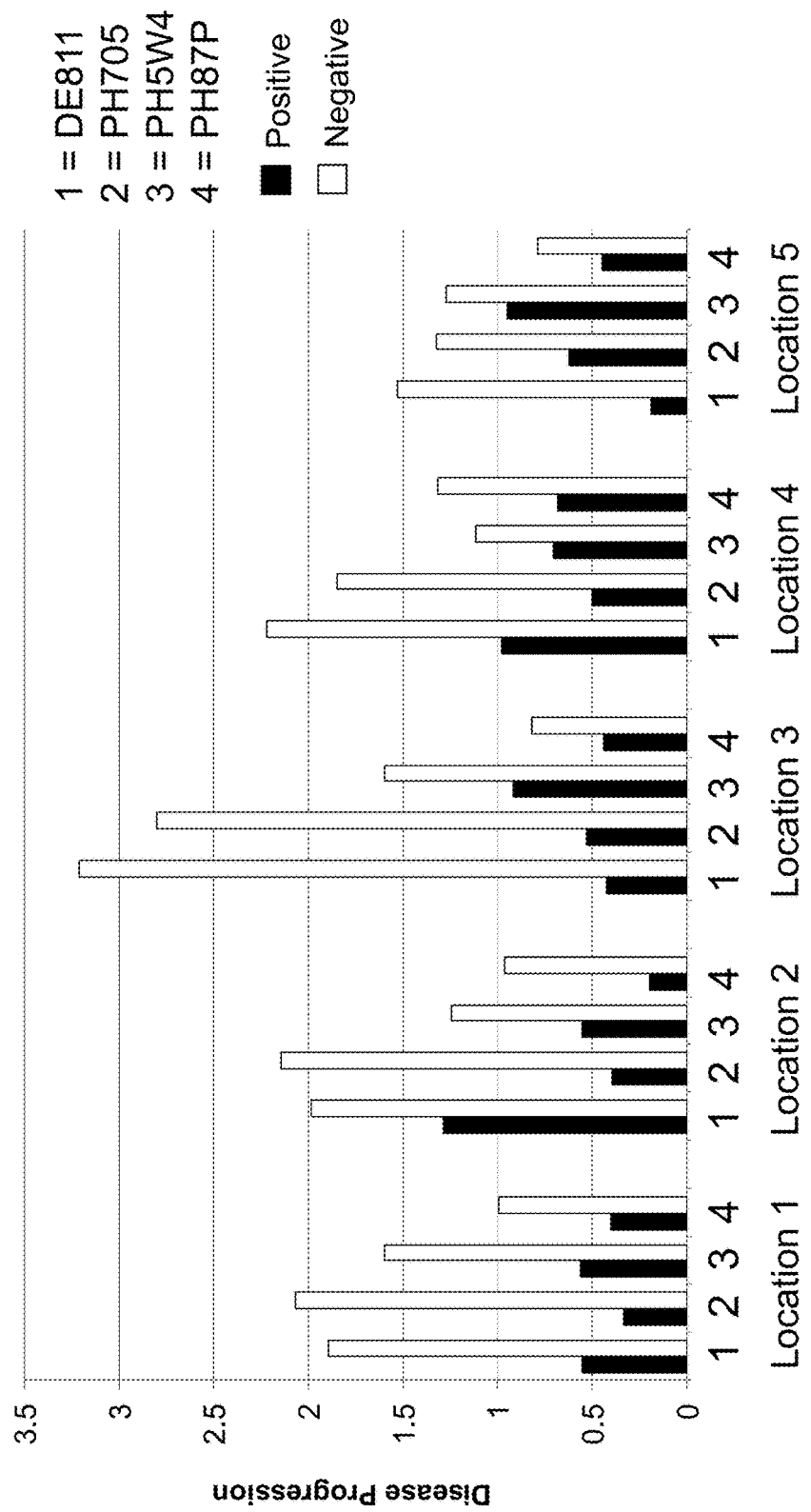
FIG. 14 shows the severity of disease at 5 different locations caused by Cg in stalks of inbred lines derived from DE811ASR(BC5) or MP305 four to five weeks after inoculation. Differences between the lines which were positive and negative for the Rcg1 gene are statistically significant at a P value of less than 0.05.
Figure 15:
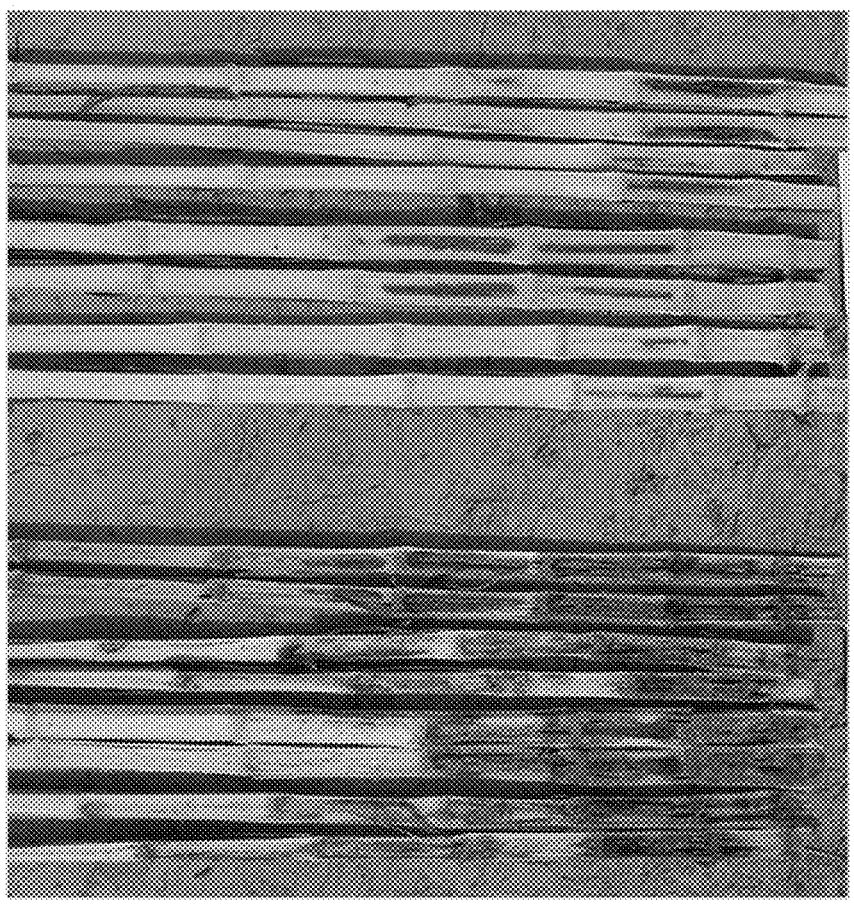
FIG. 15 shows disease progression in representative stalks from inbred PH705 lines which are positive and negative for Rcg1.
Figure 16:
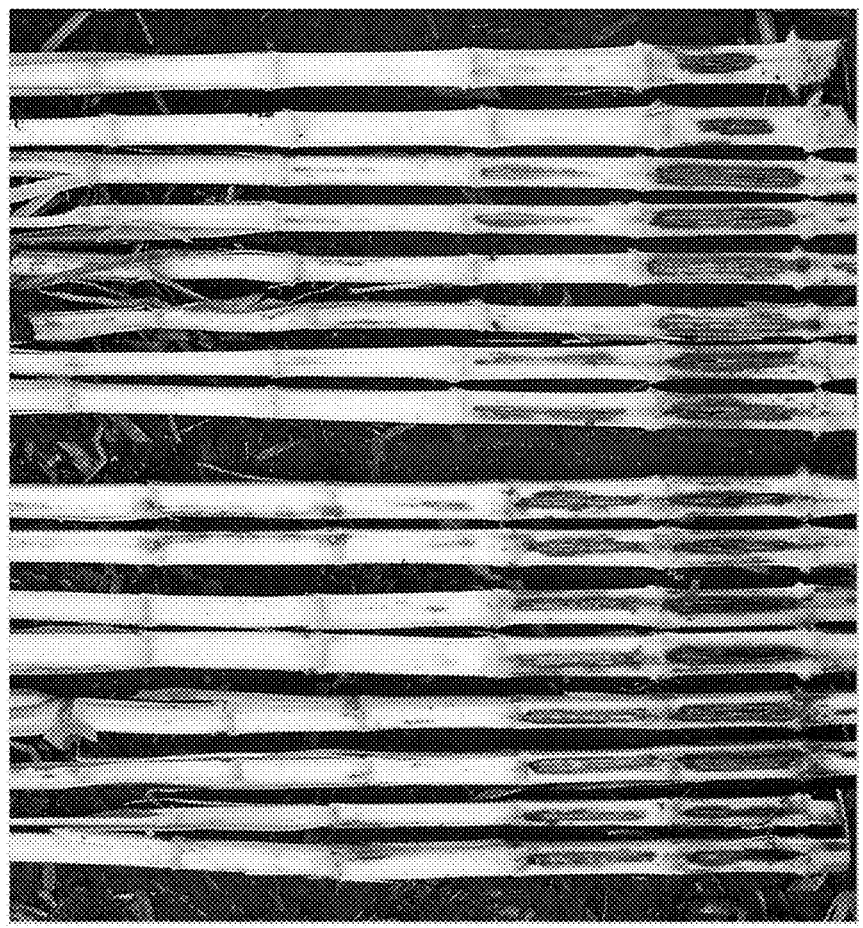
FIG. 16 shows disease progression in representative stalks from inbred PH87P lines which are positive and negative for Rcg1.

The near isogenic lines DE811 and DE811ASR described in Example 1 were tested for differences in resistance to leaf blight caused by Cg using the following procedure. Four common household sewing needles were glued to a metal support such that the holes for the thread extended out from the piece of metal, with all four needles extending an equal distance. This apparatus was dipped in a suspension of Cg spores at $5\times10^6$ spores/mL and then pushed through the surface of a young corn leaf such that the leaf was wounded and the wounds simultaneously inoculated with the spores. A wet cotton swab was placed on the midrib near the inoculation site and the entire area covered with plastic film and, over that, reflective cloth, both attached with tape, to keep it moist and shaded. The plants were left in this state for 50-54 hours in a standard greenhouse, after which the tape, cloth and plastic film were removed. At 7 and 15 days after inoculation the size of the lesion was measured and recorded in units of square centimeters.

FIG. 10(*a-b*) shows the distribution of lesion sizes 15 days after inoculation across all the individual leaves. Lesion sizes vary in each data set, but virtually all of the DE811 leaves (FIG. 10*b*) had lesion sizes significantly larger than the largest lesions to be found on the DE811ASR(BC5) leaves (FIG. 10*a*). The data are summarized for both the 7 day and 15 day post-inoculation data sets in FIG. 11. At both 7 and 15 days, the average lesion size was smaller on the leaves carrying the Rcg1 gene. The difference becomes larger over time as the fungus has time to grow and cause further damage, so that while the difference is approximately two fold at 7 days, by 15 days it is more than four fold and in fact the fungus has made only minor progress on the DE811ASR(BC5) leaves. These results clearly demonstrate that the presence of the locus containing the Rcg1 gene confers resistance to anthracnose leaf blight.

Example 11

Hybrid Lines Derived from DE811ASR(BC5) have Higher Yield than Hybrids Derived from DE811 when Infected with *Colletotrichum graminicola*

In order to demonstrate that corn hybrids containing the Rcg1 gene have higher yield potential when infected with Cg than hybrid lines without Rcg1, DE811ASR (BC5) and DE811, the isogenic lines described in Example 1, were each crossed to inbred lines B73Ht and Mo17Ht, which are both susceptible to Cg.

The hybrid lines were grown and evaluated for response to Cg in 2005 at six locations in five different states of the USA. For each hybrid line, three replications of four rows were planted at approximately 74,000 plants per hectare. Plants were inoculated with Cg at the base of the stalk approximately 10 days after flowering. The first row of each four-row plot was evaluated to determine if the inoculations had been successful by determining the response to Cg four to five weeks after inoculation. The stalks were split and the progression of the disease was scored by observation of the characteristic black color of the fungus as it grows up the stalk. Disease ratings were conducted as described by Jung et al. (1994) *Theoretical and Applied Genetics,* 89:413-418). The total number of internodes discolored greater than 75% (antgr75) was recorded on the first five internodes (See FIG. 20). This provided a disease score ranging from 0 to 5, with zero indicating no internodes more than 75% discolored and 5 indicating complete discoloration of the first five internodes. The center two plots were harvested via combine at physiological maturity and grain yield in kg/ha was determined.

The results summarized over all locations are shown in FIG. 12 for disease severity and in FIG. 13 for yield. The data show that hybrids containing Rcg1 (DE811ASR(BC5)/B73Ht and DE811ASR(BC5)/Mo17Ht) have much less disease progression than hybrids without Rcg1 (DE811/B73Ht and DE811/Mo17Ht). The high scores for disease progression in the susceptible hybrids (lacking Rcg1) show the successful infection of the experiment with Cg. Furthermore, the data show that when infected with Cg, hybrids containing Rcg1 have a higher yield than hybrids lacking Rcg1. Differences of the individual pairwise comparisons are significant at $P<0.05$. These results clearly demonstrate that by using the methods of the embodiments one can create hybrids which yield more kg of grain per hectare when infected with Cg.

Example 12

Inbred and Hybrid Rcg1 Locus Conversions Derived from DE811ASR (BC5) or MP305 are Resistant to *Colletotrichum graminicola* Induced Stalk Rot In order to demonstrate that commercial corn lines can be made resistant to Cg-induced stalk rot, MP305 and DE811ASR (BC5) were crossed with PH87P, PH5W4, and PH705. The resulting progeny were crossed again to the same three lines (i.e., the lines were used as recurrent parents in a backcrossing program) three more times, each time selecting for the presence of the Rcg1 gene using molecular markers as described in Example 5 above. As controls, selected backcross lines which lacked the Rcg1 gene were also collected from the same backcrossing program. After three backcrosses were completed, several versions were selected and selfed to obtain BC3S1 families. Individual BC3S1 plants were genotyped and plants homozygous positive and homozygous negative for Rcg1 were selfed to obtain BC3S2 families, which were then phenotyped. BC3S2 versions containing Rcg1 and, as controls, selected versions without the gene, were planted in single row plots containing approximately 25 plants per row. The experiment was planted in five different locations in five different states of the United States, designated Locations 1, 2, 3, 4, and 5. At approximately two weeks after flowering, plants were inoculated with Cg at the base of the stalk. Four to five weeks later the stalks were split and progression of the disease evaluated by visually estimating the amount of disease in the stalk. A visual score was assigned to each stalk based on the degree of infection of each internode for the inoculated internode and the four internodes above the inoculation internode. A low score thus indicates resistance to the disease. The compiled results for all rows and locations are summarized in FIG. 14. Representative pictures of two lines are shown in FIGS. 15 and 16. The data show that at all locations, each of the elite inbred lines was made more resistant to the disease by the presence of the Rcg1 gene.

Figure 17:
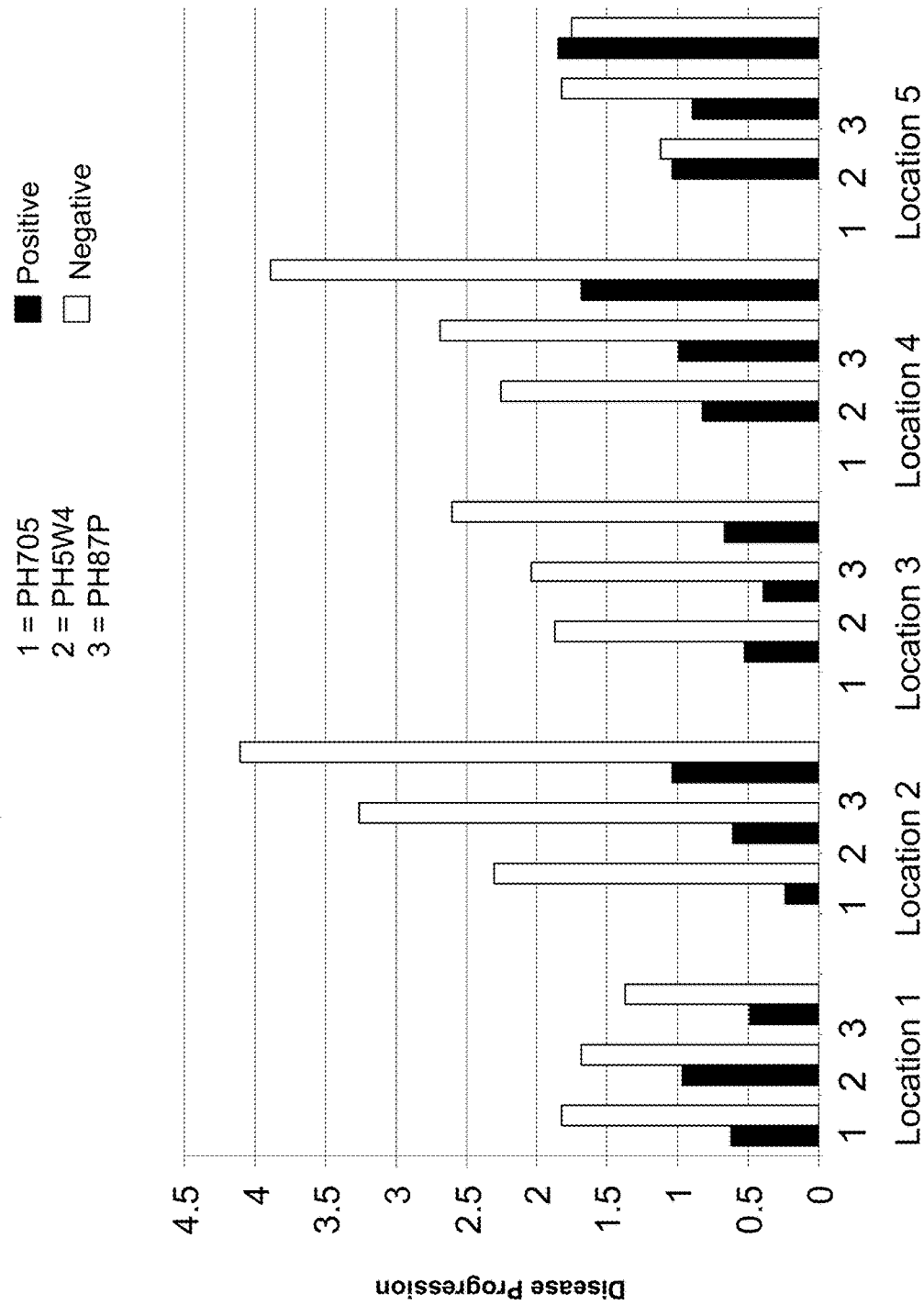
FIG. 17 shows the severity of disease four to five weeks after inoculation at 5 different locations caused by Cg in stalks of hybrids derived from crossing DE811ASR(BC5) to the line indicated. Differences between the lines which were positive and negative for the Rcg1 gene are statistically significant at a P value of less than 0.05, except for location 5.
Figure 18:
FIG. 18 shows disease progression in representative stalks from hybrids created from PH4CV and PH705 lines which are positive and negative for Rcg1.
Figure 19:
FIG. 19 shows disease progression in representative stalks from hybrids created from PH705 and PH87P lines which are positive and negative for Rcg1.

Corn seed sold to farmers is "hybrid," meaning that it is most commonly the result of a cross of two inbred parents, referred to as a single cross hybrid. Many years of breeding and production experience have shown that the use of single cross hybrids result in higher yields. It is thus important for commercial applications that the Rcg1 gene function in the hybrid plants (those in the farmer's production field) even when it is present in only one of the two parents used to make single cross hybrid seed. One of the inbred lines into which the Rcg1 line had been crossed, PH705, was thus used to create hybrid seed by crossing with PH4CV, an elite inbred that does not carry the Rcg1 gene. The resulting hybrid seeds were used in experiments identical to those described for the inbred lines as discussed above and scored in the same way at all five locations. The data are summarized in FIG. 17, which also shows the performance of the inbred PH705, and representative pictures shown in FIGS. 18 and 19. As can be seen, a clear difference in disease progression was observed in all locations for hybrid PH705×PH5W4 and in four of the five locations for PH705×PH87P. In the fifth location, environmental conditions were very stressful for plant growth, resulting in plants that were in poor condition. Under these conditions, measurements of plant disease resistance are often not reliable.

The results with both inbred lines and hybrid combinations containing Rcg1 clearly demonstrate that using the methods of the embodiments one can create commercially useful lines which are resistant to Cg-induced stalk rot.

Example 13

Markers within the Rcg1 Coding Sequence, Marker Locations and Designs within the Rcg1 Locus, and Haplotypes for the Flanking Chromosomal Region Three levels of marker locations may be utilized as a result of the fine mapping and cloning of the Rcg1 gene, markers designed within the Rcg1 coding sequence, markers designed within the non-colinear region that identify the Rcg1 locus (but outside of the Rcg1 coding sequence), and markers designed within the flanking colinear region.

Markers within the Rcg1 Coding Sequence

Following the identification and fine mapping of the Rcg1 gene, hybridization markers were designed that will function on SNP platforms. Since the Rcg1 gene occurs in a non-colinear region of the maize genome, the hybridization marker will be present in lines comprising the Rcg1 gene and absent on lines that do not comprise the Rcg1 gene. These markers identify polynucleotide sequences specific to the Rcg1 coding sequence listed on SEQ ID NO: 1. As noted in Table 7, there are other corn lines with variants of the Rcg1 coding sequence set forth in SEQ ID NO: 1, and these markers were also designed to also identify these Rcg1 coding sequence variants.

To accomplish this, a consensus map of variant Rcg1 coding sequence from different sources was created, as shown on Table 7. This consensus map aligned 4209 bases of the Rcg1 coding sequence isolated from MP305 with 3451 bases from PHBTB and 3457 bases from PH26T. The Rcg1 gene in both PHBTB and PH26T show resistance to anthracnose. Next, segments of the Rcg1 coding sequence were BLASTed against several databases including NT (Public DNA from NCBI) and the highest homology hits were aligned with the Rcg1 consensus sequence to determine the segments that shared high homology and had common segments with other resistance genes in the NBS-LRR family. Regions unique to the Rcg1 coding sequence and common across the different sources of Rcg1 were selected for marker design. Specifically, since FLP111F and FLP111R primers produced a single amplicon that reliably diagnosed the presence of Rcg1 from different sources, the regions where FLP111F and FLP111R hybridized were therefore targeted for development of a SNP marker design.

Figure 23:
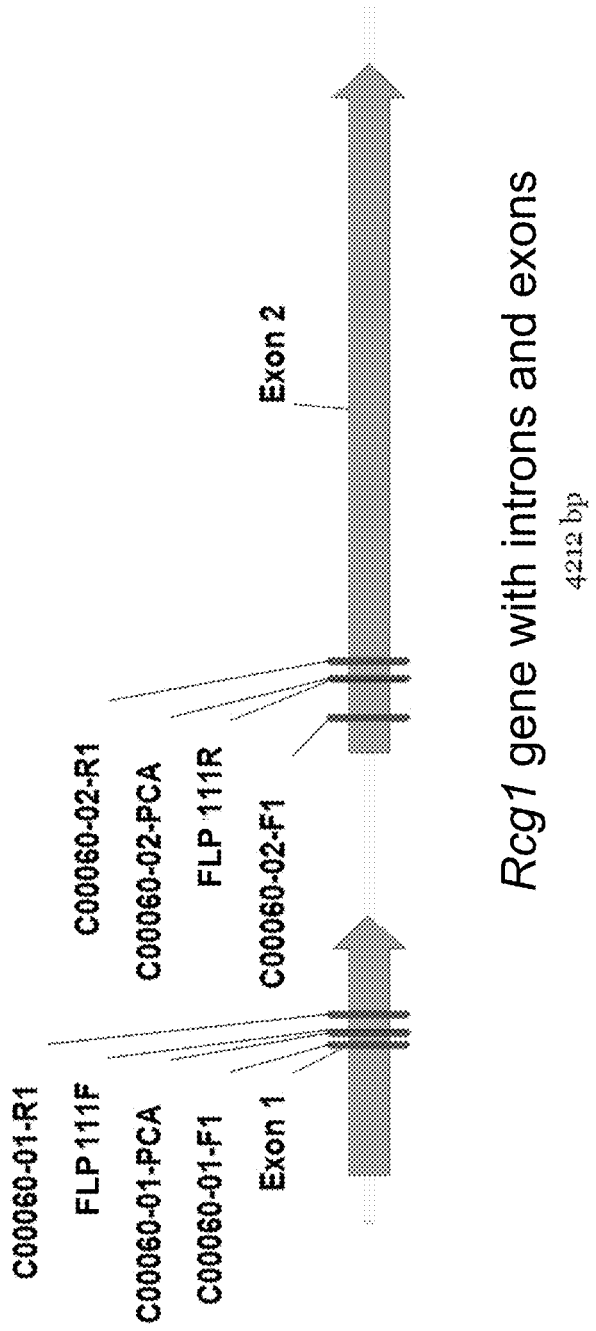
FIG. 23 shows the oligos for the Rcg1 hybridization markers designed for use with Invader™ reactions.
Figure 24:
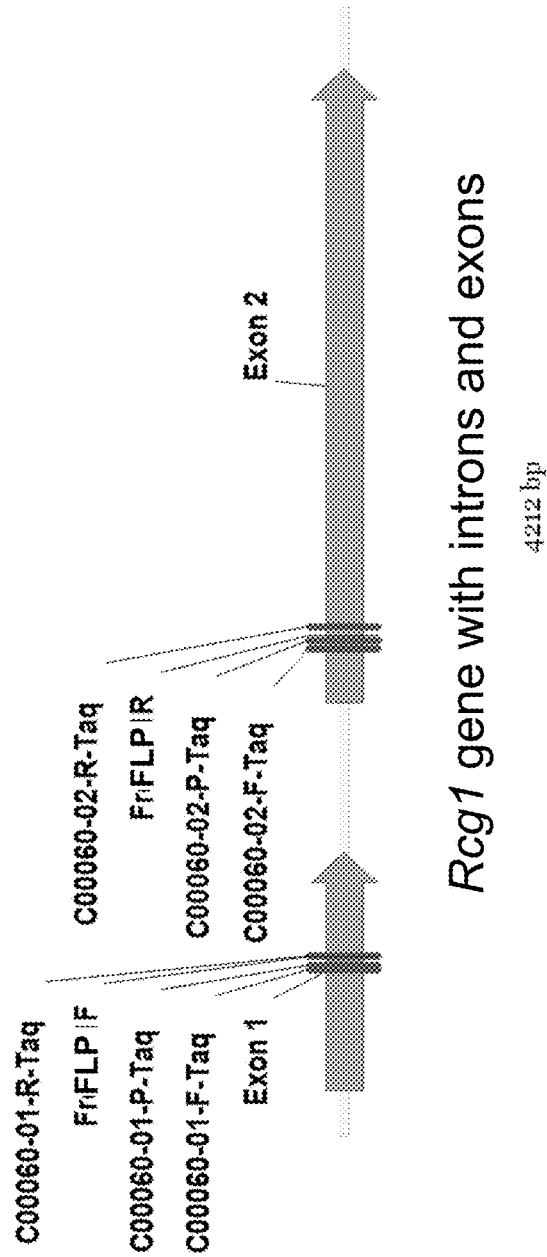
FIG. 24 shows the oligos for the Rcg1 hybridization markers designed for use with TaqMan® reactions.
Figure 25:
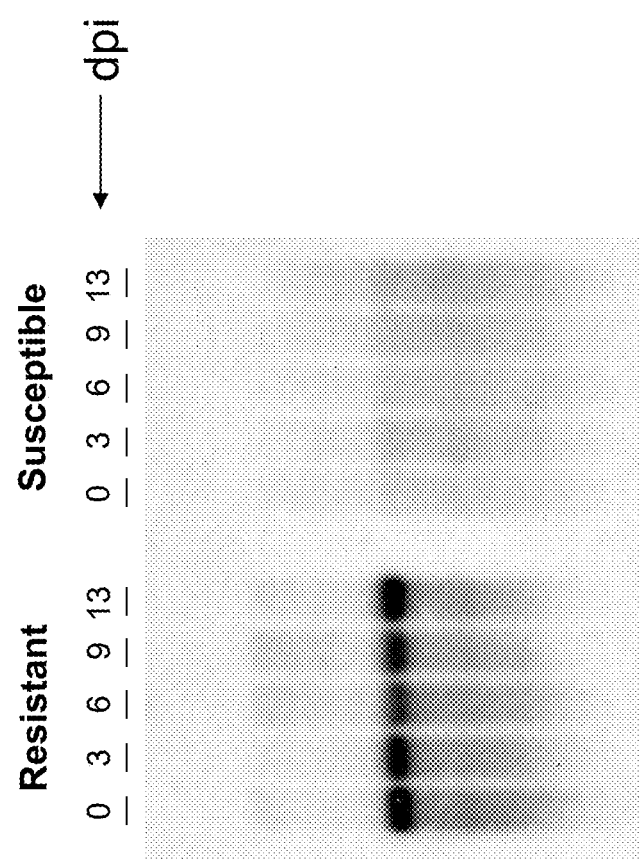
FIG. 25 shows the results of a northern blot obtained from approximately 1.5 mg of polyA-enriched RNA isolated from resistant and susceptible plants 0, 3, 6, 9, and 13 days post inoculation (dpi). The membrane was probed with a random primer labeled 420 bp Rcg1 fragment. Resistant tissue is from DE811ASR(BC5) and susceptible tissue is from DE811.

An Invader™ (Third Wave Technologies, Madison, Wis.) marker was designed using a 1413 bp segment from the consensus sequence that contained both primer sites, with the primer regions themselves being targeted for probe and Invader™ oligo hybridization. Primers were designed around each probe site to give an amplicon size below 150 bp. This marker indicated the presence of the Rcg1 coding sequence with fluorescence due to hybridization, with the absence of the Rcg1 coding sequence resulting in no fluorescence. A control fluorescence signal can also be generated by designing a marker that hybridizes to a second highly conserved maize gene, so that the presence of the Rcg1 coding sequence results in fluorescence of two dyes (Rcg1 and the conserved gene) and the absence of Rcg1 results in fluorescence due to the conserved gene only. This 'control' florescence may be used to reduce lab error by distinguishing between the situations where the Rcg1 is in fact absent and the situation where a false negative has occurred because of a failed reaction. Such markers are not limited to a specific marker detection platform. Taqman® markers (Applied Biosystems) were also designed to the same location (primer pairs FLP111F and FLP111R), that were used as for the Invader™ markers. The markers are shown on Table 15 and FIGS. 23 and 24.

The marker designs C00060-01-A and C00060-02-A were tested across a wide variety of sources and were highly successful at identifying plants that contained the Rcg1 locus and the Rcg1 gene, regardless of the source of the Rcg1 locus or Rcg1 gene. These markers were also used against a control set of nearly 100 diverse inbred lines known not to carry the gene, and no fluorescence was detected in the control set. Plants in which one or both of marker designs C00060-01-A and C00060-02-A confirmed as having Rcg1 include those shown in Table 7.

Therefore, this example shows that, based on the teaching provided herein, markers can be constructed that identify the Rcg1 coding sequence in a variety of sources.

Markers within the Rcg1 Locus

Markers may be designed to the Rcg1 locus in addition to or instead of using markers within the Rcg1 coding sequence itself. The close physical distance between the Rcg1 coding sequence and the non-colinear region makes it unlikely that the linkage between markers within the non-colinear region but outside of the Rcg1 coding sequence would be lost through recombination. As with markers for the Rcg1 coding sequence, a marker showing as present or absent would be sufficient to identify the Rcg1 locus.

To design markers for this region, a 64,460 bp segment of non-colinear region including the Rcg1 gene and the region directly north of the Rcg1 gene was sequenced. BACs in this sequence were broken up into sub-clones of approximately 800 nucleotides in length and sequenced. These sequences were then assembled to construct the BAC sequence, and genic and repetitive regions were identified. Repetitive regions were identified in order to avoid placing markers in repetitive regions. Similarly, sequences with high homology with known maize sequences were easily avoided by a simple BLAST search. Potential sequences were avoided that contained SSRs, runs of As, Ts or Gs, or that would result in the generation of probes low in GC content which can cause problems within the Invader™ platform. See FIG. 9(b) and Table 17.

Selected segments were then put into Invader Creator™ software (Third Wave, Madison, Wis.), which generates oligos for an Invader™ reaction. This produced a sense and an anti-sense design for all SNPs. The sense designs with the best scores and no penalties were selected. Although these markers have been designed, they have not yet been tested.

Primers were designed using Primer3 (Steve Rozen and Helen J. Skaletsky (2000) Primer3 available on the world wide web for general users and for biologist programmers. In: Krawetz S, Misener S (eds) *Bioinformatics Methods and Protocols: Methods in Molecular Biology*. Humana Press, Totowa, N.J., pp 365-386). Primers were selected outside of the Invader™ components, and preferred primers close to or below 150 bp long were selected. Primer temperature and length was adjusted to be most useful for the Invader™ platform, although if using other detection platforms primers would be optimized for use with such platforms.

Markers in the Colinear Region and Associated Haplotypes

Closely linked markers flanking the Rcg1 locus may be effectively used to select for a progeny plant that has inherited the Rcg1 locus from a parent that comprises the Rcg1 locus. The markers described herein, such as those listed on Table 16, as well as other markers genetically or physically mapped to the same chromosomal segment, may be used to select for a truncated chromosomal segment comprising the Rcg1 locus. Typically, a set of these markers will be used, (e.g., 2 or more, 3 or more, 4 or more, 5 or more) in the flanking region above the gene and a similar set in the flanking region below the gene. Optionally, as described above, a marker within the Rcg1 gene and/or Rcg1 locus may also be used. The parents and their progeny are screened for these sets of markers, and the markers that are polymorphic between the two parents are used for selection. The most proximal polymorphic markers to the Rcg1 gene or Rcg1 locus are used to select for the gene or locus, and the more distal polymorphic markers are used to select against the gene or locus. In an introgression program, this allows for selection of the Rcg1 gene or Rcg1 locus genotype at the more proximal polymorphic markers, and selection for the recurrent parent genotype at the more distal polymorphic markers. As described in more detail in Example 5 above, this process allowed for the efficient selection of a truncated chromosomal segment comprising the Rcg1 locus.

The process described above requires knowledge of the parental genotypes used in the cross. Optionally, haplotypes may be used so that the Rcg1 gene or Rcg1 locus can be selected for without first genotyping the specific parents used in the cross. This is a highly efficient way to select for the Rcg1 locus, especially in the absence of using markers within the Rcg1 gene or the Rcg1 locus.

All plants to be used in the breeding program, such as a gene introgression program, are screened with markers. The markers disclosed herein or equivalent markers on the same chromosomal segment may be used. The plant haplotypes (a series of SNP or other markers in linkage disequilibrium) are noted. The haplotype of the resistant plant around the Rcg1 locus is compared with the haplotype of the other plants to be used that do not comprise the Rcg1 locus. A haplotype unique to the resistant plant around the Rcg1 locus is then used for selection, and this haplotype will specifically identify the chromosomal segment from the resistant plant with the Rcg1 locus.

Based on an analysis of MP305 and a diverse set of several hundred corn lines, including 50 public corn lines shown in Table 18, a unique SNP haplotype for the MP305 chromosomal segment with the Rcg1 locus was identified. This SNP haplotype uniquely identifies the MP305 chromosomal segment that extends across MZA3434, MZA2591 and MZA11123. See FIG. 22, SEQ ID NO: 140, 141 and 142, and Tables 8, 9 and 10.

First, the primer pairs described in Table 2 for these three MZA's were used to identify haplotypes. The primer pairs MZA3434 E forward and reverse were used to amplify the genomic DNA of the set of corn lines. The PCR fragments were further purified by amplification with MZA3434 I forward and reverse primer pairs. This process was repeated for MZA2591 and MZA11123. The resulting PCR fragments were sequenced in the forward and reverse direction and the sequences were aligned to give a consensus sequence (see the sequences set forth in SEQ ID NOs: 140, 141 and 142). SNPs and indels within these consensus sequences are shown in Tables 8, 9 and 10. These series of SNPs and indels were compared across the set of genotypes.

For MZA3434, haplotype 8 was a rare haplotype allele, and was unique to MP305 and only one other corn line. This process was repeated for MZA2591, and MP305 was found to have haplotype 2 at MZA2591, which was shared by only two other corn lines. MP305 was the only corn line to have both haplotype 8 at MZA3434 and haplotype 2 at MZA2591, and therefore, the combination of these two haplotypes, 8 at MZA3434 and 2 at MZA2591, uniquely identifies the MP305 chromosomal region comprising the Rcg1 locus. MP305 also had an informative haplotype at MZA11123. MP305 was found to have haplotype 7, which was shared by 66 other corn lines, but none of these corn lines had haplotype 8 at MZA3434, or haplotype 2 at MZA2591. Therefore, any combination of 2 haplotypes at MZA3434, MZA2591 or MZA11123 could be used to uniquely identify MP305 among these genotypes. The haplotypes can then be interrogated by sequencing the fragment or by designing markers to each SNP or indel within a fragment.

Polymorphisms within haplotypes can be used to tag the haplotype. So called 'Tag-SNPs', or 'haplotype-tags' can be very useful in plant breeding, as more information than the polymorphism itself can be determined via extrapolation to the haplotype. A haplotype can also be defined as a series of polymorphisms across sequences, and these may be termed 'long-range haplotypes'.

Rare polymorphisms were observed within haplotypes that could be used as 'haplotype tags'. For example, either the SNPs MZA2591.32 (allele c) or MZA2591.35 (allele t) could be used to tag the haplotype 2 at MZA2591, and like haplotype 2, both were unique to MP305 and two other corn lines. The combination of SNPs MZA2591.32 (allele c) and MZA2591.35 (allele t) combined with MZA3434.17 (allele c) gave a 'long-range' haplotype that could be used to distinguish MP305 from all of the other genotypes in the study.

In addition, other markers, MZA15842, MZA11455, MZA8761 and MZA1851 also showed polymorphism with MP305. For MZA15842, only 18 of the other corn lines shared the same haplotype as MP305; for MZA11455, only 43 of the other corn lines shared the same haplotype as MP305; for MZA8761, only about half of the other corn lines shared the same haplotype as MP305; and for MZA1851, only about half of the other corn lines shared the same haplotype as MP305. Consensus sequences were developed for these markers, and are set forth in SEQ ID NOs: 143-146. SNPs and indels within these consensus sequences are shown in Tables 11-14. Four examples of unique haplotypes using the MZA markers are:

MZA11123 (haplotype 7)
MZA15842 (haplotype 3)
MZA8761 (haplotype 1)
and
MZA11123 (haplotype 7)
MZA15842 (haplotype 3)
MZA1851 (haplotype 1)
And
MZA11455 (haplotype 6)
MZA11123 (haplotype 7)
MZA15842 (haplotype 3)
MZA16510 (haplotype 4)
and
MZA11455 (haplotype 6)
MZA11123 (haplotype 7)
MZA15842 (haplotype 3)
MZA11394 (haplotype 6).

Multiple combination within all of the markers disclosed herein, or other markers within the region, also will contain unique haplotypes that identify the Rcg1 locus.

TABLE 8

MZA3434 Polymorphisms
M = " Mutant': differs to consensus W = 'wild type': same as consensus,

|  | MZA3434.3 | MZA3434.4 | MZA3434.6 | MZA3434.17 | MZA3434.2 | MZA3434.5 |
|---|---|---|---|---|---|---|
| Nucleotide position on SEQ ID NO: 140 | 282 | 283 | 327 | 343 | 377 | 387 |
| Type | DEL | DEL | DEL | SNP | DEL | DEL |
| Size of indel | 6 | 1 | 4 |  | 2 | 2 |
| MP305 | W | M | W | C | W | M |
| Counter allele | M | W | M | T | M | W |

TABLE 9

MZA2591 Polymorphisms
M = " Mutant': differs to consensus W = 'wild type': same as consensus,

|  | MZA2591.43 | MZA2591.20 | MZA2591.21 | MZA2591.8 | MZA2591.12 | MZA2591.4 | MZA2591.31 |
|---|---|---|---|---|---|---|---|
| Nucleotide position on SEQ ID NO: 141 | 101 | 114 | 124 | 131 | 160 | 176 | 213 |
| Type | INS | SNP | SNP | DEL | DEL | INS | SNP |
| Size of indel | 3 |  |  | 2 | 3 |  |  |
| MP305 | W | T | C | W | W | W | T |
| Counter allele | M | A | T | M | M | M | C |

|  | MZA2591.32 | MZA2591.1 | MZA2591.33 | MZA2591.35 | MZA2591.36 | MZA2591.37 |
|---|---|---|---|---|---|---|
| Nucleotide position on SEQ ID NO: 141 | 223 | 238 | 250 | 257 | 264 | 271 |
| Type | SNP | DEL | SNP | SNP | SNP | SNP |
| Size of indel |  | 2 |  |  |  |  |
| MP305 | C | M | C | T | C | G |
| Counter allele | T | W | G | A | G | A |

|  | MZA2591.38 | MZA2591.10 | MZA2591.39 | MZA2591.3 | MZA2591.40 | MZA2591.41 |
|---|---|---|---|---|---|---|
| Nucleotide position on SEQ ID NO: 141 | 282 | 290 | 310 | 313 | 325 | 332 |
| Type | SNP | DEL | SNP | DEL | SNP | SNP |
| Size of indel |  | 4 |  | 2 |  |  |
| MP305 | C | M | T | M | T | C |
| Counter allele | T | W | C | W | C | T |

TABLE 9-continued

MZA2591 Polymorphisms
M = "Mutant': differs to consensus W = 'wild type': same as consensus,

|  | MZA2591.6 | MZA2591.7 | MZA2591.9 |
|---|---|---|---|
| Nucleotide position on SEQ ID NO: 141 | 332 | 371 | 404 |
| Type | DEL | DEL | DEL |
| Size of indel |  |  | 1 |
| MP305 | W | W | W |
| Counter Allele | M | M | M |

TABLE 10

MZA11123 Polymorphisms
M = "Mutant': differs to consensus W = 'wild type': same as consensus,

|  | MZA11123.5 | MZA11123.18 | MZA11123.2 | MZA11123.13 | MZA11123.34 | MZA11123.37 | MZA11123.40 | MZA11123.41 |
|---|---|---|---|---|---|---|---|---|
| Nucleotide position on SEQ ID NO: 142 | 631 | 641 | 650 | 671 | 703 | 727 | 744 | 786 |
| Type | DEL | INS | INS | INS | SNP | SNP | SNP | SNP |
| Size of indel | 1 | 1 | 1 | 10 |  |  |  |  |
| MP305 | W | W | W | W | G | T | C | A |
| Counter allele | M | M | M | M | A | C | A | G |

|  | MZA11123.45 | MZA11123.48 | MZA11123.9 | MZA11123.19 | MZA11123.59 | MZA11123.17 | MZA11123.16 |
|---|---|---|---|---|---|---|---|
| Nucleotide position on SEQ ID NO: 142 | 807 | 864 | 915 | 934 | 956 | 991 | 1010 |
| Type | SNP | SNP | INS | DEL | SNP | DEL | DEL |
| Size of indel |  |  | 18 | 1 |  | 3 | 3 |
| MP305 | C | T | W | W | C | M | W |
| Counter allele | A | A | M | M | T | W | M |

TABLE 11

MZA15842 Polymorphisms
M = "Mutant': differs to consensus W = 'wild type': same as consensus,

|  | MZA15842.3 | MZA15842.4 | MZA15842.5 | MZA15842.7 | MZA15842.8 | MZA15842.9 |
|---|---|---|---|---|---|---|
| Nucleotide position on SEQ ID NO: 143 | 287 | 295 | 313 | 337 | 353 | 366 |
| Type | SNP | SNP | SNP | SNP | SNP | SNP |
| MP305 | T | A | T | C | T | T |
| Counter Allele | C | G | A | T | C | C |

|  | MZA15842.10 | MZA15842.11 | MZA15842.12 | MZA15842.3 |
|---|---|---|---|---|
| Nucleotide position on SEQ ID NO: 143 | 436 | 439 | 463 | 287 |
| Type | SNP | SNP | SNP | SNP |
| MP305 | G | A | A | T |
| Counter Allele | A | G | G | C |

TABLE 12

MZA8761 Polymorphisms
M = "Mutant': differs to consensus W = 'wild type': same as consensus,

|  | MZA8761.3 | MZA8761.6 | MZA8761.7 | MZA8761.8 | MZA8761.9 | MZA8761.10 | MZA8761.11 | MZA8761.4 |
|---|---|---|---|---|---|---|---|---|
| Nucleotide position on SEQ ID NO: 145 | 595 | 633 | 671 | 681 | 687 | 696 | 702 | 710 |
| Type | DEL | SNP | SNP | SNP | SNP | SNP | SNP | DEL |
| Size of indel | 7 | | | | | | | 1 |
| MP305 | W | G | T | G | T | G | C | W |
| Counter allele | M | A | C | C | C | T | A | M |

|  | MZA8761.2 | MZA8761.1 | MZA8761.5 | MZA8761.12 | MZA8761.13 | MZA8761.14 |
|---|---|---|---|---|---|---|
| Nucleotide position on SEQ ID NO: 145 | 710 | 710 | 722 | 779 | 882 | 901 |
| Type | DEL | INS | DEL | SNP | SNP | SNP |
| Size of indel | 1 | 1 | 1 | | | |
| MP305 | W | W | W | T | C | T |
| Counter allele | M | M | M | G | T | C |

TABLE 13

MZA1851 Polymorphisms
M = "Mutant': differs to consensus W = 'wild type': same as consensus,

|  | MZA1851.24 | MZA1851.41 | MZA1851.32 | MZA1851.49 | MZA1851.51 | MZA1851.52 | MZA1851.53 |
|---|---|---|---|---|---|---|---|
| Nucleotide position on SEQ ID NO: 144 | 1213 | 1236 | 1271 | 1465 | 1615 | 1617 | 1686 |
| Type | INS | SNP | INS | SNP | SNP | SNP | SNP |
| Size of indel | 19 | | 34 | | | | |
| MP305 | W | G | W | A | C | A | T |
| Counter Allele | M | A | M | G | A | C | C |

|  | MZA1851.54 | MZA1851.55 | MZA1851.56 | MZA1851.35 |
|---|---|---|---|---|
| Nucleotide position | 1697 | 1698 | 1701 | 1717 |
| Type | SNP | SNP | SNP | DEL |
| Size of indel | | | | 6 |
| MP305 | A | G | T | W |
| Counter Allele | C | C | C | M |

TABLE 14

MZA11455 Polymorphisms
M = "Mutant': differs to consensus W = 'wild type': same as consensus,

|  | MZA11455.3 | MZA11455.5 | MZA11455.2 | MZA11455.7 | MZA11455.8 | MZA11455.10 | MZA11455.11 |
|---|---|---|---|---|---|---|---|
| Nucleotide position on SEQ ID NO: 146 | 373 | 392 | 402 | 425 | 426 | 432 | 435 |
| Type | DEL | SNP | DEL | SNP | SNP | SNP | SNP |
| Size of indel | 1 | | 10 | | | | |
| MP305 | M | G | M | G | C | C | A |
| Counter allele | W | C | W | A | G | G | G |

|  | MZA11455.12 | MZA11455.4 | MZA11455.13 | MZA11455.14 | MZA11455.15 | MZA11455.1 | MZA11455.17 |
|---|---|---|---|---|---|---|---|
| Nucleotide position on SEQ ID NO: 146 | 491 | 526 | 552 | 581 | 599 | 610 | 611 |
| Type | SNP | DEL | SNP | SNP | SNP | DEL | SNP |
| Size of indel | | 1 | | | | 3 | |

TABLE 14-continued

MZA11455 Polymorphisms
M = " Mutant': differs to consensus W = 'wild type': same as consensus,

| MP305 | T | M | A | G | G | W | G |
|---|---|---|---|---|---|---|---|
| Counter allele | A | W | G | A | C | M | A |

|  | MZA11455.18 | MZA11455.19 |
|---|---|---|
| Nucleotide position on SEQ ID NO: 146 | 628 | 634 |
| Type | SNP | SNP |
| Size of indel |  |  |
| MP305 | C | A |
| Counter allele | G | C |

TABLE 15

Markers within the Rcg1 Coding Sequence

| SNP Platform | INVADER | INVADER | TAQMAN | TAQMAN | PCR |
|---|---|---|---|---|---|
| Marker Name | C00060-01-A | C00060-02-A | C00060-01 | C00060-02 | FLP111 |
| Forward Primer Name | C00060-01-F1 | C00060-02-F1 | C00060-01-F-Taq | C00060-02-F-Taq | FLP111F |
| Position on SEQ ID NO: 1 | 550-567 | 1562-1586 | 552-568 | 1634-1659 | 595-619 |
| Forward Primer Sequence | SEQ ID NO: 145 | SEQ ID NO: 146 | SEQ ID NO: 147 | SEQ ID NO: 148 | SEQ ID NO: 37 |
| Reverse Primer Name | C00060-01-R1 | C00060-02-R1 | C00060-01-R-Taq | C00060-02-R-Taq | FLP111RB |
| Position on SEQ ID NO: 1 | 641-658 | 1739-1767 | 599-620 | 1707-1730 | 1676-1700 |
| Reverse Primer Sequence | SEQ ID NO: 149 | SEQ ID NO: 150 | SEQ ID NO: 151 | SEQ ID NO: 152 | SEQ ID NO: 153 |
| Probe Name | C00060-01-PCA | C00060-02-PCA | C00060-01-P-Taq | C00060-02-P-Taq |  |
| Position on SEQ ID NO: 1 | 586-603 | 1685-1701 | 570-595 | 1662-1693 |  |
| Probe Sequence | SEQ ID NO: 154 | SEQ ID NO: 155 | SEQ ID NO: 156 | SEQ ID NO: 157 |  |

TABLE 16

Markers contained within defined chromosomal intervals that can be used to select for Rcg1.

| Interval (and position on IBM2 neighbors 4 map in cM) | Position relative to Rcg1 | Markers that could be used for selection of Rcg1 |
|---|---|---|
| UMC2041 (483.93)- UMC2200 (543.44) | Above the Rcg1 gene UMC2041 - Rcg1 Below the Rcg1 gene Rcg1 - UMC2200 | UMC2041, AY112127, UMC1086, AY110631, UMC2285, MZA8136, MZA6064, NPI270, NPI300C, PHP20071, CDO127a, RGPI102, UAZ122, BNL17.05, MZA11455, MZA15842, MZA11123, MZA2591 PHI093, MZA1215, MZA1216, MZA3434, CL12681_1, NPI444, UMC15a, MZA8761, CSU166a, CDO365, CSU1038b, CSU1073b, CSU597a, RGPG111, UMN433, PHP20562, C2, NPI910, CSU178a, CSU202, TDA44, MZA1851, UMC1051, MZA11394, PCO136722, UMC2187, NPI410, PSR109B, UMC1371, UMC1842, UMC1856, AY109980, UMC1132, NFD106, AY105971, AY110989, ENSI002A, RZ596B, BNL23A, BNL29, UMC2200 |

TABLE 16-continued

Markers contained within defined chromosomal intervals that can be used to select for Rcg1.

| Interval (and position on IBM2 neighbors 4 map in cM) | Position relative to Rcg1 | Markers that could be used for selection of Rcg1 |
|---|---|---|
| UMC1086 (500.59)- UMC2200 (543.44) | Above the Rcg1 gene UMC1086 - Rcg1 | UMC1086, AY110631, UMC2285, MZA8136, MZA6064, NPI270, NPI300C, PHP20071, CDO127a, RGPI102, UAZ122, BNL17.05, MZA11455, MZA15842, MZA11123, MZA2591 |
|  | Below the Rcg1 gene Rcg1 - UMC2200 | PHI093, MZA1215, MZA1216, MZA3434, CL12681_1, NPI444, UMC15a, MZA8761, CSU166a, CDO365, CSU1038b, CSU1073b, CSU597a, RGPG111, UMN433, PHP20562, C2, NPI910, CSU178a, CSU202, TDA44, MZA1851, UMC1051, MZA11394, PCO136722, UMC2187, NPI410, PSR109B, UMC1371, UMC1842, UMC1856, AY109980, UMC1132, NFD106, AY105971, AY110989, ENSI002A, RZ596B, BNL23A, BNL29, UMC2200 |
| UMC2285 (514.9)- UMC2187 (531.7) | Above the Rcg1 gene UMC2285 - Rcg1 | UMC2285, MZA8136, MZA6064, NPI270, NPI300C, PHP20071, CDO127a, RGPI102, UAZ122, BNL17.05, MZA11455, MZA15842, MZA11123, MZA2591 |
|  | Below the Rcg1 gene Rcg1 - UMC2187 | PHI093, MZA1215, MZA1216, MZA3434, CL12681_1, NPI444, UMC15a, MZA8761, CSU166a, CDO365, CSU1038b, CSU1073b, CSU597a, RGPG111, UMN433, PHP20562, C2, NPI910, CSU178a, CSU202, TDA44, MZA1851, UMC1051, MZA11394, PCO136722, UMC2187 |
| Within UMC2285 (514.9)- UMC15a (525.8) | Above the Rcg1 gene, within UMC2285 - Rcg1 | MZA8136, MZA6064, NPI270, NPI300C, PHP20071, CDO127a, RGPI102, UAZ122, BNL17.05, MZA11455, MZA15842, MZA11123, MZA2591 |
|  | Below the Rcg1 gene, within Rcg1 - UMC15a | PHI093, MZA1215, MZA1216, MZA3434, CL12681_1, NPI444 |

The public markers are taken from the IBM2 neighbors 4 map, while the relative locations of the Pioneer markers (prefix 'MZA') were determined by mapping to the same genetic map, and by location on the physical map.

TABLE 17

Markers Within the Rcg1 Locus

| Marker Name | SNP sequence position on SEQ ID NO: 137 | SNP Sequence | Invader Oligo | Invader Probe | Forward Primer | Reverse Primer |
|---|---|---|---|---|---|---|
| PHD0001-01 | 12-270 | SEQ ID NO: 158 | SEQ ID NO: 159 | SEQ ID NO: 160 | SEQ ID NO: 161 | SEQ ID NO: 162 |
| PHD0002-01 | 272-530 | SEQ ID NO: 163 | SEQ ID NO: 164 | SEQ ID NO: 165 | SEQ ID NO: 166 | SEQ ID NO: 167 |
| PHD0003-01 | 7232-7500 | SEQ ID NO: 168 | SEQ ID NO: 169 | SEQ ID NO: 170 | SEQ ID NO: 171 | SEQ ID NO: 172 |
| PHD0004-01 | 11302-11580 | SEQ ID NO: 173 | SEQ ID NO: 174 | SEQ ID NO: 175 | SEQ ID NO: 176 | SEQ ID NO: 177 |
| PHD0005-01 | 11581-11880 | SEQ ID NO: 178 | SEQ ID NO: 179 | SEQ ID NO: 180 | SEQ ID NO: 181 | SEQ ID NO: 182 |
| PHD0006-01 | 11881-12170 | SEQ ID NO: 183 | SEQ ID NO: 184 | SEQ ID NO: 185 | SEQ ID NO: 186 | SEQ ID NO: 187 |
| PHD0007-01 | 12171-12470 | SEQ ID NO: 188 | SEQ ID NO: 189 | SEQ ID NO: 190 | SEQ ID NO: 191 | SEQ ID NO: 192 |
| PHD0008-01 | 25417-25690 | SEQ ID NO: 193 | SEQ ID NO: 194 | SEQ ID NO: 195 | SEQ ID NO: 196 | SEQ ID NO: 197 |
| PHD0009-01 | 25692-25950 | SEQ ID NO: 198 | SEQ ID NO: 199 | SEQ ID NO: 200 | SEQ ID NO: 201 | SEQ ID NO: 202 |
| PHD0010-01 | 25951-26200 | SEQ ID NO: 203 | SEQ ID NO: 204 | SEQ ID NO: 205 | SEQ ID NO: 206 | SEQ ID NO: 207 |
| PHD0011-01 | 26602-26860 | SEQ ID NO: 208 | SEQ ID NO: 209 | SEQ ID NO: 210 | SEQ ID NO: 211 | SEQ ID NO: 212 |
| PHD0012-01 | 26932-27200 | SEQ ID NO: 213 | SEQ ID NO: 214 | SEQ ID NO: 215 | SEQ ID NO: 216 | SEQ ID NO: 217 |
| PHD0013-01 | 27322-27580 | SEQ ID NO: 218 | SEQ ID NO: 219 | SEQ ID NO: 220 | SEQ ID NO: 221 | SEQ ID NO: 222 |
| PHD0014-01 | 28472-28740 | SEQ ID NO: 223 | SEQ ID NO: 224 | SEQ ID NO: 225 | SEQ ID NO: 226 | SEQ ID NO: 227 |
| PHD0015-01 | 28791-2900? | SEQ ID NO: 228 | SEQ ID NO: 229 | SEQ ID NO: 230 | SEQ ID NO: 231 | SEQ ID NO: 232 |

TABLE 18

List of Public Lines use in Haplotype Analysis

| | | | | | |
|---|---|---|---|---|---|
| 38-11 | CO109 | MP305 | A509 | F2 | OH40B |
| A165 | D02 | N28 | A556 | F252 | OH43 |
| A188 | D146 | OH07 | A619 | F257 | OH45 |

TABLE 18-continued

List of Public Lines use in Haplotype Analysis

| | | |
|---|---|---|
| A632 | F283 | OS420 |
| B | F7 | OS426 |
| B14 | GT119 | PA91 |
| B37 | H84 | R159 |
| B42 | H99 | SC213R |
| B64 | HATO4 | SD105 |
| B73 | HY | SRS303 |
| B84 | Indiana H60 | T232 |
| B89 | K187-11217 | TR9-1-1-6 |
| B94 | K55 | TX601 |
| C103 | L1546 | V3 |
| C106 | L317 | W153R |
| CI66 | Minn49 | WF9 |
| CM49 | MO13 | |
| CM7 | Mo17 | |

---

What is claimed is:

1. An isolated polynucleotide comprising a polynucleotide operably linked to a heterologous promoter selected from the group consisting of: wherein the polynucleotide comprises a nucleotide sequence encoding a polypeptide conferring or enhancing resistance to *Colletotrichum*, wherein the polypeptide has an amino acid sequence of at least 95% identity, when compared to SEQ ID NO: 3 based on the Needleman-Wunsch alignment algorithm.

2. The polynucleotide of claim 1, wherein the nucleotide sequence comprises SEQ ID NO: 2.

3. The polynucleotide of claim 1, wherein the nucleotide sequence comprises the sequence of the plasmid deposited as Patent Deposit No. NRRL B-30895.

4. A DNA construct comprising the polynucleotide of claim 1.

5. A process for transforming a host cell, comprising transforming the host cell with the polynucleotide of claim 1.

6. The process of claim 5 wherein the host cell is a plant cell.

7. The process of claim 6 wherein the plant cell is from maize.

8. A plant cell comprising the DNA construct of claim 4.

9. A plant cell comprising the polynucleotide of claim 1.

10. The plant cell of claim 9, wherein said plant cell is from maize.

11. A process for producing a plant comprising transforming a plant cell with the recombinant DNA construct of claim 4 and regenerating a plant from the transformed plant cell.

12. A plant comprising the recombinant DNA construct of claim 4.

13. The plant of claim 12, wherein said plant is maize.

14. A seed comprising the recombinant DNA construct of claim 4.

15. The seed of claim 14, wherein said seed is maize seed.

16. A process of conferring or enhancing resistance to *Colletotrichum*, comprising transforming a plant with the recombinant DNA construct of claim 4, thereby conferring or enhancing resistance to *Colletotrichum*.

* * * * *